US 9,273,053 B2

(12) United States Patent
Matsumoto et al.

(10) Patent No.: US 9,273,053 B2
(45) Date of Patent: *Mar. 1, 2016

(54) SULFUR-CONTAINING HETEROCYCLIC DERIVATIVE HAVING BETA SECRETASE INHIBITORY ACTIVITY

(71) Applicant: Shionogi & Co., Ltd., Osaka-shi, Osaka (JP)

(72) Inventors: Sae Matsumoto, Osaka (JP); Yuuji Kooriyama, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 190 days.

This patent is subject to a terminal disclaimer.

(21) Appl. No.: 13/952,073

(22) Filed: Jul. 26, 2013

(65) Prior Publication Data
US 2015/0105379 A1    Apr. 16, 2015

Related U.S. Application Data

(62) Division of application No. 12/997,802, filed as application No. PCT/JP2009/060696 on Jun. 11, 2009, now Pat. No. 8,637,504.

(30) Foreign Application Priority Data

Jun. 13, 2008  (JP) ................. 2008-154990
Oct. 22, 2008  (JP) ................. 2008-271689
Apr. 22, 2009  (JP) ................. 2009-103616

(51) Int. Cl.
C07D 487/04    (2006.01)
C07D 417/12    (2006.01)
C07D 417/14    (2006.01)
C07D 279/06    (2006.01)
C07D 417/10    (2006.01)

(52) U.S. Cl.
CPC ............ *C07D 487/04* (2013.01); *C07D 279/06* (2013.01); *C07D 417/10* (2013.01); *C07D 417/12* (2013.01); *C07D 417/14* (2013.01)

(58) Field of Classification Search
CPC .. C07D 487/04; C07D 417/12; C07D 417/14; C07D 279/06
USPC ................... 514/227.2; 544/53, 55
See application file for complete search history.

(56) References Cited

U.S. PATENT DOCUMENTS

| | | |
|---|---|---|
| 2,899,426 A | 8/1959 | Bloom et al. |
| 3,115,494 A | 12/1963 | Joseph et al. |
| 3,227,713 A | 1/1966 | Behner et al. |
| 3,235,551 A | 2/1966 | Schubert et al. |
| 3,577,428 A | 5/1971 | Suh et al. |
| 3,636,116 A | 1/1972 | Trepanier |
| 3,719,674 A | 3/1973 | Trepanier |
| 3,775,409 A | 11/1973 | Harsanyi et al. |
| 4,049,807 A | 9/1977 | Paulus et al. |
| 4,311,840 A | 1/1982 | Condon |
| 4,895,841 A | 1/1990 | Sugimoto et al. |
| 4,906,626 A | 3/1990 | Amrein et al. |

(Continued)

FOREIGN PATENT DOCUMENTS

| | | |
|---|---|---|
| CA | 2163724 | 5/1996 |
| CA | 2165386 | 6/1996 |

(Continued)

OTHER PUBLICATIONS

Bathich, "Synthesis of branched amino polyols and amino hydroxy acids: stereoselective addition of C-Nucleophiles to isoxazoline and isoxazolinium salts and assignment of configurations," 2006, pp. 148.
Dörwald, "Side reactions in organic synthesis: a guide to successful synthesis design" 2005 Wiley-VCH Verlag GmbH & Co., KGaA, Wienheim, chapter 1, 32 pages total.
Wermuth; Practice of Medicinal Chemistry, Third Ed., 2008, Elsevier, chapter 15.
Co-pending U.S. Appl. No. 14/112,400, entitled Pyridine Derivatives and a Pharmaceutical Composition for Inhibiting Bace1 Containing Them, filed Oct. 17, 2013.
Co-pending U.S. Appl. No. 14/113,327, entitled Oxazine Derivatives and a Pharmaceutical Composition for Inhibiting Bace1 Containing Them, filed Oct. 22, 2013.
Co-pending U.S. Appl. No. 14/070,202, entitled A Pharmaceutical Composition for Treating Alzheimer's Disease, filed Nov. 1, 2013.
Emilio Testa et al.: "Auf das Zentralnervensystem wirkende Substanzen, XXXVI, Weitere Untersuchungen über die 2-substituierten Azetidine"; Justus Liebigs Annalen Der Chemie, vol. 673, No. 1., May 4, 1964, pp. 60-70 XP055091964.

(Continued)

*Primary Examiner* — Kahsay Habte
(74) *Attorney, Agent, or Firm* — Hamre, Schumann, Mueller & Larson, P.C.

(57) ABSTRACT

The following compound is provided as an agent for treating a disease induced by production, secretion and/or deposition of amyloid β protein, for example, a compound represented by the formula:

(III)

$$\begin{array}{c}R^{3b}\underset{R^{3c}}{\overset{R^{3a}}{\diagdown}}\overset{S}{\underset{N}{\diagup}}NR^{2a}R^{2b}\\R^{3d}\overset{|}{\underset{A}{\diagup}}R^{y}\end{array}$$

wherein $R^y$ is halogeno lower alkyl;
ring A is an optionally substituted carbocyclic group or an optionally substituted heterocyclic group,
$R^1$ is optionally substituted lower alkyl or the like,
$R^{2a}$ and $R^{2b}$ are each independently hydrogen, optionally substituted lower alkyl or the like,
$R^{3a}$, $R^{3b}$, $R^{3c}$ and $R^{3d}$ are each independently hydrogen, halogen, hydroxy, optionally substituted lower alkyl or the like, or a pharmaceutically acceptable salt thereof, or a solvate thereof.

13 Claims, No Drawings

(56) References Cited

U.S. PATENT DOCUMENTS

| | | | |
|---|---|---|---|
| 5,100,901 A | 3/1992 | Sugimoto et al. | |
| 5,236,942 A | 8/1993 | Miller | |
| 5,328,915 A | 7/1994 | Long et al. | |
| 5,880,147 A | 3/1999 | Yoshida et al. | |
| 5,952,374 A | 9/1999 | Clarkson, Jr. et al. | |
| 6,096,753 A | 8/2000 | Spohr et al. | |
| 6,590,123 B2 | 7/2003 | Bekesi et al. | |
| 6,713,276 B2 | 3/2004 | Cordell et al. | |
| 7,183,070 B2 | 2/2007 | Cordell et al. | |
| 7,309,706 B2 | 12/2007 | Rupp et al. | |
| 7,326,792 B2 | 2/2008 | Shum et al. | |
| 7,414,050 B2 | 8/2008 | Illig et al. | |
| 7,763,609 B2 | 7/2010 | Zhu et al. | |
| 7,902,238 B2 | 3/2011 | Galley et al. | |
| 8,173,642 B2 | 5/2012 | Kobayashi et al. | |
| 8,338,413 B1 | 12/2012 | Rueeger | |
| 8,541,408 B2 * | 9/2013 | Tamura et al. | 514/227.2 |
| 2002/0019427 A1 | 2/2002 | Carry et al. | |
| 2005/0165080 A1 | 7/2005 | Rupp et al. | |
| 2006/0173006 A1 | 8/2006 | Sun et al. | |
| 2006/0183790 A1 | 8/2006 | Cole et al. | |
| 2006/0183792 A1 | 8/2006 | Fobare et al. | |
| 2006/0183943 A1 | 8/2006 | Hu et al. | |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0224656 A1 | 9/2007 | Cordell et al. | |
| 2008/0200445 A1 | 8/2008 | Zhu et al. | |
| 2009/0023729 A1 | 1/2009 | Nakamura et al. | |
| 2009/0082560 A1 | 3/2009 | Kobayashi et al. | |
| 2010/0075957 A1 | 3/2010 | Tamura et al. | |
| 2010/0093999 A1 | 4/2010 | Motoki et al. | |
| 2010/0125087 A1 | 5/2010 | Holenz et al. | |
| 2010/0160290 A1 | 6/2010 | Kobayashi et al. | |
| 2010/0234365 A1 | 9/2010 | Liu et al. | |
| 2010/0261727 A1 | 10/2010 | Chi et al. | |
| 2011/0009395 A1 | 1/2011 | Audia et al. | |
| 2011/0046122 A1 | 2/2011 | Andreini et al. | |
| 2011/0065695 A1 | 3/2011 | Beauchamp et al. | |
| 2011/0190279 A1 | 8/2011 | Hori et al. | |
| 2011/0237576 A1 | 9/2011 | Yonezawa et al. | |
| 2012/0015961 A1 | 1/2012 | Tamura et al. | |
| 2012/0016116 A1 | 1/2012 | Kobayashi et al. | |
| 2012/0022249 A1 | 1/2012 | Kobayashi et al. | |
| 2012/0172355 A1 | 7/2012 | Tamura et al. | |
| 2012/0202828 A1 | 8/2012 | Castro Pineiro et al. | |
| 2012/0238548 A1 | 9/2012 | Gabellieri et al. | |
| 2012/0238557 A1 | 9/2012 | Masui et al. | |
| 2012/0245154 A1 | 9/2012 | Anan et al. | |
| 2012/0245155 A1 | 9/2012 | Yoshida et al. | |
| 2012/0245157 A1 | 9/2012 | Masui et al. | |
| 2012/0253035 A1 | 10/2012 | Narquizian et al. | |
| 2012/0258961 A1 | 10/2012 | Suzuki et al. | |
| 2012/0258962 A1 | 10/2012 | Hilpert et al. | |
| 2012/0295900 A1 | 11/2012 | Hilpert et al. | |
| 2013/0158260 A1 | 6/2013 | Kobayashi et al. | |
| 2013/0210839 A1 | 8/2013 | Masui et al. | |
| 2013/0217705 A1 | 8/2013 | Mitsuoka et al. | |
| 2013/0303755 A1 | 11/2013 | Kobayashi et al. | |

FOREIGN PATENT DOCUMENTS

| | | |
|---|---|---|
| EP | 140144 | 2/1980 |
| EP | 0798 292 | 10/1995 |
| EP | 0713704 | 5/1996 |
| EP | 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1 942 105 | 7/2008 |
| EP | 1942105 | 7/2008 |
| EP | 2147914 | 1/2010 |
| EP | 2151435 | 2/2010 |
| EP | 2 233 474 | 9/2010 |
| EP | 2305672 | 4/2011 |
| EP | 2332943 | 6/2011 |
| EP | 2 360 155 | 8/2011 |
| EP | 2360155 | 8/2011 |
| EP | 2415756 | 2/2012 |
| EP | 2500344 | 9/2012 |
| EP | 2511268 | 10/2012 |
| EP | 2511269 | 10/2012 |
| EP | 2514747 | 10/2012 |
| EP | 2518059 | 10/2012 |
| EP | 2634186 | 9/2013 |
| EP | 2634188 | 9/2013 |
| EP | 2689780 | 1/2014 |
| EP | 2703399 | 3/2014 |
| EP | 2703401 | 3/2014 |
| GB | 1001093 | 8/1965 |
| JP | 62-120374 | 6/1987 |
| JP | 8-231521 | 9/1996 |
| JP | 9-67355 | 3/1997 |
| JP | 10-505862 | 12/1999 |
| JP | 11-349572 | 12/1999 |
| JP | 2004-149429 | 5/2004 |
| JP | 2005-509651 | 4/2005 |
| JP | 2005-517634 | 6/2005 |
| JP | 2005-526005 | 9/2005 |
| JP | 2005-531520 | 10/2005 |
| JP | 2009-051828 | 3/2009 |
| JP | 2009-520685 | 5/2009 |
| JP | 2012250933 | 12/2012 |
| JP | 2014101354 | 6/2014 |
| WO | 94/12165 | 6/1994 |
| WO | 95/09619 | 4/1995 |
| WO | 96/09286 | 3/1996 |
| WO | 96/14842 | 5/1996 |
| WO | 96/18608 | 6/1996 |
| WO | 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | 01/19788 | 3/2001 |
| WO | 01/78709 | 10/2001 |
| WO | 01/87293 | 11/2001 |
| WO | 02/062766 | 8/2002 |
| WO | 02/088101 | 11/2002 |
| WO | 02/096897 | 12/2002 |
| WO | 03/039446 | 5/2003 |
| WO | 03/040096 | 5/2003 |
| WO | 03/040115 | 5/2003 |
| WO | 03/040142 | 5/2003 |
| WO | 03/082191 | 10/2003 |
| WO | 2004/009549 | 1/2004 |
| WO | 2004/014843 | 2/2004 |
| WO | 2004/031154 | 4/2004 |
| WO | 2004/039404 | 5/2004 |
| WO | 2004/043916 | 5/2004 |
| WO | 2004/096795 | 11/2004 |
| WO | 2005/014555 | 2/2005 |
| WO | 2005/032493 | 4/2005 |
| WO | 2005/058311 | 6/2005 |
| WO | 2005/097767 | 10/2005 |
| WO | 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | 2006/041404 | 4/2006 |
| WO | 2006/041405 | 4/2006 |
| WO | 2006/065204 | 6/2006 |
| WO | 2006/065277 | 6/2006 |
| WO | 2006/076284 | 7/2006 |
| WO | 2006-519758 | 8/2006 |
| WO | 2006/099379 | 9/2006 |
| WO | 2006/138192 | 12/2006 |
| WO | 2006/138217 | 12/2006 |
| WO | 2006/138265 | 12/2006 |
| WO | 2006/138304 | 12/2006 |
| WO | 2007/002220 | 1/2007 |

(56) References Cited

FOREIGN PATENT DOCUMENTS

| | | |
|---|---|---|
| WO | 2007/005366 | 1/2007 |
| WO | 2007/005404 | 1/2007 |
| WO | 2007/016012 | 2/2007 |
| WO | 2007/038271 | 4/2007 |
| WO | 2007/049532 | 5/2007 |
| WO | 2007/058580 | 5/2007 |
| WO | 2007/058582 | 5/2007 |
| WO | 2007/058583 | 5/2007 |
| WO | 2007/058601 | 5/2007 |
| WO | 2007/058602 | 5/2007 |
| WO | WO 2007049532 A1 * | 5/2007 |
| WO | 2007/073284 | 6/2007 |
| WO | 2007/078813 | 7/2007 |
| WO | 2007/092846 | 8/2007 |
| WO | 2007/092854 | 8/2007 |
| WO | 2007/114771 | 10/2007 |
| WO | 2007/120096 | 10/2007 |
| WO | 2007/146225 | 12/2007 |
| WO | 2008/011560 | 1/2008 |
| WO | 2008/022024 | 2/2008 |
| WO | 2008/073365 | 6/2008 |
| WO | 2008/073370 | 6/2008 |
| WO | 2008/103351 | 8/2008 |
| WO | 2008/133273 | 11/2008 |
| WO | 2008/133274 | 11/2008 |
| WO | 2009/010454 | 1/2009 |
| WO | 2009/064418 | 5/2009 |
| WO | 2009/091016 | 7/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/013302 | 2/2010 |
| WO | 2010/013794 | 2/2010 |
| WO | 2010/019392 | 2/2010 |
| WO | 2010/019393 | 2/2010 |
| WO | 2010/038686 | 4/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/128058 | 11/2010 |
| WO | 2010/129864 | 11/2010 |
| WO | 2011/005738 | 1/2011 |
| WO | 2011/009897 | 1/2011 |
| WO | 2011/009898 | 1/2011 |
| WO | 2011/009943 | 1/2011 |
| WO | 2011/020806 | 2/2011 |
| WO | 2011/029803 | 3/2011 |
| WO | 2011/044181 | 4/2011 |
| WO | 2011/044184 | 4/2011 |
| WO | 2011/044185 | 4/2011 |
| WO | 2011/044187 | 4/2011 |
| WO | 2011/058763 | 5/2011 |
| WO | 2011/060207 | 5/2011 |
| WO | 2011057973 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | 2011/080176 | 7/2011 |
| WO | 2011/138293 | 11/2011 |
| WO | 2011/154374 | 12/2011 |
| WO | 2011/154431 | 12/2011 |
| WO | 2012/000933 | 1/2012 |
| WO | 2012/006953 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095469 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012095451 | 7/2012 |
| WO | 2012095463 | 7/2012 |
| WO | 2012095469 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |
| WO | 2013027188 | 2/2013 |
| WO | 2013041499 | 3/2013 |
| WO | 2013083556 | 6/2013 |
| WO | 2013083557 | 6/2013 |
| WO | 2013110622 | 8/2013 |
| WO | 2013142613 | 9/2013 |

OTHER PUBLICATIONS

Portnyagin et al.: Russian Journal of Organic Chemistry, Consultants Bureau, US, vol. 10, Jan. 1, 1974, pp. 95-98, XP009174887.

Database Caplus [Online]; Chemical Abstracts Service, Columbus, OH, US; 2006, Bathich, Yaser: "Synthesis of Branched Amino Polyoly and Aminohydroxy Acids: Stereoselective Additiom of C-Nucleophiles ti Isoxazolines and Isoxazolinium Salts and Assignment of Configurations", XP002717806.

Database Registry [Online]; Chemical Abstracts Service, Columbus, OH, US; 3-Pyridinepropanol, .beta., .gamma.-diamino-6-fluoro-.gamma.-(4-fluorophenyl)-, (.beta.-R,.gamma.S)-, Apr. 29, 2004, XP002717807.

Church J et al.: "Anticonvulsant actions of phencyclidine receptor ligands: Correlation with N-Methylaspartate Antagonism in vivo"; General Phamacology, Pergamon Press, Oxford, GB, vol. 21, No. 2, Jan. 1, 1990, pp. 165-170, XP023834032.

Cohen et al. "Synthesis of 2-Amino-5, +-dihydro-4H-1, 3-thiazines and Related Compounds by Acid Catalyzed Cyclization of Allylic Isothiuronium Salts." Journal of Heterocyclic Chemistry 14(5), 1977, p. 717-723.

Kuo et al. "A Synthesis of Estrone via Novel Intermediates. Mechanism of Coupling Reaction of a Vinyl Carbinol with a β Diketone." Journal of Organic Chemistry 33(8), Aug. 1968, p. 3126-3132.

Liebscher et al. "2-Arylimino-3-Thiazolines—Formation of Unusual Tautomers of 2-Acylamino-Thiazolines—A Revision." Tetrahedron Letters, 26(35), 1985, p. 4179-4180.

Fernández et al. "Syntheses and Spectral Properties of β-Iodoureas ans 2-Amino-4, 4-diphenyl-2-oxazolines." Journal of Heterocyclic Chemistry, 28(3), Apr.-May 1991, p. 777-780.

Schaumann et al. "Stickstoffhaltige Fünfring-Heterocyclen aus Carbodiimiden orderKeteniminen mit 3-Dimethylamino-2H-azirinen." Liebigs Annalen der Chemie, 1981, p. 290-305.

Fernández et al. "Syntheses of β-iodourea derivatives of carbohydrates and glycosylamino-ozazolines." Carbohydrate Research, 216, 1991, p. 21-32.

Cambie et al. "vic-Iodothiocyanates and Iodoisothiocyanates. Part 2. New Syntheses of Thiazolidin-2-ones and 2-Amino-thiazolines." Journal of the Chemical Society, Perkin Transactions I, 3, 1979, p. 765-770.

(56) References Cited

OTHER PUBLICATIONS

Kondrat'Eva et al. "Noncyclic dimer of 4-methyl-2-(dimenthylamino)oxazole." Akademii Nauk SSSR, Seriya Khimicheskaya, 7, 1977, p. 1680-1682.
Hünig et al. "Azo dyes by oxidative coupling, XVIII. Synthesis of 3-substituted 2-thiazolone hydrazones and 2-thiazolone benzenesulfonylhydrazones." Ann. 647, 1961, p. 66-76.
Edwards et al., "Application of fragment-based lead generation to the discovery of novel, cyclic amidine β-secretase inhibitors with nanomolar potency, cellular activity, and high ligand efficiency", Journal of Medicinal Chemistry., vol. 50, No. 24, 2007, pp. 5912-5925.
Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.
Fujisawa et al., "Switchover of diastereofacial selectivity in the condensation reaction of optically active N-sulfmimine with ester enolate," Tetrahedron Letters, vol. 37, No. 22, 1996, pp. 3881-3884.
Vilaivan et al., "Recent Advances in Catalytic Asymmetric Addition to Imines and Related C=N Systems," Current Organic Chemistry, vol. 9, 2005, pp. 1315-1392.
Hua et al., "N-Alkylidenesulfmamides," Sulfur Reports, vol. 21, 1999, pp. 211-239.
Savoca et al., "1,5-Diazabicyclo[4.3.0]non-5-ene[1]," Encyclopedia of Reagents for Organic Synthesis, 2006, 10 pages total.
Creeke et al., "Synthesis and elaboration of heterocycles via iodocyclisation of unsaturated thioureas," Tetrahedron Letters, 1989, vol. 30, No. 33, pp. 4435-4438.
Mellor et al., A general route to spirocycles by radical additions to exocyclic unsaturated sulphides and related compounds, Tetrahedron Letters, 1991, vol. 32, No. 48, pp. 7111-7114.
Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.
Singh et al., "Synthesis of heterocyclic compounds via enamines. Part 8.[t] Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.
Vippagunta et al. "Crystalline Solids". Advanced Drug Delivery Reviews, vol. 48, 2001, pp. 3-26.
Gavezzotti. "Are Crystal Structures Predictable". Accounts of Chemical Research, vol. 27, 1994, pp. 309-314.
Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).
Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.
Schubert et al., "Neue synthesen von 2-Amino-5,6-dihydro-4H-1,3-thiazinen," Archiv der Pharmazie, 1968, vol. 301, No. 10, pp. 750-762.
Huang et al., "Pharmacophore model construction of β-secretase inhibitors," 2008, Acta Chimica Sinica, vol. 66, No. 16, pp. 1889-1897 (English language abstract provided).
Clark, et al., "Antitumor Imidazotetrazines. 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.
Congreve, et al., "Application of Fragment Screening by X-ray Crystallography to the Discovery of Aminopyridines as Inhibitors of β-Secretase[§]", J. Med. Chem., vol. 50, 2007, pp. 1124-1132.
Huang, et al., "Progress in the Development of Nonpeptidomimetic BACE 1 Inhibitors for Alzheimer's Disease", Current Medicinal Chemistry, vol. 16, 2009, pp. 1806-1820.
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.
Siddiqui et al., "Some extensions of Von Bruan (BrCN) reaction on organic bases," Proc. Pakistan Acad Sci., 1988, vol. 25, No. 3, pp. 231-240.
Ozawa et al., Pharmacological actions of 2-Aminoethylisothiuronium (AET) derivatives. I[1]), Yakugaku Zasshi, 1968, vol. 88, No. 2, pp. 156-162 (with English language abstract).
Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.
Burton et al., "Addition reactions of quinones. Part I. The reaction of cysteine and thiourea and its derivatives with some quinones," Journal of the Chemical Society, 1952, pp. 2193-2196.
Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).
Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.
Cole et al., "Acylguanidines as small-molecule beta-secretase inhibitors," J. Med. Chem., 2006, pp. 6158-6161.
Bol'but et al., Heterocyclizations of Functionalized Heterocumulenes with C,N- and C,O-Dinucleophiles: III.* Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 29, No. 2, pp. 1789-1791.
Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.
Sayed et al., "α-Enones in heterocyclic synthesis of indazole, thiazine, chromene and quinolone derivatives with their antimicrobial activities," Journal of Chemical Research, 2009, vol. 12, pp. 726-728.
Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.
Bol'but et al., "Synthesis of 4-imino-2-trifluoromethyl-3,4-dihydro-2h-Benzo-[1,3]Thiazines," Chemistry of Heterocyclic Compounds, 2001, vol. 37, No. 4, pp. 522-523.
Vovk et al., "Intramolecular thermal cyclization of N-(1-Aryl-1-aryloxy-2,2,2-trifluoroethyl)-N'-arylcarbodiimides," Russian Journal of Organic Chemistry, 2000, vol. 36, No. 12, pp. 1739-1742.
Vovk et al., "Regioselective cyclization of 1-chloroalkylcarbodiimides with 1,1- and 1,2-bifunctional nucleophilic reagents," Russian Journal of Organic Chemistry, 1997, vol. 22, No. 1, pp. 96-102.
Potts et al., "N-Acyl-β-enamino Ketones: Versatile Heterocyclic Synthons," J. Org. Chem., 1983, 48, pp. 625-626.
Rivkin et al., "Piperazinyl pyrimidine derivatives as potent γ-secretase modulators," Bioorganic & Medicinal Chemistry Letters, 2010, 20, pp. 1269-1271.
Rivkin et al., "Purine derivatives as potent γ-secretase modulators," Bioorganic & Medicinal Chemistry Letters, 2010, 20, pp. 2279-2282.
STN a the Web, RN 79005-45-1, 1964.
Zhu et al., Two novel Diastereoselective Three-Component Reactions of Alkenes or 3,4-Dihydro-(2H)-pyran with Urea/Thiourea-Aldehyde Mixtures: [4 +2] Cycloaddition vs Biginelli-Type Reaction, Organic Letters, 2006, vol. 8, No. 12, pp. 2599-2602.
Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).

(56) References Cited

OTHER PUBLICATIONS

Kavya et al. "Nitric oxide synthase regulation and diversity: Implications in Parkinson's Disease". Nitric Oxide: Biology and Chemistry, vol. 15, No. 4, pp. 280-294 (2006).
Chiou et al. "Review: Effects of Nitric Oxide on Eye Diseases and Their Treatment". Journal of Ocular Pharmacology and Therapeutics, vol. 17, No. 2, pp. 189-198 (2001).
Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).
Pak et al. "Morphine via nitric oxide modulates β-amyloid metabolism: a novel protective mechanism for Alzheimer's disease". Medical Science Monitor, vol. 11, No. 10, pp. BR357-BR366 (2005).
Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.
Mulcahy et al., "A stereoselective synthesis of (+)-Gonyautoxin 3," Journal of the American Chemical Society, 2008, vol. 130, pp. 12630-12631.
"Diphenyl Cyanocarbonimidate," e-EROS Encyclopedia of Reagents for Organic Synthesis, 2001, 2 pages total.
Shafik et al., "Synthesis of novel 2-[2-(substituted amino)phenethyl]-1$H$-benzimidazoles; 3,4-dihydro and 1,2,3,4-tetrahydropyrimido[1,6-α]-benzimidazoles as potential antiulcer agents," 2004, Pharmazie, vol. 59, No. 12, pp. 899-905.
Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.
Buschauer et al., "Isohistamine und Homologe als Bausteine von $H_2$-Antagonisten,"Arzneimittel-Forschung, 1985, vol. 35, pp. 1025-1029 (English language abstract provided).
Buschauer et al., "7,8-Dihydroimidazo[1,2-c]pyrimidin-5(6$H$)-one, -5(6$H$)-thione and -5(6$H$)-ylidencyanamide," Chemische Berichte, 1984, vol. 117, pp. 2597-2614.
Borchers et al., "$H_2$-Antihystaminika, 19. Mitt.[1]) Synthesen und $H_2$-antihistaminische Wirkung N$^α$-substituierter Histamine," Archiv der Pharmazie (Weinheim, Germany), 1984, vol. 317, pp. 455-459.
Cheong et al., "Pharmacophore elucidation for a new series of 2-aryl-pyrazolo-triazolo-pyrimidines as potent human $A_3$ adenosine receptor antagonists," Bioorganic & Medicinal Chemistry Letters, 2011, vol. 21, pp. 2898-2905.
Xu et al., "Copper-catalyzed cascade synthesis of benzimidazoquinazoline derivatives under mild condition," Chemical Communications, 2011, vol. 47, pp. 5596-5598.
Kishore et al., "QSAR of adenosine receptor antagonists: exploring physicochemical requirements for binding of pyrazolo[4,3-e]-1,2,4-triazolo[1,5-c]pyrimidine derivatives with human adenosine $A_3$ receptor subtype," Bioorganic & Medicinal Chemistry Letters, 2011, vol. 21, No. 2, pp. 818-823.
Dolzhenko et al., "8-methyl-2-[4-(trifluoromethyl)phenyl]-8$H$-pyrazolo[4,3-e][1,2,4]triazolo[1,5-c]-pyrimidin-5-amine methanol disolvate," Acta Crystallographica, Section E: Structure Reports Online, 2010, E66(7), 12 pages total.
Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.
Beaton et al., "The synthesis of 1-aminodihydroisoquinolines by an imine addition cyclisation reaction," 1998, Tetrahedron Letters, vol. 39, pp. 1227-1230.
Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.
Weinhardt et al. "Synthesis and antidepressant profiles of phenyl-substituted 2-amino- and 2- ((alkoxycarbonyl)amino)11,4,5,6-tetrahydropyrimidines," Journal of Medicinal Chemistry, vol. 28, No. 6, 1985, pp. 694-698.
Meschino et al., "2-Amino-5,6-dihydro-1,3-oxazines. The reduction of carboxylic esters with sodium borohydride," J. Org. Chem., vol. 28, 1963, pp. 3129-3134.
Poos et al., "2-amino-5-aryl-2-oxazolines. Potent new anorectic agent," J. Med. Chem., vol. 6, 1963, pp. 266-272.
Sandin et al., "A fast and parallel route to cyclic isothioureas and guanidines with use of microwave-assisted chemistry," J. Org. Chem., vol. 69, 2004, pp. 1571-1580.
Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.
Woodgate et al., "A new synthesis of 2-amino-2-thiazolines," Heterocycles, vol. 7, No. 1, 1977, pp. 109-112.
Co-pending U.S. Appl. No. 13/881,112, entitled Fused Aminodihydropyrimidine Derivative, filed Apr. 23, 2013.
Co-pending U.S. Appl. No. 13/881,250, entitled Naphthyridine Derivative, filed Apr. 24, 2013.
Co-pending U.S. Appl. No. 13/887,745, entitled Aminodihydrothiazine Derivatives Substituted With a Cyclic Group, filed May 6, 2013.
Co-pending U.S. Appl. No. 13/941,082, entitled Aminodihydrothiazine Derivatives, filed Jul. 12, 2013.
Hilpert et al., "Beta-secretase (BACE1) inhibitors with high in vivo efficacy suitable for clinical evaluation in Alzheimer's disease," Journal of Medicinal Chemistry, 2013, 56, pp. 3980-3995.
Delgado et al., "A practical entry to beta-aryl-beta-alkyl amino alcohols: application to the synthesis of a potent BACE1 inhibitor," Organic & Biomolecular Chemistry 2012, 10, pp. 6758-6766.
Woltering et al., "BACE1 inhibitors: a head group scan on a series of amides," Bioorganic & Medicinal Chemistry Letters, 2013, vol. 23, issue14, pp. 4239-4243.
Co-pending U.S. Appl. No. 14/434,013, entitled Dihydrooxazine or Oxazepine Derivatives Having BACE1 Inhibitory Activity, filed Apr. 7, 2015 (271 pages total).
Medicinal Chemistry, Nozaki et al., Kagaku-Dojin, Jul. 1, 1995, p. 98-99 and English translation thereof, 4 pages total.

* cited by examiner

SULFUR-CONTAINING HETEROCYCLIC DERIVATIVE HAVING BETA SECRETASE INHIBITORY ACTIVITY

TECHNICAL FIELD

The present invention relates to a compound which has amyloid β production inhibitory activity, and is useful as an agent for treating disease induced by production, secretion and/or deposition of amyloid β protein.

BACKGROUND ART

In the brain of Alzheimer's patient, the peptide composed of about 40 amino acids residue as is called amyloid β protein, that accumulates to form insoluble specks (senile specks) outside nerve cells is widely observed. It is concerned that this senile specks kill nerve cells to cause Alzheimer's disease, so the therapeutic agents for Alzheimer's disease, such as decomposition agents of amyloid β protein and amyloid vaccine, are under investigation.

Secretase is an enzyme which cleaves a protein called amyloid β precursor protein (APP) in cell and produces amyloid β protein. The enzyme which controls the production of N terminus of amyloid β protein is called as β-secretase (beta-site APP-cleaving enzyme 1, BACE-1). It is thought that inhibition of this enzyme leads to reduction of producing amyloid β protein and that the therapeutic agent for Alzheimer's disease will be created due to the inhibition.

Patent Literature 1 describes the compounds which are similar to those of the present invention, and the compounds have NO synthase enzyme inhibitory activity and are useful for dementia.

Patent Literatures 2 to 5 and Non-patent Literatures 1 and 2 describe the compounds which are similar to those of the present invention, and are useful for hypertensive agent, morphine like analgesic, tranquilizers, intermediate for medicament, NPYY5 antagonist, analgesic, or the like, respectively.

Patent Literature 6 to 24 are known as β serectase inhibitor, however, all compounds in these literatures have different structures from the present invention.

PRIOR ART LITERATURES

Patent Literatures

[Patent Literature 1] International Patent Application Publication WO 96/014842
[Patent Literature 2] U.S. Pat. No. 3,235,551
[Patent Literature 3] U.S. Pat. No. 3,227,713
[Patent Literature 4] JP Application Publication JP09-067355
[Patent Literature 5] International Patent Application Publication WO 2005/111031
[Patent Literature 6] International Patent Application Publication WO 02/96897
[Patent Literature 7] International Patent Application Publication WO 04/043916
[Patent Literature 8] International Patent Application Publication WO 2005/058311
[Patent Literature 9] International Patent Application Publication WO 2005/097767
[Patent Literature 10] International Patent Application Publication WO 2006/041404
[Patent Literature 11] International Patent Application Publication WO 2006/041405
[Patent Literature 12] US Patent Publication 2007/0004786
[Patent Literature 13] US Patent Publication 2007/0004730
[Patent Literature 14] US Patent Publication 2007/27199
[Patent Literature 15] International Patent Application Publication WO 2007/049532
[Patent Literature 16] International Patent Application Publication WO 2007/146225
[Patent Literature 17] International Patent Application Publication WO 2007/114771
[Patent Literature 18] International Patent Application Publication WO 2007/073284
[Patent Literature 19] International Patent Application Publication WO 2007/058583
[Patent Literature 20] International Patent Application Publication WO 2007/058580
[Patent Literature 21] International Patent Application Publication WO 2006/138217
[Patent Literature 22] International Patent Application Publication WO 2006/138192
[Patent Literature 23] International Patent Application Publication WO 2006/065277
[Patent Literature 24] International Patent Application Publication WO 2005/058311
[Patent Literature 25] International Patent Application Publication WO 2008/103351

Non-Patent Literatures

[Non-Patent Literature 1] Journal of Heterocyclic Chemistry, 14, 717-723 (1977)
[Non-Patent Literature 2] Journal of Organic Chemistry, 33, 8, 3126-3132 (1968)
[Non-Patent Literature 3] Journal of Medicinal Chemistry, 50, 24, 5912-5925 (2007)

DISCLOSURE OF INVENTION

Problems to be solved by the Invention

The present invention provides compounds which have reducing effects to produce amyloid 1 protein, especially β secretase inhibitory activity, and are useful as an agent for treating disease induced by production, secretion and/or deposition of amyloid β protein.

Means to Solve the Problems

The present invention provides:
1) a compound represented by the following formula (I):

[Chemical formula 1]

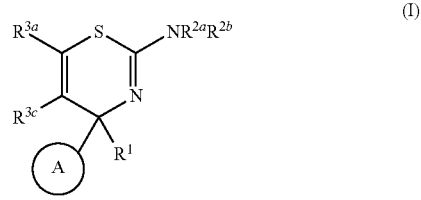

wherein ring A is an optionally substituted carbocyclic group or an optionally substituted heterocyclic group;
$R^1$ is optionally substituted lower alkyl, optionally substituted lower alkenyl, optionally substituted lower alkynyl, cyano, an optionally substituted carbocyclic group or an optionally substituted heterocyclic group;

$R^{2a}$ and $R^{2b}$ are each independently hydrogen, optionally substituted lower alkyl or optionally substituted acyl;

$R^{3a}$ and $R^{3c}$ are each independently hydrogen, halogen, hydroxy, optionally substituted lower alkyl, optionally substituted lower alkenyl, optionally substituted lower alkynyl, optionally substituted acyl, optionally substituted lower alkoxy, optionally substituted aryl lower alkyl, optionally substituted heteroaryl lower alkyl, optionally substituted aryl lower alkoxy, optionally substituted heteroaryl lower alkoxy, optionally substituted lower alkylthio, carboxy, lower alkoxycarbonyl optionally having a cyano substituent, optionally substituted amino, optionally substituted carbamoyl, an optionally substituted carbocyclic group or an optionally substituted heterocyclic group, or $R^{3a}$ and $R^{3c}$ may be taken together to form a ring;

or its pharmaceutically acceptable salt; or a solvate thereof, 2) a compound represented by the following formula (II):

[Chemical formula 2]

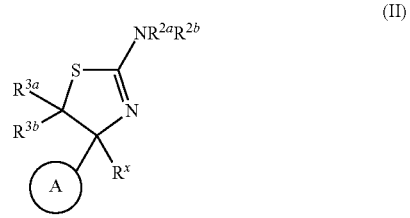

(II)

wherein $R^x$ is an optionally substituted carbocyclic group or an optionally substituted heterocyclic group;

$R^{3a}$ and $R^{3b}$ are each independently hydrogen, halogen, hydroxy, optionally substituted lower alkyl, optionally substituted lower alkenyl, optionally substituted lower alkynyl, optionally substituted acyl, optionally substituted lower alkoxy, optionally substituted aryl lower alkyl, optionally substituted heteroaryl lower alkyl, optionally substituted aryl lower alkoxy, optionally substituted heteroaryl lower alkoxy, optionally substituted lower alkylthio, carboxy, cyano, optionally substituted lower alkoxycarbonyl, optionally substituted amino, optionally substituted carbamoyl, an optionally substituted carbocyclic group or an optionally substituted heterocyclic group;

ring A, $R^{2a}$ and $R^{2b}$ are as defined in the above 1);

or its pharmaceutically acceptable salt; or a solvate thereof, 3) a compound represented by the following formula (III):

[Chemical formula 3]

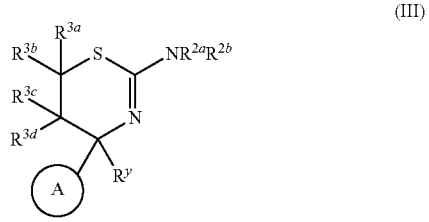

(III)

wherein $R^y$ is halogeno lower alkyl;

$R^{3a}$, $R^{3b}$, $R^{3c}$ and $R^{3d}$ are each independently hydrogen, halogen, hydroxy, optionally substituted lower alkyl, optionally substituted lower alkenyl, optionally substituted lower alkynyl, optionally substituted acyl, optionally substituted lower alkoxy, optionally substituted aryl lower alkyl, optionally substituted heteroaryl lower alkyl, optionally substituted aryl lower alkoxy, optionally substituted heteroaryl lower alkoxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group; and ring A, $R^{2a}$, and $R^{2b}$ are as defined in the above 1) or 2);

or its pharmaceutically acceptable salt; or a solvate thereof;

4) a compound represented by the following formula (IV):

[Chemical formula 4]

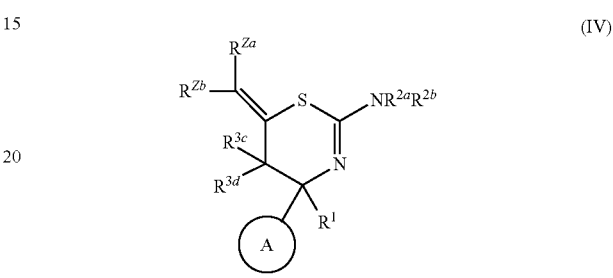

(IV)

wherein $R^{Za}$ and $R^{Zb}$ are each independently optionally substituted lower alkyl, or are taken together with a carbon atom to which they bind to form a carbocycle;

ring A, $R^{2a}$, and $R^{2b}$ are as defined in the above 1);

and $R^{3c}$ and $R^{3d}$ are as defined in the above 3);

or its pharmaceutically acceptable salt; or a solvate thereof,

4') a compound represented by the above formula (IV):

wherein $R^{Za}$ and $R^{Zb}$ are each independently hydrogen, halogen, optionally substituted lower alkyl, or $R^{Za}$ and $R^{Zb}$ are taken together with a carbon atom to which they bind to form a carbocycle; and ring A, $R^{2a}$, and $R^{2b}$ are as defined in the above 1);

and $R^{3c}$ and $R^{3d}$ are as defined in the above 3);

or its pharmaceutically acceptable salt; or a solvate thereof, 5) the compound according to the above 1), wherein $R^{3a}$ or $R^{3c}$ is hydrogen, or its pharmaceutically acceptable salt; or a solvate thereof, 6) the compound according to the above 1), wherein $R^{3a}$ and $R^{3c}$ are both hydrogen, or its pharmaceutically acceptable salt; or a solvate thereof, 7) the compound according to any one of 1), 4), 5) and 6), wherein $R^1$ is alkyl of a carbon number of 1 to 3, or its pharmaceutically acceptable salt; or a solvate thereof, 8) the compound according to the above 2), wherein $R^x$ is optionally substituted cycloalkyl, optionally substituted phenyl, or an optionally substituted nitrogen-containing aromatic heterocyclic group, or its pharmaceutically acceptable salt; or a solvate thereof, 9) the compound according to the above 2) or 8), wherein $R^{3a}$ and $R^{3b}$ are both hydrogen, or its pharmaceutically acceptable salt; or a solvate thereof, 10) the compound according to the above 3), wherein $R^{3a}$, $R^{3b}$, $R^{3c}$ and $R^{3d}$ are all hydrogen, or its pharmaceutically acceptable salt, or a solvate thereof, 11) the compound according to any one of the above 1) to 10), wherein $R^{2a}$ and $R^{2b}$ are both hydrogen, or its pharmaceutically acceptable salt; or a solvate thereof, 12) the compound according to any one of the above 1) to 11), wherein ring A is

[Chemical formula 5]

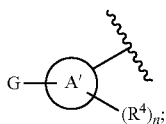

wherein ring A' is a carbocyclic group or a heterocyclic group;
G is

[Chemical formula 6]

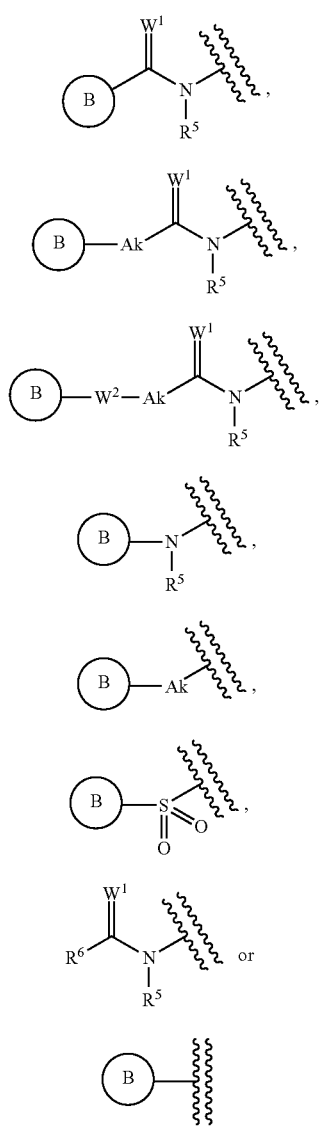

wherein $R^5$ is hydrogen, lower alkyl or acyl;
$R^6$ is optionally substituted lower alkyl, optionally substituted lower alkenyl, or optionally substituted lower alkynyl;
$W^1$ is O or S;
$W^2$ is O, S or $NR^5$;

Ak is optionally substituted lower alkylene, optionally substituted lower alkenylene, or optionally substituted lower alkynylene;
ring B is an optionally substituted carbocyclic group or an optionally substituted heterocyclic group;
each $R^4$ is independently halogen, hydroxy, mercapto, halogeno lower alkyl, lower alkyl, lower alkoxy, optionally substituted amino or lower alkylthio, and n is an integer of 0 to 2;
or its pharmaceutically acceptable salt; or a solvate thereof, 13) the compound according to the above 12), wherein ring A' is phenyl or a nitrogen-containing aromatic heterocyclic group, or its pharmaceutically acceptable salt; or a solvate thereof, 14) the compound according to the above 12), wherein ring A' is a nitrogen-containing aromatic heteromonocyclic group, or its pharmaceutically acceptable salt; or a solvate thereof, 15) the compound according to the above 12), wherein ring A' is phenyl, or its pharmaceutically acceptable salt; or a solvate thereof, 16) the compound according to any one of the above 12) to 15), wherein ring B is a nitrogen-containing aromatic heteromonocyclic group, or its pharmaceutically acceptable salt; or a solvate thereof, 17) a pharmaceutical composition comprising, as an effective ingredient, the compound according to any one of the above 1) to 16), or its pharmaceutically acceptable salt; or a solvate thereof, 18) a pharmaceutical composition having β secretase inhibitory activity, comprising, as an effective ingredient, the compound according to any one of the above 1) to 16), or its pharmaceutically acceptable salt; or a solvate thereof, 19) a method for inhibiting β secretase activity, comprising administering the compound according to any one of the above 1) to 16), or its pharmaceutically acceptable salt; or a solvate thereof, 20) use of the compound according to any one of the above 1) to 16), or its pharmaceutically acceptable salt; or a solvate thereof in the manufacture of a medicament for inhibiting β secretase activity, 21) the compound according to any one of the above 1) to 16), or its pharmaceutically acceptable salt; or a solvate thereof for use in a method for inhibiting β secretase activity, 22) a method for treating disease induced by production, secretion or deposition of amyloid β protein, comprising administering the compound according to any one of the above 1) to 16), or its pharmaceutically acceptable salt; or a solvate thereof, 23) use of the compound according to any one of the above 1) to 16), or its pharmaceutically acceptable salt; or a solvate thereof in the manufacture of a medicament for treating disease induced by production, secretion or deposition of amyloid β protein, 24) the compound according to any one of the above 1) to 16), or its pharmaceutically acceptable salt; or a solvate thereof for use in a method for treating disease induced by production, secretion or deposition of amyloid β protein, 25) a method for treating Alzheimer's disease comprising administering the compound according to any one of the above 1) to 16), or its pharmaceutically acceptable salt; or a solvate thereof, 26) use of the compound according to any one of the above 1) to 16), or its pharmaceutically acceptable salt; or a solvate thereof in the manufacture of a medicament for treating Alzheimer's disease, 27) the compound according to any one of the above 1) to 16), or its pharmaceutically acceptable salt; or a solvate thereof for use in a method for treating Alzheimer's disease.

Effect of the Invention

The compounds of the present invention are useful as an agent for treating disease induced by production, secretion or deposition of amyloid β protein (Alzheimer's disease and the like).

BEST MODE FOR CARRYING OUT THE INVENTION

As used herein, the "halogen" includes fluorine, chlorine, bromine, and iodine.

A halogen part of the "halogeno lower alkyl", the "halogeno lower alkoxy", and the "halogeno lower alkoxycarbonyl" is the same as the above "halogen".

The "lower alkyl" includes straight or branched alkyl of a carbon number of 1 to 15, preferably a carbon number of 1 to 10, further preferably a carbon number of 1 to 6, and more further preferably a carbon number of 1 to 3, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

A lower alkyl part of the "lower alkoxy", the "halogeno lower alkyl", the "hydroxy lower alkyl", the "halogeno lower alkoxy", the "hydroxy lower alkoxy", the "lower alkoxycarbonyl", the "halogeno lower alkoxycarbonyl", the "lower alkoxycarbonyl lower alkyl", the "lower alkylamino", the "lower alkoxy lower alkyl", the "hydroxyimino lower alkyl", the "lower alkoxyimino lower alkyl,", the "amino lower alkyl", the "lower alkoxy lower alkoxy", the "lower alkoxy lower alkenyl", the "lower alkoxy lower alkenyloxy", the "lower alkoxycarbonyl lower alkenyl", the "lower alkoxy lower alkynyl", the "lower alkoxycarbonyl lower alkynyl", the "lower alkylcarbamoyl", the "hydroxy lower alkylcarbamoyl", the "lower alkoxyimino", the "lower alkylthio", the "lower alkylsulfonyl", the "lower alkylsulfonyloxy", the "lower alkylsulfonylamino", the "lower alkylsulfonyl lower alkylamino", the "lower alkylsulfonylimino", the "lower alkylsulfinylamino", the "lower alkylsulfinyl lower alkylamino", the "lower alkylsulfinylimino", the "lower alkylsulfamoyl", the "lower alkylsulfinyl", the "carbocyclyl lower alkyl", the "carbocyclyl lower alkoxy", the "carbocyclyl lower alkoxycarbonyl", the "carbocyclyl lower alkylamino", the "carbocyclyl lower alkylcarbamoyl", the "cycloalkyl lower alkyl", the "cycloalkyl lower alkoxy", the "cycloalkyl lower alkylamino", the "cycloalkyl lower alkoxycarbonyl", the "cycloalkyl lower alkylcarbamoyl", the "aryl lower alkyl", the "aryl lower alkoxy", the "aryl lower alkylamino", the "aryl lower alkoxycarbonyl", the "aryl lower alkylcarbamoyl", the "heterocyclyl lower alkyl", the "heterocyclyl lower alkoxy", the "heterocyclyl lower alkylamino", the "heterocyclyl lower alkoxycarbonyl", the "heterocyclyl lower alkylcarbamoyl", the "heteroaryl lower alkyl", and the "heteroaryl lower alkoxy" is the same as the above "lower alkyl".

The "optionally substituted lower alkyl" may be substituted with one or more substituents selected from a substituent group α.

As used herein, the substituent group α is a group consisting of halogen, hydroxy, lower alkoxy, halogeno lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfinyl, lower alkylsulfonylamino, lower alkylsulfonyl lower alkylamino, lower alkylsulfonylimino, lower alkylsulfinylamino, lower alkylsulfinyl lower alkylamino, lower alkylsulfinylimino, cyano, nitro, a carbocyclic group and a heterocyclic group wherein the carbocycle and the heterocycle may be each substituted with halogen and/or hydroxy.

Examples of the substituent of the "optionally substituted lower alkoxy", the "optionally substituted lower alkoxycarbonyl", and the "optionally substituted lower alkylthio" include one or more groups selected from the above substituent group α.

Examples of a preferable embodiment of the "halogeno lower alkyl" include trifluoromethyl, fluoromethyl, and trichloromethyl.

The "lower alkylidene" includes a divalent group of the above "lower alkyl", and examples include methylidene, ethylidene, propylidene, isopropylidene, butylidene, pentylidene, and hexylidene.

The "lower alkenyl" includes straight or branched alkenyl of a carbon number of 2 to 15, preferably a carbon number of 2 to 10, more preferably a carbon number of 2 to 6, further preferably a carbon number of 2 to 4, having one or more double bonds at an optional position. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

The "lower alkynyl" includes straight or branched alkynyl of a carbon number of 2 to 10, preferably a carbon number of 2 to 8, further preferably a carbon number of 3 to 6, having one or more triple bonds at an optional position. Examples include ethynyl, propynyl, butynyl, pentynyl, hexynyl, heptynyl, octynyl, nonynyl, and decynyl. These may further a double bond at an optional position.

Examples of the substituent of the "optionally substituted lower alkenyl" and the "optionally substituted lower alkynyl" include one or more substituents selected from the above substituent group α. A lower alkenyl part of the "hydroxy lower alkenyl", the "lower alkoxy lower alkenyl", the "lower alkoxy carbonyl lower alkenyl", the "carbocyclyl lower alkenyl", the "lower alkenyloxy", the "lower alkoxy lower alkenyloxy", the "lower alkenylthio", and the "lower alkenylamino" is the same as the above "lower alkenyl".

A lower alkynyl part of the "hydroxy lower alkynyl", the "lower alkoxy lower alkynyl", the "lower alkoxycarbonyl lower alkynyl", the "carbocyclyl lower alkynyl", the "lower alkynyloxy", the "lower alkoxy lower alkynyloxy", the "lower alkynylthio", and the "lower alkynylamino" is the same as the above "lower alkynyl".

Examples of the substituent of the "optionally substituted amino" and the "optionally substituted carbamoyl" include 1 to 2 substituents selected from lower alkyl, acyl, hydroxy, lower alkoxy, lower alkoxycarbonyl, a carbocyclic group and a heterocyclic group.

The "acyl" includes aliphatic acyl, carbocyclylcarbonyl and heterocyclylcarbonyl of a carbon number of 1 to 10. Examples include formyl, acetyl, propionyl, butyryl, isobutyryl, valeryl, pivaloyl, hexanoyl, acryloyl, propioyl, methacryloyl, crotonoyl, benzoyl, cyclohexanecarbonyl, pyridinecarbonyl, furancarbonyl, thiophenecarbonyl, benzothiazolecarbonyl, pyrazinecarbonyl, piperidinecarbonyl, and thiomorpholino.

An acyl part of the "acyl amino" and the "acyloxy" is as described above.

Examples of the substituent of the "optionally substituted acyl" include one or more substituents selected from the substituent group α. In addition, a ring part of the carbocyclylcarbonyl and the heterocyclylcarbonyl may be substituted with one or more substituents selected from lower alkyl, a substituent group α, and lower alkyl substituted with one or more groups selected from the substituent group α.

The "carbocyclic group" includes cycloalkyl, cycloalkenyl, aryl and a non-aromatic fused carbocyclic group.

The "cycloalkyl" is a carbocyclic group of a carbon number of 3 to 10, preferably a carbon number of 3 to 8, more preferably a carbon number of 4 to 8, and examples include cyclopropyl, cyclobutyl, cyclopentyl, cyclohexyl, cycloheptyl, cyclooctyl, cyclononyl, and cyclodecyl.

A cycloalkyl part of the "cycloalkyl lower alkyl", the "cycloalkoxy", the "cycloalkyl lower alkoxy", the "cycloalkylthio", the "cycloalkylamino", the "cycloalkyl lower alkylamino", the "cycloalkylsulfamoyl", the "cycloalkylsulfonyl", the "cycloalkylcarbamoyl", the "cycloalkyl lower alkyl carbamoyl", the "cycloalkyl lower alkoxycarbonyl", and the "cycloalkoxycarbonyl" is the same as the above "cycloalkyl".

The "cycloalkenyl" includes the cycloalkyl having one or more double bonds at an optional position in the ring, and examples include cyclopropenyl, cyclobutenyl, cyclopentenyl, cyclohexenyl, cycloheptynyl, cyclooctynyl and cyclohexadienyl.

The "aryl" includes phenyl, naphthyl, anthryl and phenanthryl, and phenyl is particularly preferable.

The "non-aromatic fused carbocyclic group" includes a non-aromatic group in which two or more cyclic groups selected from the above "cycloalkyl", the above"cycloalkenyl" and the above "aryl" are fused, and examples include indanyl, indenyl, tetrahydronaphthyl and fluorenyl.

The "taken together with a carbon atom to which they bind to form a carbocycle" refers to that two substituents are taken together to form the "cycloalkyl" or the "cycloalkenyl".

A carbocyclyl part of the "carbocyclyloxy", the "carbocyclyl lower alkyl", the "carbocyclyl lower alkenyl", the "carbocyclyl lower alkynyl", the "carbocyclyl lower alkoxy", the "carbocyclyl lower alkoxycarbonyl", the "carbocyclylthio", the "carbocyclyl amino", the "carbocyclyl lower alkylamino", the "carbocyclyl carbonyl", the "carbocyclyl sulfamoyl", the "carbocyclylsulfonyl", the "carbocyclylcarbamoyl", the "carbocyclyl lower alkylcarbamoyl", and the "carbocyclyloxycarbonyl" is the same as the "carbocyclic group".

An aryl part of the "aryl lower alkyl", the "aryloxy", the "aryloxycarbonyl", the "aryloxycarbonyloxy", the "aryl lower alkoxycarbonyl", the "arylthio", the "arylamino", the "aryl lower alkoxy", the "aryl lower alkylamino", the "arylsulfonyl", the "arylsulfonyloxy", the "arylsulfinyl", the "arylsulfamoyl", the "arylcarbamoyl", and the "aryl lower alkylcarbamoyl" is the same as the "aryl".

The "heterocyclic group" includes a heterocyclic group having one or more hetero atoms optionally selected from O, S and N in a ring, and examples include 5- to 6-membered heteroaryl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl; non-aromatic heterocyclic groups such as dioxanyl, thiiranyl, oxyranyl, oxetanyl, oxathioranyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, and tetrahydropyridazinyl;

dicyclic fused heterocyclic groups such as indolyl, isoindolyl, indazolyl, indolidinyl, indolinyl, isoindolinyl, quinolyl, isoquinolyl, cinnolinyl, phthalazinyl, quinazolinyl, naphthrydinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, imidazopyrazolyl, pyrazolopyridyl, pyrazolopyrazinyl, thiazolopyridyl, pyrazolopyrimidinyl, pyrazolotrianidyl, pyridazolopyridyl, triazolopyridyl, imidazothiazolyl, pyrazinopyridadinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzoxazinyl, dihydrobenzodioxepynyl, and dihydrothienodioxynyl;

tricyclic fused heterocyclic groups such as carbazolyl, acrydinyl, xanthenyl, phenothiadinyl, phenoxathiinyl, phenoxadinyl, dibenzofuryl, imidazoquinolyl, and tetrahydrocarbazolyl. Preferable is a 5- to 6-membered heteroaryl or a non-aromatic heterocyclic group.

A heterocyclyl part of the "heterocyclyl lower alkyl", the "heterocyclyloxy", the "heterocyclylthio", the "heterocyclylcarbonyl", the "heterocyclyl lower alkoxy", the "heterocyclylamino", the "heterocyclylcarbonylamino", the "heterocyclylsulfamoyl", the "heterocyclylsulfonyl", the "heterocyclylcarbamoyl", the "heterocyclyloxycarbonyl", the "heterocyclyl lower alkylamino", the "heterocyclyl lower alkoxycarbonyl" and the "heterocyclyl lower alkylcarbamoyl" is the same as the "heterocyclic group".

The "nitrogen-containing aromatic heterocyclic group" is a group containing at least one nitrogen among the "heterocyclic group", and examples include 5- or 6-membered heteroaryls such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, and thiadiazolyl; dicyclic fused heterocyclic groups such as indolyl, isoindolyl, indazolyl, indolidinyl, indolinyl, isoindolinyl, quinolyl, isoquinolyl, cinnolinyl, phthalazinyl, quinazolinyl, naphthyrdinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzotriazolyl, imidazopyridyl, pyrazolopyridine, triazolopyridyl, imidazothiazolyl, pyrazinopyridadinyl, quinazolinyl, quinolyl, isoquinolyl, naphthyridinyl, dihydrobenzofuryl, tetrahydroquinolyl, tetrahydroisoquinolyl, and dihydrobenzoxazine; tricyclic fused heterocyclic groups such as carbazolyl, acrydinyl, xanthenyl, and imidazoquinolyl; pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, dihydrobenzimidazolyl, tetrahydropyridyl, tetrahydrothiazolyl, and tetrahydroisothiazolyl.

A bond of the "heterocyclic group" and the "nitrogen-aromatic heterocyclic group" may be situated on any ring.

The "nitrogen-containing aromatic heteromonocyclic group" refers to monocyclic group among the "nitrogen-containing aromatic heterocyclic group". Examples include 5- to 6-membered heteroaryls such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, and thiadiazolyl.

A bond of the "nitrogen-containing aromatic heteromonocyclic group" may be situated on any carbon atom.

The "heteroaryl" includes an aromatic cyclic group among the "heterocyclic group". A heteroaryl part of the "heteroaryl lower alkyl" and the "heteroaryl lower alkoxy" is the same.

Examples of the substituent of the "optionally substituted carbocyclic group" and "optionally substituted heterocyclic group" in ring A, ring B and $R^X$ include:

a substituent group α, preferably, halogen, hydroxy, acyl, acyloxy, carboxy, lower alkoxycarbonyl, carbamoyl, amino, cyano, lower alkylamino and/or lower alkylthio etc.;

lower alkyl optionally substituted with one or more substituents selected from the group consisting of a substituent group α, hydroxyimino and lower alkoxyimino, herein, the substituent is preferably halogen, hydroxy, lower alkoxy and/or lower alkoxycarbonyl etc.;

amino lower alkyl substituted with one or more groups selected from a substituent group α; herein, the substituent is preferably acyl, lower alkyl and/or lower alkoxy etc., hydroxyimino lower alkyl;

lower alkoxyimino lower alkyl;

lower alkenyl optionally substituted with one or more substituents selected from a substituent group α, herein, the substituent is preferably lower alkoxycarbonyl, halogen, and/or halogeno lower alkoxycarbonyl etc.;

lower alkynyl optionally substituted with one or more substituents selected from a substituent group α, herein, the substituent is preferably lower alkoxycarbonyl etc., lower alkoxy optionally substituted with one or more substituents selected from a substituent group α, herein, the substituent is preferably halogen, carbamoyl, lower alkylcarbamoyl and/or hydroxy lower alkylcarbamoyl etc.;

lower alkoxy lower alkoxy optionally substituted with one or more substituents selected from a substituent group α;

lower alkenyloxy optionally substituted with one or more substituents selected from a substituent group α, herein, the substituent is preferably halogen, hydroxy, amino and/or lower alkylamino etc.;

lower alkoxy lower alkenyloxy optionally substituted with one or more substituents selected from a substituent group α;

lower alkynyloxy optionally substituted with one or more substituents selected from a substituent group α, herein, the substituent is preferably halogen and/or hydroxy etc.;

lower alkoxy lower alkynyloxy optionally substituted with one or more groups selected from a substituent group α;

lower alkylthio optionally substituted with one or more substituents selected from a substituent group α;

lower alkenylthio optionally substituted with one or more substituents selected from a substituent group α;

lower alkynylthio optionally substituted with one or more substituents selected from a substituent group α;

lower alkylamino substituted with one or more substituents selected from a substituent group α;

lower alkenylamino substituted with one or more substituents selected from a substituent group α;

lower alkynylamino substituted with one or more substituents selected from a substituent group α;

aminooxy optionally substituted with one or more substituents selected from a substituent group α and lower alkylydene;

acyl substituted with one or more substituents selected from a substituent group α;

lower alkylsulfonyl optionally substituted with one or more substituents selected from a substituent group α;

lower alkylsulfinyl optionally substituted with one or more substituents selected from a substituent group α;

lower alkylsulfamoyl optionally substituted with one or more substituents selected from a substituent group α;

a carbocyclic group, e.g. cycloalkyl, aryl and the like, optionally substituted with one or more substituents selected from the group consisting of a substituent group α, azido, lower alkyl and halogeno lower alkyl;

heterocyclic group optionally substituted with one or more substituents selected from the group consisting of a substituent group α, azido, lower alkyl and halogeno lower alkyl;

carbocyclyl lower alkyl, e.g. cycloalkyl lower alkyl, aryl lower alkyl and the like, optionally substituted with one or more substituents selected from the group consisting of a substituent group α, azido, lower alkyl and halogeno lower alkyl; heterocyclyl lower alkyl optionally substituted with one or more substituents selected from the group consisting of a substituent group α, azido, lower alkyl and halogeno lower alkyl;

carbocyclyloxy, e.g. cycloalkoxy, aryloxy and the like, optionally substituted with one or more substituents selected from the group consisting of a substituent group α, azido, lower alkyl and halogeno lower alkyl;

heterocyclyloxy optionally substituted with one or more substituents selected from the group consisting of a substituent group α, azido, lower alkyl and halogeno lower alkyl;

carbocyclyl lower alkoxy, e.g. cycloalkyl lower alkoxy, aryl lower alkoxy and the like, optionally substituted with one or more substituents selected from the group consisting of a substituent group α, azido, lower alkyl and halogeno lower alkyl;

heterocyclyl lower alkoxy optionally substituted with one or more substituents selected from the group consisting of a substituent group α, azido, lower alkyl and halogeno lower alkyl;

carbocyclyl lower alkoxycarbonyl, e.g. cycloalkyl lower alkoxycarbonyl, aryl lower alkoxycarbonyl and the like, optionally substituted with one or more substituents selected from the group consisting of a substituent group α, azido, lower alkyl and halogeno lower alkyl;

heterocyclyl lower alkoxycarbonyl optionally substituted with one or more substituents selected from the group consisting of a substituent group α, azido, lower alkyl and halogeno lower alkyl;

carbocyclylthio, e.g. cycloalkylthio, arylthio and the like, optionally substituted with one or more substituents selected from the group consisting of a substituent group α, azido, lower alkyl and halogeno lower alkyl;

heterocyclylthio optionally substituted with one or more substituents selected from the group consisting of a substituent group α, azido, lower alkyl and halogeno lower alkyl;

carbocyclylamino, e.g. cycloalkylamino, arylamino and the like, optionally substituted with one or more substituents selected from the group consisting of a substituent group α, azido, lower alkyl and halogeno lower alkyl;

heterocyclylamino optionally substituted with one or more substituents selected from the group consisting of a substituent group α, azido, lower alkyl and halogeno lower alkyl;

carbocyclyl lower alkylamino, e.g. cycloalkyl lower alkylamino, aryl lower alkylamino and the like, optionally substituted with one or more substituents selected from the group consisting of a substituent group α, azido, lower alkyl and halogeno lower alkyl;

heterocyclyl lower alkylamino optionally substituted with one or more substituents selected from the group consisting of a substituent group α, azido, lower alkyl and halogeno lower alkyl;

lower alkylsulfamoyl optionally substituted with one or more substituents selected from the group consisting of a substituent group α;
carbocyclylsulfamoyl, e.g. cycloalkylsulfamoyl, arylsulfamoyl and the like, optionally substituted with one or more substituents selected from the group consisting of a substituent group α, azido, lower alkyl and halogeno lower alkyl;
heterocyclylsulfamoyl optionally substituted with one or more substituents selected from the group consisting of a substituent group α, azido, lower alkyl and halogeno lower alkyl;
carbocyclylsulfonyl, e.g. cycloalkylsulfonyl, arylsulfonyl and the like, optionally substituted with one or more substituents selected from the group consisting of a substituent group α, azido, lower alkyl and halogeno lower alkyl;
heterocyclylsulfonyl optionally substituted with one or more substituents selected from the group consisting of a substituent group α, azido, lower alkyl and halogeno lower alkyl;
carbocyclylcarbamoyl, e.g. cycloalkylcarbamoyl, arylcarbamoyl and the like, optionally substituted with one or more substituents selected from the group consisting of a substituent group α, azido, lower alkyl and halogeno lower alkyl;
heterocyclylcarbamoyl optionally substituted with one or more substituents selected from the group consisting of a substituent group α, azido, lower alkyl and halogeno lower alkyl;
carbocyclyl lower alkylcarbamoyl, e.g. cycloalkyl lower alkylcarbamoyl, aryl lower alkylcarbamoyl, optionally substituted with one or more substituents selected from the group consisting of a substituent group α, azido, lower alkyl and halogeno lower alkyl;
heterocyclyl lower alkylcarbamoyl optionally substituted with one or more substituents selected from the group consisting of a substituent group α, azido, lower alkyl and halogeno lower alkyl;
carbocyclyloxycarbonyl, e.g. cycloalkoxycarbonyl, aryloxycarbonyl and the like, optionally substituted with one or more substituents selected from the group consisting of a substituent group α, azido, lower alkyl and halogeno lower alkyl;
heterocyclyloxycarbonyl optionally substituted with one or more substituents selected from the group consisting of a substituent group α, azido, lower alkyl and halogeno lower alkyl;
lower alkylenedioxy optionally substituted with halogen; oxo, and azido. "Optionally substituted carbocyclic group" and "optionally substituted heterocyclic group" may be substituted with one or more substituents selected from them.

As other embodiment, ring A may be substituted with one or more substituents selected from the following substituents

[Chemical formula 7]

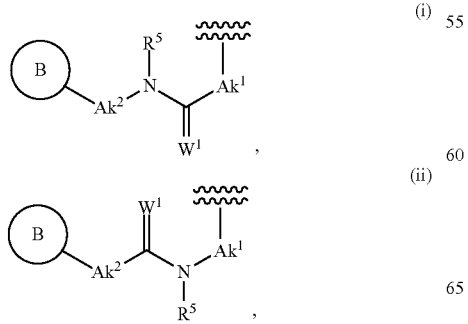

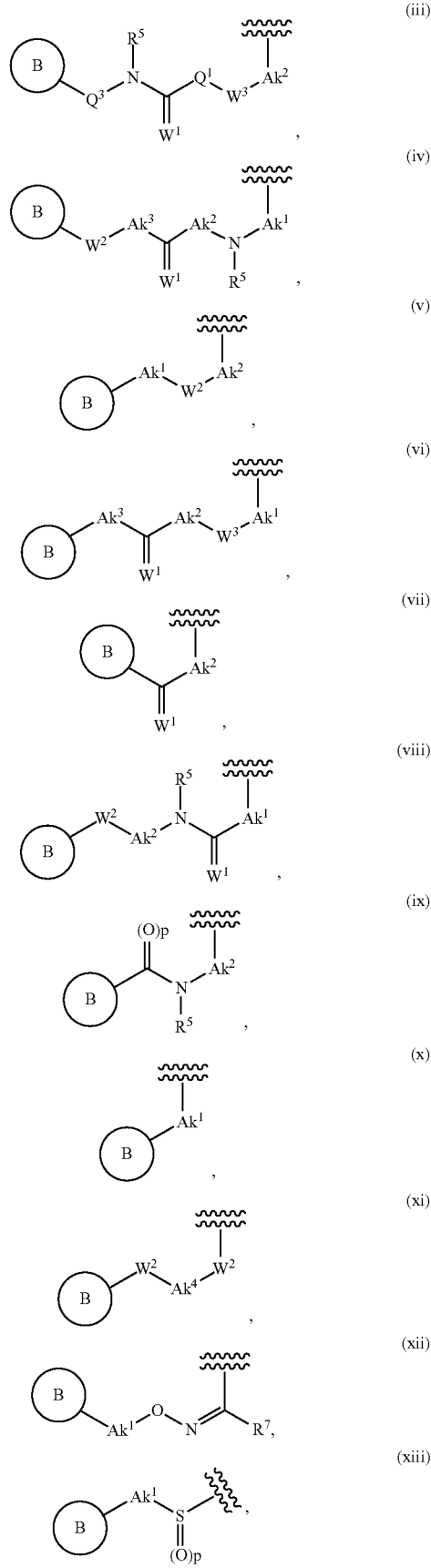

-continued

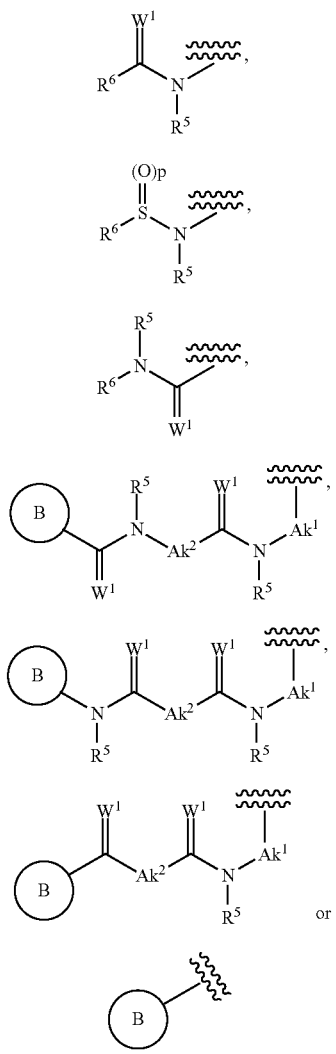

Among groups shown in (i) to (xixi), preferable are:

[Chemical formula 8]

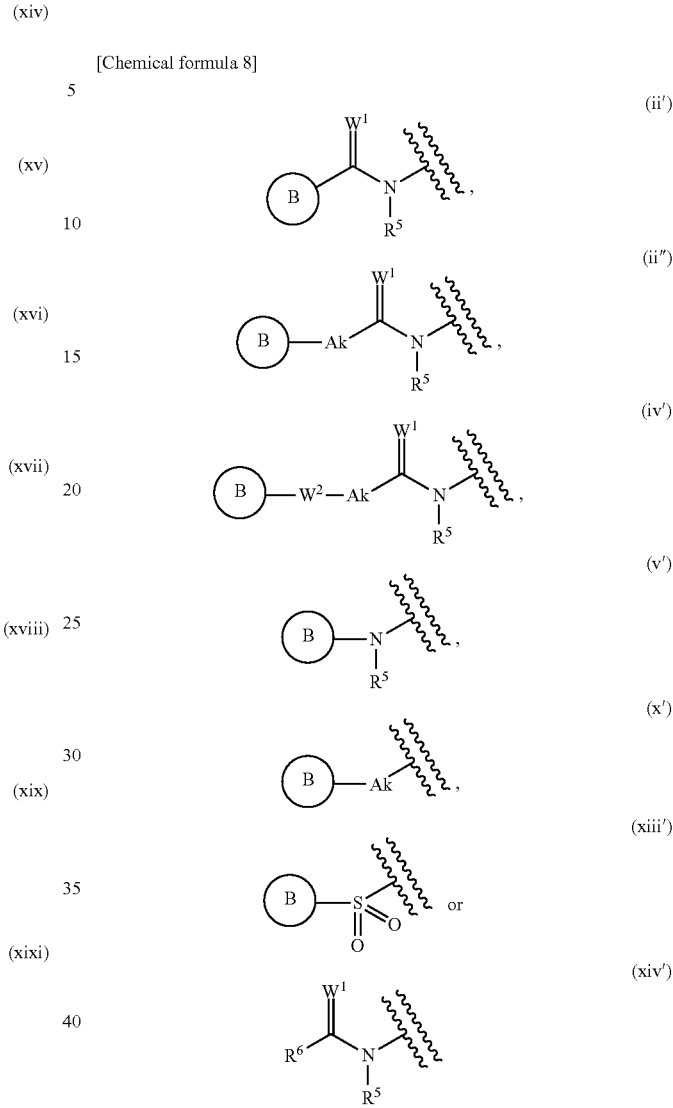

wherein Ak¹, Ak² and Ak³ are each independently a bond, optionally substituted lower alkylene, optionally substituted lower alkenylene or optionally substituted lower alkynylene; Ak⁴ is optionally substituted lower alkylene, optionally substituted lower alkenylene or optionally substituted lower alkynylene,
W¹ and W³ are each independently O or S;
each W² is independently O, S or NR⁵;
R⁵ and R⁶ are each independently hydrogen, lower alkyl, hydroxy lower alkyl, lower alkoxy lower alkyl, lower alkoxycarbonyl lower alkyl, carbocyclyl lower alkyl, lower alkenyl, hydroxy lower alkenyl, lower alkoxy lower alkenyl, lower alkoxycarbonyl lower alkenyl, carbocyclyl lower alkenyl, lower alkynyl, hydroxy lower alkynyl, lower alkoxy lower alkynyl, lower alkoxycarbonyl lower alkynyl, carbocyclyl lower alkynyl or acyl;
R⁷ is hydrogen or lower alkyl;
ring B is an optionally substituted carbocyclic group or an optionally substituted heterocyclic group;
p is 1 or 2.
When a plurality of W¹s, a plurality of W³s, and a plurality of R⁵s are present, they may be each independently different.
An oxygen atom in (xii) may place at cis or trans position to the substituent R⁷.

wherein Ak is optionally substituted lower alkylene, optionally substituted lower alkenylene or optionally substituted lower alkynylene, and other symbols are as defined above.
As the substituent of B ring, one or more groups selected from the substituent group α are preferable.
In those other than ring A, ring B and R$^x$, examples of the substituent of the "optionally substituted carbocyclic group", the "optionally substituted heterocyclic group", the "optionally substituted aryl lower alkyl", the "optionally substituted aryl lower alkoxy", the "optionally substituted heteroaryl lower alkyl", the "optionally substituted heteroaryl lower alkoxy", the "optionally substituted cycloalkyl", the "optionally substituted phenyl", and the "optionally substituted nitrogen-containing aromatic heterocyclic group" include lower alkyl optionally substituted with one or more groups selected from the substituent group α, and one or more substituents selected from the group consisting of the substituent group α.
Preferable examples of R⁴ include halogen, lower alkyl, halogeno lower alkyl, lower alkoxy, and halogeno lower alkoxy.
"Lower alkylene" includes a straight or branched divalent carbon chain of a carbon number of 1 to 10, preferably a carbon number of 1 to 6, more preferably a carbon number of 1 to 3. Examples include methylene, dimethylene, trimethylene, tetramethylene, and methyltrimethylene.

A lower alkylene part of the "lower alkylenedioxy" is the same as the "lower alkylene".

The "lower alkenylene" includes a straight or branched divalent carbon chain of a carbon number of 2 to 10, preferably a carbon number of 2 to 6, more preferably a carbon number of 2 to 4, having a double bond at an optional position. Examples include vinylene, propenylene, butenylene, butadienylene, methylpropenylene, pentenylene and hexenylene.

The "lower alkynylene" includes a straight or branched divalent carbon chain of a carbon number of 2 to 10, more preferably a carbon number of 2 to 6, more preferably a carbon number of 2 to 4, having a triple bond at an optional position and, further, optionally having a double bond. Examples include ethynylene, propynylene, butynylene, pentynylene and hexynylene.

Examples of the substituent of the "optionally substituted lower alkylene", the "optionally substituted lower alkenylene", and the "optionally substituted lower alkynylene" include the substituent group α, preferably halogen, and hydroxy.

In the formula (I), the "$R^{3a}$ and $R^{3c}$ may be taken together to form a ring" includes the following formula (I''):

[Chemical formula 9]

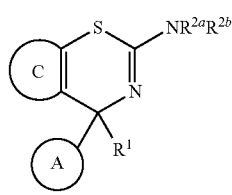

(I'')

wherein ring C is an optionally substituted carbocyclic group or an optionally substituted heterocyclic group, and other symbols are defined as in formula (I),
and examples of a preferable embodiment of ring C include benzene, pyridine, pyrimidine, cyclohexene, tetrahydropyridine, and dihydropyran.

In the present specification, the "solvate" includes, for example, a solvate with an organic solvent, and a hydrate. When a hydrate is formed, an arbitrary number of water molecules may be coordinated.

The compound represented by the formula (I) includes a pharmaceutically acceptable salt. Examples include salts with alkali metals such as lithium, sodium or potassium; alkaline earth metals such as magnesium or calcium; ammonium; organic bases; and amino acids; or salts with inorganic acids such as hydrochloric acid, sulfuric, nitric acid, hydrobromic acid, phosphoric acid or hydroiodic acid; and organic acids such as acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluenesulfonic acid, methanesulfonic acid or ethane sulfonic acid. Particularly, hydrochloric acid, phosphoric acid, tartaric acid or methanesulfonic acid is preferable. These salts can be formed by ordinary methods.

In addition, the compound represented by the formula (I) is not limited to a specific isomer, but includes all possible isomers, such as keto-enol isomers, imine-enamine isomers, diastereoisomers, optical isomers and rotation isomers; and racemate. For example, the compound represented by the formula (I) in which $R^{2a}$ is hydrogen includes the following tautomers.

[Chemical formula 10]

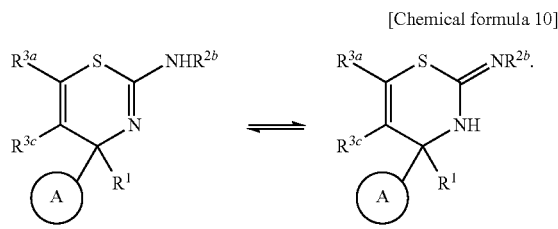

Compounds represented by the formulas (II); (III) and (IV) include the similar tautomers.

The present compound represented by the formula (I), (II), (III) or (IV) can be produced, for example, according to the method described in Patent Literature 15 or Non-Patent Literature 1, or by the following method.

In the following all steps, when a substituent which impedes a reaction, e.g. hydroxy, mercapto, amino, formyl, carbonyl, carboxy, is possessed, the substituent is protected by the method described in Protective Groups in organic Synthesis, and Theodora W Greene (John Wiley & Sons) in advance, and the protective group may be removed at a desirable stage.

In addition, in the all steps, an order of steps to be implemented may be appropriately changed, and each intermediate may be isolated, and used in a next step.

A. Production of Compound Represented by the Formula (I)

The compound represented by the formula (I) can be produced, for example, according to a method of synthesizing a compound v or a compound ab shown below.

A-1) Synthesis of Compound v

[Chemical formula 11]

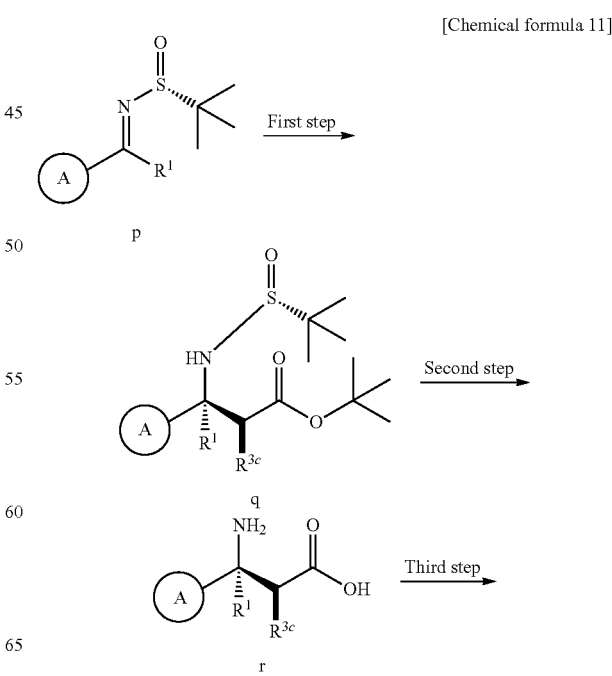

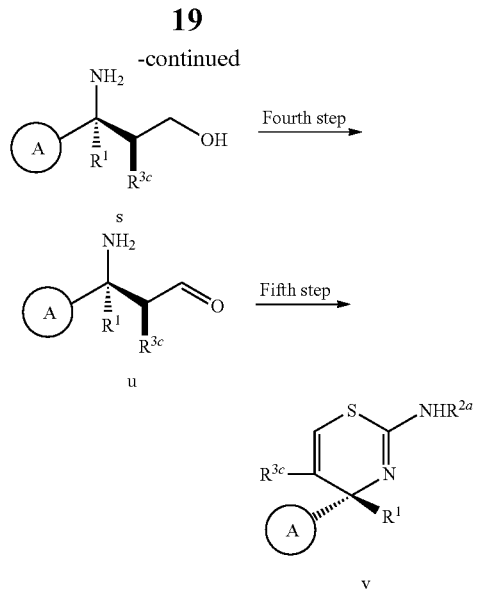

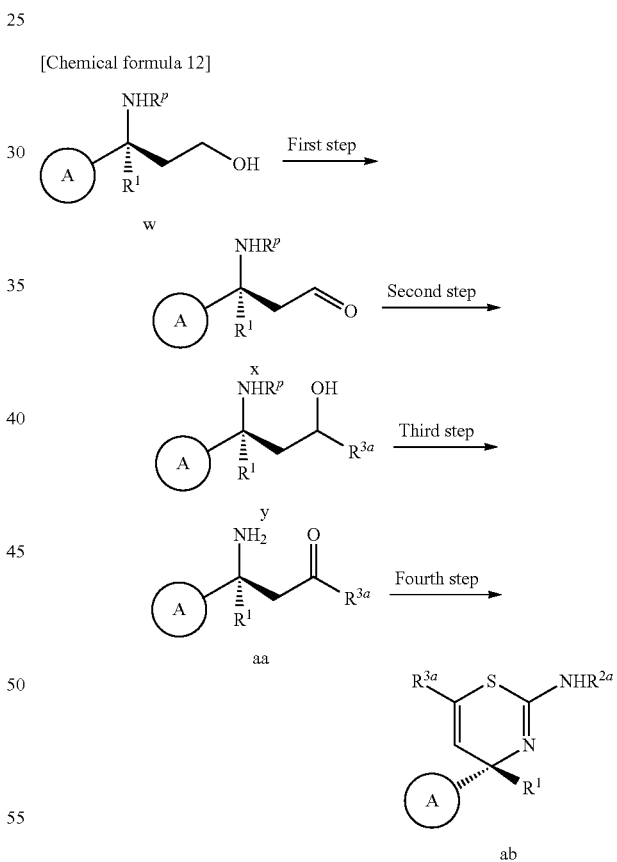

wherein ring A is an optionally substituted carbocyclic group or an optionally substituted heterocyclic group;

$R^1$ is optionally substituted lower alkyl, optionally substituted lower alkenyl, optionally substituted lower alkynyl, an optionally substituted carbocyclic group or an optionally substituted heterocyclic group;

$R^{2a}$ is hydrogen, optionally substituted lower alkyl or optionally substituted acyl;

$R^{3c}$ is each independently hydrogen, halogen, hydroxy, optionally substituted lower alkyl, optionally substituted lower alkenyl, optionally substituted acyl, optionally substituted lower alkoxy, optionally substituted aralkyl, optionally substituted heteroarylalkyl, optionally substituted aralkyloxy, optionally substituted heteroarylalkoxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group.

First Step

A compound q can be diastereoselectively obtained by adding a titanium reagent such as chlorotitanium triisopropoxide to enolate, which is obtained by reacting an objective ester such as t-butyl propionate in the presence of a base such as lithium diisopropylamide in a solvent such as toluene, dichloromethane, and tetrahydrofuran, or a mixed solvent of them, adding a compound p which can be prepared by the known method, and reacting them at −80° C. to 30° C., preferably −80° C. to 0° C., for 0.1 to 24 hours, preferably 0.1 to 12 hours.

Second Step

A compound r can be obtained by reacting the compound q at 0° C. to 80° C., preferably 0° C. to 30° C., for 0.5 to 48 hours, preferably 1 to 24 hours in the presence of an acid such as hydrochloric acid, hydrobromic acid, sulfuric acid and trifluoroacetic acid in a solvent such as dioxane, methanol, and dichloromethane, or a mixed solvent of them.

Third Step A compound s can be obtained by adding a reducing agent such as borane, sodium hydride, and lithium aluminum hydride to the compound r and reacting at −80° C. to 80° C., preferably −20° C. to 30° C., for 0.5 to 48 hours, preferably 1 to 12 hours in a solvent such as dioxane, tetrahydrofuran, and toluene, or a mixed solvent of them.

Fourth Step

A compound u can be obtained by adding an oxidizing agent such as 2-iodoxybenzoic acid to the compound s and reacting at 0° C. to 80° C., preferably 10° C. to 40° C., for 0.5 to 48 hours, preferably 1 to 12 hours in a solvent such as dimethyl sulfoxide, and dichloromethane.

In third step and fourth step, amine and/or aldehyde groups of the compound and the compound u can be protected by the method described in Protective Groups in Organic Synthesis, Theodora W Green (John Wiley & Sons), and deprotected at an appropriate time, if necessary.

Fifth Step

A compound v can be obtained by adding isothiocyanate having a protective group, e.g. benzoyl isothiocyanate, which is commercially available or prepared by the known method to the compound u, reacting at −30° C. to 50° C., preferably −10° C. to 25° C., for 0.1 to 12 hours, preferably 0.1 to 3 hours in a solvent such as dioxane, tetrahydrofuran, toluene and acetone, or a mixed solvent of them, and subsequently, adding concentrated sulfuric acid or concentrated nitric acid, followed by a reaction at 0° C. to 100° C., preferably 0° C. to 60° C., for 0.5 to 24 hours, preferably 1 to 12 hours.

A-2) Synthesis of Compound ab

[Chemical formula 12]

wherein $R^p$ represents a protective group of amine;

$R^{3a}$ is each independently hydrogen, halogen, hydroxy, optionally substituted lower alkyl, optionally substituted lower alkenyl, optionally substituted acyl, optionally substituted lower alkoxy, optionally substituted aralkyl, optionally substituted heteroarylalkyl, optionally substituted aralkyloxy, optionally substituted heteroarylalkoxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group;

and other symbols are as defined above:

First Step

A compound x can be obtained by reacting a compound w, which can be prepared by protecting an amino group of the compound s with a protective group, at 0° C. to 80° C., preferably 10° C. to 40° C., for 0.5 to 48 hours, preferably 1 to 12 hours under the condition of a Swern oxidation reaction in which oxalyl chloride-dimethyl sulfoxide are used, or by adding an oxidizing agent of an alcohol group such as 2-iodoxybenzoic acid, in a solvent such as toluene, dichloromethane, and tetrahydrofuran, or a mixed solvent of them.

Second Step

A compound y can be obtained by adding a Grignard reagent corresponding to an objective substance such as methylmagnesium bromid to the compound x and reacting at −80° C. to 50° C., preferably −20° C. to 20° C., for 0.2 to 48 hours, preferably 1 to 24 hours in a solvent such as toluene, ether, and tetrahydrofuran, or a mixed solvent of them. Upon the reaction, the yield can be improved by adding titanium tetrachloride.

Third Step

A compound aa can be obtained by adding an oxidizing agent of an alcohol group such as oxalyl chloride-dimethyl sulfoxide or 2-iodoxybenzoic acid to the compound y and reacting at 0° C. to 80° C., preferably 10° C. to 40° C., for 0.5 to 48 hours, preferably 1 to 6 hours in a solvent such as dimethyl sulfoxide.

Fourth Step

A compound ab can be obtained by adding isothiocyanate having a protective group, e.g. benzoyl isothiocyanate, which is commercially available or is prepared by the known method, to the compound aa, reacting at −30° C. to 50° C., preferably −10° C. to 25° C., for 0.1 to 12 hours, preferably 0.1 to 3 hours in a solvent such as dioxane, tetrahydrofuran, toluene, and acetone, or a mixed solvent of them and, subsequently, adding concentrated sulfuric acid or concentrated nitric acid, followed by a reaction at 0° C. to 100° C., preferably 0° C. to 60° C., for 0.5 to 12 hours, preferably 1 to 6 hours.

B. Production of Compound Represented by the Formula (II)

The compound represented by the formula (II) can be produced, for example, according to a method of synthesizing a compound f or a compound o shown below.

B-1) Synthesis of Compound f

[Chemical formula 13]

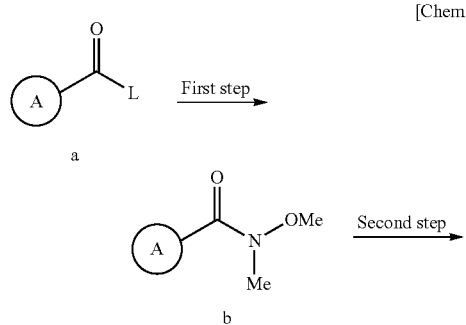

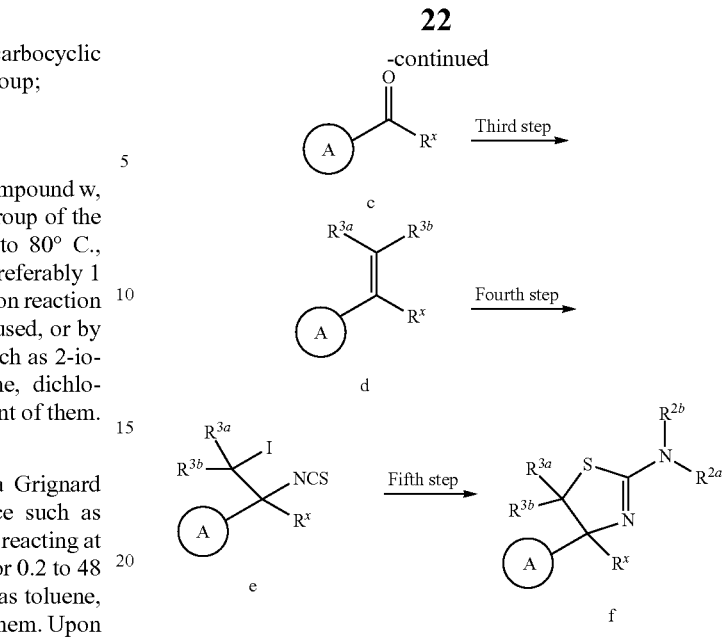

wherein $R^X$ is an optionally substituted carbocyclic group, or an optionally substituted heterocyclic group;

$R^{2a}$ and $R^{2b}$ are each independently hydrogen, optionally substituted lower alkyl or optionally substituted acyl;

$R^{3a}$ and $R^{3b}$ are each independently hydrogen, halogen, hydroxy, optionally substituted lower alkyl, optionally substituted lower alkenyl, optionally substituted acyl, optionally substituted lower alkoxy, optionally substituted aralkyl, optionally substituted heteroarylalkyl, optionally substituted aralkyloxy, optionally substituted heteroarylalkoxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group;

L is a leaving group such as halogen or a lower alkylsulfonyloxy group;

and other symbols are as defined above.

First Step

A compound b can be obtained by reacting a compound a which is commercially available, or can be prepared by the known method, with N,O-dimethylhydroxylamine hydrochloride or its free form at −40° C. to 60° C., preferably −20° C. to 30° C., for 0.1 to 24 hours, preferably 0.3 to 6 hours in the presence of a base such as pyridine, triethylamine, diisopropylethylamine, and 4-dimethylaminopyridine in a solvent such as toluene, dichloromethane, and tetrahydrofuran, or a mixed solvent of them.

Second Step

A compound c can be obtained by adding a Grignard reagent corresponding to an objective substance such as cyclohexylmagnesium bromide at −80° C. to 50° C., preferably −20° C. to 20° C., to the compound b and reacting for 0.2 to 48 hours, preferably 1 to 24 hours in a solvent such as ether and tetrahydrofuran, or a mixed solvent of them.

In the first step and the second step, if a compound c is directly obtained from a compound a by a reaction of the second step, the first step may be omitted.

Third Step

A compound d can be obtained by reacting the compound c dissolved in a solvent such as ether, tetrahydrofuran, and dioxane, or a mixed solvent of them with a Wittig regent corresponding to an objective substance, which is prepared by adding a strong base such as an alkyl metal regent, e.g. n-butyllithium to $R^{3a}R^{3b}CHPPh_3L$, e.g. methyltriphenylphosphonium iodide, which is commercially available or can be synthesized by the known method, at −40° C. to 60° C., preferably −20° C. to 30° C., for 0.1 to 24 hours, preferably 0.3 to 6 hours, in a solvent such as ether, tetrahydrofuran, and dioxane, or mixed solvent of them.

Fourth Step

A compound e can be obtained by adding thiophosgene or iodine, and thiocyanate to the compound d and reacting for 1 to 72 hours, preferably 6 to 48 hours in a solvent such as toluene, dichloromethane, tetrahydrofuran, and water, or a mixed solvent of them. Upon the reaction, if necessary, an appropriate amount of phase transfer catalyst, e.g. tetra-n-butyl ammonium chloride, tetramethyl ammonium bromide, is placed therein, and the reaction can be performed.

Fifth Step

A compound f can be obtained by adding $R^{2a}R^{2b}$-amine to the compound e and reacting at 0° C. to 120° C., preferably 20° C. to 80° C., for 1 to 72 hours, preferably 6 to 48 hours in a solvent such as toluene, dichloromethane, and tetrahydrofuran, or a mixed solvent of them.

B-2) Synthesis of Compound o

[Chemical formula 14]

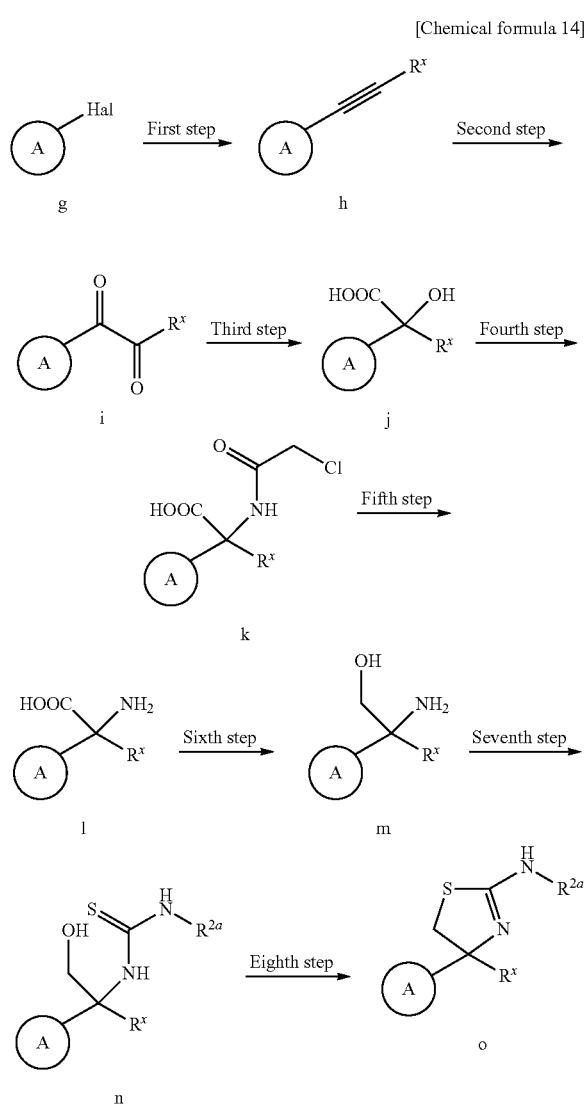

wherein Hal is halogen, and other symbols are as defined above.

First Step

A compound h can be obtained by adding ethynyl-$R^x$ and trisbenzylideneacetone dipalladium, palladium acetate, tetrakistriphenylphosphine palladium, or a Pd(0) catalyst which is prepared in situ, and a ligand such as tri-t-butylphosphine, and dicyclohexylbiphenylphosphine and, further, adding copper iodide to a compound g, which is commercially available or can be prepared by the known method, and reacting at 20° C. to 120° C., preferably 30° C. to 80° C., for 0.1 to 24 hours, preferably 0.1 to 12 hours in the presence of a base such as diisopropylethylamine, triethylamine, and trimethylamine, in a solvent such as toluene, dichloromethane, and tetrahydrofuran, or a mixed solvent of them.

Second Step

A compound i can be obtained by dissolving the compound h in dimethyl sulfoxide, and adding iodide, followed by a reaction at 20° C. to 200° C., preferably 100° C. to 180° C., for 0.1 to 24 hours, preferably 1 to 12 hours.

Third Step

A compound j can be obtained by reacting the compound i at 20° C. to 100° C., preferably 50° C. to 100° C., for 0.5 to 24 hours, preferably 1 to 12 hours in the presence of water and a base such as potassium hydroxide, sodium hydroxide and lithium hydroxide in a solvent such as methanol, ethanol, and isopropyl alcohol according to the method described in Chem. Lett., 3, 373-376 (1990).

Fourth Step

A compound k can be obtained by adding 2-chloroacetonitrile and concentrated sulfuric acid to the compound j, followed by a reaction at −20° C. to 100° C., preferably 0° C. to 40° C., for 0.2 to 24 hours, preferably 1 to 12 hours in the presence of carboxylic acid such as acetic acid, formic acid and trifluoroacetic acid.

Fifth Step

A compound l can be obtained by adding acetic acid and thiourea to the compound k, followed by a reaction at −20° C. to 100° C., preferably 0° C. to 40° C., for 0.2 to 24 hours, preferably 1 to 12 hours in a solvent such as methanol, ethanol, and isopropyl alcohol.

Fourth step and fifth step can be performed according to the method described in Synthesis 12, 1709-1712 (2000).

Sixth Step

A compound m can be obtained by adding a reducing agent such as borane, sodium hydride, and lithium aluminum hydride to the compound l and reacting at −80° C. to 100° C., preferably −20° C. to 40° C., for 0.2 to 24 hours, preferably 1 to 12 hours in a solvent such as tetrahydrofuran, toluene, and dichloromethane.

Seventh Step

A compound n can be obtained by adding isothiocyanate having a protective group, e.g. benzoyl isothiocyanate, which is commercially available or is prepared by the known method to the compound m and reacting at −30° C. to 50° C., preferably −10° C. to 20° C., for 0.5 to 24 hours, preferably 0.5 to 12 hours in a solvent such as dichloromethane, tetrahydrofuran, and toluene, or a mixed solvent of them.

Eighth Step

A compound o can be obtained by adding oxalyl chloride, thionyl chloride or the like, and a catalytic amount of N,N-dimethylformamide, or adding a chlorinating reagent such as 1-chloro-2-trimethylpropenylamine to the compound n and reacting at 0° C. to 100° C., preferably 20° C. to 50° C., for 0.5 to 72 hours, preferably 0.5 to 12 hours in a solvent such as dichloromethane, tetrahydrofuran, and toluene.

B-2')

The compound j can be also synthesized by the following method.

[Chemical formula 15]

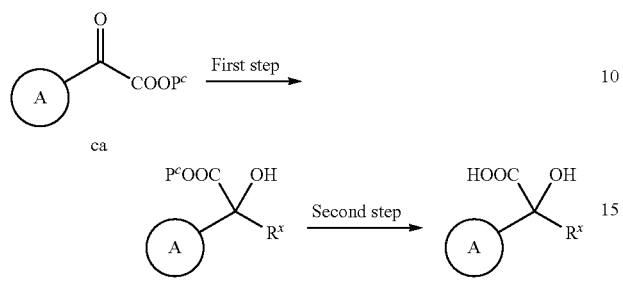

wherein $P^c$ is a protective group of carboxylic acid, and other symbols are as defined above.

First Step

A compound cb can be obtained by adding a corresponding Grignard reagent such as Rx magnesium bromide, and reacting a compound ca which is commercially available or can be prepared by the known method at −80° C. to 30° C., preferably −40° C. to 10° C., for 0.1 to 24 hours, preferably 0.1 to 12 hours in a solvent such as toluene, dichloromethane, and tetrahydrofuran, or a mixed solvent of them.

Second Step

A compound j can be obtained by subjecting a protective group Pc of carboxylic acid to a deprotecting reaction by an ordinary method.

C. Production of Compound Represented by the Formula (III)

The compound represented by the formula (III) can be produced, for example, according to the following method for synthesizing a compound ai or a compound al.

C-1) Synthesis of Compound ai

[Chemical formula 16]

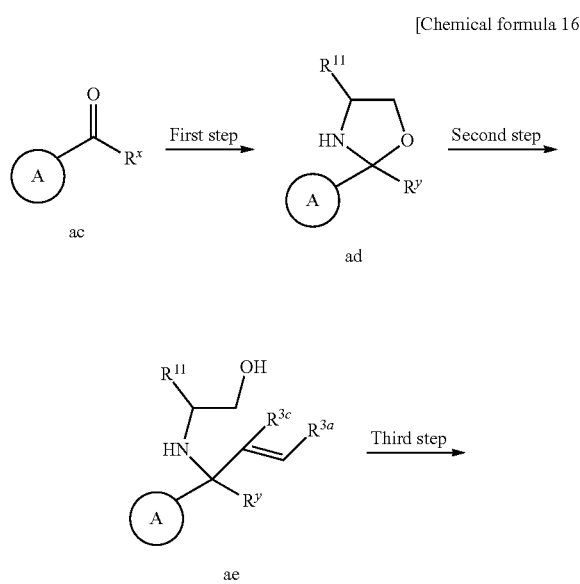

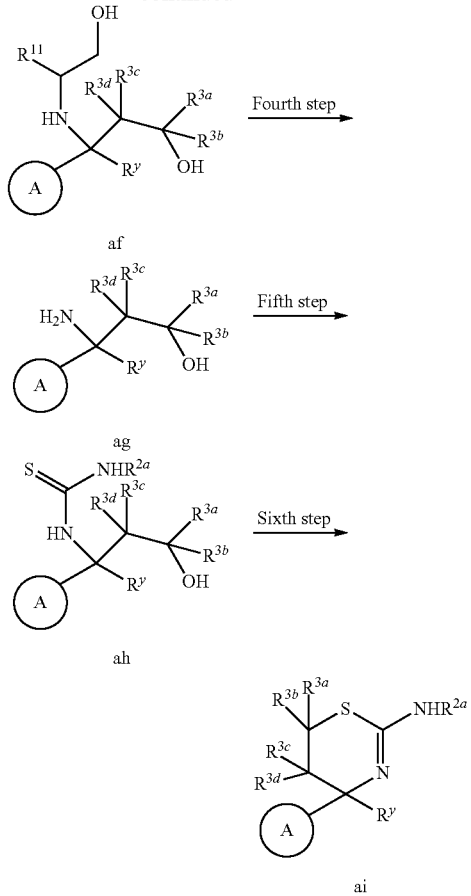

wherein $R^{11}$ is optionally substituted aryl;
$R^y$ is halogeno lower alkyl;
$R^{3d}$ is hydrogen, halogen, hydroxy, optionally substituted lower alkyl, optionally substituted lower alkenyl, optionally substituted acyl, optionally substituted lower alkoxy, optionally substituted aralkyl, optionally substituted heteroarylalkyl, optionally substituted aralkyloxy, optionally substituted heteroarylalkoxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group;
and other symbols are as defined above.

First Step

A compound ad can be obtained by reacting a compound ac which is commercially available or can be prepared by the known method, at 50° C. to 200° C., preferably 80° C. to 150° C., for 1 to 48 hours, preferably 2 to 24 hours under the dehydration condition in the presence of a reagent corresponding to an objective compound such as 2-amino-2-phenylethanol, a catalytic amount of sulfuric acid, and an acid such as pyridinium para-toluenesulfonic acid in a solvent such as dioxane, tetrahydrofuran, and toluene, or a mixed solvent of them.

Second Step

A compound ae can be obtained by adding a vinyllithium reagent corresponding to an objective substance to the compound ad and reacting at −80° C. to 50° C., preferably −80° C. to 0° C., for 0.2 to 24 hours, preferably 0.5 to 12 hours in a solvent such as ether, and tetrahydrofuran, or a mixed solvent of them.

The vinyllithium reagent can be prepared by adding an alkyllithium reagent such as butyllithium to objective tetravinyltin.

Third Step

A compound af can be obtained by adding a borane reagent to the compound ae and reacting at 0° C. to 60° C., preferably 20° C. to 50° C., for 0.2 to 12 hours, preferably 0.5 to 6 hours in a solvent such as dioxane, and tetrahydrofuran, or a mixed solvent of them, adding aqueous alkali such as a sodium hydroxide aqueous solution, and aqueous hydrogen peroxide, and reacting them for 0.5 to 12 hours.

Fourth Step

A compound ag can be obtained by adding a palladium catalyst such as $Pd(OH)_2$, or Pd—C to the compound af and reacting at 0° C. to 60° C., preferably 20° C. to 50° C., for 1 to 24 hours, preferably 1 to 12 hours under flow hydrogen in a solvent such as methanol, ethanol, ethyl acetate, and tetrahydrofuran, or a mixed solvent of them.

Fifth Step

A compound ah can be obtained by adding isothiocyanate having a protective group, e.g. benzoyl isothiocyanate, which is commercially available or is prepared by the known method to the compound ag and reacting at −30° C. to 70° C., preferably 0° C. to 50° C., for 1 to 12 hours, preferably 1 to 6 hours in a solvent such as dioxane, tetrahydrofuran, toluene, and acetone, or a mixed solvent of them.

Sixth Step

A compound ai can be obtained by adding oxalyl chloride, thionyl chloride or the like with a catalytic amount of N,N-dimethylformamide, or adding a chlorinating reagent such as 1-chloro-2-trimethylpropenylamine, to the compound ah and reacting at 0° C. to 100° C., preferably 10° C. to 50° C. for, 0.5 to 72 hours, preferably 0.5 to 6 hours in a solvent such as dichloromethane, tetrahydrofuran, and toluene.

C-2) Synthesis of Compound al wherein $R^{12}$ is optionally substituted aryl, or optionally substituted heteroaryl; and other symbols are as defined above.

First Step

A compound aj can be stereoselectively obtained by adding a compound p which can be prepared by the known method, to enolate obtained by reacting corresponding phenyl alkyl ketone, e.g. acetophenone, in the presence of a base such as lithium diisopropylamide, and potassium hexamethyldisilazide, and reacting them at −80° C. to 30° C., preferably −80° C. to 0° C. for 0.1 to 24 hours, preferably 0.1 to 12 hours in a solvent such as toluene, dichloromethane, and tetrahydrofuran, or a mixed solvent of them.

Second Step

A compound ak can be obtained by adding hydrochloric acid, hydrobromic acid, trifluoroacetic acid or the like, to the compound aj obtained in the first step, and reacting them at 0° C. to 60° C., preferably 0° C. to 30° C., for 0.1 to 24 hours, preferably 0.5 to 12 hours.

Third Step

A compound al can be obtained by adding isothiocyanate having a protective group, e.g. benzoyl isothiocyanate, which is commercially available or is prepared by the known method, to the compound ak and reacting at −30° C. to 70° C., preferably −20° C. to 50° C. for 0.1 to 12 hours, preferably 0.1 to 6 hours in a solvent such as dioxane, tetrahydrofuran, toluene, and acetone, or a mixed solvent of them, subsequently, distilling off the solvent, adding concentrated sulfuric acid, concentrated nitric acid or the like, and reacting them at −30° C. to 70° C., preferably −20° C. to 50° C., for 1 to 12 hours, preferably 1 to 6 hours.

D. Production of Compound (IV)

The compound (IV) can be produced, for example, according to the following method for synthesizing a compound ao, a compound be or a compound bh.

D-1) Synthesis of Compound ao

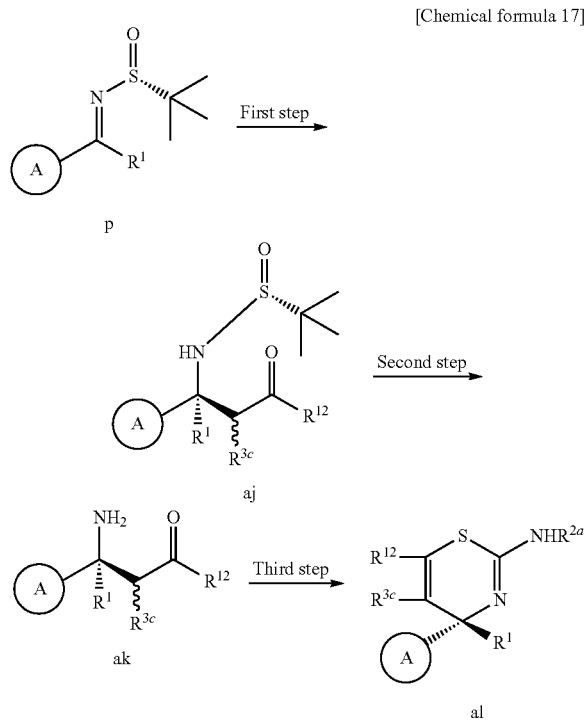

[Chemical formula 17]

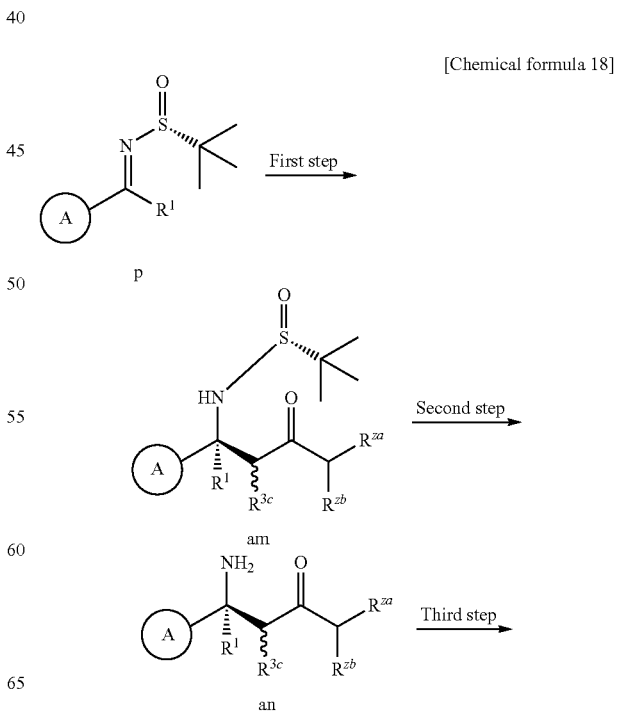

[Chemical formula 18]

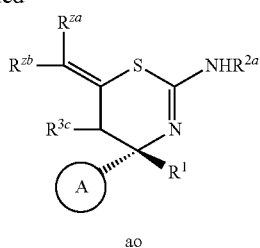

ao wherein $R^{Za}$ and $R^{Zb}$ each independently represent optionally substituted lower alkyl, or are taken together with a carbon atom to which they bind to form a carbocycle;

and other symbols are as defined above.

First Step A compound am can be stereoselectively obtained by adding a compound p which can be prepared by the known method, to enolate obtained by reacting corresponding alkyl ketone, e.g. 3-methyl-2-butanone, in the presence of a base such as lithium diisopropylamide and potassium hexamethyldisilazide, and reacting them at −80° C. to 30° C., preferably −80° C. to 0° C., for 0.1 to 24 hours, preferably 0.1 to 12 hours in a solvent such as toluene, dichloromethane, and tetrahydrofuran, or a mixed solvent of them.

Second Step

A compound an can be obtained by adding hydrochloric acid, hydrobromic acid, trifluoroacetic acid or the like, to the compound am obtained in the first step, and reacting them at 0° C. to 60° C., preferably 0° C. to 30° C., for 0.1 to 24 hours, preferably 0.5 to 12 hours.

Third Step

A compound ao can be obtained by adding isothiocyanate having a protective group, e.g. benzoyl isothiocyanate, which is commercially available or is prepared by the known method, to the compound an, reacting at −30° C. to 70° C., preferably −20° C. to 50° C. for 0.1 to 12 hours, preferably 0.1 to 6 hours in a solvent such as dioxane, tetrahydrofuran, toluene, and acetone, or a mixed solvent of them, subsequently, distilling off the solvent, adding concentrated sulfuric acid, concentrated nitric acid or the like, and reacting them at −30° C. to 70° C., preferably −20° C. to 50° C. for 1 to 12 hours, preferably 1 to 6 hours.

D-2) Synthesis of Compound be

[Chemical formula 19]

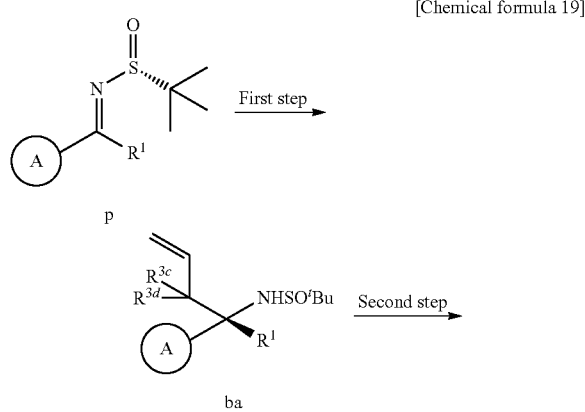

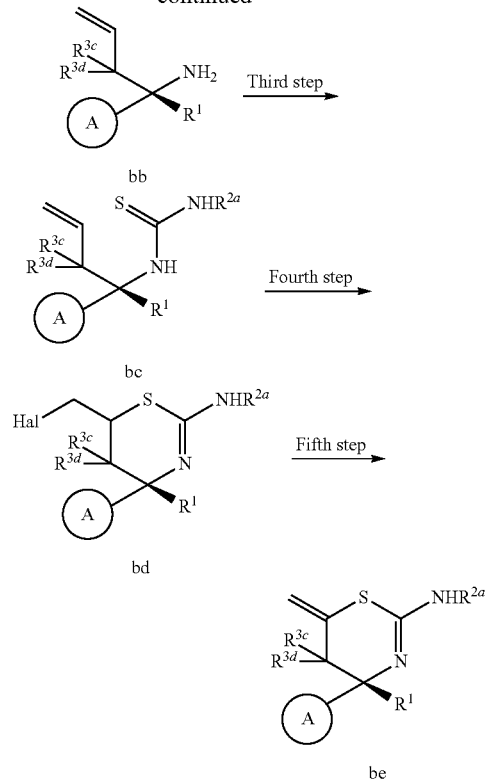

wherein respective symbols are as defined above.

First Step

A compound am can be stereoselectively obtained by reacting with a Grignard reagent such as allylmagnesium bromide at −80° C. to 30° C., preferably −80° C. to 0° C., for 0.1 to 24 hours, preferably 0.1 to 12 hours in a solvent such as toluene, dichloromethane, and tetrahydrofuran, or a mixed solvent of them.

Second Step

A compound bb can be obtained by adding a hydrogen chloride solution to the compound ba obtained in the first step, and reacting at −20° C. to 80° C., preferably 0° C. to 30° C., for 0.1 to 24 hours, preferably 0.1 to 12 hours in a solvent such as methanol, ethanol and water, or a mixed solvent of them.

Third Step

A compound bc can be obtained by adding isothiocyanate having a protective group, e.g. benzoyl isothiocyanate, which is commercially available or is prepared by the known method, to the compound bb and reacting at −30° C. to 70° C., preferably −20° C. to 50° C., for 0.1 to 12 hours, preferably 0.1 to 6 hours, in a solvent such as dichloromethane, dioxane, tetrahydrofuran, toluene, and acetone, or a mixed solvent of them.

Fourth Step

A compound bd can be obtained by adding a halogenium cation source such as iodine, bromine, and NBS to the compound bc and reacting at −20° C. to 40° C., preferably 0° C. to 20° C., for 0.1 to 12 hours, preferably 0.1 to 6 hours in a solvent such as dichloromethane.

Fifth Step

A compound bd can be obtained by adding a base such as pyrrolidine, piperidine, piperazine, and morpholine to the compound bd and reacting at 20° C. to 100° C., preferably 40°

C. to 80° C., for 0.1 to 24 hours, preferably 1 to 12 hours in a solvent such as dioxane, tetrahydrofuran, and toluene, or a mixed solvent of them.

D-3) Synthesis of Compound bh

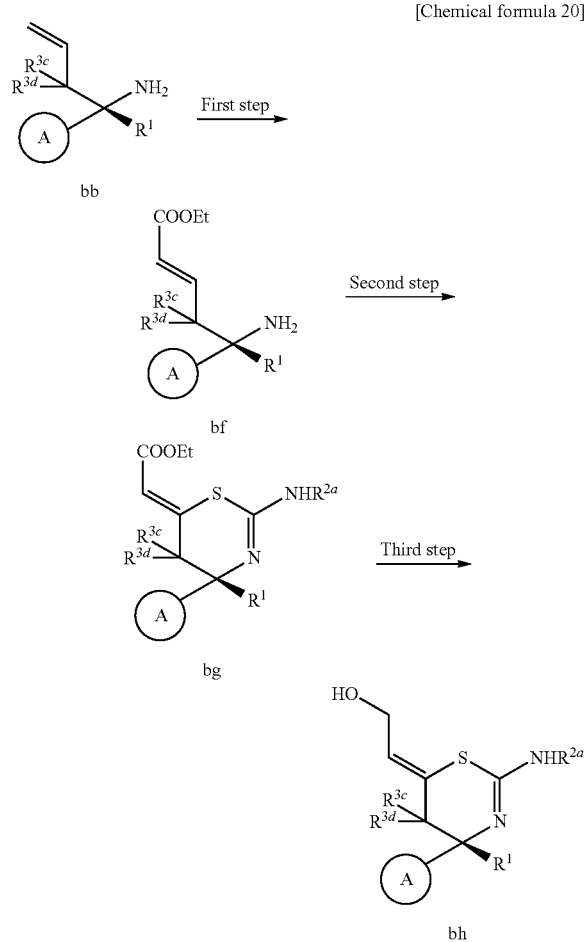

[Chemical formula 20]

wherein respective symbols are as defined above.

First Step

A compound bf can be obtained by adding ethyl acrylate and Grubbs' reagent to the compound bb in which an amino group is appropriately protected with a protective group, and subjecting to an olefinmetathesis reaction in a solvent such as toluene, dichloromethane, and tetrahydrofuran, or a mixed solvent of them. A reaction temperature is −20° C. to 60° C., preferably 0° C. to 30° C., and a reaction time is 0.5 to 24 hours, preferably 1 to 12 hours.

Second Step

A compound bg can be obtained by adding isothiocyanate having a protective group, e.g. benzoyl isothiocyanate, which is commercially available or is prepared by the known method, to the compound bf and reacting at −30° C. to 70° C., preferably −20° C. to 50° C. for 0.1 to 12 hours, preferably 0.1 to 6 hours in a solvent such as dichloromethane, dioxane, tetrahydrofuran, toluene, and acetone, or a mixed solvent of them.

Third Step

A compound bh can be obtained by adding diisobutylaluminum hydride, lithium aluminum hydride, or sodium hydride to the compound bg, subjecting to a reducing reaction, and reacting them at −80° C. to 0° C., preferably −80° C. to −20° C., for 0.1 to 12 hours, preferably 0.1 to 3 hours in a solvent such as dioxane, tetrahydrofuran, and toluene, or a mixed solvent of them.

The compound bh can be subjected to an appropriately reaction to further convert an alcohol group.

E. Conversion of Substituent (1)

The synthesis of compound ab-2 obtained by a conversion of a substituent, is described below.

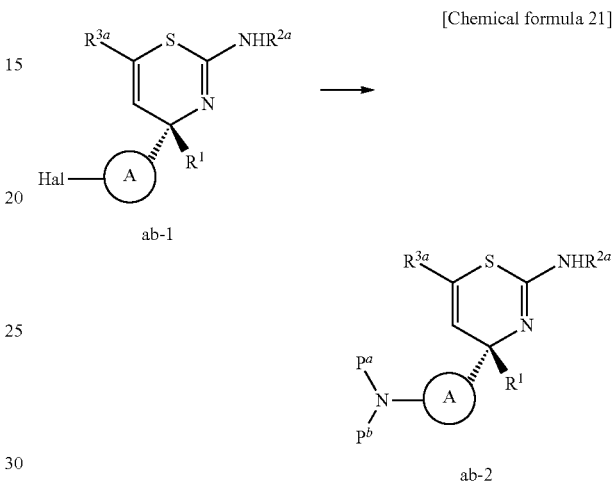

[Chemical formula 21]

wherein $P^a$ and $P^b$ are an amino protective group; and other symbols are as defined above.

A compound af-1 can be obtained by adding tris(dibenzylideneacetone)dipalladium, palladium acetate, palladium (0) prepared in situ or the like, and a phosphine ligand such as tritert-butylphosphine, and dicyclohexylbiphenylphosphine to the compound ab-1 in a solvent such as tetrahydrofuran, toluene, and xylene, adding a reagent having a substituent corresponding to an objective compound such as lithium hexamethyldisilazide, and benzophenoneimine at −10° C. to 30° C., and reacting them at 30° C. to 120° C., preferably 50° C. to 100° C., for 0.5 to 48 hours, preferably 3 to 20 hours.

The amino protective group may be a substituent which can be deprotected by the method described in Protective Groups in Organic Synthesis, Theodora W Green (John Wiley & Sons), and examples include lower alkoxycarbonyl, lower alkenyloxycarbonyl, trialkylsilyl, acyl, methane sulfonyl, trifluoroethanesulfonyl, toluenesulfonyl and the like.

F. Conversion of Substituent (2)

The synthesis of a compound ab-4 obtained by a conversion of a substituent, is described below.

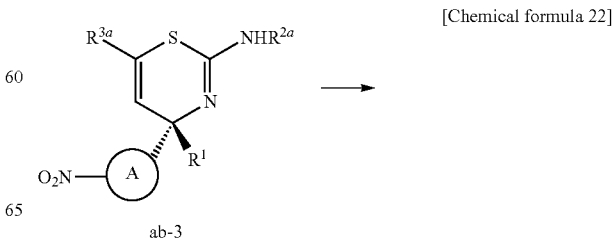

[Chemical formula 22]

-continued

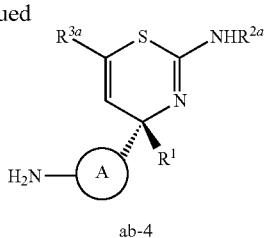

ab-4 wherein respective symbols are as defined above.

A compound ab-4 can be obtained by adding iron to a compound ab-3 in a mixed solvent of acetic acid and water, followed by a reaction at 20° C. to 120° C., preferably 50° C. to 80° C., for 0.5 to 48 hours, preferably 6 to 20 hours.

Besides, the compound ab-4 can be also obtained by adding a catalytic reducing catalyst such as 10% palladium/carbon to the compound ab-3 in a solvent such as tetrahydrofuran, ethyl acetate, and methanol, and reacting them at 30° C. to 120° C., preferably 50° C. to 80° C., for 0.5 to 48 hours, preferably 6 to 20 hours under the hydrogen atmosphere at a normal pressure to 5 atm, preferably a normal pressure to 2 atm, or by the method described in Comprehensive Organic Transformations, Richard C Larock (Mcgraw-Hill).

The compounds v, ab, al, ao, be and bh can be produced by an optical resolution of each intermediate and a final product, or the following method, for example, according to the method described in (1) T. Fujisawa et al., Tetrahedron Lett., 37, 3881-3884 (1996), (2) D. H. Hua et al., Sulfur Reports, vol. 21, pp. 211-239 (1999), (3) Y. Koriyama et al., Tetrahedron, 58, 9621-9628 (2002) or (4) T. Vilavan et al., Current Organic Chemistry, 9, 1315-1392 (2005). As a procedure of the optical resolution, there are a method of separating an optical isomer using an optically active column; kinetic optical resolution utilizing an enzymatic reaction and the like; crystallization resolution of a diastereomer by salt formation using a chiral acid or a chiral base; preference crystallization method and the like.

Of the present compound, the following compounds are preferable.

In the formula (I'):

[Chemical formula 23]

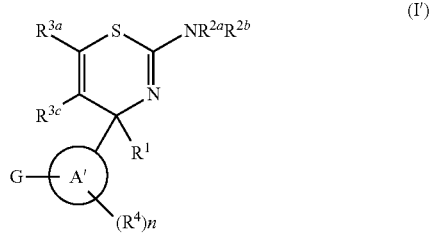

(I')

1) the compound, wherein ring A' is phenyl or a nitrogen-containing aromatic heterocyclic group (hereinafter, referred to as compound in which ring A' is A'1), the compound, wherein ring A' is phenyl, pyridyl, indolyl, benzoisoxazolyl, benzopyrazolyl or benzofuryl, benzothienyl, benzodioxolyl, or dihydrobenzodioxolanyl (hereinafter, referred to as compound in which ring A' is A'2),
the compound, wherein ring A' is phenyl (hereinafter, referred to as compound in which ring A' is A'3),
the compound, wherein ring A' is pyridyl, (hereinafter, referred to as compound in which ring A' is A'4), 2) the compound, wherein $R^1$ is optionally substituted lower alkyl (hereinafter, referred to as compound in which $R^1$ is R1-1),
the compound, wherein $R^1$ is methyl (hereinafter, referred to as compound in which $R^1$ is R1-2),
3) the compound, wherein $R^{2a}$ and $R^{2b}$ are each independently hydrogen, lower alkyl or acyl (hereinafter, referred to as compound in which $R^{2a}$ and $R^{2b}$ are R2-1),
the compound, wherein $R^{2a}$ and $R^{2b}$ are both hydrogen (hereinafter, referred to as compound in which $R^{2a}$ and $R^{2a}$q are R2-2),
4) the compound, wherein $R^{3a}$ and $R^{3c}$ are each independently hydrogen, halogen, hydroxyl, lower alkyl or amino (hereinafter, referred to as compound in which $R^{3a}$ and $R^{3c}$ are R3-1),
the compound, wherein $R^{3a}$ and $R^{3c}$ are the same substituent selected from halogen or lower alkyl (hereinafter, referred to as compound in which $R^{3a}$ and $R^{3c}$ are R3-2),
the compound, wherein $R^{3a}$ and $R^{3c}$ are all hydrogen (hereinafter, referred to as compound in which $R^{3a}$ and $R^{3c}$ are R3-3),
5) the compound, wherein n is 0 to 2, and each $R^4$ is independently halogen, lower alkoxy, lower alkylamino, lower alkylthio, oxo, or lower alkylenedioxy (hereinafter, referred to as compound in which $R^4$ is R4-1),
the compound, wherein n is 0 to 2, and each $R^4$ is independently halogen (hereinafter, referred to as compound in which $R^4$ is R4-2),
6) the compound, wherein G is the above (ii), (iv), (v), (x), (xiii), or (xiv) (hereinafter, referred to as compound in which G is G1),
the compound, wherein G is the above (ii'), (ii''), (iv'), (v'), (x'), (xiii') or (xiv') (hereinafter, referred to as compound in which G is G2),
the compound, wherein G is the above (ii'), (ii''), (iv'), (v'), (x'), (xiii') or (xiv'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl, or optionally substituted pyridopyrimidinyl, herein, the substituent is 1 to 3 groups selected from the group consisting of the substituent group α and lower alkyl optionally substituted one or more groups selected from the substituent group α (hereinafter, referred to as compound in which G is G3),
the compound, wherein G is the above (ii'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl, or optionally substituted pyridopyrimidinyl, herein, the substituent is 1 to 3 groups selected from the group consisting of the substituent group α and lower alkyl optionally substituted one or more groups selected from the substituent group α (hereinafter, referred to as compound in which G is G4),
the compound, wherein G is the above (ii'), $R^5$ is hydrogen or lower alkyl, $W^1$ is O, ring B is optionally substituted pyridyl, or optionally substituted pyrazinyl, herein, the substituent is 1 to 3 groups selected from the group consisting of the substituent group α and lower alkyl optionally substituted one or more groups selected from the substituent group α (hereinafter, referred to as compound in which G is G5), compounds in which, in the formula (I'), a combination of ring A', $R^1$, $R^{2a}$ and $R^{2b}$, $R^{3a}$, $R^{3c}$, n and $R^4$, and G is as follows.

(A'1, R1-1, R2-1, R3-1, R4-1, G1), (A'1, R1-1, R2-1, R3-1, R4-1, G2),
(A'1, R1-1, R2-1, R3-1, R4-1, G3), (A'1, R1-1, R2-1, R3-1, R4-1, G4),
(A'1, R1-1, R2-1, R3-1, R4-1, G5), (A'1, R1-1, R2-1, R3-1, R4-2, G1),
(A'1, R1-1, R2-1, R3-1, R4-2, G2), (A'1, R1-1, R2-1, R3-1, R4-2, G3),
(A'1, R1-1, R2-1, R3-1, R4-2, G4), (A'1, R1-1, R2-1, R3-1, R4-2, G5),
(A'1, R1-1, R2-1, R3-2, R4-1, G1), (A'1, R1-1, R2-1, R3-2, R4-1, G2),
(A'1, R1-1, R2-1, R3-2, R4-1, G3), (A'1, R1-1, R2-1, R3-2, R4-1, G4),
(A'1, R1-1, R2-1, R3-2, R4-1, G5), 1, R2-1, R3-2, R4-2, G1),
(A'1, R1-1, R2-1, R3-2, R4-2, G2), (A'1, R1-1, R2-1, R3-2, R4-2, G3),
(A'1, R1-1, R2-1, R3-2, R4-2, G4), (A'1, R1-1, R2-1, R3-2, R4-2, G5),
(A'1, R1-1, R2-1, R3-3, R4-1, G1), (A'1, R1-1, R2-1, R3-3, R4-1, G2),
(A'1, R1-1, R2-1, R3-3, R4-1, G3), (A'1, R1-1, R2-1, R3-3, R4-1, G4),
(A'1, R1-1, R2-1, R3-3, R4-1, G5), (A'1, R1-1, R2-1, R3-3, R4-2, G1),
(A'1, R1-1, R2-1, R3-3, R4-2, G2), (A'1, R1-1, R2-1, R3-3, R4-2, G3),
(A'1, R1-1, R2-1, R3-3, R4-2, G4), (A'1, R1-1, R2-1, R3-3, R4-2, G5),
(A'1, R1-1, R2-2, R3-1, R4-1, G1), (A'1, R1-1, 112-2, R3-1, R4-1, G2),
(A'1, R1-1, R2-2, R3-1, R4-1, G3), (A'1, R1-1, R2-2, R3-1, R4-1, G4),
(A'1, R1-1, R2-2, R3-1, R4-1, G5), (A'1, R1-1, R2-2, R3-1, R4-2, G1),
(A'1, R1-1, R2-2, R3-1, R4-2, G2), (A'1, R1-1, R2-2, R3-1, R4-2, G3),
(A'1, R1-1, R2-2, R3-1, R4-2, G4), (A'1, R1-1, R2-2, R3-1, R4-2, G5),
(A'1, R1-1, R2-2, R3-2, R4-1, G1), (A'1, R1-1, R2-2, R3-2, R4-1, G2),
(A'1, R1-1, R2-2, R3-2, R4-1, G3), (A'1, R1-1, R2-2, R3-2, R4-1, G4),
(A'1, R1-1, R2-2, R3-2, R4-1, G5), (A'1, R1-1, R2-2, R3-2, R4-2, G1),
(A'1, R1-1, R2-2, R3-2, R4-2, G2), (A'1, R1-1, R2-2, R3-2, R4-2, G3),
(A'1, R1-1, R2-2, R3-2, R4-2, G4), (A'1, R1-1, R2-2, R3-2, R4-2, G5),
(A'1, R1-1, R2-2, R3-3, R4-1, G1), (A'1, R1-1, R2-2, R3-3, R4-1, G2),
(A'1, R1-1, R2-2, R3-3, R4-1, G3), (A'1, R1-1, R2-2, R3-3, R4-1, G4),
(A'1, R1-1, R2-2, R3-3, R4-1, G5), (A'1, R1-1, R2-2, R3-3, R4-2, G1),
(A'1, R1-1, R2-2, R3-3, R4-2, G2), (A'1, R1-1, R2-2, R3-3, R4-2, G3),
(A'1, R1-1, R2-2, R3-3, R4-2, G4), (A'1, R1-1, R2-2, R3-3, R4-2, G5),
(A'1, R1-2, R2-1, R3-1, R4-1, G1), (A'1, R1-2, R2-1, R3-1, R4-1, G2),
(A'1, R1-2, R2-1, R3-1, R4-1, G3), (A'1, R1-2, R2-1, R3-1, R4-1, G4),
(A'1, R1-2, R2-1, R3-1, R4-1, G5), (A'1, R1-2, R2-1, R3-1, R4-2, G1),
(A'1, R1-2, R2-1, R3-1, R4-2, G2), (A'1, R1-2, R2-1, R3-1, R4-2, G3),
(A'1, R1-2, R2-1, R3-1, R4-2, G4),
(A'1, R1-2, R2-1, R3-2, R4-1, G1), (A'1, R1-2, R2-1, R3-2, R4-1, G2),
(A'1, R1-2, R2-1, R3-2, R4-1, G3), (A'1, R1-2, R2-1, R3-2, R4-1, G4),
(A'1, R1-2, R2-1, R3-2, R4-1, G5), (A'1, R1-2, R2-1, R3-2, R4-2, G1),
(A'1, R1-2, R2-1, R3-2, R4-2, G2), (A'1, R1-2, R2-1, R3-2, R4-2, G3),
(A'1, R1-2, R2-1, R3-2, R4-2, G4), (A'1, R1-2, R2-1, R3-2, R4-2, G5),
(A'1, R1-2, R2-1, R3-3, R4-1, G1),
(A'1, R1-2, R2-1, R3-3, R4-1, G3), (A'1, R1-2, R2-1, R3-3, R4-1, G4),
(A'1, R1-2, R2-1, R3-3, R4-1, G5), (A'1, R1-2, R2-1, R3-3, R4-2, G1),
(A'1, R1-2, R2-1, R3-3, R4-2, G2), (A'1, R1-2, R2-1, R3-3, R4-2, G3),
(A'1, R1-2, R2-1, R3-3, R4-2, G4), (A'1, R1-2, R2-1, R3-3, R4-2, G5),
(A'1, R1-2, R2-2, R3-1, R4-1, G1), (A'1, R1-2, R2-2, R3-1, R4-1, G2),
(A'1, R1-2, R2-2, R3-1, R4-1, G3), (A'1, R1-2, R2-2, R3-1, R4-1, G4),
(A'1, R1-2, R2-2, R3-1, R4-1, G5), (A'1, R1-2, R2-2, R3-1, R4-2, G1),
(A'1, R1-2, R2-2, R3-1, R4-2, G2), (A'1, R1-2, R2-2, R3-1, R4-2, G3),
(A'1, R1-2, R2-2, R3-1, R4-2, G4), (A'1, R1-2, R2-2, R3-1, R4-2, G5),
(A'1, R1-2, R2-2, R3-2, R4-1, G1), (A'1, R1-2, R2-2, R3-2, R4-1, G2),
(A'1, R1-2, R2-2, R3-2, R4-1, G3), (A'1, R1-2, R2-2, R3-2, R4-1, G4),
(A'1, R1-2, R2-2, R3-2, R4-1, G5), (A'1, R1-2, R2-2, R3-2, R4-2, G1),
(A'1, R1-2, R2-2, R3-2, R4-2, G2), (A'1, R1-2, R2-2, R3-2, R4-2, G3),
(A'1, R1-2, R2-2, R3-2, R4-2, G4), (A'1, R1-2, R2-2, R3-2, R4-2, G5),
(A'1, R1-2, R2-2, R3-3, R4-1, G1), (A'1, R1-2, R2-2, R3-3, R4-1, G2),
(A'1, R1-2, R2-2, R3-3, R4-1, G3), (A'1, R1-2, R2-2, R3-3, R4-1, G4),
(A'1, R1-2, R2-2, R3-3, R4-1, G5), (A'1, R1-2, R2-2, R3-3, R4-2, G1),
(A'1, R1-2, R2-2, R3-3, R4-2, G2), (A'1, R1-2, R2-2, R3-3, R4-2, G3),
(A'1, R1-2, R2-2, R3-3, R4-2, G4),
(A'2, R1-1, R2-1, R3-1, R4-1, G1), (A'2, R1-1, R2-1, R3-1, R4-1, G2),
(A'2, R1-1, R2-1, R3-1, R4-1, G3), (A'2, R1-1, R2-1, R3-1, R4-1, G4),
(A'2, R1-1, R2-1, R3-1, R4-1, G5), (A'2, R1-1, R2-1, R3-1, R4-2, G1),
(A'2, R1-1, R2-1, R3-1, R4-2, G2), (A'2, R1-1, R2-1, R3-1, R4-2, G3),
(A'2, R1-1, R2-1, R3-1, R4-2, G4), (A'2, R1-1, R2-1, R3-1, R4-2, G5),
(A'2, R1-1, R2-1, R3-2, R4-1, G1), (A'2, R1-1, R2-1, R3-2, R4-1, G2),
(A'2, R1-1, R2-1, R3-2, R4-1, G3), (A'2, R1-1, R2-1, R3-2, R4-1, G4), (A'2, R1-1, R2-1, R3-2, R4-1, G5), (A'2, R1-1, R2-1, R3-2, R4-2, G1),
(A'2, R1-1, R2-1, R3-2, R4-2, G2), (A'2, R1-1, R2-1, R3-2, R4-2, G3),
(A'2, R1-1, R2-1, R3-2, R4-2, G4), (A'2, R1-1, R2-1, R3-2, R4-2, G5),
(A'2, R1-1, R2-1, R3-3, R4-1, G1), (A'2, R1-1, R2-1, R3-3, R4-1, G2),
(A'2, R1-1, R2-1, R3-3, R4-1, G3), (A'2, R1-1, R2-1, R3-3, R4-1, G4),
(A'2, R1-1, R2-1, R3-3, R4-1, G5), (A'2, R1-1, R2-1, R3-3, R4-2, G1),
(A'2, R1-1, R2-1, R3-3, R4-2, G2), (A'2, R1-1, R2-1, R3-3, R4-2, G3),
(A'2, R1-1, R2-1, R3-3, R4-2, G4), (A'2, R1-1, R2-1, R3-3, R4-2, G5),
(A'2, R1-1, R2-2, R3-1, R4-1, G1), (A'2, R1-1, R2-2, R3-1, R4-1, G2),
(A'2, R1-1, R2-2, R3-1, R4-1, G3), (A'2, R1-1, R2-2, R3-1, R4-1, G4),
(A'2, R1-1, R2-2, R3-1, R4-1, G5), (A'2, R1-1, R2-2, R3-1, R4-2, G1),
(A'2, R1-1, R2-2, R3-1, R4-2, G2), (A'2, R1-1, R2-2, R3-1, R4-2, G3),
(A'2, R1-1, R2-2, R3-1, R4-2, G4), (A'2, R1-1, R2-2, R3-1, R4-2, G5),
(A'2, R1-1, R2-2, R3-2, R4-1, G1), (A'2, R1-1, R2-2, R3-2, R4-1, G2),
(A'2, R1-1, R2-2, R3-2, R4-1, G3), (A'2, R1-1, R2-2, R3-2, R4-1, G4),
(A'2, R1-1, R2-2, R3-2, R4-1, G5), (A'2, R1-1, R2-2, R3-2, R4-2, G1),
(A'2, R1-1, R2-2, R3-2, R4-2, G2), (A'2, R1-1, R2-2, R3-2, R4-2, G3),
(A'2, R1-1, R2-2, R3-2, R4-2, G4), (A'2, R1-1, R2-2, R3-2, R4-2, G5),
(A'2, R1-1, R2-2, R3-3, R4-1, G1), (A'2, R1-1, R2-2, R3-3, R4-1, G2),
(A'2, R1-1, R2-2, R3-3, R4-1, G3), (A'2, R1-1, R2-2, R3-3, R4-1, G4),
(A'2, R1-1, R2-2, R3-3, R4-1, G5), (A'2, R1-1, R2-2, R3-3, R4-2, G1),
(A'2, R1-1, R2-2, R3-3, R4-2, G2), (A'2, R1-1, R2-2, R3-3, R4-2, G3),
(A'2, R1-1, R2-2, R3-3, R4-2, G4), (A'2, R1-1, R2-2, R3-3, R4-2, G5),
(A'2, R1-2, R2-1, R3-1, R4-1, G1), (A'2, R1-2, R2-1, R3-1, R4-1, G2),
(A'2, R1-2, R2-1, R3-1, R4-1, G3), (A'2, R1-2, R2-1, R3-1, R4-1, G4),
(A'2, R1-2, R2-1, R3-1, R4-1, G5), (A'2, R1-2, R2-1, R3-1, R4-2, G1),
(A'2, R1-2, R2-1, R3-1, R4-2, G2), (A'2, R1-2, R2-1, R3-1, R4-2, G3),
(A'2, R1-2, R2-1, R3-1, R4-2, G4), (A'2, R1-2, R2-1, R3-1, R4-2, G5),
(A'2, R1-2, R2-1, R3-2, R4-1, G1), (A'2, R1-2, R2-1, R3-2, R4-1, G2),
(A'2, R1-2, R2-1, R3-2, R4-1, G3), (A'2, R1-2, R2-1, R3-2, R4-1, G4),
(A'2, R1-2, R2-1, R3-2, R4-1, G5), (A'2, R1-2, R2-1, R3-2, R4-2, G1),
(A'2, R1-2, R2-1, R3-2, R4-2, G2), (A'2, R1-2, R2-1, R3-2, R4-2, G3),
(A'2, R1-2, R2-1, R3-2, R4-2, G4), (A'2, R1-2, R2-1, R3-2, R4-2, G5),
(A'2, R1-2, R2-1, R3-3, R4-1, G1), (A'2, R1-2, R2-1, R3-3, R4-1, G2),
(A'2, R1-2, R2-1, R3-3, R4-1, G3), (A'2, R1-2, R2-1, R3-3, R4-1, G4),
(A'2, R1-2, R2-1, R3-3, R4-1, G5), (A'2, R1-2, R2-1, R3-3, R4-2, G1),
(A'2, R1-2, R2-1, R3-3, R4-2, G2), (A'2, R1-2, R2-1, R3-3, R4-2, G3),
(A'2, R1-2, R2-1, R3-3, R4-2, G4), (A'2, R1-2, R2-1, R3-3, R4-2, G5),
(A'2, R1-2, R2-2, R3-1, R4-1, G1), (A'2, R1-2, R2-2, R3-1, R4-1, G2),
(A'2, R1-2, R2-2, R3-1, R4-1, G3), (A'2, R1-2, R2-2, R3-1, R4-1, G4),
(A'2, R1-2, R2-2, R3-1, R4-1, G5), (A'2, R1-2, R2-2, R3-1, R4-2, G1),
(A'2, R1-2, R2-2, R3-1, R4-2, G2), (A'2, R1-2, R2-2, R3-1, R4-2, G3),
(A'2, R1-2, R2-2, R3-1, R4-2, G4), (A'2, R1-2, R2-2, R3-1, R4-2, G5),
(A'2, R1-2, R2-2, R3-2, R4-1, G1), (A'2, R1-2, R2-2, R3-2, R4-1, G2),
(A'2, R1-2, R2-2, R3-2, R4-1, G3), (A'2, R1-2, R2-2, R3-2, R4-1, G4),
(A'2, R1-2, R2-2, R3-2, R4-1, G5), (A'2, R1-2, R2-2, R3-2, R4-2, G1),
(A'2, R1-2, R2-2, R3-2, R4-2, G2), (A'2, R1-2, R2-2, R3-2, R4-2, G3),
(A'2, R1-2, R2-2, R3-2, R4-2, G4), (A'2, R1-2, R2-2, R3-2, R4-2, G5),
(A'2, R1-2, R2-2, R3-3, R4-1, G1), (A'2, R1-2, R2-2, R3-3, R4-1, G2),
(A'2, R1-2, R2-2, R3-3, R4-1, G3), (A'2, R1-2, R2-2, R3-3, R4-1, G4),
(A'2, R1-2, R2-2, R3-3, R4-1, G5), (A'2, R1-2, R2-2, R3-3, R4-2, G1),
(A'2, R1-2, R2-2, R3-3, R4-2, G2), (A'2, R1-2, R2-2, R3-3, R4-2, G3),
(A'2, R1-2, R2-2, R3-3, R4-2, G4), (A'2, R1-2, R2-2, R3-3, R4-2, G5),
(A'3, R1-1, R2-1, R3-1, R4-1, G0, (A'3, R1-1, R2-1, R3-1, R4-1, G2),
(A'3, R1-1, R2-1, R3-1, R4-1, G3), (A'3, R1-1, R2-1, R3-1, R4-1, G4),
(A'3, R1-1, R2-1, R3-1, R4-1, G5), (A'3, R1-1, R2-1, R3-1, R4-2, G1),
(A'3, R1-1, R2-1, R3-1, R4-2, G2), (A'3, R1-1, R2-1, R3-1, R4-2, G3),
(A'3, R1-1, R2-1, R3-1, R4-2, G4), (A'3, R1-1, R2-1, R3-1, R4-2, G5),
(A'3, R1-1, R2-1, R3-2, R4-1, G1), (A'3, R1-1, R2-1, R3-2, R4-1, G2),
(A'3, R1-1, R2-1, R3-2, R4-1, G3), (A'3, R1-1, R2-1, R3-2, R4-1, G4),
(A'3, R1-1, R2-1, R3-2, R4-1, G5), (A'3, R1-1, R2-1, R3-2, R4-2, G1),
(A'3, R1-1, R2-1, R3-2, R4-2, G2), (A'3, R1-1, R2-1, R3-2, R4-2, G3),
(A'3, R1-1, R2-1, R3-2, R4-2, G4), (A'3, R1-1, R2-1, R3-2, R4-2, G5),
(A'3, R1-1, R2-1, R3-3, R4-1, G1), (A'3, R1-1, R2-1, R3-3, R4-1, G2),
(A'3, R1-1, R2-1, R3-3, R4-1, G3), (A'3, R1-1, R2-1, R3-3, R4-1, G4),
(A'3, R1-1, R2-1, R3-3, R4-1, G5), (A'3, R1-1, R2-1, R3-3, R4-2, G1), (A'3, R1-1, R2-1, R3-3, R4-2, G2), (A'3, R1-1, R2-1, R3-3, R4-2, G3),
(A'3, R1-1, R2-1, R3-3, R4-2, G4), (A'3, R1-1, R2-1, R3-3, R4-2, G5),
(A'3, R1-1, R2-2, R3-1, R4-1, G1), (A'3, R1-1, R2-2, R3-1, R4-1, G2),
(A'3, R1-1, R2-2, R3-1, R4-1, G3), (A'3, R1-1, R2-2, R3-1, R4-1, G4),
(A'3, R1-1, R2-2, R3-1, R4-1, G5), (A'3, R1-1, R2-2, R3-1, R4-2, G1),
(A'3, R1-1, R2-2, R3-1, R4-2, G2), (A'3, R1-1, R2-2, R3-1, R4-2, G3),
(A'3, R1-1, R2-2, R3-1, R4-2, G4), (A'3, R1-1, R2-2, R3-1, R4-2, G5),
(A'3, R1-1, R2-2, R3-2, R4-1, G1), (A'3, R1-1, R2-2, R3-2, R4-1, G2),
(A'3, R1-1, R2-2, R3-2, R4-1, G3), (A'3, R1-1, R2-2, R3-2, R4-1, G4),
(A'3, R1-1, R2-2, R3-2, R4-1, G5), (A'3, R1-1, R2-2, R3-2, R4-2, G1),
(A'3, R1-1, R2-2, R3-2, R4-2, G2), (A'3, R1-1, R2-2, R3-2, R4-2, G3),
(A'3, R1-1, R2-2, R3-2, R4-2, G4), (A'3, R1-1, R2-2, R3-2, R4-2, G5),
(A'3, R1-1, R2-2, R3-3, R4-1, G0, (A'3, R1-1, R2-2, R3-3, R4-1, G2),
(A'3, R1-1, R2-2, R3-3, R4-1, G3), (A'3, R1-1, R2-2, R3-3, R4-1, G4),
(A'3, R1-1, R2-2, R3-3, R4-1, G5), (A'3, R1-1, R2-2, R3-3, R4-2, G1),
(A'3, R1-1, R2-2, R3-3, R4-2, G2), (A'3, R1-1, R2-2, R3-3, R4-2, G3),
(A'3, R1-1, R2-2, R3-3, R4-2, G4), (A'3, R1-1, R2-2, R3-3, R4-2, G5),
(A'3, R1-2, R2-1, R3-1, R4-1, G1), (A'3, R1-2, R2-1, R3-1, R4-1, G2),
(A'3, R1-2, R2-1, R3-1, R4-1, G3), (A'3, R1-2, R2-1, R3-1, R4-1, G4),
(A'3, R1-2, R2-1, R3-1, R4-1, G5), (A'3, R1-2, R2-1, R3-1, R4-2, G1),
(A'3, R1-2, R2-1, R3-1, R4-2, G2), (A'3, R1-2, R2-1, R3-1, R4-2, G3),
(A'3, R1-2, R2-1, R3-1, R4-2, G4), (A'3, R1-2, R2-1, R3-1, R4-2, G5),
(A'3, R1-2, R2-1, R3-2, R4-1, G1), (A'3, R1-2, R2-1, R3-2, R4-1, G2),
(A'3, R1-2, R2-1, R3-2, R4-1, G3), (N3, R1-2, R2-1, R3-2, R4-1, G4),
(A'3, R1-2, R2-1, R3-2, R4-1, G5), (A'3, R1-2, R2-1, R3-2, R4-2, G1),
(A'3, R1-2, R2-1, R3-2, R4-2, G2), (A'3, R1-2, R2-1, R3-2, R4-2, G3),
(A'3, R1-2, R2-1, R3-2, R4-2, G4), (A'3, R1-2, R2-1, R3-2, R4-2, G5),
(A'3, R1-2, R2-1, R3-3, R4-1, G1), (A'3, R1-2, R2-1, R3-3, R4-1, G2),
(A'3, R1-2, R2-1, R3-3, R4-1, G3), (A'3, R1-2, R2-1, R3-3, R4-1, G4),
(A'3, R1-2, R2-1, R3-3, R4-1, G5), (A'3, R1-2, R2-1, R3-3, R4-2, G1),
(A'3, R1-2, R2-1, R3-3, R4-2, G2), (A'3, R1-2, R2-1, R3-3, R4-2, G3),
(A'3, R1-2, R2-1, R3-3, R4-2, G4), (A'3, R1-2, R2-1, R3-3, R4-2, G5),
(A'3, R1-2, R2-2, R3-1, R4-1, G1), (A'3, R1-2, R2-2, R3-1, R4-1, G2),
(A'3, R1-2, R2-2, R3-1, R4-1, G3), (A'3, R1-2, R2-2, R3-1, R4-1, G4),
(A'3, R1-2, R2-2, R3-1, R4-1, G5), (A'3, R1-2, R2-2, R3-1, R4-2, G1),
(A'3, R1-2, R2-2, R3-1, R4-2, G2), (A'3, R1-2, R2-2, R3-1, R4-2, G3),
(A'3, R1-2, R2-2, R3-1, R4-2, G4), (A'3, R1-2, R2-2, R3-1, R4-2, G5),
(A'3, R1-2, R2-2, R3-2, R4-1, G1), (N3, R1-2, R2-2, R3-2, R4-1, G2),
(A'3, R1-2, R2-2, R3-2, R4-1, G3), (A'3, R1-2, R2-2, R3-2, R4-1, G4),
(A'3, R1-2, R2-2, R3-2, R4-1, G5), (A'3, R1-2, R2-2, R3-2, R4-2, G1),
(A'3, R1-2, R2-2, R3-2, R4-2, G2), (A'3, R1-2, R2-2, R3-2, R4-2, G3),
(A'3, R1-2, R2-2, R3-2, R4-2, G4), (A'3, R1-2, R2-2, R3-2, R4-2, G5),
(A'3, R1-2, R2-2, R3-3, R4-1, G1), (A'3, R1-2, R2-2, R3-3, R4-1, G2),
(A'3, R1-2, R2-2, R3-3, R4-1, G3), (A'3, R1-2, R2-2, R3-3, R4-1, G4),
(A'3, R1-2, R2-2, R3-3, R4-1, G5), (A'3, R1-2, R2-2, R3-3, R4-2, G1),
(A'3, R1-2, R2-2, R3-3, R4-2, G2), (A'3, R1-2, R2-2, R3-3, R4-2, G3),
(A'3, R1-2, R2-2, R3-3, R4-2, G4), (A'3, R1-2, R2-2, R3-3, R4-2, G5),
(A'4, R1-1, R2-1, R3-1, R4-1, G1), (A'4, R1-1, R2-1, R3-1, R4-1, G2),
(A'4, R1-1, R2-1, R3-1, R4-1, G3), (A'4, R1-1, R2-1, R3-1, R4-1, G4),
(A'4, R1-1, R2-1, R3-1, R4-1, G5), (A'4, R1-1, R2-1, R3-1, R4-2, G1),
(A'4, R1-1, R2-1, R3-1, R4-2, G2), (A'4, R1-1, R2-1, R3-1, R4-2, G3),
(A'4, R1-1, R2-1, R3-1, R4-2, G4), (A'4, R1-1, R2-1, R3-1, R4-2, G5),
(A'4, R1-1, R2-1, R3-2, R4-1, G1), (A'4, R1-1, R2-1, R3-2, R4-1, G2),
(A'4, R1-1, R2-1, R3-2, R4-1, G3), (A'4, R1-1, R2-1, R3-2, R4-1, G4),
(A'4, R1-1, R2-1, R3-2, R4-1, G5), (A'4, R1-1, R2-1, R3-2, R4-2, G1),
(A'4, R1-1, R2-1, R3-2, R4-2, G2), (A'4, R1-1, R2-1, R3-2, R4-2, G3),
(A'4, R1-1, R2-1, R3-2, R4-2, G4), (A'4, R1-1, R2-1, R3-2, R4-2, G5),
(A'4, R1-1, R2-1, R3-3, R4-1, G1), (A'4, R1-1, R2-1, R3-3, R4-1, G2),
(A'4, R1-1, R2-1, R3-3, R4-1, G3), (A'4, R1-1, R2-1, R3-3, R4-1, G4),
(A'4, R1-1, R2-1, R3-3, R4-1, G5), (A'4, R1-1, R2-1, R3-3, R4-2, G1),
(A'4, R1-1, R2-1, R3-3, R4-2, G2), (A'4, R1-1, R2-1, R3-3, R4-2, G3),
(A'4, R1-1, R2-1, R3-3, R4-2, G4), (A'4, R1-1, R2-1, R3-3, R4-2, G5),
(A'4, R1-1, R2-2, R3-1, R4-1, G1), (A'4, R1-1, R2-2, R3-1, R4-1, G2),
(A'4, R1-1, R2-2, R3-1, R4-1, G3), (A'4, R1-1, R2-2, R3-1, R4-1, G4),
(A'4, R1-1, R2-2, R3-1, R4-1, G5), (A'4, R1-1, R2-2, R3-1, R4-2, G1),
(A'4, R1-1, R2-2, R3-1, R4-2, G2), (A'4, R1-1, R2-2, R3-1, R4-2, G3), (A'4, R1-1, R2-2, R3-1, R4-2, G4), (A'4, R1-1, R2-2, R3-1, R4-2, G5),
(A'4, R1-1, R2-2, R3-2, R4-1, G1), (A'4, R1-1, R2-2, R3-2, R4-1, G2),
(A'4, R1-1, R2-2, R3-2, R4-1, G3), (A'4, R1-1, R2-2, R3-2, R4-1, G4),
(A'4, R1-1, R2-2, R3-2, R4-1, G5), (A'4, R1-1, R2-2, R3-2, R4-2, G1),
(A'4, R1-1, R2-2, R3-2, R4-2, G2), (A'4, R1-1, R2-2, R3-2, R4-2, G3),
(A'4, R1-1, R2-2, R3-2, R4-2, G4), (A'4, R1-1, R2-2, R3-2, R4-2, G5),
(A'4, R1-1, R2-2, R3-3, R4-1, G1), (A'4, R1-1, R2-2, R3-3, R4-1, G2),
(A'4, R1-1, R2-2, R3-3, R4-1, G3), (A'4, R1-1, R2-2, R3-3, R4-1, G4),
(A'4, R1-1, R2-2, R3-3, R4-1, G5), (A'4, R1-1, R2-2, R3-3, R4-2, G1),
(A'4, R1-1, R2-2, R3-3, R4-2, G2), (A'4, R1-1, R2-2, R3-3, R4-2, G3),
(A'4, R1-1, R2-2, R3-3, R4-2, G4), (A'4, R1-1, R2-2, R3-3, R4-2, G5),
(A'4, R1-2, R2-1, R3-1, R4-1, G1), (A'4, R1-2, R2-1, R3-1, R4-1, G2),
(A'4, R1-2, R2-1, R3-1, R4-1, G3), (A'4, R1-2, R2-1, R3-1, R4-1, G4),
(A'4, R1-2, R2-1, R3-1, R4-1, G5), (A'4, R1-2, R2-1, R3-1, R4-2, G1),
(A'4, R1-2, R2-1, R3-1, R4-2, G2), (A'4, R1-2, R2-1, R3-1, R4-2, G3),
(A'4, R1-2, R2-1, R3-1, R4-2, G4), (A'4, R1-2, R2-1, R3-1, R4-2, G5),
(A'4, R1-2, R2-1, R3-2, R4-1, G1), (A'4, R1-2, R2-1, R3-2, R4-1, G2),
(A'4, R1-2, R2-1, R3-2, R4-1, G3), (A'4, R1-2, R2-1, R3-2, R4-1, G4),
(A'4, R1-2, R2-1, R3-2, R4-1, G5), (A'4, R1-2, R2-1, R3-2, R4-2, G1),
(A'4, R1-2, R2-1, R3-2, R4-2, G2), (A'4, R1-2, R2-1, R3-2, R4-2, G3),
(A'4, R1-2, R2-1, R3-2, R4-2, G4), (A'4, R1-2, R2-1, R3-2, R4-2, G5),
(A'4, R1-2, R2-1, R3-3, R4-1, G1), (A'4, R1-2, R2-1, R3-3, R4-1, G2),
(A'4, R1-2, R2-1, R3-3, R4-1, G3), (A'4, R1-2, R2-1, R3-3, R4-1, G4),
(A'4, R1-2, R2-1, R3-3, R4-1, G5), (A'4, R1-2, R2-1, R3-3, R4-2, G1),
(A'4, R1-2, R2-1, R3-3, R4-2, G2), (A'4, R1-2, R2-1, R3-3, R4-2, G3),
(A'4, R1-2, R2-1, R3-3, R4-2, G4), (A'4, R1-2, R2-1, R3-3, R4-2, G5),
(A'4, R1-2, R2-2, R3-1, R4-1, G1), (A'4, R1-2, R2-2, R3-1, R4-1, G2),
(A'4, R1-2, R2-2, R3-1, R4-1, G3), (A'4, R1-2, R2-2, R3-1, R4-1, G4),
(A'4, R1-2, R2-2, R3-1, R4-1, G5), (A'4, R1-2, R2-2, R3-1, R4-2, G1),
(A'4, R1-2, R2-2, R3-1, R4-2, G2), (A'4, R1-2, R2-2, R3-1, R4-2, G3),
(A'4, R1-2, R2-2, R3-1, R4-2, G4), (A'4, R1-2, R2-2, R3-1, R4-2, G5),
(A'4, R1-2, R2-2, R3-2, R4-1, G1), (A'4, R1-2, R2-2, R3-2, R4-1, G2),
(A'4, R1-2, R2-2, R3-2, R4-1, G3), (A'4, R1-2, R2-2, R3-2, R4-1, G4),
(A'4, R1-2, R2-2, R3-2, R4-1, G5), (A'4, R1-2, R2-2, R3-2, R4-2, G1),
(A'4, R1-2, R2-2, R3-2, R4-2, G2), (A'4, R1-2, R2-2, R3-2, R4-2, G3),
(A'4, R1-2, R2-2, R3-2, R4-2, G4), (A'4, R1-2, R2-2, R3-2, R4-2, G5),
(A'4, R1-2, R2-2, R3-3, R4-1, G1), (N4, R1-2, R2-2, R3-3, R4-1, G2),
(A'4, R1-2, R2-2, R3-3, R4-1, G3), (A'4, R1-2, R2-2, R3-3, R4-1, G4),
(A'4, R1-2, R2-2, R3-3, R4-1, G5), (A'4, R1-2, R2-2, R3-3, R4-2, G1),
(A'4, R1-2, R2-2, R3-3, R4-2, G2), (A'4, R1-2, R2-2, R3-3, R4-2, G3),
(A'4, R1-2, R2-2, R3-3, R4-2, G4), (A'4, R1-2, R2-2, R3-3, R4-2, G5).

In the formula (II')

[Chemical formula 24]

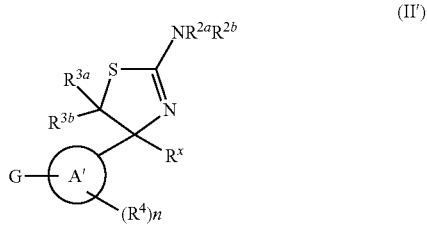

1) the compound, wherein ring A' is phenyl or a nitrogen-containing aromatic heterocyclic group (hereinafter, referred to as compound in which ring A' is A'1), the compound, wherein ring A' is phenyl, pyridyl, indolyl, benzisoxazolyl, benzopyrazolyl, or benzofuryl, benzothienyl, benzodioxolyl, or dihydrobenzodioxolanyl (hereinafter, referred to as compound in which rig A' is A'2), the compound, wherein ring A' is phenyl (hereinafter, referred to as compound in which ruing A' is A'3), the compound, wherein a ring A' is pyridyl (hereinafter, referred to as compound in which ring A' is A'4), 2) the compound, wherein $R^X$ is an optionally substituted carbocyclic group or an optionally substituted heterocyclic group (hereinafter, referred to as compound in which $R^X$ is Rx-1), the compound, wherein $R^X$ is optionally substituted phenyl, optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl, or optionally substituted pyridopyrimidinyl (hereinafter, referred to as compound in which $R^X$ is Rx-2), the compound, wherein $R^X$ is cyclohexyl, pyrrolinyl, morpholinyl, piperidyl, or piperazinyl (hereinafter, referred to as compound in which $R^X$ is Rx-3), 3) the compound, wherein $R^{2a}$ and $R^{2b}$ are each independently hydrogen, lower alkyl or acyl (hereinafter, referred to as compound in which $R^{2a}$ and $R^{2b}$ are R2-1), the compound wherein $R^{2a}$ and $R^{2b}$ are both hydrogen (hereinafter, referred to as compound in which $R^{2a}$ and $R^{2b}$ are R2-2), 4) the compound, wherein $R^{3a}$ and $R^{3b}$ are each independently hydrogen, halogen, hydroxy, lower alkyl or amino (hereinafter, referred to as compound in which $R^{3a}$ and $R^{3b}$ are R3-1), the compound, wherein $R^{3a}$ and $R^{3b}$ are taken together to form cyclopropyl, cyclobutyl, cyclopentyl, or cyclohexyl (hereinafter, referred to as compound in which $R^{3a}$ and $R^{3b}$ are R3-2), the compound, wherein $R^{3a}$ and $R^{3b}$ are the same substituent selected from halogen or lower alkyl (hereinafter, referred to as compound in which $R^{3a}$ and $R^{3b}$ are R3-3), the compound, wherein $R^{3a}$ and $R^{3b}$ are all hydrogen (hereinafter, referred to as compound in which $R^{3a}$ and $R^{3b}$ are R3-4), 5) the compound, wherein n is 0 to 2, and each $R^4$ is independently halogen, lower alkoxy, lower alkylamino, lower alkylthio, oxo, or lower alkylenedioxy (hereinafter, referred to as compound in which $R^4$ is R4-1), the compound, wherein n is 0 to 2, and each $R^4$ is independently halogen (hereinafter, referred to as compound in which $R^4$ is R4-2), 6) the compound, wherein G is the above (ii), (iv), (v), (x), (xiii) or (xiv) (hereinafter, referred to as compound in which G is G1), the compound, wherein G is the above (ii'), (ii''), (iv'), (v'), (x'), (xiii') or (xiv') (hereinafter, referred to as compound in which G is G2), the compound, wherein G is the above (ii'), (ii''), (iv'), (v'), (x'), (xiii') or (xiv') and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl, or optionally substituted pyridopyrimidinyl, herein, the substituent is 1 to 3 groups selected from the group consisting of the substituent group α and lower alkyl optionally substituted one or more groups selected from the substituent group α (hereinafter, referred to as compound in which G is G3), the compound, wherein G is the above (ii'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl, or optionally substituted pyridopyrimidinyl, herein, the substituent is 1 to 3 groups selected from the group consisting of the substituent group α and lower alkyl optionally substituted one or more groups selected from the substituent group α (hereinafter, referred to as compound in which G is G4), the compound, wherein G is the above (ii'), $R^5$ is hydrogen or lower alkyl, $W^1$ is O, and ring B is optionally substituted pyridyl or optionally substituted pyrazinyl, herein, the substituent is 1 to 3 groups selected from the group consisting of the substituent group α and lower alkyl optionally substituted one or more groups selected from the substituent group α (hereinafter, referred to as compound in which G is G5), compounds in which, in the formula (II'), a combination of ring A', $R^X$, $R^{2a}$ and $R^{2b}$, $R^{3a}$ $R^{3b}$, n and $R^4$, and G is as follows.

(A'1, Rx-1, R2-1, R3-1, R4-1, G1), (A'1, Rx-1, R2-1, R3-1, R4-1, G2),
(A'1, Rx-1, R2-1, R3-1, R4-1, G3), (A'1, Rx-1, R2-1, R3-1, R4-1, G4),
(A'1, Rx-1, R2-1, R3-1, R4-1, G5), (A'1, Rx-1, R2-1, R3-1, R4-2, G1),
(A'1, Rx-1, R2-1, R3-1, R4-2, G2), (A'1, Rx-1, R2-1, R3-1, R4-2, G3),
(A'1, Rx-1, R2-1, R3-1, R4-2, G4), (A'1, Rx-1, R2-1, R3-1, R4-2, G5),
(A'1, Rx-1, R2-1, R3-2, R4-1, G1), (A'1, Rx-1, R2-1, R3-2, R4-1, G2),
(A'1, Rx-1, R2-1, R3-2, R4-1, G3), (A'1, Rx-1, R2-1, R3-2, R4-1, G4),
(A'1, Rx-1, R2-1, R3-2, R4-1, G5), (A'1, Rx-1, R2-1, R3-2, R4-2, G1),
(A'1, Rx-1, R2-1, R3-2, R4-2, G2), (A'1, Rx-1, R2-1, R3-2, R4-2, G3),
(A'1, Rx-1, R2-1, R3-2, R4-2, G4), (A'1, Rx-1, R2-1, R3-2, R4-2, G5),
(A'1, Rx-1, R2-1, R3-3, R4-1, G1), (A'1, Rx-1, R2-1, R3-3, R4-1, G2),
(A'1, Rx-1, R2-1, R3-3, R4-1, G3), (A'1, Rx-1, R2-1, R3-3, R4-1, G4),
(A'1, Rx-1, R2-1, R3-3, R4-1, G5), (A'1, Rx-1, R2-1, R3-3, R4-2, G1),
(A'1, Rx-1, R2-1, R3-3, R4-2; G2), (A'1, Rx-1, R2-1, R3-3, R4-2, G3),
(A'1, Rx-1, R2-1, R3-3, R4-2, G4), (A'1, Rx-1, R2-1, R3-3, R4-2, G5),
(A'1, Rx-1, R2-1, R3-4, R4-1, G1), (A'1, Rx-1, R2-1, R3-4, R4-1, G2),
(A'1, Rx-1, R2-1, R3-4, R4-1, G3), (All, Rx-1, R2-1, R3-4, R4-1, G4),
(A'1, Rx-1, R2-1, R3-4, R4-1, G5), (A'1, Rx-1, R2-1, R3-4, R4-2, G1),
(A'1, Rx-1, R2-1, R3-4, R4-2, G2), (A'1, Rx-1, R2-1, R3-4, R4-2, G3),
(A'1, Rx-1, R2-1, R3-4, R4-2, G4), (A'1, Rx-1, R2-1, R3-4, R4-2, G5),
(A'1, Rx-1, R2-2, R3-1, R4-1, G1), (A'1, Rx-1, R2-2, R3-1, R4-1, G2),
(A'1, Rx-1, R2-2, R3-1, R4-1, G3), (A'1, Rx-1, R2-2, R3-1, R4-1, G4),
(A'1, Rx-1, R2-2, R3-1, R4-1, G5), (A'1, Rx-1, R2-2, R3-1, R4-2, G1),
(A'1, Rx-1, R2-2, R3-1, R4-2, G2), (A'1, Rx-1, R2-2, R3-1, R4-2, G3),
(A'1, Rx-1, R2-2, R3-1, R4-2, G4), (A'1, Rx-1, R2-2, R3-1, R4-2, G5),
(A'1, Rx-1, R2-2, R3-2, R4-1, G1), (A'1, Rx-1, R2-2, R3-2, R4-1, G2),
(A'1, Rx-1, R2-2, R3-2, R4-1, G3), (A'1, Rx-1, R2-2, R3-2, R4-1, G4),
(A'1, Rx-1, R2-2, R3-2, R4-1, G5), (A'1, Rx-1, R2-2, R3-2, R4-2, G1),
(A'1, Rx-1, R2-2, R3-2, R4-2, G2), (A'1, Rx-1, R2-2, R3-2, R4-2, G3),
(A'1, Rx-1, R2-2, R3-2, R4-2, G4), (A'1, Rx-1, R2-2, R3-2, R4-2, G5),
(A'1, Rx-1, R2-2, R3-3, R4-1, G1), (A'1, Rx-1, R2-2, R3-3, R4-1, G2),
(A'1, Rx-1, R2-2, R3-3, R4-1, G3), (A'1, Rx-1, R2-2, R3-3, R4-1, G4),
(A'1, Rx-1, R2-2, R3-3, R4-1, G5), (A'1, Rx-1, R2-2, R3-3, R4-2, G1),
(A'1, Rx-1, R2-2, R3-3, R4-2, G2), (A'1, Rx-1, R2-2, R3-3, R4-2, G3),
(A'1, Rx-1, R2-2, R3-3, R4-2, G4), (A'1, Rx-1, R2-2, R3-3, R4-2, G5),
(A'1, R2-2, R3-4, R4-1, G1), (A'1, Rx-1, R2-2, R3-4, R4-1, G2),
(A'1, Rx-1, R2-2, R3-4, R4-1, G3), (A'1, Rx-1, R2-2, R3-4, R4-1, G4), (A'1, Rx-1, R2-2, R3-4, R4-1, G5), (A'1, Rx-1, R2-2, R3-4, R4-2, G1),
(A'1, Rx-1, R2-2, R3-4, R4-2, G2), (A'1, Rx-1, R2-2, R3-4, R4-2, G3),
(A'1, Rx-1, R2-2, R3-4, R4-2, G4), (A'1, Rx-1, R2-2, R3-4, R4-2, G5),
(A'1, Rx-2, R2-1, R3-1, R4-1, G1), (A'1, Rx-2, R2-1, R3-1, R4-1, G2),
(A'1, R3-1, R4-1, G3), (A'1, Rx-2, R2-1, R3-1, R4-1, G4),
(A'1, Rx-2, R2-1, R3-1, R4-1, G5), (A'1, Rx-2, R2-1, R3-1, R4-2, G1),
(A'1, Rx-2, R2-1, R3-1, R4-2, G2), (A'1, Rx-2, R2-1, R3-1, R4-2, G3),
(A'1, Rx-2, R2-1, R3-1, R4-2, G4), (A'1, Rx-2, R2-1, R3-1, R4-2, G5),
(A'1, Rx-2, R2-1, R3-2, R4-1, G1), (A'1, Rx-2, R2-1, R3-2, R4-1, G2),
(A'1, Rx-2, R2-1, R3-2, R4-1, G3), (A'1, Rx-2, R2-1, R3-2, R4-1, G4),
(A'1, Rx-2, R2-1, R3-2, R4-1, G5), (A'1, Rx-2, R2-1, R3-2, R4-2, G1),
(A'1, Rx-2, R2-1, R3-2, R4-2, G2), (A'1, Rx-2, R2-1, R3-2, R4-2, G3),
(A'1, Rx-2, R2-1, R3-2, R4-2, G4), (A'1, Rx-2, R2-1, R3-2, R4-2, G5),
(A'1, Rx-2, R2-1, R3-3, R4-1, G1), (A'1, Rx-2, R2-1, R3-3, R4-1, G2),
(A'1, Rx-2, R2-1, R3-3, R4-1, G3), (A'1, Rx-2, R2-1, R3-3, R4-1, G4),
(A'1, Rx-2, R2-1, R3-3, R4-1, G5), (A'1, Rx-2, R2-1, R3-3, R4-2, G1),
(A'1, Rx-2, R2-1, R3-3, R4-2, G2), (A'1, Rx-2, R2-1, R3-3, R4-2, G3),
(A'1, Rx-2, R2-1, R3-3, R4-2, G4), (A'1, Rx-2, R2-1, R3-3, R4-2, G5),
(A'1, Rx-2, R2-1, R3-4, R4-1, G1), (A'1, Rx-2, R2-1, R3-4, R4-1, G2),
(A'1, Rx-2, R2-1, R3-4, R4-1, G3), (A'1, Rx-2, R2-1, R3-4, R4-1, G4),
(A'1, Rx-2, R2-1, R3-4, R4-1, G5), (A'1, Rx-2, R2-1, R3-4, R4-2, G1),
(A'1, Rx-2, R2-1, R3-4, R4-2, G2), (A'1, Rx-2, R2-1, R3-4, R4-2, G3),
(A'1, Rx-2, R2-1, R3-4, R4-2, G4), (A'1, Rx-2, R2-1, R3-4, R4-2, G5),
(A'1, Rx-2, R2-2, R3-1, R4-1, G1), (A'1, Rx-2, R2-2, R3-1, R4-1, G2),
(A'1, Rx-2, R2-2, R3-1, R4-1, G3), (A'1, Rx-2, R2-2, R3-1, R4-1, G4),
(A'1, Rx-2, R2-2, R3-1, R4-1, G5), (A'1, Rx-2, R2-2, R3-1, R4-2, G1),
(A'1, Rx-2, R2-2, R3-1, R4-2, G2), (A'1, Rx-2, R2-2, R3-1, R4-2, G3),
(A'1, Rx-2, R2-2, R3-1, R4-2, G4), (A'1, Rx-2, R2-2, R3-1, R4-2, G5),
(A'1, Rx-2, R2-2, R3-2, R4-1, G1), (A'1, Rx-2, R2-2, R3-2, R4-1, G2),
(A'1, Rx-2, R2-2, R3-2, R4-1, G3), (A'1, Rx-2, R2-2, R3-2, R4-1, G4),
(A'1, Rx-2, R2-2, R3-2, R4-1, G5), (A'1, Rx-2, R2-2, R3-2, R4-2, G1),
(A'1, Rx-2, R2-2, R3-2, R4-2, G2), (A'1, Rx-2, R2-2, R3-2, R4-2, G3),
(A'1, Rx-2, R2-2, R3-2, R4-2, G4), (A'1, Rx-2, R2-2, R3-2, R4-2, G5),
(A'1, Rx-2, R2-2, R3-3, R4-1, G1), (A'1, Rx-2, R2-2, R3-3, R4-1, G2),
(A'1, Rx-2, R2-2, R3-3, R4-1, G3), (A'1, Rx-2, R2-2, R3-3, R4-1, G4),
(A'1, Rx-2, R2-2, R3-3, R4-1, G5), (A'1, Rx-2, R2-2, R3-3, R4-2, G1),
(A'1, Rx-2, R2-2, R3-3, R4-2, G2), (A'1, Rx-2, R2-2, R3-3, R4-2, G3),
(A'1, Rx-2, R2-2, R3-3, R4-2, G4), (All, Rx-2, R2-2, R3-3, R4-2, G5),
(A'1, Rx-2, R2-2, R3-4, R4-1, G1), (A'1, Rx-2, R2-2, R3-4, R4-1, G2),
(A'1, Rx-2, R2-2, R3-4, R4-1, G3), (A'1, Rx-2, R2-2, R3-4, R4-1, G4),
(A'1, Rx-2, R2-2, R3-4, R4-1, G5), (A'1, Rx-2, R2-2, R3-4, R4-2, G1),
(A'1, Rx-2, R2-2, R3-4, R4-2, G2), (A'1, Rx-2, R2-2, R3-4, R4-2, G3),
(A'1, Rx-2, R2-2, R3-4, R4-2, G4), (A'1, Rx-2, R2-2, R3-4, R4-2, G5),
(A'1, Rx-3, R2-1, R3-1, R4-1, G1), (A'1, Rx-3, R2-1, R3-1, R4-1, G2),
(A'1, Rx-3, R2-1, R3-1, R4-1, G4),
(A'1, Rx-3, R2-1, R3-1, R4-1, G5), (A'1, Rx-3, R2-1, R3-1, R4-2, G1),
(A'1, Rx-3, R2-1, R3-1, R4-2, G2), (A'1, Rx-3, R2-1, R3-1, R4-2, G3),
(A'1, Rx-3, R2-1, R3-1, R4-2, G4), (A'1, Rx-3, R2-1, R3-1, R4-2, G5),
(A'1, Rx-3, R2-1, R3-2, R4-1, G1), (A'1, Rx-3, R2-1, R3-2, R4-1, G2),
(A'1, Rx-3, R2-1, R3-2, R4-1, G3), (A'1, Rx-3, R2-1, R3-2, R4-1, G4),
(A'1, Rx-3, R2-1, R3-2, R4-1, G5), (A'1, Rx-3, R2-1, R3-2, R4-2, G1),
(A'1, Rx-3, R2-1, R3-2, R4-2, G2), (A'1, Rx-3, R2-1, R3-2, R4-2, G3),
(A'1, Rx-3, R2-1, R3-2, R4-2, G4), (A'1, Rx-3, R2-1, R3-2, R4-2, G5),
(A'1, Rx-3, R2-1, R3-3, R4-1, G1), (A'1, Rx-3, R2-1, R3-3, R4-1, G2),
(A'1, Rx-3, R2-1, R3-3, R4-1, G3), (A'1, Rx-3, R2-1, R3-3, R4-1, G4),
(A'1, Rx-3, R2-1, R3-3, R4-1, G5), (A'1, Rx-3, R2-1, R3-3, R4-2, G1),
(A'1, Rx-3, R2-1, R3-3, R4-2, G2), 1, R3-3, R4-2, G3),
(A'1, Rx-3, R2-1, R3-3, R4-2, G4), (A'1, Rx-3, R2-1, R3-3, R4-2, G5),
(A'1, Rx-3, R2-1, R3-4, R4-1, G1), (A'1, Rx-3, R2-1, R3-4, R4-1, G2),
(A'1, Rx-3, R2-1, R3-4, R4-1, G3), (A'1, Rx-3, R2-1, R3-4, R4-1, G4),
(A'1, Rx-3, R2-1, R3-4, R4-1, G5), (A'1, Rx-3, R2-1, R3-4, R4-2, G1),
(A'1, Rx-3, R2-1, R3-4, R4-2, G2), (A'1, Rx-3, R2-1, R3-4, R4-2, G3),
(A'1, Rx-3, R2-1, R3-4, R4-2, G4), (A'1, Rx-3, R2-1, R3-4, R4-2, G5),
(A'1, Rx-3, R2-2, R3-1, R4-1, G1), (A'1, Rx-3, R2-2, R3-1, R4-1, G2),
(A'1, Rx-3, R2-2, R3-1, R4-1, G3), (A'1, Rx-3, R2-2, R3-1, R4-1, G4),
(A'1, Rx-3, R2-2, R3-1, R4-1, G5), (A'1, Rx-3, R2-2, R3-1, R4-2, G1),
(A'1, Rx-3, R2-2, R3-1, R4-2, G2), (A'1, Rx-3, R2-2, R3-1, R4-2, G3),
(A'1, Rx-3, R2-2, R3-1, R4-2, G4), (A'1, Rx-3, R2-2, R3-1, R4-2, G5), (A'1, Rx-3, R2-2, R3-2, R4-1, G1), (A'1, Rx-3, R2-2, R3-2, R4-1, G2),
(A'1, Rx-3, R2-2, R3-2, R4-1, G3), (A'1, Rx-3, R2-2, R3-2, R4-1, G4),
(A'1, Rx-3, R2-2, R3-2, R4-1, G5), (A'1, Rx-3, R2-2, R3-2, R4-2, G1),
(A'1, Rx-3, R2-2, R3-2, R4-2, G2), (A'1, Rx-3, R2-2, R3-2, R4-2, G3),
(A'1, Rx-3, R2-2, R3-2, R4-2, G4), (A'1, Rx-3, R2-2, R3-2, R4-2, G5),
(A'1, Rx-3, R2-2, R3-3, R4-1, G1), (A'1, Rx-3, R2-2, R3-3, R4-1, G2),
(A'1, Rx-3, R2-2, R3-3, R4-1, G3), (A'1, Rx-3, R2-2, R3-3, R4-1, G4),
(A'1, Rx-3, R2-2, R3-3, R4-1, G5), (A'1, Rx-3, R2-2, R3-3, R4-2, G1),
(A'1, Rx-3, R2-2, R3-3, R4-2, G2), (A'1, Rx-3, R2-2, R3-3, R4-2, G3),
(A'1, Rx-3, R2-2, R3-3, R4-2, G4), (A'1, Rx-3, R2-2, R3-3, R4-2, G5),
(A'1, Rx-3, R2-2, R3-4, R4-1, G1), (A'1, Rx-3, R2-2, R3-4, R4-1, G2),
(A'1, Rx-3, R2-2, R3-4, R4-1, G3), (A'1, Rx-3, R2-2, R3-4, R4-1, G4),
(A'1, Rx-3, R2-2, R3-4, R4-1, G5), (A'1, Rx-3, R2-2, R3-4, R4-2, G1),
(A'1, Rx-3, R2-2, R3-4, R4-2, G2), (A'1, Rx-3, R2-2, R3-4, R4-2, G3),
(A'1, Rx-3, R2-2, R3-4, R4-2, G4), (A'1, Rx-3, R2-2, R3-4, R4-2, G5),
(A'2, Rx-1, R2-1, R3-1, R4-1, G1), (A'2, Rx-1, R2-1, R3-1, R4-1, G2),
(A'2, Rx-1, R2-1, R3-1, R4-1, G3), (A'2, Rx-1, R2-1, R3-1, R4-1, G4),
(A'2, Rx-1, R2-1, R3-1, R4-1, G5), (A'2, Rx-1, R2-1, R3-1, R4-2, G1),
(A'2, Rx-1, R2-1, R3-1, R4-2, G2), (A'2, Rx-1, R2-1, R3-1, R4-2, G3),
(A'2, Rx-1, R2-1, R3-1, R4-2, G4), (A'2, Rx-1, R2-1, R3-1, R4-2, G5),
(A'2, Rx-1, R2-1, R3-2, R4-1, G1), (A'2, Rx-1, R2-1, R3-2, R4-1, G2),
(A'2, Rx-1, R2-1, R3-2, R4-1, G3), (A'2, Rx-1, R2-1, R3-2, R4-1, G4),
(A'2, Rx-1, R2-1, R3-2, R4-1, G5), (A'2, Rx-1, R2-1, R3-2, R4-2, G1),
(A'2, Rx-1, R2-1, R3-2, R4-2, G2), (A'2, Rx-1, R2-1, R3-2, R4-2, G3),
(A'2, Rx-1, R2-1, R3-2, R4-2, G4), (A'2, Rx-1, R2-1, R3-2, R4-2, G5),
(A'2, Rx-1, R2-1, R3-3, R4-1, G1), (A'2, Rx-1, R2-1, R3-3, R4-1, G2),
(A'2, Rx-1, R2-1, R3-3, R4-1, G3), (A'2, Rx-1, R2-1, R3-3, R4-1, G4),
(A'2, Rx-1, R2-1, R3-3, R4-1, G5), (A'2, Rx-1, R2-1, R3-3, R4-2, G1),
(A'2, Rx-1, R2-1, R3-3, R4-2, G2), (A'2, Rx-1, R2-1, R3-3, R4-2, G3),
(A'2, Rx-1, R2-1, R3-3, R4-2, G4), (A'2, Rx-1, R2-1, R3-3, R4-2, G5),
(A'2, Rx-1, R2-1, R3-4, R4-1, G1), (A'2, Rx-1, R2-1, R3-4, R4-1, G2),
(A'2, Rx-1, R2-1, R3-4, R4-1, G3), (A'2, Rx-1, R2-1, R3-4, R4-1, G4),
(A'2, Rx-1, R2-1, R3-4, R4-1, G5), (A'2, Rx-1, R2-1, R3-4, R4-2, G1),
(A'2, Rx-1, R2-1, R3-4, R4-2, G2), (A'2, Rx-1, R2-1, R3-4, R4-2, G3),
(A'2, Rx-1, R2-1, R3-4, R4-2, G4), (A'2, Rx-1, R2-1, R3-4, R4-2, G5),
(A'2, Rx-1, R2-2, R3-1, R4-1, G1), (A'2, Rx-1, R2-2, R3-1, R4-1, G2),
(A'2, Rx-1, R2-2, R3-1, R4-1, G3), (A'2, Rx-1, R2-2, R3-1, R4-1, G4),
(A'2, Rx-1, R2-2, R3-1, R4-1, G5), (A'2, Rx-1, R2-2, R3-1, R4-2, G1),
(A'2, Rx-1, R2-2, R3-1, R4-2, G2), (A'2, Rx-1, R2-2, R3-1, R4-2, G3),
(A'2, Rx-1, R2-2, R3-1, R4-2, G4), (A'2, Rx-1, R2-2, R3-1, R4-2, G5),
(A'2, Rx-1, R2-2, R3-2, R4-1, G1), (A'2, Rx-1, R2-2, R3-2, R4-1, G2),
(A'2, Rx-1, R2-2, R3-2, R4-1, G3), (A'2, Rx-1, R2-2, R3-2, R4-1, G4),
(A'2, Rx-1, R2-2, R3-2, R4-1, G5), (A'2, Rx-1, R2-2, R3-2, R4-2, G1),
(A'2, Rx-1, R2-2, R3-2, R4-2, G2), (A'2, Rx-1, R2-2, R3-2, R4-2, G3),
(A'2, Rx-1, R2-2, R3-2, R4-2, G4), (A'2, Rx-1, R2-2, R3-2, R4-2, G5),
(A'2, Rx-1, R2-2, R3-3, R4-1, G1), (A'2, Rx-1, R2-2, R3-3, R4-1, G2),
(A'2, Rx-1, R2-2, R3-3, R4-1, G3), (A'2, Rx-1, R2-2, R3-3, R4-1, G4),
(A'2, Rx-1, R2-2, R3-3, R4-1, G5), (A'2, Rx-1, R2-2, R3-3, R4-2, G1), (A'2, Rx-1, R2-2, R3-3, R4-2, G2), (A'2, Rx-1, R2-2, R3-3, R4-2, G3),
(A'2, Rx-1, R2-2, R3-3, R4-2, G4), (A'2, Rx-1, R2-2, R3-3, R4-2, G5),
(A'2, Rx-1, R2-2, R3-4, R4-1, G1), (A'2, Rx-1, R2-2, R3-4, R4-1, G2),
(A'2, Rx-1, R2-2, R3-4, R4-1, G3), (A'2, Rx-1, R2-2, R3-4, R4-1, G4),
(A'2, Rx-1, R2-2, R3-4, R4-1, G5), (A'2, Rx-1, R2-2, R3-4, R4-2, G1),
(A'2, Rx-1, R2-2, R3-4, R4-2, G2), (A'2, Rx-1, R2-2, R3-4, R4-2, G3),
(A'2, Rx-1, R2-2, R3-4, R4-2, G4), (A'2, Rx-1, R2-2, R3-4, R4-2, G5),
(A'2, Rx-2, R2-1, R3-1, R4-1, G1), (A'2, Rx-2, R2-1, R3-1, R4-1, G2),
(A'2, Rx-2, R2-1, R3-1, R4-1, G3), (A'2, Rx-2, R2-1, R3-1, R4-1, G4),
(A'2, Rx-2, R2-1, R3-1, R4-1, G5), (A'2, Rx-2, R2-1, R3-1, R4-2, G1),
(A'2, Rx-2, R2-1, R3-1, R4-2, G2), (A'2, Rx-2, R2-1, R3-1, R4-2, G3),
(A'2, Rx-2, R2-1, R3-1, R4-2, G4), (A'2, Rx-2, R2-1, R3-1, R4-2, G5),
(A'2, Rx-2, R2-1, R3-2, R4-1, G1), (A'2, Rx-2, R2-1, R3-2, R4-1, G2),
(A'2, Rx-2, R2-1, R3-2, R4-1, G3), (A'2, Rx-2, R2-1, R3-2, R4-1, G4),
(A'2, Rx-2, R2-1, R3-2, R4-1, G5), (A'2, Rx-2, R2-1, R3-2, R4-2, G1),
(A'2, Rx-2, R2-1, R3-2, R4-2, G2), (A'2, Rx-2, R2-1, R3-2, R4-2, G3),
(A'2, Rx-2, R2-1, R3-2, R4-2, G4), (A'2, Rx-2, R2-1, R3-2, R4-2, G5),
(A'2, Rx-2, R2-1, R3-3, R4-1, G1), (A'2, Rx-2, R2-1, R3-3, R4-1, G2),
(A'2, Rx-2, R2-1, R3-3, R4-1, G3), (A'2, Rx-2, R2-1, R3-3, R4-1, G4), (A'2, Rx-2, R2-1, R3-3, R4-1, G5), (A'2, Rx-2, R2-1, R3-3, R4-2, G1),
(A'2, Rx-2, R2-1, R3-3, R4-2, G2), (A'2, Rx-2, R2-1, R3-3, R4-2, G3),
(A'2, Rx-2, R2-1, R3-3, R4-2, G4), (A'2, Rx-2, R2-1, R3-3, R4-2, G5),
(A'2, Rx-2, R2-1, R3-4, R4-1, G1), (A'2, Rx-2, R2-1, R3-4, R4-1, G2),
(A'2, Rx-2, R2-1, R3-4, R4-1, G3), (A'2, Rx-2, R2-1, R3-4, R4-1, G4),
(A'2, Rx-2, R2-1, R3-4, R4-1, G5), (A'2, Rx-2, R2-1, R3-4, R4-2, G1),
(A'2, Rx-2, R2-1, R3-4, R4-2, G2), (A'2, Rx-2, R2-1, R3-4, R4-2, G3),
(A'2, Rx-2, R2-1, R3-4, R4-2, G4), (A'2, Rx-2, R2-1, R3-4, R4-2, G5),
(A'2, Rx-2, R2-2, R3-1, R4-1, G1), (A'2, Rx-2, R2-2, R3-1, R4-1, G2),
(A'2, Rx-2, R2-2, R3-1, R4-1, G3), (A'2, Rx-2, R2-2, R3-1, R4-1, G4),
(A'2, Rx-2, R2-2, R3-1, R4-1, G5), (A'2, Rx-2, R2-2, R3-1, R4-2, G1),
(A'2, Rx-2, R2-2, R3-1, R4-2, G2), (A'2, Rx-2, R2-2, R3-1, R4-2, G3),
(A'2, Rx-2, R2-2, R3-1, R4-2, G4), (A'2, Rx-2, R2-2, R3-1, R4-2, G5),
(A'2, Rx-2, R2-2, R3-2, R4-1, G1), (A'2, Rx-2, R2-2, R3-2, R4-1, G2),
(A'2, Rx-2, R2-2, R3-2, R4-1, G3), (A'2, Rx-2, R2-2, R3-2, R4-1, G4),
(A'2, Rx-2, R2-2, R3-2, R4-1, G5), (A'2, Rx-2, R2-2, R3-2, R4-2, G1),
(A'2, Rx-2, R2-2, R3-2, R4-2, G2), (A'2, Rx-2, R2-2, R3-2, R4-2, G3),
(A'2, Rx-2, R2-2, R3-2, R4-2, G4), (A'2, Rx-2, R2-2, R3-2, R4-2, G5),
(A'2, Rx-2, R2-2, R3-3, R4-1, G1), (A'2, Rx-2, R2-2, R3-3, R4-1, G2),
(A'2, Rx-2, R2-2, R3-3, R4-1, G3), (A'2, Rx-2, R2-2, R3-3, R4-1, G4),
(A'2, Rx-2, R2-2, R3-3, R4-1, G5), (A'2, Rx-2, R2-2, R3-3, R4-2, G1),
(A'2, Rx-2, R2-2, R3-3, R4-2, G2), (A'2, Rx-2, R2-2, R3-3, R4-2, G3),
(A'2, Rx-2, R2-2, R3-3, R4-2, G4), (A'2, Rx-2, R2-2, R3-3, R4-2, G5),
(A'2, Rx-2, R2-2, R3-4, R4-1, G1), (A'2, Rx-2, R2-2, R3-4, R4-1, G2),
(A'2, Rx-2, R2-2, R3-4, R4-1, G3), (A'2, Rx-2, R2-2, R3-4, R4-1, G4),
(A'2, Rx-2, R2-2, R3-4, R4-1, G5), (A'2, Rx-2, R2-2, R3-4, R4-2, G1),
(A'2, Rx-2, R2-2, R3-4, R4-2, G2), (A'2, Rx-2, R2-2, R3-4, R4-2, G3),
(A'2, Rx-2, R2-2, R3-4, R4-2, G4), (A'2, Rx-2, R2-2, R3-4, R4-2, G5),
(A'2, Rx-3, R2-1, R3-1, R4-1, G1), (A'2, Rx-3, R2-1, R3-1, R4-1, G2),
(A'2, Rx-3, R2-1, R3-1, R4-1, G3), (A'2, Rx-3, R2-1, R3-1, R4-1, G4),
(A'2, Rx-3, R2-1, R3-1, R4-1, G5), (A'2, Rx-3, R2-1, R3-1, R4-2, G1),
(A'2, Rx-3, R2-1, R3-1, R4-2, G2), (A'2, Rx-3, R2-1, R3-1, R4-2, G3),
(A'2, Rx-3, R2-1, R3-1, R4-2, G4), (A'2, Rx-3, R2-1, R3-1, R4-2, G5),
(A'2, Rx-3, R2-1, R3-2, R4-1, G1), (A'2, Rx-3, R2-1, R3-2, R4-1, G2),
(A'2, Rx-3, R2-1, R3-2, R4-1, G3), (A'2, Rx-3, R2-1, R3-2, R4-1, G4),
(A'2, Rx-3, R2-1, R3-2, R4-1, G5), (A'2, Rx-3, R2-1, R3-2, R4-2, G1),
(A'2, Rx-3, R2-1, R3-2, R4-2, G2), (A'2, Rx-3, R2-1, R3-2, R4-2, G3),
(A'2, Rx-3, R2-1, R3-2, R4-2, G4), (A'2, Rx-3, R2-1, R3-2, R4-2, G5),
(A'2, Rx-3, R2-1, R3-3, R4-1, G1), (A'2, Rx-3, R2-1, R3-3, R4-1, G2),
(A'2, Rx-3, R2-1, R3-3, R4-1, G3), (A'2, Rx-3, R2-1, R3-3, R4-1, G4),
(A'2, Rx-3, R2-1, R3-3, R4-1, G5), (A'2, Rx-3, R2-1, R3-3, R4-2, G1),
(A'2, Rx-3, R2-1, R3-3, R4-2, G2), (A'2, Rx-3, R2-1, R3-3, R4-2, G3),
(A'2, Rx-3, R2-1, R3-3, R4-2, G4), (A'2, Rx-3, R2-1, R3-3, R4-2, G5),
(A'2, Rx-3, R2-1, R3-4, R4-1, G1), (A'2, Rx-3, R2-1, R3-4, R4-1, G2),
(A'2, Rx-3, R2-1, R3-4, R4-1, G3), (A'2, Rx-3, R2-1, R3-4, R4-1, G4),
(A'2, Rx-3, R2-1, R3-4, R4-1, G5), (A'2, Rx-3, R2-1, R3-4, R4-2, G1),
(A'2, Rx-3, R2-1, R3-4, R4-2, G2), (A'2, Rx-3, R2-1, R3-4, R4-2, G3),
(A'2, Rx-3, R2-1, R3-4, R4-2, G4), (A'2, Rx-3, R2-1, R3-4, R4-2, G5),
(A'2, Rx-3, R2-2, R3-1, R4-1, G1), (A'2, Rx-3, R2-2, R3-1, R4-1, G2),
(A'2, Rx-3, R2-2, R3-1, R4-1, G3), (A'2, Rx-3, R2-2, R3-1, R4-1, G4),
(A'2, Rx-3, R2-2, R3-1, R4-1, G5), (A'2, Rx-3, R2-2, R3-1, R4-2, G1),
(A'2, Rx-3, R2-2, R3-1, R4-2, G2), (A'2, Rx-3, R2-2, R3-1, R4-2, G3),
(A'2, Rx-3, R2-2, R3-1, R4-2, G4), (A'2, Rx-3, R2-2, R3-1, R4-2, G5),
(A'2, Rx-3, R2-2, R3-2, R4-1, G1), (A'2, Rx-3, R2-2, R3-2, R4-1, G2),
(A'2, Rx-3, R2-2, R3-2, R4-1, G3), (A'2, Rx-3, R2-2, R3-2, R4-1, G4),
(A'2, Rx-3, R2-2, R3-2, R4-1, G5), (A'2, Rx-3, R2-2, R3-2, R4-2, G1),
(A'2, Rx-3, R2-2, R3-2, R4-2, G2), (A'2, Rx-3, R2-2, R3-2, R4-2, G3),
(A'2, Rx-3, R2-2, R3-2, R4-2, G4), (A'2, Rx-3, R2-2, R3-2, R4-2, G5),
(A'2, Rx-3, R2-2, R3-3, R4-1, G1), (A'2, Rx-3, R2-2, R3-3, R4-1, G2),
(A'2, Rx-3, R2-2, R3-3, R4-1, G3), (A'2, Rx-3, R2-2, R3-3, R4-1, G4),
(A'2, Rx-3, R2-2, R3-3, R4-1, G5), (A'2, Rx-3, R2-2, R3-3, R4-2, G1),
(A'2, Rx-3, R2-2, R3-3, R4-2, G2), (A'2, Rx-3, R2-2, R3-3, R4-2, G3),
(A'2, Rx-3, R2-2, R3-3, R4-2, G4), (A'2, Rx-3, R2-2, R3-3, R4-2, G5),
(A'2, Rx-3, R2-2, R3-4, R4-1, G1), (A'2, Rx-3, R2-2, R3-4, R4-1, G2),
(A'2, Rx-3, R2-2, R3-4, R4-1, G3), (A'2, Rx-3, R2-2, R3-4, R4-1, G4),
(A'2, Rx-3, R2-2, R3-4, R4-1, G5), (A'2, Rx-3, R2-2, R3-4, R4-2, G1), (A'2, Rx-3, R2-2, R3-4, R4-2, G2), (A'2, Rx-3, R2-2, R3-4, R4-2, G3),
(A'2, Rx-3, R2-2, R3-4, R4-2, G4), (A'2, Rx-3, R2-2, R3-4, R4-2, G5),
(A'3, Rx-1, R2-1, R3-1, R4-1, G1), (A'3, Rx-1, R2-1, R3-1, R4-1, G2),
(A'3, Rx-1, R2-1, R3-1, R4-1, G3), (A'3, Rx-1, R2-1, R3-1, R4-1, G4),
(A'3, Rx-1, R2-1, R3-1, R4-1, G5), (A'3, Rx-1, R2-1, R3-1, R4-2, G1),
(A'3, Rx-1, R2-1, R3-1, R4-2, G2), (A'3, Rx-1, R2-1, R3-1, R4-2, G3),
(A'3, Rx-1, R2-1, R3-1, R4-2, G4), (A'3, Rx-1, R2-1, R3-1, R4-2, G5),
(A'3, Rx-1, R2-1, R3-2, R4-1, G1), (A'3, Rx-1, R2-1, R3-2, R4-1, G2),
(A'3, Rx-1, R2-1, R3-2, R4-1, G3), (A'3, Rx-1, R2-1, R3-2, R4-1, G4),
(A'3, Rx-1, R2-1, R3-2, R4-1, G5), (A'3, Rx-1, R2-1, R3-2, R4-2, G1),
(A'3, Rx-1, R2-1, R3-2, R4-2, G2), (A'3, Rx-1, R2-1, R3-2, R4-2, G3),
(A'3, Rx-1, R2-1, R3-2, R4-2, G4), (A'3, Rx-1, R2-1, R3-2, R4-2, G5),
(A'3, Rx-1, R2-1, R3-3, R4-1, G1), (A'3, Rx-1, R2-1, R3-3, R4-1, G2),
(A'3, Rx-1, R2-1, R3-3, R4-1, G3), (A'3, Rx-1, R2-1, R3-3, R4-1, G4),
(A'3, Rx-1, R2-1, R3-3, R4-1, G5), (A'3, Rx-1, R2-1, R3-3, R4-2, G1),
(A'3, Rx-1, R2-1, R3-3, R4-2, G2), (A'3, Rx-1, R2-1, R3-3, R4-2, G3),
(A'3, Rx-1, R2-1, R3-3, R4-2, G4), (A'3, Rx-1, R2-1, R3-3, R4-2, G5),
(A'3, Rx-1, R2-1, R3-4, R4-1, G1), (A'3, Rx-1, R2-1, R3-4, R4-1, G2),
(A'3, Rx-1, R2-1, R3-4, R4-1, G3), (A'3, Rx-1, R2-1, R3-4, R4-1, G4),
(A'3, Rx-1, R2-1, R3-4, R4-1, G5), (A'3, Rx-1, R2-1, R3-4, R4-2, G1),
(A'3, Rx-1, R2-1, R3-4, R4-2, G2), (A'3, Rx-1, R2-1, R3-4, R4-2, G3),
(A'3, Rx-1, R2-1, R3-4, R4-2, G4), (A'3, Rx-1, R2-1, R3-4, R4-2, G5),
(A'3, Rx-1, R2-2, R3-1, R4-1, G1), (A'3, Rx-1, R2-2, R3-1, R4-1, G2),
(A'3, Rx-1, R2-2, R3-1, R4-1, G3), (A'3, Rx-1, R2-2, R3-1, R4-1, G4),
(A'3, Rx-1, R2-2, R3-1, R4-1, G5), (A'3, Rx-1, R2-2, R3-1, R4-2, G1),
(A'3, Rx-1, R2-2, R3-1, R4-2, G2), (A'3, Rx-1, R2-2, R3-1, R4-2, G3),
(A'3, Rx-1, R2-2, R3-1, R4-2, G4), (A'3, Rx-1, R2-2, R3-1, R4-2, G5),
(A'3, Rx-1, R2-2, R3-2, R4-1, G1), (A'3, Rx-1, R2-2, R3-2, R4-1, G2),
(A'3, Rx-1, R2-2, R3-2, R4-1, G3), (A'3, Rx-1, R2-2, R3-2, R4-1, G4),
(A'3, Rx-1, R2-2, R3-2, R4-1, G5), (A'3, Rx-1, R2-2, R3-2, R4-2, G1),
(A'3, Rx-1, R2-2, R3-2, R4-2, G2), (A'3, Rx-1, R2-2, R3-2, R4-2, G3),
(A'3, Rx-1, R2-2, R3-2, R4-2, G4), (A'3, Rx-1, R2-2, R3-2, R4-2, G5),
(A'3, Rx-1, R2-2, R3-3, R4-1, G1), (A'3, Rx-1, R2-2, R3-3, R4-1, G2),
(A'3, Rx-1, R2-2, R3-3, R4-1, G3), (A'3, Rx-1, R2-2, R3-3, R4-1, G4),
(A'3, Rx-1, R2-2, R3-3, R4-1, G5), (A'3, Rx-1, R2-2, R3-4, R4-2, G1),
(A'3, Rx-1, R2-2, R3-3, R4-2, G2), (A'3, Rx-1, R2-2, R3-3, R4-2, G3),
(A'3, Rx-1, R2-2, R3-3, R4-2, G4), (A'3, Rx-1, R2-2, R3-3, R4-2, G5),
(A'3, Rx-1, R2-2, R3-4, R4-1, G1), (A'3, Rx-1, R2-2, R3-4, R4-1, G2),
(A'3, Rx-1, R2-2, R3-4, R4-1, G3), (A'3, Rx-1, R2-2, R3-4, R4-1, G4),
(A'3, Rx-1, R2-2, R3-4, R4-1, G5), (A'3, Rx-1, R2-2, R3-4, R4-2, G1),
(A'3, Rx-1, R2-2, R3-4, R4-2, G2), (A'3, Rx-1, R2-2, R3-4, R4-2, G3),
(A'3, Rx-1, R2-2, R3-4, R4-2, G4), (A'3, Rx-1, R2-2, R3-4, R4-2, G5),
(A'3, Rx-2, R2-1, R3-1, R4-1, G1), (A'3, Rx-2, R2-1, R3-1, R4-1, G2),
(A'3, Rx-2, R2-1, R3-1, R4-1, G3), (A'3, Rx-2, R2-1, R3-1, R4-1, G4),
(A'3, Rx-2, R2-1, R3-1, R4-1, G5), (A'3, Rx-2, R2-1, R3-1, R4-2, G1),
(A'3, Rx-2, R2-1, R3-1, R4-2, G2), (A'3, Rx-2, R2-1, R3-1, R4-2, G3),
(A'3, Rx-2, R2-1, R3-1, R4-2, G4), (A'3, Rx-2, R2-1, R3-1, R4-2, G5),
(A'3, Rx-2, R2-1, R3-2, R4-1, G1), (A'3, Rx-2, R2-1, R3-2, R4-1, G2),
(A'3, Rx-2, R2-1, R3-2, R4-1, G3), (A'3, Rx-2, R2-1, R3-2, R4-1, G4),
(A'3, Rx-2, R2-1, R3-2, R4-1, G5), (A'3, Rx-2, R2-1, R3-2, R4-2, G1),
(A'3, Rx-2, R2-1, R3-2, R4-2, G2), (A'3, Rx-2, R2-1, R3-2, R4-2, G3),
(A'3, Rx-2, R2-1, R3-2, R4-2, G4), (A'3, Rx-2, R2-1, R3-2, R4-2, G5),
(A'3, Rx-2, R2-1, R3-3, R4-1, G1), (A'3, Rx-2, R2-1, R3-3, R4-1, G2),
(A'3, Rx-2, R2-1, R3-3, R4-1, G3), (A'3, Rx-2, R2-1, R3-3, R4-1, G4),
(A'3, Rx-2, R2-1, R3-3, R4-1, G5), (A'3, Rx-2, R2-1, R3-3, R4-2, G1),
(A'3, Rx-2, R2-1, R3-3, R4-2, G2), (A'3, Rx-2, R2-1, R3-3, R4-2, G3),
(A'3, Rx-2, R2-1, R3-3, R4-2, G4), (A'3, Rx-2, R2-1, R3-3, R4-2, G5),
(A'3, Rx-2, R2-1, R3-4, R4-1, G1), (A'3, Rx-2, R2-1, R3-4, R4-1, G2),
(A'3, Rx-2, R2-1, R3-4, R4-1, G3), (A'3, Rx-2, R2-1, R3-4, R4-1, G4),
(A'3, Rx-2, R2-1, R3-4, R4-1, G5), (A'3, Rx-2, R2-1, R3-4, R4-2, G1),
(A'3, Rx-2, R2-1, R3-4, R4-2, G2), (A'3, Rx-2, R2-1, R3-4, R4-2, G3),
(A'3, Rx-2, R2-1, R3-4, R4-2, G4), (A'3, Rx-2, R2-1, R3-4, R4-2, G5),
(A'3, Rx-2, R2-2, R3-1, R4-1, G1), (A'3, Rx-2, R2-2, R3-1, R4-1, G2),
(A'3, Rx-2, R2-2, R3-1, R4-1, G3), (A'3, Rx-2, R2-2, R3-1, R4-1, G4),
(A'3, Rx-2, R2-2, R3-1, R4-1, G5), (A'3, Rx-2, R2-2, R3-1, R4-2, G1),
(A'3, Rx-2, R2-2, R3-1, R4-2, G2), (A'3, Rx-2, R2-2, R3-1, R4-2, G3), (A'3, Rx-2, R2-2, R3-1, R4-2, G4), (A'3, Rx-2, R2-2, R3-1, R4-2, G5),
(A'3, Rx-2, R2-2, R3-2, R4-1, G1), (A'3, Rx-2, R2-2, R3-2, R4-1, G2),
(A'3, Rx-2, R2-2, R3-2, R4-1, G3), (A'3, Rx-2, R2-2, R3-2, R4-1, G4),
(A'3, Rx-2, R2-2, R3-2, R4-1, G5), (A'3, Rx-2, R2-2, R3-2, R4-2, G1),
(A'3, Rx-2, R2-2, R3-2, R4-2, G2), (A'3, Rx-2, R2-2, R3-2, R4-2, G3),
(A'3, Rx-2, R2-2, R3-2, R4-2, G4), (A'3, Rx-2, R2-2, R3-2, R4-2, G5),
(A'3, Rx-2, R2-2, R3-3, R4-1, G1), (A'3, Rx-2, R2-2, R3-3, R4-1, G2),
(A'3, Rx-2, R2-2, R3-3, R4-1, G3), (A'3, Rx-2, R2-2, R3-3, R4-1, G4),
(A'3, Rx-2, R2-2, R3-3, R4-1, G5), (A'3, Rx-2, R2-2, R3-3, R4-2, G1),
(A'3, Rx-2, R2-2, R3-3, R4-2, G2), (A'3, Rx-2, R2-2, R3-3, R4-2, G3),
(A'3, Rx-2, R2-2, R3-3, R4-2, G4), (A'3, Rx-2, R2-2, R3-3, R4-2, G5),
(A'3, Rx-2, R2-2, R3-4, R4-1, G1), (A'3, Rx-2, R2-2, R3-4, R4-1, G2),
(A'3, Rx-2, R2-2, R3-4, R4-1, G3), (A'3, Rx-2, R2-2, R3-4, R4-1, G4),
(A'3, Rx-2, R2-2, R3-4, R4-1, G5), (A'3, Rx-2, R2-2, R3-4, R4-2, G1),
(A'3, Rx-2, R2-2, R3-4, R4-2, G2), (A'3, Rx-2, R2-2, R3-4, R4-2, G3),
(A'3, Rx-2, R2-2, R3-4, R4-2, G4), (A'3, Rx-2, R2-2, R3-4, R4-2, G5),
(A'3, Rx-3, R2-1, R3-1, R4-1, G1), (A'3, Rx-3, R2-1, R3-1, R4-1, G2),
(A'3, Rx-3, R2-1, R3-1, R4-1, G3), (A'3, Rx-3, R2-1, R3-1, R4-1, G4),
(A'3, Rx-3, R2-1, R3-1, R4-1, G5), (A'3, Rx-3, R2-1, R3-1, R4-2, G1),
(A'3, Rx-3, R2-1, R3-1, R4-2, G2), (A'3, Rx-3, R2-1, R3-1, R4-2, G3),
(A'3, Rx-3, R2-1, R3-1, R4-2, G4), (A'3, Rx-3, R2-1, R3-1, R4-2, G5),
(A'3, Rx-3, R2-1, R3-2, R4-1, G1), (A'3, Rx-3, R2-1, R3-2, R4-1, G2),
(A'3, Rx-3, R2-1, R3-2, R4-1, G3), (A'3, Rx-3, R2-1, R3-2, R4-1, G4),
(A'3, Rx-3, R2-1, R3-2, R4-1, G5), (A'3, Rx-3, R2-1, R3-2, R4-2, G1),
(A'3, Rx-3, R2-1, R3-2, R4-2, G2), (A'3, Rx-3, R2-1, R3-2, R4-2, G3),
(A'3, Rx-3, R2-1, R3-2, R4-2, G4), (A'3, Rx-3, R2-1, R3-2, R4-2, G5),
(A'3, Rx-3, R2-1, R3-3, R4-1, G1), (A'3, Rx-3, R2-1, R3-3, R4-1, G2),
(A'3, Rx-3, R2-1, R3-3, R4-1, G3), (A'3, Rx-3, R2-1, R3-3, R4-1, G4),
(A'3, Rx-3, R2-1, R3-3, R4-1, G5), (A'3, Rx-3, R2-1, R3-3, R4-2, G1),
(A'3, Rx-3, R2-1, R3-3, R4-2, G2), (A'3, Rx-3, R2-1, R3-3, R4-2, G3),
(A'3, Rx-3, R2-1, R3-3, R4-2, G4), (A'3, Rx-3, R2-1, R3-3, R4-2, G5),
(A'3, Rx-3, R2-1, R3-4, R4-1, G1), (A'3, Rx-3, R2-1, R3-4, R4-1, G2),
(A'3, Rx-3, R2-1, R3-4, R4-1, G3), (A'3, Rx-3, R2-1, R3-4, R4-1, G4),
(A'3, Rx-3, R2-1, R3-4, R4-1, G5), (A'3, Rx-3, R2-1, R3-4, R4-2, G1),
(A'3, Rx-3, R2-1, R3-4, R4-2, G2), (A'3, Rx-3, R2-1, R3-4, R4-2, G3),
(A'3, Rx-3, R2-1, R3-4, R4-2, G4), (A'3, Rx-3, R2-1, R3-4, R4-2, G5),
(A'3, Rx-3, R2-2, R3-1, R4-1, G1), (A'3, Rx-3, R2-2, R3-1, R4-1, G2),
(A'3, Rx-3, R2-2, R3-1, R4-1, G3), (A'3, Rx-3, R2-2, R3-1, R4-1, G4),
(A'3, Rx-3, R2-2, R3-1, R4-1, G5), (A'3, Rx-3, R2-2, R3-1, R4-2, G1),
(A'3, Rx-3, R2-2, R3-1, R4-2, G2), (A'3, Rx-3, R2-2, R3-1, R4-2, G3),
(A'3, Rx-3, R2-2, R3-1, R4-2, G4), (A'3, Rx-3, R2-2, R3-1, R4-2, G5),
(A'3, Rx-3, R2-2, R3-2, R4-1, G1), (A'3, Rx-3, R2-2, R3-2, R4-1, G2),
(A'3, Rx-3, R2-2, R3-2, R4-1, G3), (A'3, Rx-3, R2-2, R3-2, R4-1, G4),
(A'3, Rx-3, R2-2, R3-2, R4-1, G5), (A'3, Rx-3, R2-2, R3-2, R4-2, G1),
(A'3, Rx-3, R2-2, R3-2, R4-2, G2), (A'3, Rx-3, R2-2, R3-2, R4-2, G3),
(A'3, Rx-3, R2-2, R3-2, R4-2, G4), (A'3, Rx-3, R2-2, R3-2, R4-2, G5),
(A'3, Rx-3, R2-2, R3-3, R4-1, G1), (A'3, Rx-3, R2-2, R3-3, R4-1, G2),
(A'3, Rx-3, R2-2, R3-3, R4-1, G3), (A'3, Rx-3, R2-2, R3-3, R4-1, G4),
(A'3, Rx-3, R2-2, R3-3, R4-1, G5), (A'3, Rx-3, R2-2, R3-3, R4-2, G1),
(A'3, Rx-3, R2-2, R3-3, R4-2, G2), (A'3, Rx-3, R2-2, R3-3, R4-2, G3),
(A'3, Rx-3, R2-2, R3-3, R4-2, G4), (A'3, Rx-3, R2-2, R3-3, R4-2, G5),
(A'3, Rx-3, R2-2, R3-4, R4-1, G1), (A'3, Rx-3, R2-2, R3-4, R4-1, G2),
(A'3, Rx-3, R2-2, R3-4, R4-1, G3), (A'3, Rx-3, R2-2, R3-4, R4-1, G4),
(A'3, Rx-3, R2-2, R3-4, R4-1, G5), (A'3, Rx-3, R2-2, R3-4, R4-2, G1),
(A'3, Rx-3, R2-2, R3-4, R4-2, G2), (A'3, Rx-3, R2-2, R3-4, R4-2, G3),
(A'3, Rx-3, R2-2, R3-4, R4-2, G4), (A'3, Rx-3, R2-2, R3-4, R4-2, G5),
(A'4, Rx-1, R2-1, R3-1, R4-1, G1), (A'4, Rx-1, R2-1, R3-1, R4-1, G2),
(A'4, Rx-1, R2-1, R3-1, R4-1, G3), (A'4, Rx-1, R2-1, R3-1, R4-1, G4),
(A'4, Rx-1, R2-1, R3-1, R4-1, G5), (A'4, Rx-1, R2-1, R3-1, R4-2, G1),
(A'4, Rx-1, R2-1, R3-1, R4-2, G2), (A'4, Rx-1, R2-1, R3-1, R4-2, G3);
(A'4, Rx-1, R2-1, R3-1, R4-2, G4), (A'4, Rx-1, R2-1, R3-1, R4-2, G5),
(A'4, Rx-1, R2-1, R3-2, R4-1, G1), (A'4, Rx-1, R2-1, R3-2, R4-1, G2),
(A'4, Rx-1, R2-1, R3-2, R4-1, G3), (A'4, Rx-1, R2-1, R3-2, R4-1, G4),
(A'4, Rx-1, R2-1, R3-2, R4-1, G5), (A'4, Rx-1, R2-1, R3-2, R4-2, G1),
(A'4, Rx-1, R2-1, R3-2, R4-2, G2), (A'4, Rx-1, R2-1, R3-2, R4-2, G3),
(A'4, Rx-1, R2-1, R3-2, R4-2, G4), (A'4, Rx-1, R2-1, R3-2, R4-2, G5), (A'4, Rx-1, R2-1, R3-3, R4-1, G1), (A'4, Rx-1, R2-1, R3-3, R4-1, G2),
(A'4, Rx-1, R2-1, R3-3, R4-1, G3), (A'4, Rx-1, R2-1, R3-3, R4-1, G4),
(A'4, Rx-1, R2-1, R3-3, R4-1, G5), (A'4, Rx-1, R2-1, R3-3, R4-2, G1),
(A'4, Rx-1, R2-1, R3-3, R4-2, G2), (A'4, Rx-1, R2-1, R3-3, R4-2, G3),
(A'4, Rx-1, R2-1, R3-3, R4-2, G4), (A'4, Rx-1, R2-1, R3-3, R4-2, G5),
(A'4, Rx-1, R2-1, R3-4, R4-1, G1), (A'4, Rx-1, R2-1, R3-4, R4-1, G2),
(A'4, Rx-1, R2-1, R3-4, R4-1, G3), (A'4, Rx-1, R2-1, R3-4, R4-1, G4),
(A'4, Rx-1, R2-1, R3-4, R4-1, G5), (A'4, Rx-1, R2-1, R3-4, R4-2, G1),
(A'4, Rx-1, R2-1, R3-4, R4-2, G2), (A'4, Rx-1, R2-1, R3-4, R4-2, G3),
(A'4, Rx-1, R2-1, R3-4, R4-2, G4), (A'4, Rx-1, R2-1, R3-4, R4-2, G5),
(A'4, Rx-1, R2-2, R3-1, R4-1, G1), (A'4, Rx-1, R2-2, R3-1, R4-1, G2),
(A'4, Rx-1, R2-2, R3-1, R4-1, G3), (A'4, Rx-1, R2-2, R3-1, R4-1, G4),
(A'4, Rx-1, R2-2, R3-1, R4-1, G5), (A'4, Rx-1, R2-2, R3-1, R4-2, G1),
(A'4, Rx-1, R2-2, R3-1, R4-2, G2), (A'4, Rx-1, R2-2, R3-1, R4-2, G3),
(A'4, Rx-1, R2-2, R3-1, R4-2, G4), (A'4, Rx-1, R2-2, R3-1, R4-2, G5),
(A'4, Rx-1, R2-2, R3-2, R4-1, G1), (A'4, Rx-1, R2-2, R3-2, R4-1, G2),
(A'4, Rx-1, R2-2, R3-2, R4-1, G3), (A'4, Rx-1, R2-2, R3-2, R4-1, G4),
(A'4, Rx-1, R2-2, R3-2, R4-1, G5), (A'4, Rx-1, R2-2, R3-2, R4-2, G1),
(A'4, Rx-1, R2-2, R3-2, R4-2, G2), (A'4, Rx-1, R2-2, R3-2, R4-2, G3),
(A'4, Rx-1, R2-2, R3-2, R4-2, G4), (A'4, Rx-1, R2-2, R3-2, R4-2, G5),
(A'4, Rx-1, R2-2, R3-3, R4-1, G1), (A'4, Rx-1, R2-2, R3-3, R4-1, G2),
(A'4, Rx-1, R2-2, R3-3, R4-1, G3), (A'4, Rx-1, R2-2, R3-3, R4-1, G4),
(A'4, Rx-1, R2-2, R3-3, R4-1, G5), (A'4, Rx-1, R2-2, R3-3, R4-2, G1),
(A'4, Rx-1, R2-2, R3-3, R4-2, G2), (A'4, Rx-1, R2-2, R3-3, R4-2, G3),
(A'4, Rx-1, R2-2, R3-3, R4-2, G4), (A'4, Rx-1, R2-2, R3-3, R4-2, G5),
(A'4, Rx-1, R2-2, R3-4, R4-1, G1), (A'4, Rx-1, R2-2, R3-4, R4-1, G2),
(A'4, Rx-1, R2-2, R3-4, R4-1, G3), (A'4, Rx-1, R2-2, R3-4, R4-1, G4),
(A'4, Rx-1, R2-2, R3-4, R4-1, G5), (A'4, Rx-1, R2-2, R3-4, R4-2, G1),
(A'4, Rx-1, R2-2, R3-4, R4-2, G2), (A'4, Rx-1, R2-2, R3-4, R4-2, G3),
(A'4, Rx-1, R2-2, R3-4, R4-2, G4), (A'4, Rx-1, R2-2, R3-4, R4-2, G5),
(A'4, Rx-2, R2-1, R3-1, R4-1, G1), (A'4, Rx-2, R2-1, R3-1, R4-1, G2),
(A'4, Rx-2, R2-1, R3-1, R4-1, G3), (A'4, Rx-2, R2-1, R3-1, R4-1, G4),
(A'4, Rx-2, R2-1, R3-1, R4-1, G5), (A'4, Rx-2, R2-1, R3-1, R4-2, G1),
(A'4, Rx-2, R2-1, R3-1, R4-2, G2), (A'4, Rx-2, R2-1, R3-1, R4-2, G3),
(A'4, Rx-2, R2-1, R3-1, R4-2, G4), (A'4, Rx-2, R2-1, R3-1, R4-2, G5),
(A'4, Rx-2, R2-1, R3-2, R4-1, G1), (A'4, Rx-2, R2-1, R3-2, R4-1, G2),
(A'4, Rx-2, R2-1, R3-2, R4-1, G3), (A'4, Rx-2, R2-1, R3-2, R4-1, G4),
(A'4, Rx-2, R2-1, R3-2, R4-1, G5), (A'4, Rx-2, R2-1, R3-2, R4-2, G1),
(A'4, Rx-2, R2-1, R3-2, R4-2, G2), (A'4, Rx-2, R2-1, R3-2, R4-2, G3),
(A'4, Rx-2, R2-1, R3-2, R4-2, G4), (A'4, Rx-2, R2-1, R3-2, R4-2, G5),
(A'4, Rx-2, R2-1, R3-3, R4-1, G1), (A'4, Rx-2, R2-1, R3-3, R4-1, G2),
(A'4, Rx-2, R2-1, R3-3, R4-1, G3), (A'4, Rx-2, R2-1, R3-3, R4-1, G4),
(A'4, Rx-2, R2-1, R3-3, R4-1, G5), (A'4, Rx-2, R2-1, R3-3, R4-2, G1),
(A'4, Rx-2, R2-1, R3-3, R4-2, G2), (A'4, Rx-2, R2-1, R3-3, R4-2, G3),
(A'4, Rx-2, R2-1, R3-3, R4-2, G4), (A'4, Rx-2, R2-1, R3-3, R4-2, G5),
(A'4, Rx-2, R2-1, R3-4, R4-1, G1), (A'4, Rx-2, R2-1, R3-4, R4-1, G2),
(A'4, Rx-2, R2-1, R3-4, R4-1, G3), (A'4, Rx-2, R2-1, R3-4, R4-1, G4),
(A'4, Rx-2, R2-1, R3-4, R4-1, G5), (A'4, Rx-2, R2-1, R3-4, R4-2, G1),
(A'4, Rx-2, R2-1, R3-4, R4-2, G2), (A'4, Rx-2, R2-1, R3-4, R4-2, G3),
(A'4, Rx-2, R2-1, R3-4, R4-2, G4), (A'4, Rx-2, R2-1, R3-4, R4-2, G5),
(A'4, Rx-2, R2-2, R3-1, R4-1, G1), (A'4, Rx-2, R2-2, R3-1, R4-1, G2),
(A'4, Rx-2, R2-2, R3-1, R4-1, G3), (A'4, Rx-2, R2-2, R3-1, R4-1, G4),
(A'4, Rx-2, R2-2, R3-1, R4-1, G5), (A'4, Rx-2, R2-2, R3-1, R4-2, G1),
(A'4, Rx-2, R2-2, R3-1, R4-2, G2), (A'4, Rx-2, R2-2, R3-1, R4-2, G3),
(A'4, Rx-2, R2-2, R3-1, R4-2, G4), (A'4, Rx-2, R2-2, R3-1, R4-2, G5),
(A'4, Rx-2, R2-2, R3-2, R4-1, G1), (A'4, Rx-2, R2-2, R3-2, R4-1, G2),
(A'4, Rx-2, R2-2, R3-2, R4-1, G3), (A'4, Rx-2, R2-2, R3-2, R4-1, G4),
(A'4, Rx-2, R2-2, R3-2, R4-1, G5), (A'4, Rx-2, R2-2, R3-2, R4-2, G1),
(A'4, Rx-2, R2-2, R3-2, R4-2, G2), (A'4, Rx-2, R2-2, R3-2, R4-2, G3),
(A'4, Rx-2, R2-2, R3-2, R4-2, G4), (A'4, Rx-2, R2-2, R3-2, R4-2, G5),
(A'4, Rx-2, R2-2, R3-3, R4-1, G1), (A'4, Rx-2, R2-2, R3-3, R4-1, G2),
(A'4, Rx-2, R2-2, R3-3, R4-1, G3), (A'4, Rx-2, R2-2, R3-3, R4-1, G4),
(A'4, Rx-2, R2-2, R3-3, R4-1, G5), (A'4, Rx-2, R2-2, R3-3, R4-2, G1),
(A'4, Rx-2, R2-2, R3-3, R4-2, G2), (A'4, Rx-2, R2-2, R3-3, R4-2, G3),
(A'4, Rx-2, R2-2, R3-3, R4-2, G4), (A'4, Rx-2, R2-2, R3-3, R4-2, G5),
(A'4, Rx-2, R2-2, R3-4, R4-1, G1), (A'4, Rx-2, R2-2, R3-4, R4-1, G2), (A'4, Rx-2, R2-2, R3-4, R4-1, G3), (A'4, Rx-2, R2-2, R3-4, R4-1, G4),
(A'4, Rx-2, R2-2, R3-4, R4-1, G5), (A'4, Rx-2, R2-2, R3-4, R4-2, G1),
(A'4, Rx-2, R2-2, R3-4, R4-2, G2), (A'4, Rx-2, R2-2, R3-4, R4-2, G3),
(A'4, Rx-2, R2-2, R3-4, R4-2, G4), (A'4, Rx-2, R2-2, R3-4, R4-2, G5),
(A'4, Rx-3, R2-1, R3-1, R4-1, G1), (A'4, Rx-3, R2-1, R3-1, R4-1, G2),
(A' 4, Rx-3, R2-1, R3-1, R4-1, G3), (A'4, Rx-3, R2-1, R3-1, R4-1, G4),
(A'4, Rx-3, R2-1, R3-1, R4-1, G5), (A'4, Rx-3, R2-1, R3-1, R4-2, G1),
(A' 4, Rx-3, R2-1, R3-1, R4-2, G2), (A' 4, Rx-3, R2-1, R3-1, R4-2, G3),
(A'4, Rx-3, R2-1, R3-1, R4-2, G4), (A'4, Rx-3, R2-1, R3-1, R4-2, G5),
(A'4, Rx-3, R2-1, R3-2, R4-1, G1), (A'4, Rx-3, R2-1, R3-2, R4-1, G2),
(A'4, Rx-3, R2-1, R3-2, R4-1, G3), (A'4, Rx-3, R2-1, R32, R41, G4),
(A'4, Rx-3, R2-1, R3-2, R4-1, G5), (A'4, Rx-3, R2-1, R3-2, R4-2, G1),
(A' 4, Rx-3, R2-1, R3-2, R4-2, G2), (A' 4, Rx-3, R2-1, R3-2, R4-2, G3),
(A'4, Rx-3, R2-1, R3-2, R4-2, G4), (A'4, Rx-3, R2-1, R3-2, R4-2, G5),
(A'4, Rx-3, R2-1, R3-3, R4-1, G1), (A'4, Rx-3, R2-1, R3-3, R4-1, G2),
(A'4, Rx-3, R2-1, R3-3, R4-1, G3), (A'4, Rx-3, R2-1, R3-3, R4-1, G4),
(A'4, Rx-3, R2-1, R3-3, R4-1, G5), (A'4, Rx-3, R2-1, R3-3, R4-2, G1),
(A'4, Rx-3, R2-1, R3-3, R4-2, G2), (A' 4, Rx-3, R2-1, R3-3, R4-2, G3),
(A'4, Rx-3, R2-1, R3-3, R4-2, G4), (A'4, Rx-3, R2-1, R3-3, R4-2, G5),
(A'4, Rx-3, R2-1, R3-4, R4-1, G1), (A'4, Rx-3, R2-1, R3-4, R4-1, G2),
(A'4, Rx-3, R2-1, R3-4, R4-1, G3), (A'4, Rx-3, R2-1, R3-4, R4-1, G4),
(A'4, Rx-3, R2-1, R3-4, R4-1, G5), (A' 4, Rx-3, R2-1, R3-4, R4-2, G1),
(A' 4, Rx-3, R2-1, R3-4, R4-2, G2), (A'4, Rx-3, R2-1, R3-4, R4-2, G3),
(A'4, Rx-3, R2-1, R3-4, R4-2, G4), (A'4, Rx-3, R2-1, R3-4, R4-2, G5),
(A'4, Rx-3, R2-2, R3-1, R4-1, G1), (A'4, Rx-3, R2-2, R3-1, R4-1, G2),
(A'4, Rx-3, R2-2, R3-1, R4-1, G3), (A'4, Rx-3, R2-2, R3-1, R4-1, G4),
(A'4, Rx-3, R2-2, R3-1, R4-1, G5), (A' 4, Rx-3, R2-2, R3-1, R4-2, G1),
(A'4, Rx-3, R2-2, R3-1, R4-2, G2), (A'4, Rx-3, R2-2, R3-1, R4-2, G3),
(A'4, Rx-3, R2-2, R3-1, R4-2, G4), (A'4, Rx-3, R2-2, R3-1, R4-2, G5),
(A'4, Rx-3, R2-2, R3-2, R4-1, G1), (A'4, Rx-3, R2-2, R3-2, R4-1, G2),
(A'4, Rx-3, R2-2, R3-2, R4-1, G3), (A'4, Rx-3, R2-2, R3-2, R4-1, G4),
(A'4, Rx-3, R2-2, R3-2, R4-1, G5), (A'4, Rx-3, R2-2, R3-2, R4-2, G1),
(A'4, Rx-3, R2-2, R3-2, R4-2, G2), (A'4, Rx-3, R2-2, R3-2, R4-2, G3),
(A'4, Rx-3, R2-2, R3-2, R4-2, G4), (A'4, Rx-3, R2-2, R3-2, R4-2, G5),
(A'4, Rx-3, R2-2, R3-3, R4-1, G1), (A'4, Rx-3, R2-2, R3-3, R4-1, G2),
(A' 4, Rx-3, R2-2, R3-3, R4-1, G3), (A'4, Rx-3, R2-2, R3-3, R4-1, G4),
(A'4, Rx-3, R2-2, R3-3, R4-1, G5), (A'4, Rx-3, R2-2, R3-3, R4-2, G1),
(A' 4, Rx-3, R2-2, R3-3, R4-2, G2), (A'4, Rx-3, R2-2, R3-3, R4-2, G3),
(A' 4, Rx-3, R2-2, R3-3, R4-2, G4), (A'4, Rx-3, R2-2, R3-3, R4-2, G5),
(A'4, Rx-3, R2-2, R3-4, R4-1, G1), (A'4, Rx-3, R2-2, R3-4, R4-1, G2),
(A'4, Rx-3, R2-2, R3-4, R4-1, G3), (A'4, Rx-3, R2-2, R3-4, R4-1, G4),
(A'4, Rx-3, R2-2, R3-4, R4-1, G5), (A'4, Rx-3, R2-2, R3-4, R4-1, G2),
(A' 4, Rx-3, R2-2, R3-4, R4-2, G2), (A'4, Rx-3, R2-2, R3-4, R4-2, G3),
(A'4, Rx-3, R2-2, R3-4, R4-2, G4), (A'4, Rx-3, R2-2, R3-4, R4-2, G5).

In the formula (III'):

[Chemical formula 25]

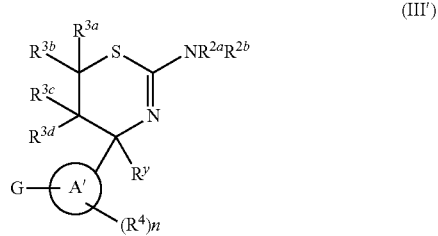

1) the compound, wherein ring A' is phenyl or a nitrogen-containing aromatic heterocyclic group (hereinafter, referred to as compound in which ring A' is A'1), the compound, wherein ring A' is phenyl, pyridyl, indolyl, benzisoxazolyl, benzopyrazolyl, benzofuryl, benzothienyl, benzodioxolyl, or dihydrobenzodioxolanyl (hereinafter, referred to as compound in which ring A' is A'2),
the compound, wherein ring A' is phenyl (hereinafter, referred to as compound in which ring A' is A'3),
the compound, wherein ring A' is pyridyl (hereinafter, referred to as compound in which ring A' is A'4),
2) the compound, wherein $R^y$ is lower alkyl substituted with halogen (hereinafter, referred to as compound in which $R^y$ is $R^y$-1),
the compound, wherein $R^y$ is trifluoromethyl (hereinafter, referred to as compound in which $R^y$ is $R^y$-2),
3) the compound, wherein $R^{2a}$ and $R^{2b}$ are each independently hydrogen, lower alkyl or acyl (hereinafter, referred to as compound in which $R^{2a}$ and $R^{2b}$ are R2-1),
the compound, wherein $R^{2a}$ and $R^{2b}$ are both hydrogen (hereinafter, referred to as compound in which $R^{2a}$ and $R^{2b}$ are R2-2),
4) the compound, wherein $R^{3a}$, $R^{3b}$, $R^{3c}$ and $R^{3d}$ are each independently hydrogen, halogen, hydroxy, lower alkyl or amino (hereinafter, referred to as compound in which $R^{3a}$, $R^{3b}$, $R^{3c}$, and $R^{3d}$ are R3-1),
the compound, wherein $R^{3a}$ and $R^{3b}$, or $R^{3c}$ and $R^{3d}$ are taken together to form cyclopropyl, cyclobutyl, cyclopentyl, or cyclohexyl (hereinafter, referred to as compound in which $R^{3a}$, $R^{3b}$, $R^{3c}$ and $R^{3d}$ are R3-2), the compound, wherein $R^{3a}$ and $R^{3b}$, or $R^{3c}$ and $R^{3d}$ are the same substituent selected from halogen or lower alkyl (hereinafter, referred to as compound in which $R^{3a}$, $R^{3b}$, $R^{3c}$ and $R^{3d}$ are R3-3), the compound, wherein $R^{3a}$, $R^{3b}$, and $R^{3c}$ and $R^{3d}$ are all hydrogen (hereinafter, referred to as compound in which $R^{3a}$, $R^{3b}$, $R^{3c}$ and $R^{3d}$ are R3-4), 5) the compound, wherein n is 0 to 2, and each $R^4$ is independently halogen, lower alkoxy, lower alkylamino, lower alkylthio, oxo, or lower alkylenedioxy (hereinafter, referred to as compound in which $R^4$ is R4-1), the compound, wherein n is 0 to 2, and each $R^4$ is independently halogen (hereinafter, referred to as compound in which $R^4$ is R4-2), 6) the compound, wherein G is the above (ii), (iv), (v), (x), (xiii), or (xiv) (hereinafter, referred to as compound in which G is G1), the compound, wherein G is the (ii'), (ii''), (iv'), (v'), (x'), (xiii') or (xiv') (hereinafter, referred to as compound in which G is G2), the compound, wherein G is the above (ii'), (ii''), (iv'), (v'), (x'), (xiii') or (xiv'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl or optionally substituted pyridopyrimidinyl, (herein, the substituent is 1 to 3 groups selected from the group consisting of the substituent group α and lower alkyl optionally substituted with one or more groups selected from the substituent group α (hereinafter, referred to as compound in which G is G3), the compound, wherein G is the above (ii'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl or optionally substituted pyridopyrimidinyl, herein, the substituent is 1 to 3 groups selected from the group consisting of the substituent group α and lower alkyl optionally substituted with one or more groups selected from the substituent group α (hereinafter, referred to as compound in which G is G4)

the compound, wherein G is the above (ii'), $R^5$ is hydrogen or lower alkyl, $W^1$ is O, and ring B is optionally substituted pyridyl or optionally substituted pyrazinyl, herein, the substituent is 1 to 3 groups selected from the group consisting of the substituent group α and lower alkyl optionally substituted with one or more groups selected from the substituent group α (hereinafter, referred to as compound in which G is G5), compounds in which a combination of ring A'; $R^y$; $R^{2a}$ and $R^{2b}$; $R^{3a}$, $R^{3b}$, $R^{3c}$, and $R^{3d}$; n, and $R^4$; and G is as follows.

(A'1, Ry-1, R2-1, R3-1, R4-1, G1), (A'1, Ry-1, R2-1, R3-1, R4-1, G2),
(A'1, Ry-1, R2-1, R3-1, R4-1, G3), (A'1, Ry-1, R2-1, R3-1, R4-1, G4),
(A'1, Ry-1, R2-1, R3-1, R4-1, G5), (A'1, Ry-1, R2-1, R3-1, R4-2, G1),
(A'1, Ry-1, R2-1, R3-1, R4-2, G2), (A'1, Ry-1, R2-1, R3-1, R4-2, G3),
(A'1, Ry-1, R2-1, R3-1, R4-2, G4), (A'1, Ry-1, R2-1, R3-1, R4-2, G5),
(A'1, Ry-1, R2-1, R3-2, R4-1, G1), (A'1, Ry-1, R2-1, R3-2, R4-1, G2),
(A'1, Ry-1, R2-1, R3-2, R4-1, G3), (A'1, Ry-1, R2-1, R3-2, R4-1, G4),
(A'1, Ry-1, R2-1, R3-2, R4-1, G5), (A'1, Ry-1, R2-1, R3-2, R4-2, G1),
(A'1, Ry-1, R2-1, R3-2, R4-2, G2), (A'1, Ry-1, R2-1, R3-2, R4-2, G3),
(A'1, Ry-1, R2-1, R3-2, R4-2, G4), (A'1, Ry-1, R2-1, R3-2, R4-2, G5),
(A'1, Ry-1, R2-1, R3-3, R4-1, G1),
(A'1, Ry-1, R2-1, R3-3, R4-1, G3), (A'1, Ry-1, R2-1, R3-3, R4-1, G4),
(A'1, Ry-1, R2-1, R3-3, R4-1, G5), (A'1, Ry-1, R2-1, R3-3, R4-2, G1),
(A'1, Ry-1, R2-1, R3-3, R4-2, G2), (A'1, Ry-1, R2-1, R3-3, R4-2, G3),
(A'1, Ry-1, R2-1, R3-3, R4-2, G4), (A'1, Ry-1, R2-1, R3-3, R4-2, G5),
(A'1, Ry-1, R2-1, R3-4, R4-1, G1), (A'1, Ry-1, R2-1, R3-4, R4-1, G2),
(A'1, Ry-1, R2-1, R3-4, R4-1, G3), (A'1, Ry-1, R2-1, R3-4, R4-1, G4),
(A'1, Ry-1, R2-1, R3-4, R4-1, G5), (A'1, Ry-1, R2-1, R3-4, R4-2, G1),
(A'1, Ry-1, R2-1, R3-4, R4-2, G2), (A'1, Ry-1, R2-1, R3-4, R4-2, G3),
(A'1, Ry-1, R2-1, R3-4, R4-2, G4), (A'1, Ry-1, R2-1, R3-4, R4-2, G5),
(A'1, Ry-1, R2-2, R3-1, R4-1, G1), (A'1, Ry-1, R2-2, R3-1, R4-1, G2),
(A'1, Ry-1, R2-2, R3-1, R4-1, G3), (A'1, Ry-1, R2-2, R3-1, R4-1, G4),
(A'1, Ry-1, R2-2, R3-1, R4-1, G5), (A'1, Ry-1, R2-2, R3-1, R4-2, G1),
(A'1, Ry-1, R2-2, R3-1, R4-2, G2), (A'1, Ry-1, R2-2, R3-1, R4-2, G3),
(A'1, Ry-1, R2-2, R3-1, R4-2, G4), (A'1, Ry-1, R2-2, R3-1, R4-2, G5),
(A'1, Ry-1, R2-2, R3-2, R4-1, G1), (A'1, Ry-1, R2-2, R3-2, R4-1, G2),
(A'1, Ry-1, R2-2, R3-2, R4-1, G3), (A'1, Ry-1, R2-2, R3-2, R4-1, G4),
(A'1, Ry-1, R2-2, R3-2, R4-1, G5), (A'1, Ry-1, R2-2, R3-2, R4-2, G1),
(A'1, Ry-1, R2-2, R3-2, R4-2, G2), (A'1, Ry-1, R2-2, R3-2, R4-2, G3),
(A'1, Ry-1, R2-2, R3-2, R4-2, G4), (A'1, Ry-1, R2-2, R3-2, R4-2, G5),
(A'1, Ry-1, R2-2, R3-3, R4-1, G1), (A'1, Ry-1, R2-2, R3-3, R4-1, G2),
(A'1, Ry-1, R2-2, R3-3, R4-1, G3), (A'1, Ry-1, R2-2, R3-3, R4-1, G4),
(A'1, Ry-1, R2-2, R3-3, R4-1, G5), (A'1, Ry-1, R2-2, R3-3, R4-2, G1),
(A'1, Ry-1, R2-2, R3-3, R4-2, G2), (A'1, Ry-1, R2-2, R3-3, R4-2, G3),
(A'1, Ry-1, R2-2, R3-3, R4-2, G4), (A'1, Ry-1, R2-2, R3-3, R4-2, G5),
(A'1, Ry-1, R2-2, R3-4, R4-1, G1), (A'1, Ry-1, R2-2, R3-4, R4-1, G2),
(A'1, Ry-1, R2-2, R3-4, R4-1, G3), (A'1, Ry-1, R2-2, R3-4, R4-1, G4),
(A'1, Ry-1, R2-2, R3-4, R4-1, G5), (A'1, Ry-1, R2-2, R3-4, R4-2, G1),
(A'1, Ry-1, R2-2, R3-4, R4-2, G2), (A'1, Ry-1, R2-2, R3-4, R4-2, G3), (A'1, Ry-1, R2-2, R3-4, R4-2, G4), (A'1, Ry-1, R2-2, R3-4, R4-2, G5),
(A'1, Ry-2, R2-1, R3-1, R4-1, G1), (A'1, Ry-2, R2-1, R3-1, R4-1, G2),
(A'1, Ry-2, R2-1, R3-1, R4-1, G3), (A'1, Ry-2, R2-1, R3-1, R4-1, G4),
(A'1, Ry-2, R2-1, R3-1, R4-1, G5), (A'1, Ry-2, R2-1, R3-1, R4-2, G1),
(A'1, Ry-2, R2-1, R3-1, R4-2, G2), (A'1, Ry-2, R2-1, R3-1, R4-2, G3),
(A'1, Ry-2, R2-1, R3-1, R4-2, G4), (A'1, Ry-2, R2-1, R3-1, R4-2, G5),
(A'1, Ry-2, R2-1, R3-2, R4-1, G1), (A'1, Ry-2, R2-1, R3-2, R4-1, G2),
(A'1, Ry-2, R2-1, R3-2, R4-1, G3), (A'1, Ry-2, R2-1, R3-2, R4-1, G4),
(A'1, Ry-2, R2-1, R3-2, R4-1, G5), (A'1, Ry-2, R2-1, R3-2, R4-2, G1),
(A'1, Ry-2, R2-1, R3-2, R4-2, G2), (A'1, Ry-2, R2-1, R3-2, R4-2, G3),
(A'1, Ry-2, R2-1, R3-2, R4-2, G4), (A'1, Ry-2, R2-1, R3-2, R4-2, G5),
(A'1, Ry-2, R2-1, R3-3, R4-1, G1), (A'1, Ry-2, R2-1, R3-3, R4-1, G2),
(A'1, Ry-2, R2-1, R3-3, R4-1, G3), (A'1, Ry-2, R2-1, R3-3, R4-1, G4),
(A'1, Ry-2, R2-1, R3-3, R4-1, G5), (A'1, Ry-2, R2-1, R3-3, R4-2, G1),
(A'1, Ry-2, R2-1, R3-3, R4-2, G2), (A'1, Ry-2, R2-1, R3-3, R4-2, G3),
(A'1, Ry-2, R2-1, R3-3, R4-2, G4), (A'1, Ry-2, R2-1, R3-3, R4-2, G5),
(A'1, Ry-2, R2-1, R3-4, R4-1, G1), (A'1, Ry-2, R2-1, R3-4, R4-1, G2),
(A'1, Ry-2, R2-1, R3-4, R4-1, G3), (A'1, Ry-2, R2-1, R3-4, R4-1, G4),
(A'1, R3-4, R4-1, G5), (A'1, Ry-2, R2-1, R3-4, R4-2, G1),
(A'1, Ry-2, R2-1, R3-4, R4-2, G2), (A'1, Ry-2, R2-1, R3-4, R4-2, G3),
(A'1, Ry-2, R2-1, R3-4, R4-2, G4), (A'1, Ry-2, R2-1, R3-4, R4-2, G5),
(A'1, Ry-2, R2-2, R3-1, R4-1, G1), (A'1, Ry-2, R2-2, R3-1, R4-1, G2),
(A'1, Ry-2, R2-2, R3-1, R4-1, G3),
(A'1, Ry-2, R2-2, R3-1, R4-1, G5), (A'1, Ry-2, R2-2, R3-1, R4-2, G1),
(A'1, Ry-2, R2-2, R3-1, R4-2, G2), (A'1, Ry-2, R2-2, R3-1, R4-2, G3),
(A'1, Ry-2, R2-2, R3-1, R4-2, G4), (A'1, Ry-2, R2-2, R3-1, R4-2, G5),
(A'1, Ry-2, R2-2, R3-2, R4-1, G1), (A'1, Ry-2, R2-2, R3-2, R4-1, G2),
(A'1, Ry-2, R2-2, R3-2, R4-1, G3), (A'1, Ry-2, R2-2, R3-2, R4-1, G4),
(A'1, Ry-2, R2-2, R3-2, R4-1, G5), (A'1, Ry-2, R2-2, R3-2, R4-2, G1),
(A'1, Ry-2, R2-2, R3-2, R4-2, G2),
(A'1, Ry-2, R2-2, R3-2, R4-2, G4), (A'1, Ry-2, R2-2, R3-2, R4-2, G5),
(A'1, Ry-2, R2-2, R3-3, R4-1, G1), (A'1, Ry-2, R2-2, R3-3, R4-1, G2),
(A'1, Ry-2, R2-2, R3-3, R4-1, G3), (A'1, Ry-2, R2-2, R3-3, R4-1, G4),
(A'1, Ry-2, R2-2, R3-3, R4-1, G5), (A'1, Ry-2, R2-2, R3-3, R4-2, G1),
(A'1, Ry-2, R2-2, R3-3, R4-2, G2), (A'1, Ry-2, R2-2, R3-3, R4-2, G3),
(A'1, Ry-2, R2-2, R3-3, R4-2, G4), (A'1, Ry-2, R2-2, R3-3, R4-2, G5),
(A'1, Ry-2, R2-2, R3-4, R4-1, G1), (A'1, Ry-2, R2-2, R3-4, R4-1, G2),
(A'1, Ry-2, R2-2, R3-4, R4-1, G3), (A'1, Ry-2, R2-2, R3-4, R4-1, G4),
(A'1, Ry-2, R2-2, R3-4, R4-1, G5), (A'1, Ry-2, R2-2, R3-4, R4-2, G1),
(A'1, Ry-2, R2-2, R3-4, R4-2, G2), (A'1, Ry-2, R2-2, R3-4, R4-2, G3),
(A'1, Ry-2, R2-2, R3-4, R4-2, G4), 4, R4-2, G5),
(A'2, Ry-1, R2-1, R3-1, R4-1, G1), (A'2, Ry-1, R2-1, R3-1, R4-1, G2),
(A'2, Ry-1, R2-1, R3-1, R4-1, G3), (A'2, Ry-1, R2-1, R3-1, R4-1, G4),
(A'2, Ry-1, R2-1, R3-1, R4-1, G5), (A'2, Ry-1, R2-1, R3-1, R4-2, G1),
(A'2, Ry-1, R2-1, R3-1, R4-2, G2), (A'2, Ry-1, R2-1, R3-1, R4-2, G3),
(A'2, Ry-1, R2-1, R3-1, R4-2, G4), (A'2, Ry-1, R2-1, R3-1, R4-2, G5),
(A'2, Ry-1, R2-1, R3-2, R4-1, G1), (A'2, Ry-1, R2-1, R3-2, R4-1, G2),
(A'2, Ry-1, R2-1, R3-2, R4-1, G3), (A'2, Ry-1, R2-1, R3-2, R4-1, G4),
(A'2, Ry-1, R2-1, R3-2, R4-1, G5), (A'2, Ry-1, R2-1, R3-2, R4-2, G1),
(A'2, Ry-1, R2-1, R3-2, R4-2, G2), (A'2, Ry-1, R2-1, R3-2, R4-2, G3),
(A'2, Ry-1, R2-1, R3-2, R4-2, G4), (A'2, Ry-1, R2-1, R3-2, R4-2, G5),
(A'2, Ry-1, R2-1, R3-3, R4-1, G1), (A'2, Ry-1, R2-1, R3-3, R4-1, G2),
(A'2, Ry-1, R2-1, R3-3, R4-1, G3), (A'2, Ry-1, R2-1, R3-3, R4-1, G4),
(A'2, Ry-1, R2-1, R3-3, R4-1, G5), (A'2, Ry-1, R2-1, R3-3, R4-2, G1),
(A'2, Ry-1, R2-1, R3-3, R4-2, G2), (A'2, Ry-1, R2-1, R3-3, R4-2, G3),
(A'2, Ry-1, R2-1, R3-3, R4-2, G4), (A'2, Ry-1, R2-1, R3-3, R4-2, G5),
(A'2, Ry-1, R2-1, R3-4, R4-1, G1), (A'2, Ry-1, R2-1, R3-4, R4-1, G2),
(A'2, Ry-1, R2-1, R3-4, R4-1, G3), (A'2, Ry-1, R2-1, R3-4, R4-1, G4),
(A'2, Ry-1, R2-1, R3-4, R4-1, G5), (A'2, Ry-1, R2-1, R3-4, R4-2, G1),
(A'2, Ry-1, R2-1, R3-4, R4-2, G2), (A'2, Ry-1, R2-1, R3-4, R4-2, G3),
(A'2, Ry-1, R2-1, R3-4, R4-2, G4), (A'2, Ry-1, R2-1, R3-4, R4-2, G5),
(A'2, Ry-1, R2-2, R3-1, R4-1, G1), (A'2, Ry-1, R2-2, R3-1, R4-1, G2),
(A'2, Ry-1, R2-2, R3-1, R4-1, G3), (A'2, Ry-1, R2-2, R3-1, R4-1, G4),
(A'2, Ry-1, R2-2, R3-1, R4-1, G5), (A'2, Ry-1, R2-2, R3-1, R4-2, G1),
(A'2, Ry-1, R2-2, R3-1, R4-2, G2), (A'2, Ry-1, R2-2, R3-1, R4-2, G3),
(A'2, Ry-1, R2-2, R3-1, R4-2, G4), (A'2, Ry-1, R2-2, R3-1, R4-2, G5),
(A'2, Ry-1, R2-2, R3-2, R4-1, G1), (A'2, Ry-1, R2-2, R3-2, R4-1, G2),
(A'2, Ry-1, R2-2, R3-2, R4-1, G3), (A'2, Ry-1, R2-2, R3-2, R4-1, G4),
(A'2, Ry-1, R2-2, R3-2, R4-1, G5), (A'2, Ry-1, R2-2, R3-2, R4-2, G1), (A'2, Ry-1, R2-2, R3-2, R4-2, G2), (A'2, Ry-1, R2-2, R3-2, R4-2, G3),
(A'2, Ry-1, R2-2, R3-2, R4-2, G4), (A'2, Ry-1, R2-2, R3-2, R4-2, G5),
(A'2, Ry-1, R2-2, R3-3, R4-1, G1), (A'2, Ry-1, R2-2, R3-3, R4-1, G2),
(A'2, Ry-1, R2-2, R3-3, R4-1, G3), (A'2, Ry-1, R2-2, R3-3, R4-1, G4),
(A'2, Ry-1, R2-2, R3-3, R4-1, G5), (A'2, Ry-1, R2-2, R3-3, R4-2, G1),
(A'2, Ry-1, R2-2, R3-3, R4-2, G2), (A'2, Ry-1, R2-2, R3-3, R4-2, G3),
(A'2, Ry-1, R2-2, R3-3, R4-2, G4), (A'2, Ry-1, R2-2, R3-3, R4-2, G5),
(A'2, Ry-1, R2-2, R3-4, R4-1, G1), (A'2, Ry-1, R2-2, R3-4, R4-1, G2),
(A'2, Ry-1, R2-2, R3-4, R4-1, G3), (A'2, Ry-1, R2-2, R3-4, R4-1, G4),
(A'2, Ry-1, R2-2, R3-4, R4-1, G5), (A'2, Ry-1, R2-2, R3-4, R4-2, G1),
(A'2, Ry-1, R2-2, R3-4, R4-2, G2), (A'2, Ry-1, R2-2, R3-4, R4-2, G3),
(A'2, Ry-1, R2-2, R3-4, R4-2, G4), (A'2, Ry-1, R2-2, R3-4, R4-2, G5),
(A'2, Ry-2, R2-1, R3-1, R4-1, G1), (A'2, Ry-2, R2-1, R3-1, R4-1, G2),
(A'2, Ry-2, R2-1, R3-1, R4-1, G3), (A'2, Ry-2, R2-1, R3-1, R4-1, G4),
(A'2, Ry-2, R2-1, R3-1, R4-1, G5), (A'2, Ry-2, R2-1, R3-1, R4-2, G1),
(A'2, Ry-2, R2-1, R3-1, R4-2, G2), (A'2, Ry-2, R2-1, R3-1, R4-2, G3),
(A'2, Ry-2, R2-1, R3-1, R4-2, G4), (A'2, Ry-2, R2-1, R3-1, R4-2, G5),
(A'2, Ry-2, R2-1, R3-2, R4-1, G1), (A'2, Ry-2, R2-1, R3-2, R4-1, G2),
(A'2, Ry-2, R2-1, R3-2, R4-1, G3), (A'2, Ry-2, R2-1, R3-2, R4-1, G4),
(A'2, Ry-2, R2-1, R3-2, R4-1, G5), (A'2, Ry-2, R2-1, R3-2, R4-2, G1),
(A'2, Ry-2, R2-1, R3-2, R4-2, G2), (A'2, Ry-2, R2-1, R3-2, R4-2, G3),
(A'2, Ry-2, R2-1, R3-2, R4-2, G4), (A'2, Ry-2, R2-1, R3-2, R4-2, G5),
(A'2, Ry-2, R2-1, R3-3, R4-1, G1), (A'2, Ry-2, R2-1, R3-3, R4-1, G2),
(A'2, Ry-2, R2-1, R3-3, R4-1, G3), (A'2, Ry-2, R2-1, R3-3, R4-1, G4),
(A'2, Ry-2, R2-1, R3-3, R4-1, G5), (A'2, Ry-2, R2-1, R3-3, R4-2, G1),
(A'2, Ry-2, R2-1, R3-3, R4-2, G2), (A'2, Ry-2, R2-1, R3-3, R4-2, G3),
(A'2, Ry-2, R2-1, R3-3, R4-2, G4), (A'2, Ry-2, R2-1, R3-3, R4-2, G5),
(A'2, Ry-2, R2-1, R3-4, R4-1, G1), (A'2, Ry-2, R2-1, R3-4, R4-1, G2),
(A'2, Ry-2, R2-1, R3-4, R4-1, G3), (A'2, Ry-2, R2-1, R3-4, R4-1, G4),
(A'2, Ry-2, R2-1, R3-4, R4-1, G5), (A'2, Ry-2, R2-1, R3-4, R4-2, G1),
(A'2, Ry-2, R2-1, R3-4, R4-2, G2), (A'2, Ry-2, R2-1, R3-4, R4-2, G3),
(A'2, Ry-2, R2-1, R3-4, R4-2, G4), (A'2, Ry-2, R2-1, R3-4, R4-2, G5),
(A'2, Ry-2, R2-2, R3-1, R4-1, G1), (A'2, Ry-2, R2-2, R3-1, R4-1, G2),
(A'2, Ry-2, R2-2, R3-1, R4-1, G3), (A'2, Ry-2, R2-2, R3-1, R4-1, G4),
(A'2, Ry-2, R2-2, R3-1, R4-1, G5), (A'2, Ry-2, R2-2, R3-1, R4-2, G1),
(A'2, Ry-2, R2-2, R3-1, R4-2, G2), (A'2, Ry-2, R2-2, R3-1, R4-2, G3),
(A'2, Ry-2, R2-2, R3-1, R4-2, G4), (A'2, Ry-2, R2-2, R3-1, R4-2, G5),
(A'2, Ry-2, R2-2, R3-2, R4-1, G1), (A'2, Ry-2, R2-2, R3-2, R4-1, G2),
(A'2, Ry-2, R2-2, R3-2, R4-1, G3), (A'2, Ry-2, R2-2, R3-2, R4-1, G4),
(A'2, Ry-2, R2-2, R3-2, R4-1, G5), (A'2, Ry-2, R2-2, R3-2, R4-2, G1),
(A'2, Ry-2, R2-2, R3-2, R4-2, G2), (A'2, Ry-2, R2-2, R3-2, R4-2, G3),
(A'2, Ry-2, R2-2, R3-2, R4-2, G4), (A'2, Ry-2, R2-2, R3-2, R4-2, G5),
(A'2, Ry-2, R2-2, R3-3, R4-1, G1), (A'2, Ry-2, R2-2, R3-3, R4-1, G2),
(A'2, Ry-2, R2-2, R3-3, R4-1, G3), (A'2, Ry-2, R2-2, R3-3, R4-1, G4),
(A'2, Ry-2, R2-2, R3-3, R4-1, G5), (A'2, Ry-2, R2-2, R3-3, R4-2, G1),
(A'2, Ry-2, R2-2, R3-3, R4-2, G2), (A'2, Ry-2, R2-2, R3-3, R4-2, G3),
(A'2, Ry-2, R2-2, R3-3, R4-2, G4), (A'2, Ry-2, R2-2, R3-3, R4-2, G5),
(A'2, Ry-2, R2-2, R3-4, R4-1, G1), (A'2, Ry-2, R2-2, R3-4, R4-1, G2),
(A'2, Ry-2, R2-2, R3-4, R4-1, G3), (A'2, Ry-2, R2-2, R3-4, R4-1, G4),
(A'2, Ry-2, R2-2, R3-4, R4-1, G5), (A'2, Ry-2, R2-2, R3-4, R4-2, G1),
(A'2, Ry-2, R2-2, R3-4, R4-2, G2), (A'2, Ry-2, R2-2, R3-4, R4-2, G3),
(A'2, Ry-2, R2-2, R3-4, R4-2, G4), (A'2, Ry-2, R2-2, R3-4, R4-2, G5),
(A'3, Ry-1, R2-1, R3-1, R4-1, G1), (A'3, Ry-1, R2-1, R3-1, R4-1, G2),
(A'3, Ry-1, R2-1, R3-1, R4-1, G3), (A'3, Ry-1, R2-1, R3-1, R4-1, G4),
(A'3, Ry-1, R2-1, R3-1, R4-1, G5), (A'3, Ry-1, R2-1, R3-1, R4-2, G1),
(A'3, Ry-1, R2-1, R3-1, R4-2, G2), (A'3, Ry-1, R2-1, R3-1, R4-2, G3),
(A'3, Ry-1, R2-1, R3-1, R4-2, G4), (A'3, Ry-1, R2-1, R3-1, R4-2, G5),
(A'3, Ry-1, R2-1, R3-2, R4-1, G1), (A'3, Ry-1, R2-1, R3-2, R4-1, G2),
(A'3, Ry-1, R2-1, R3-2, R4-1, G3), (A'3, Ry-1, R2-1, R3-2, R4-1, G4),
(A'3, Ry-1, R2-1, R3-2, R4-1, G5), (A'3, Ry-1, R2-1, R3-2, R4-2, G1),
(A'3, Ry-1, R2-1, R3-2, R4-2, G2), (A'3, Ry-1, R2-1, R3-2, R4-2, G3),
(A'3, Ry-1, R2-1, R3-2, R4-2, G4), (A'3, Ry-1, R2-1, R3-2, R4-2, G5),
(A'3, Ry-1, R2-1, R3-3, R4-1, G1), (A'3, Ry-1, R2-1, R3-3, R4-1, G2),
(A'3, Ry-1, R2-1, R3-3, R4-1, G3), (A'3, Ry-1, R2-1, R3-3, R4-1, G4),
(A'3, Ry-1, R2-1, R3-3, R4-1, G5), (A'3, Ry-1, R2-1, R3-3, R4-2, G1),
(A'3, Ry-1, R2-1, R3-3, R4-2, G2), (A'3, Ry-1, R2-1, R3-3, R4-2, G3), (A'3, Ry-1, R2-1, R3-3, R4-2, G4), (A'3, Ry-1, R2-1, R3-3, R4-2, G5),
(A'3, Ry-1, R2-1, R3-4, R4-1, G1), (A'3, Ry-1, R2-1, R3-4, R4-1, G2),
(A'3, Ry-1, R2-1, R3-4, R4-1, G3), (A'3, Ry-1, R2-1, R3-4, R4-1, G4),
(A'3, Ry-1, R2-1, R3-4, R4-1, G5), (A'3, Ry-1, R2-1, R3-4, R4-2, G1),
(A'3, Ry-1, R2-1, R3-4, R4-2, G2), (A'3, Ry-1, R2-1, R3-4, R4-2, G3),
(A'3, Ry-1, R2-1, R3-4, R4-2, G4), (A'3, Ry-1, R2-1, R3-4, R4-2, G5),
(A'3, Ry-1, R2-2, R3-1, R4-1, G1), (A'3, Ry-1, R2-2, R3-1, R4-1, G2),
(A'3, Ry-1, R2-2, R3-1, R4-1, G3), (A'3, Ry-1, R2-2, R3-1, R4-1, G4),
(A'3, Ry-1, R2-2, R3-1, R4-1, G5), (A'3, Ry-1, R2-2, R3-1, R4-2, G1),
(A'3, Ry-1, R2-2, R3-1, R4-2, G2), (A'3, Ry-1, R2-2, R3-1, R4-2, G3),
(A'3, Ry-1, R2-2, R3-1, R4-2, G4), (A'3, Ry-1, R2-2, R3-1, R4'2, G5),
(A'3, Ry-1, R2-2, R3-2, R4-1, G1), (A'3, Ry-1, R2-2, R3-2, R4-1, G2),
(A'3, Ry-1, R2-2, R3-2, R4-1, G3), (A'3, Ry-1, R2-2, R3-2, R4-1, G4),
(A'3, Ry-1, R2-2, R3-2, R4-1, G5), (A'3, Ry-1, R2-2, R3-2, R4-2, G1),
(A'3, Ry-1, R2-2, R3-2, R4-2, G2), (A'3, Ry-1, R2-2, R3-2, R4-2, G3),
(A'3, Ry-1, R2-2, R3-2, R4-2, G4), (A'3, Ry-1, R2-2, R3-2, R4-2, G5),
(A'3, Ry-1, R2-2, R3-3, R4-1, G1), (A'3, Ry-1, R2-2, R3-3, R4-1, G2),
(A'3, Ry-1, R2-2, R3-3, R4-1, G3), (A'3, Ry-1, R2-2, R3-3, R4-1, G4),
(A'3, Ry-1, R2-2, R3-3, R4-1, G5), (A'3, Ry-1, R2-2, R3-3, R4-2, G1),
(A'3, Ry-1, R2-2, R3-3, R4-2, G2), (A'3, Ry-1, R2-2, R3-3, R4-2, G3),
(A'3, Ry-1, R2-2, R3-3, R4-2, G4), (A'3, Ry-1, R2-2, R3-3, R4-2, G5),
(A'3, Ry-1, R2-2, R3-4, R4-1, G1), (A'3, Ry-1, R2-2, R3-4, R4-1, G2),
(A'3, Ry-1, R2-2, R3-4, R4-1, G3), (A'3, Ry-1, R2-2, R3-4, R4-1, G4),
(A'3, Ry-1, R2-2, R3-4, R4-1, G5), (A'3, Ry-1, R2-2, R3-4, R4-2, G1),
(A'3, Ry-1, R2-2, R3-4, R4-2, G2), (A'3, Ry-1, R2-2, R3-4, R4-2, G3),
(A'3, Ry-1, R2-2, R3-4, R4-2, G4), (A'3, Ry-1, R2-2, R3-4, R4-2, G5),
(A'3, Ry-2, R2-1, R3-1, R4-1, G1), (A'3, Ry-2, R2-1, R3-1, R4-1, G2),
(A'3, Ry-2, R2-1, R3-1, R4-1, G3), (A'3, Ry-2, R2-1, R3-1, R4-1, G4),
(A'3, Ry-2, R2-1, R3-1, R4-1, G5), (A'3, Ry-2, R2-1, R3-1, R4-2, G1),
(A'3, Ry-2, R2-1, R3-1, R4-2, G2), (A'3, Ry-2, R2-1, R3-1, R4-2, G3),
(A'3, Ry-2, R2-1, R3-1, R4-2, G4), (A'3, Ry-2, R2-1, R3-1, R4-2, G5),
(A'3, Ry-2, R2-1, R3-2, R4-1, G1), (A'3, Ry-2, R2-1, R3-2, R4-1, G2),
(A'3, Ry-2, R2-1, R3-2, R4-1, G3), (A'3, Ry-2, R2-1, R3-2, R4-1, G4),
(A'3, Ry-2, R2-1, R3-2, R4-1, G5), (A'3, Ry-2, R2-1, R3-2, R4-2, G1),
(A'3, Ry-2, R2-1, R3-2, R4-2, G2), (A'3, Ry-2, R2-1, R3-2, R4-2, G3),
(A'3, Ry-2, R2-1, R3-2, R4-2, G4), (A'3, Ry-2, R2-1, R3-2, R4-2, G5),
(A'3, Ry-2, R2-1, R3-3, R4-1, G1), (A'3, Ry-2, R2-1, R3-3, R4-1, G2),
(A'3, Ry-2, R2-1, R3-3, R4-1, G3), (A'3, Ry-2, R2-1, R3-3, R4-1, G4),
(A'3, Ry-2, R2-1, R3-3, R4-1, G5), (A'3, Ry-2, R2-1, R3-3, R4-2, G1),
(A'3, Ry-2, R2-1, R3-3, R4-2, G2), (A'3, Ry-2, R2-1, R3-3, R4-2, G3),
(A'3, Ry-2, R2-1, R3-3, R4-2, G4), (A'3, Ry-2, R2-1, R3-3, R4-2, G5),
(A'3, Ry-2, R2-1, R3-4, R4-1, G1), (A'3, Ry-2, R2-1, R3-4, R4-1, G2),
(A'3, Ry-2, R2-1, R3-4, R4-1, G3), (A'3, Ry-2, R2-1, R3-4, R4-1, G4),
(A'3, Ry-2, R2-1, R3-4, R4-1, G5), (A'3, Ry-2, R2-1, R3-4, R4-2, G1),
(A'3, Ry-2, R2-1, R3-4, R4-2, G2), (A'3, Ry-2, R2-1, R3-4, R4-2, G3),
(A'3, Ry-2, R2-1, R3-4, R4-2, G4), (A'3, Ry-2, R2-1, R3-4, R4-2, G5),
(A'3, Ry-2, R2-2, R3-1, R4-1, G1), (A'3, Ry-2, R2-2, R3-1, R4-1, G2),
(A'3, Ry-2, R2-2, R3-1, R4-1, G3), (A'3, Ry-2, R2-2, R3-1, R4-1, G4),
(A'3, Ry-2, R2-2, R3-1, R4-1, G5), (A'3, Ry-2, R2-2, R3-1, R4-2, G1),
(A'3, Ry-2, R2-2, R3-1, R4-2, G2), (A'3, Ry-2, R2-2, R3-1, R4-2, G3),
(A'3, Ry-2, R2-2, R3-1, R4-2, G4), (A'3, Ry-2, R2-2, R3-1, R4-2, G5),
(A'3, Ry-2, R2-2, R3-2, R4-1, G1), (A'3, Ry-2, R2-2, R3-2, R4-1, G2),
(A'3, Ry-2, R2-2, R3-2, R4-1, G3), (A'3, Ry-2, R2-2, R3-2, R4-1, G4),
(A'3, Ry-2, R2-2, R3-2, R4-1, G5), (A'3, Ry-2, R2-2, R3-2, R4-2, G1),
(A'3, Ry-2, R2-2, R3-2, R4-2, G2), (A'3, Ry-2, R2-2, R3-2, R4-2, G3),
(A'3, Ry-2, R2-2, R3-2, R4-2, G4), (A'3, Ry-2, R2-2, R3-2, R4-2, G5),
(A'3, Ry-2, R2-2, R3-3, R4-1, G1), (A'3, Ry-2, R2-2, R3-3, R4-1, G2),
(A'3, Ry-2, R2-2, R3-3, R4-1, G3), (A'3, Ry-2, R2-2, R3-3, R4-1, G4),
(A'3, Ry-2, R2-2, R3-3, R4-1, G5), (A'3, Ry-2, R2-2, R3-3, R4-2, G1),
(A'3, Ry-2, R2-2, R3-3, R4-2, G2), (A'3, Ry-2, R2-2, R3-3, R4-2, G3),
(A'3, Ry-2, R2-2, R3-3, R4-2, G4), (A'3, Ry-2, R2-2, R3-3, R4-2, G5),
(A'3, Ry-2, R2-2, R3-4, R4-1, G1), (A'3, Ry-2, R2-2, R3-4, R4-1, G2),
(A'3, Ry-2, R2-2, R3-4, R4-1, G3), (A'3, Ry-2, R2-2, R3-4, R4-1, G4),
(A'3, Ry-2, R2-2, R3-4, R4-1, G5), (A'3, Ry-2, R2-2, R3-4, R4-2, G1),
(A'3, Ry-2, R2-2, R3-4, R4-2, G2), (A'3, Ry-2, R2-2, R3-4, R4-2, G3),
(A'3, Ry-2, R2-2, R3-4, R4-2, G4), (A'3, Ry-2, R2-2, R3-4, R4-2, G5), (A'4, Ry-1, R2-1, R3-1, R4-1, G1), (A'4, Ry-1, R2-1, R3-1, R4-1, G2),
(A'4, Ry-1, R2-1, R3-1, R4-1, G3), (A'4, Ry-1, R2-1, R3-1, R4-1, G4),
(A'4, Ry-1, R2-1, R3-1, R4-1, G5), (A'4, Ry-1, R2-1, R3-1, R4-2, G1),
(A'4, Ry-1, R2-1, R3-1, R4-2, G2), (A'4, Ry-1, R2-1, R3-1, R4-2, G3),
(A'4, Ry-1, R2-1, R3-1, R4-2, G4), (A'4, Ry-1, R2-1, R3-1, R4-2, G5),
(A'4, Ry-1, R2-1, R3-2, R4-1, G1), (A'4, Ry-1, R2-1, R3-2, R4-1, G2),
(A'4, Ry-1, R2-1, R3-2, R4-1, G3), (A'4, Ry-1, R2-1, R3-2, R4-1, G4),
(A'4, Ry-1, R2-1, R3-2, R4-1, G5), (A'4, Ry-1, R2-1, R3-2, R4-2, G1),
(A'4, Ry-1, R2-1, R3-2, R4-2, G2), (A'4, Ry-1, R2-1, R3-2, R4-2, G3),
(A'4, Ry-1, R2-1, R3-2, R4-2, G4), (A'4, Ry-1, R2-1, R3-2, R4-2, G5),
(A'4, Ry-1, R2-1, R3-3, R4-1, G1), (A'4, Ry-1, R2-1, R3-3, R4-1, G2),
(A'4, Ry-1, R2-1, R3-3, R4-1, G3), (A'4, Ry-1, R2-1, R3-3, R4-1, G4),
(A'4, Ry-1, R2-1, R3-3, R4-1, G5), (A'4, Ry-1, R2-1, R3-3, R4-2, G1),
(A'4, Ry-1, R2-1, R3-3, R4-2, G2), (A'4, Ry-1, R2-1, R3-3, R4-2, G3),
(A'4, Ry-1, R2-1, R3-3, R4-2, G4), (A'4, Ry-1, R2-1, R3-3, R4-2, G5),
(A'4, Ry-1, R2-1, R3-4, R4-1, G1), (A'4, Ry-1, R2-1, R3-4, R4-1, G2),
(A'4, Ry-1, R2-1, R3-4, R4-1, G3), (A'4, Ry-1, R2-1, R3-4, R4-1, G4),
(A'4, Ry-1, R2-1, R3-4, R4-1, G5), (A'4, Ry-1, R2-1, R3-4, R4-2, G1),
(A'4, Ry-1, R2-1, R3-4, R4-2, G2), (A'4, Ry-1, R2-1, R3-4, R4-2, G3),
(A'4, Ry-1, R2-1, R3-4, R4-2, G4), (A'4, Ry-1, R2-1, R3-4, R4-2, G5),
(A'4, Ry-1, R2-2, R3-1, R4-1, G1), (A'4, Ry-1, R2-2, R3-1, R4-1, G2),
(A'4, Ry-1, R2-2, R3-1, R4-1, G3), (A'4, Ry-1, R2-2, R3-1, R4-1, G4),
(A'4, Ry-1, R2-2, R3-1, R4-1, G5), (A'4, Ry-1, R2-2, R3-1, R4-2, G1),
(A'4, Ry-1, R2-2, R3-1, R4-2, G2), (A'4, Ry-1, R2-2, R3-1, R4-2, G3),
(A'4, Ry-1, R2-2, R3-1, R4-2, G4), (A'4, Ry-1, R2-2, R3-1, R4-2, G5),
(A'4, Ry-1, R2-2, R3-2, R4-1, G1), (A'4, Ry-1, R2-2, R3-2, R4-1, G2),
(A'4, Ry-1, R2-2, R3-2, R4-1, G3), (A'4, Ry-1, R2-2, R3-2, R4-1, G4),
(A'4, Ry-1, R2-2, R3-2, R4-1, G5), (A'4, Ry-1, R2-2, R3-2, R4-2, G1),
(A'4, Ry-1, R2-2, R3-2, R4-2, G2), (A'4, Ry-1, R2-2, R3-2, R4-2, G3),
(A'4, Ry-1, R2-2, R3-2, R4-2, G4), (A'4, Ry-1, R2-2, R3-2, R4-2, G5),
(A'4, Ry-1, R2-2, R3-3, R4-1, G1), (A'4, Ry-1, R2-2, R3-3, R4-1, G2),
(A'4, Ry-1, R2-2, R3-3, R4-1, G3), (A'4, Ry-1, R2-2, R3-3, R4-1, G4),
(A'4, Ry-1, R2-2, R3-3, R4-1, G5), (A'4, Ry-1, R2-2, R3-3, R4-2, G1),
(A'4, Ry-1, R2-2, R3-3, R4-2, G2), (A'4, Ry-1, R2-2, R3-3, R4-2, G3),
(A'4, Ry-1, R2-2, R3-3, R4-2, G4), (A'4, Ry-1, R2-2, R3-3, R4-2, G5),
(A'4, Ry-1, R2-2, R3-4, R4-1, G1), (A'4, Ry-1, R2-2, R3-4, R4-1, G2),
(A'4, Ry-1, R2-2, R3-4, R4-1, G3), (A'4, Ry-1, R2-2, R3-4, R4-1, G4),
(A'4, Ry-1, R2-2, R3-4, R4-1, G5), (A'4, Ry-1, R2-2, R3-4, R4-2, G1),
(A'4, Ry-1, R2-2, R3-4, R4-2, G2), (A'4, Ry-1, R2-2, R3-4, R4-2, G3),
(A'4, Ry-1, R2-2, R3-4, R4-2, G4), (A'4, Ry-1, R2-2, R3-4, R4-2, G5),
(A'4, Ry-2, R2-1, R3-1, R4-1, G1), (A'4, Ry-2, R2-1, R3-1, R4-1, G2),
(A'4, Ry-2, R2-1, R3-1, R4-1, G3), (A'4, Ry-2, R2-1, R3-1, R4-1, G4),
(A'4, Ry-2, R2-1, R3-1, R4-1, G5), (A'4, Ry-2, R2-1, R3-1, R4-2, G1),
(A'4, Ry-2, R2-1, R3-1, R4-2, G2), (A'4, Ry-2, R2-1, R3-1, R4-2, G3),
(A'4, Ry-2, R2-1, R3-1, R4-2, G4), (A'4, Ry-2, R2-1, R3-1, R4-2, G5),
(A'4, Ry-2, R2-1, R3-2, R4-1, G1), (A'4, Ry-2, R2-1, R3-2, R4-1, G2),
(A'4, Ry-2, R2-1, R3-2, R4-1, G3), (A'4, Ry-2, R2-1, R3-2, R4-1, G4),
(A'4, Ry-2, R2-1, R3-2, R4-1, G5), (A'4, Ry-2, R2-1, R3-2, R4-2, G1),
(A'4, Ry-2, R2-1, R3-2, R4-2, G2), (A'4, Ry-2, R2-1, R3-2, R4-2, G3),
(A'4, Ry-2, R2-1, R3-2, R4-2, G4), (A'4, Ry-2, R2-1, R3-2, R4-2, G5),
(A'4, Ry-2, R2-1, R3-3, R4-1, G1), (A'4, Ry-2, R2-1, R3-3, R4-1, G2),
(A'4, Ry-2, R2-1, R3-3, R4-1, G3), (A'4, Ry-2, R2-1, R3-3, R4-1, G4),
(A'4, Ry-2, R2-1, R3-3, R4-1, G5), (A'4, Ry-2, R2-1, R3-3, R4-2, G1),
(A'4, Ry-2, R2-1, R3-3, R4-2, G2), (A'4, Ry-2, R2-1, R3-3, R4-2, G3),
(A'4, Ry-2, R2-1, R3-3, R4-2, G4), (A'4, Ry-2, R2-1, R3-3, R4-2, G5),
(A'4, Ry-2, R2-1, R3-4, R4-1, G1), (A'4, Ry-2, R2-1, R3-4, R4-1, G2),
(A'4, Ry-2, R2-1, R3-4, R4-1, G3), (A'4, Ry-2, R2-1, R3-4, R4-1, G4),
(A'4, Ry-2, R2-1, R3-4, R4-1, G5), (A'4, Ry-2, R2-1, R3-4, R4-2, G1),
(A'4, Ry-2, R2-1, R3-4, R4-2, G2), (A'4, Ry-2, R2-1, R3-4, R4-2, G3),
(A'4, Ry-2, R2-1, R3-4, R4-2, G4), (A'4, Ry-2, R2-1, R3-4, R4-2, G5),
(A'4, Ry-2, R2-2, R3-1, R4-1, G1), (A'4, Ry-2, R2-2, R3-1, R4-1, G2),
(A'4, Ry-2, R2-2, R3-1, R4-1, G3), (A'4, Ry-2, R2-2, R3-1, R4-1, G4),
(A'4, Ry-2, R2-2, R3-1, R4-1, G5), (A'4, Ry-2, R2-2, R3-1, R4-2, G1),
(A'4, Ry-2, R2-2, R3-1, R4-2, G2), (A'4, Ry-2, R2-2, R3-1, R4-2, G3),
(A'4, Ry-2, R2-2, R3-1, R4-2, G4), (A'4, Ry-2, R2-2, R3-1, R4-2, G5),
(A'4, Ry-2, R2-2, R3-2, R4-1, G1), (A'4, Ry-2, R2-2, R3-2, R4-1, G2), (A'4, Ry-2, R2-2, R3-2, R4-1, G3), (A'4, Ry-2, R2-2, R3-2, R4-1, G4),
(A'4, Ry-2, R2-2, R3-2, R4-1, G5), (A'4, Ry-2, R2-2, R3-2, R4-2, G1),
(A'4, Ry-2, R2-2, R3-2, R4-2, G2), (A'4, Ry-2, R2-2, R3-2, R4-2, G3),
(A'4, Ry-2, R2-2, R3-2, R4-2, G4), (A'4, Ry-2, R2-2, R3-2, R4-2, G5),
(A'4, Ry-2, R2-2, R3-3, R4-1, G1), (A'4, Ry-2, R2-2, R3-3, R4-1, G2),
(A'4, Ry-2, R2-2, R3-3, R4-1, G3), (A'4, Ry-2, R2-2, R3-3, R4-1, G4),
(A'4, Ry-2, R2-2, R3-3, R4-1, G5), (A'4, Ry-2, R2-2, R3-3, R4-2, G1),
(A'4, Ry-2, R2-2, R3-3, R4-2, G2), (A'4, Ry-2, R2-2, R3-3, R4-2, G3),
(A'4, Ry-2, R2-2, R3-3, R4-2, G4), (A'4, Ry-2, R2-2, R3-3, R4-2, G5),
(A'4, Ry-2, R2-2, R3-4, R4-1, G1), (A'4, Ry-2, R2-2, R3-4, R4-1, G2),
(A'4, Ry-2, R2-2, R3-4, R4-1, G3), (A'4, Ry-2, R2-2, R3-4, R4-1, G4),
(A'4, Ry-2, R2-2, R3-4, R4-1, G5), (A'4, Ry-2, R2-2, R3-4, R4-2, G1),
(A'4, Ry-2, R2-2, R3-4, R4-2, G2), (A'4, Ry-2, R2-2, R3-4, R4-2, G3),
(A'4, Ry-2, R2-2, R3-4, R4-2, G4), (A'4, Ry-2, R2-2, R3-4, R4-2, G5).
In the formula (IV):

[Chemical formula 26]

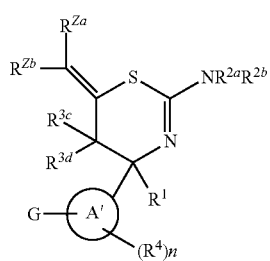

(IV')

wherein $R^{Za}$ and $R^{Zb}$ are each independently hydrogen, halogen, or optionally substituted lower alkyl, 1) the compound, wherein ring A' is phenyl or a nitrogen-containing aromatic heterocyclic group (hereinafter, referred to as compound in which ring A' is A'1),
the compound, wherein ring A' is phenyl, pyridyl, indolyl, benzoisoxazolyl, benzopyrazolyl, benzofuryl, benzothienyl, benzodioxolyl, or dihydrobenzodioxolanyl (hereinafter, referred to as compound in which ring A' is A'2),
the compound, wherein ring A' is phenyl (hereinafter, referred to as compound in which ring A' is A'3),
the compound, wherein ring A' is pyridyl (hereinafter, referred to as compound in which ring A' is A'4),
2) the compound, wherein IV is optionally substituted lower alkyl (hereinafter, referred to as compound in which $R^1$ is R1-1),
the compound, wherein which $R^1$ is methyl (hereinafter, referred to as compound in which $R^1$ is R1-2),
3) the compound, wherein $R^{2a}$ and $R^{2b}$ are each independently hydrogen, lower alkyl or acyl (hereinafter, referred to as compound in which $R^{2a}$ and $R^{2b}$ are R2-1),
the compound, wherein $R^{2a}$ and $R^{2b}$ are both hydrogen (hereinafter, referred to as compound in which $R^{2a}$ and $R^{2b}$ are R2-2),
4) the compound, wherein $R^{3c}$ and $R^{3d}$ are each independently hydrogen, halogen, hydroxy, lower alkyl or amino (hereinafter, referred to as compound in which $R^{3c}$ and $R^{3d}$ are R3-1),
the compound, wherein $R^{3c}$ and $R^{3d}$ are the same substituent selected from halogen and lower alkyl (hereinafter, referred to as compound in which $R^{3c}$ and $R^{3d}$ are R3-2),
the compound, wherein $R^{3c}$ and $R^{3d}$ are all hydrogen (hereinafter, referred to as compound in which $R^{3c}$ and $R^{3d}$ are R3-3),
5) the compound, wherein n is 0 to 2, and each $R^4$ is independently halogen, lower alkoxy, lower alkylamino, lower alkylthio, oxo, or lower alkylenedioxy (hereinafter, referred to as compound in which $R^4$ is R4-1),
the compound, wherein n is 0 to 2, and each $R^4$ is independently halogen (hereinafter, referred to as compound in which $R^4$ is R4-2),
6) the compound, wherein G is the above (ii), (iv), (v), (x), (xiii), or (xiv) (hereinafter, referred to as compound in which G is G1),
the compound, wherein G is the above (ii'), (ii''), (iv'), (v'), (x'), (xiii') or (xiv') (hereinafter, referred to as compound in which G is G2),
the compound, wherein G is the above (ii'), (ii''), (iv'), (v'), (x'), (xiii') or (xiv'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl or optionally substituted pyridopyrimidinyl, herein, the substituent is 1 to 3 groups selected from the group consisting of the substituent group α and lower alkyl optionally substituted with one or more groups selected from the substituent group α (hereinafter, referred to as compound in which G is G3),
the compound, wherein G is the above (ii'), and ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl, optionally substituted naphthyridinyl, optionally substituted quinazolinyl or optionally substituted pyridopyrimidinyl, herein, the substituent is 1 to 3 groups selected from the group consisting of the substituent group α and lower alkyl optionally substituted with one or more groups selected from the substituent group α (hereinafter, referred to as compound in which G is G4),
the compound, wherein G is the above (ii'), $R^5$ is hydrogen or lower alkyl, $W^1$ is O, and ring B is optionally substituted pyridyl or optionally substituted pyrazinyl, herein, the substituent is 1 to 3 groups selected from the group consisting of the substituent group α and lower alkyl optionally substituted with one or more groups selected from the substituent group α, (hereinafter, referred to as compound in which G is G5),
compounds in which a combination of ring A', $R^1$, $R^{2a}$ and $R^{2b}$, $R^{3c}$ and $R^{3d}$, n and $R^4$, and G is as follows.
(A'1, R1-1, R2-1, R3-1, R4-1, G1), (A'1, R1-1, R2-1, R3-1, R4-1, G2),
(A'1, R1-1, R2-1, R3-1, R4-1, G3), (A'1, R1-1, R2-1, R3-1, R4-1, G4),
(A'1, R1-1, R2-1, R3-1, R4-1, G5), (A'1, R1-1, R2-1, R3-1, R4-2, G1), (A'1, R1-1, R2-1, R3-1, R4-2, G2), (A'1, R1-1, R2-1, R3-1, R4-2, G3),
(A'1, R1-1, R2-1, R3-1, R4-2, G4), (A'1, R1-1, R2-1, R3-1, R4-2, G5),
(A'1, R1-1, R2-1, R3-2, R4-1, G1), (A'1, R1-1, R2-1, R3-2, R4-1, G2),
(A'1, R1-1, R2-1, R3-2, R4-1, G3), (A'1, R1-1, R2-1, R3-2, R4-1, G4),
(A'1, R1-1, R2-1, R3-2, R4-1, G5), (A'1, R1-1, R2-1, R3-2, R4-2, G1),
(A'1, R1-1, R2-1, R3-2, R4-2, G2), (A'1, R1-1, R2-1, R3-2, R4-2, G3),
(A'1, R1-1, R2-1, R3-2, R4-2, G4), (A'1, R1-1, R2-1, R3-2, R4-2, G5),
(A'1, R1-1, R2-1, R3-3, R4-1, G1), (A'1, R1-1, R2-1, R3-3, R4-1, G2),
(A'1, R1-1, R2-1, R3-3, R4-1, G3), (A'1, R1-1, R2-1, R3-3, R4-1, G4),
(A'1, R1-1, R2-1, R3-3, R4-1, G5), (A'1, R1-1, R2-1, R3-3, R4-2, G1),
(A'1, R1-1, R2-1, R3-3, R4-2, G2), (A'1, R1-1, R2-1, R3-3, R4-2, G3),
(A'1, R1-1, R2-1, R3-3, R4-2, G4),
(A'1, R1-1, R2-2, R3-1, R4-1, G1), (A'1, R1-1, R2-2, R3-1, R4-1, G2),
(A'1, R1-1, R2-2, R3-1, R4-1, G3), (A'1, R1-1, R2-2, R3-1, R4-1, G4),
(A'1, R1-1, R2-2, R3-1, R4-1, G5), (A'1, R1-1, R2-2, R3-1, R4-2, G1),
(A'1, R1-1, R2-2, R3-1, R4-2, G2), (A'1, R1-1, R2-2, R3-1, R4-2, G3),
(A'1, R1-1, R2-2, R3-1, R4-2, G4), (A'1, R1-1, R2-2, R3-1, R4-2, G5),
(A'1, R1-1, R2-2, R3-2, R4-1, G1), (A'1, R1-1, R2-2, R3-2, R4-1, G2),
(A'1, R1-1, R2-2, R3-2, R4-1, G3), (A'1, R1-1, R2-2, R3-2, R4-1, G4),
(A'1, R1-1, R2-2, R3-2, R4-1, G5), (A'1, R1-1, R2-2, R3-2, R4-2, G1),
(A'1, R1-1, R2-2, R3-2, R4-2, G2), (A'1, R1-1, R2-2, R3-2, R4-2, G3),
(A'1, R1-1, R2-2, R3-2, R4-2, G4), (A'1, R1-1, R2-2, R3-2, R4-2, G5),
(A'1, R1-1, R2-2, R3-3, R4-1, (A'1, R1-1, R2-2, R3-3, R4-1, G2),
(A'1, R1-1, R2-2, R3-3, R4-1, G3), (A'1, R1-1, R2-2, R3-3, R4-1, G4),
(A'1, R1-1, R2-2, R3-3, R4-1, G5), (A'1, R1-1, R2-2, R3-3, R4-2, G1),
(A'1, R1-1, R2-2, R3-3, R4-2, G2), (A'1, R1-1, R2-2, R3-3, R4-2, G3),
(A'1, R1-1, R2-2, R3-3, R4-2, G4), (A'1, R1-1, R2-2, R3-3, R4-2, G5),
(A'1, R1-2, R2-1, R3-1, R4-1, G1), (A'1, R1-2, R2-1, R3-1, R4-1, G2),
(A'1, R1-2, R2-1, R3-1, R4-1, G3), (A'1, R1-2, R2-1, R3-1, R4-1, G4),
(A'1, R1-2, R2-1, R3-1, R4-1, G5), (A'1, R1-2, R2-1, R3-1, R4-2, G1),
(A'1, R1-2, R2-1, R3-1, R4-2, G2), (A'1, R1-2, R2-1, R3-1, R4-2, G3),
(A'1, R1-2, R2-1, R3-1, R4-2, G4), (A'1, R1-2, R2-1, R3-1, R4-2, G5),
(A'1, R1-2, R2-1, R3-2, R4-1, G1), (A'1, R1-2, R2-1, R3-2, R4-1, G2),
(A'1, R1-2, R2-1, R3-2, R4-1, G3), (A'1, R1-2, R2-1, R3-2, R4-1, G4),
(A'1, R1-2, R2-1, R3-2, R4-1, G5), (A'1, R1-2, R2-1, R3-2, R4-2, G1),
(A'1, R1-2, R2-1, R3-2, R4-2, G2), (A'1, R1-2, R2-1, R3-2, R4-2, G3),
(A'1, R1-2, R2-1, R3-2, R4-2, G4), (A'1, R1-2, R2-1, R3-2, R4-2, G5),
(A'1, R1-2, R2-1, R3-3, R4-1, G1), (A'1, R1-2, R2-1, R3-3, R4-1, G2),
(A'1, R1-2, R2-1, R3-3, R4-1, G3), (A'1, R1-2, R2-1, R3-3, R4-1, G4),
(A'1, R1-2, R2-1, R3-3, R4-1, G5), (A'1, R1-2, R2-1, R3-3, R4-2, G1),
(A'1, R1-2, R2-1, R3-3, R4-2, G2), (A'1, R1-2, R2-1, R3-3, R4-2, G3),
(A'1, R1-2, R2-1, R3-3, R4-2, G4), (A'1, R1-2, R2-1, R3-3, R4-2, G5),
(A'1, R1-2, R2-2, R3-1, R4-1, G1), (A'1, R1-2, R2-2, R3-1, R4-1, G2),
(A'1, R1-2, R2-2, R3-1, R4-1, G3), (A'1, R1-2, R2-2, R3-1, R4-1, G4),
(A'1, R1-2, R2-2, R3-1, R4-1, G5), (A'1, R1-2, R2-2, R3-1, R4-2, G1),
(A'1, R1-2, R2-2, R3-1, R4-2, G2), (A'1, R1-2, R2-2, R3-1, R4-2, G3),
(A'1, R1-2, R2-2, R3-1, R4-2, G4), (A'1, R1-2, R2-2, R3-1, R4-2, G5),
(A'1, R1-2, R2-2, R3-2, R4-1, G1), (A'1, R1-2, R2-2, R3-2, R4-1, G2),
(A'1, R1-2, R2-2, R3-2, R4-1, G3), (A'1, R1-2, R2-2, R3-2, R4-1, G4),
(A'1, R1-2, R2-2, R3-2, R4-1, G5), (A'1, R1-2, R2-2, R3-2, R4-2, G1),
(A'1, R1-2, R2-2, R3-2, R4-2, G2), (A'1, R1-2, R2-2, R3-2, R4-2, G3),
(A'1, R1-2, R2-2, R3-2, R4-2, G4), (A'1, R1-2, R2-2, R3-2, R4-2, G5),
(A'1, R1-2, R2-2, R3-3, R4-1, G1), (A'1, R1-2, R2-2, R3-3, R4-1, G2),
(A'1, R1-2, R2-2, R3-3, R4-1, G3), (A'1, R1-2, R2-2, R3-3, R4-1, G4),
(A'1, R1-2, R2-2, R3-3, R4-1, G5), (A'1, R1-2, R2-2, R3-3, R4-2, G1),
(A'1, R1-2, R2-2, R3-3, R4-2, G2), (A'1, R1-2, R2-2, R3-3, R4-2, G3),
(A'1, R1-2, R2-2, R3-3, R4-2, G4), (A'1, R1-2, R2-2, R3-3, R4-2, G5),
(A'2, R1-1, R2-1, R3-1, R4-1, G1), (A'2, R1-1, R2-1, R3-1, R4-1, G2),
(A'2, R1-1, R2-1, R3-1, R4-1, G3), (A'2, R1-1, R2-1, R3-1, R4-1, G4),
(A'2, R1-1, R2-1, R3-1, R4-1, G5), (A'2, R1-1, R2-1, R3-1, R4-2, G1),
(A'2, R1-1, R2-1, R3-1, R4-2, G2), (A'2, R1-1, R2-1, R3-1, R4-2, G3),
(A'2, R1-1, R2-1, R3-1, R4-2, G4), (A'2, R1-1, R2-1, R3-1, R4-2, G5),
(A'2, R1-1, R2-1, R3-2, R4-1, G1), (A'2, R1-1, R2-1, R3-2, R4-1, G2),
(A'2, R1-1, R2-1, R3-2, R4-1, G3), (A'2, R1-1, R2-1, R3-2, R4-1, G4),
(A'2, R1-1, R2-1, R3-2, R4-1, G5), (A'2, R1-1, R2-1, R3-2, R4-2, G1),
(A'2, R1-1, R2-1, R3-2, R4-2, G2), (A'2, R1-1, R2-1, R3-2, R4-2, G3),
(A'2, R1-1, R2-1, R3-2, R4-2, G4), (A'2, R1-1, R2-1, R3-2, R4-2, G5), (A'2, R1-1, R2-1, R3-3, R4-1, G1), (A'2, R1-1, R2-1, R3-3, R4-1, G2),
(A'2, R1-1, R2-1, R3-3, R4-1, G3), (A'2, R1-1, R2-1, R3-3, R4-1, G4),
(A'2, R1-1, R2-1, R3-3, R4-1, G5), (A'2, R1-1, R2-1, R3-3, R4-2, G1),
(A'2, R1-1, R2-1, R3-3, R4-2, G2), (A'2, R1-1, R2-1, R3-3, R4-2, G3),
(A'2, R1-1, R2-1, R3-3, R4-2, G4), (A'2, R1-1, R2-1, R3-3, R4-2, G5),
(A'2, R1-1, R2-2, R3-1, R4-1, G1), (A'2, R1-1, R2-2, R3-1, R4-1, G2),
(A'2, R1-1, R2-2, R3-1, R4-1, G3), (A'2, R1-1, R2-2, R3-1, R4-1, G4),
(A'2, R1-1, R2-2, R3-1, R4-1, G5), (A'2, R1-1, R2-2, R3-1, R4-2, G1),
(A'2, R1-1, R2-2, R3-1, R4-2, G2), (A'2, R1-1, R2-2, R3-1, R4-2, G3),
(A'2, R1-1, R2-2, R3-1, R4-2, G4), (A'2, R1-1, R2-2, R3-1, R4-2, G5),
(A'2, R1-1, R2-2, R3-2, R4-1, G1), (A'2, R1-1, R2-2, R3-2, R4-1, G2),
(A'2, R1-1, R2-2, R3-2, R4-1, G3), (A'2, R1-1, R2-2, R3-2, R4-1, G4),
(A'2, R1-1, R2-2, R3-2, R4-1, G5), (A'2, R1-1, R2-2, R3-2, R4-2, G1),
(A'2, R1-1, R2-2, R3-2, R4-2, G2), (A'2, R1-1, R2-2, R3-2, R4-2, G3),
(A'2, R1-1, R2-2, R3-2, R4-2, G4), (A'2, R1-1, R2-2, R3-2, R4-2, G5),
(A'2, R1-1, R2-2, R3-3, R4-1, G1), (A'2, R1-1, R2-2, R3-3, R4-1, G2),
(A'2, R1-1, R2-2, R3-3, R4-1, G3), (A'2, R1-1, R2-2, R3-3, R4-1, G4),
(A'2, R1-1, R2-2, R3-3, R4-1, G5), (A'2, R1-1, R2-2, R3-3, R4-2, G1),
(A'2, R1-1, R2-2, R3-3, R4-2, G2), (A'2, R1-1, R2-2, R3-3, R4-2, G3),
(A'2, R1-1, R2-2, R3-3, R4-2, G4), (A'2, R1-1, R2-2, R3-3, R4-2, G5),
(A'2, R1-2, R2-1, R3-1, R4-1, G1), (A'2, R1-2, R2-1, R3-1, R4-1, G2),
(A'2, R1-2, R2-1, R3-1, R4-1, G3), (A'2, R1-2, R2-1, R3-1, R4-1, G4),
(A'2, R1-2, R2-1, R3-1, R4-1, G5), (A'2, R1-2, R2-1, R3-1, R4-2, G1),
(A'2, R1-2, R2-1, R3-1, R4-2, G2), (A'2, R1-2, R2-1, R3-1, R4-2, G3),
(A'2, R1-2, R2-1, R3-1, R4-2, G4), (A'2, R1-2, R2-1, R3-1, R4-2, G5),
(A'2, R1-2, R2-1, R3-2, R4-1, G1), (A'2, R1-2, R2-1, R3-2, R4-1, G2),
(A'2, R1-2, R2-1, R3-2, R4-1, G3), (A'2, R1-2, R2-1, R3-2, R4-1, G4),
(A'2, R1-2, R2-1, R3-2, R4-1, G5), (A'2, R1-2, R2-1, R3-2, R4-2, G1),
(A'2, R1-2, R2-1, R3-2, R4-2, G2), (A'2, R1-2, R2-1, R3-2, R4-2, G3),
(A'2, R1-2, R2-1, R3-2, R4-2, G4), (A'2, R1-2, R2-1, R3-2, R4-2, G5),
(A'2, R1-2, R2-1, R3-3, R4-1, G1), (A'2, R1-2, R2-1, R3-3, R4-1, G2),
(A'2, R1-2, R2-1, R3-3, R4-1, G3), (A'2, R1-2, R2-1, R3-3, R4-1, G4),
(A'2, R1-2, R2-1, R3-3, R4-1, G5), (A'2, R1-2, R2-1, R3-3, R4-2, G1),
(A'2, R1-2, R2-1, R3-3, R4-2, G2), (A'2, R1-2, R2-1, R3-3, R4-2, G3),
(A'2, R1-2, R2-1, R3-3, R4-2, G4), (A'2, R1-2, R2-1, R3-3, R4-2, G5),
(A'2, R1-2, R2-2, R3-1, R4-1, G1), (A'2, R1-2, R2-2, R3-1, R4-1, G2),
(A'2, R1-2, R2-2, R3-1, R4-1, G3), (A'2, R1-2, R2-2, R3-1, R4-1, G4),
(A'2, R1-2, R2-2, R3-1, R4-1, G5), (A'2, R1-2, R2-2, R3-1, R4-2, G1),
(A'2, R1-2, R2-2, R3-1, R4-2, G2), (A'2, R1-2, R2-2, R3-1, R4-2, G3),
(A'2, R1-2, R2-2, R3-1, R4-2, G4), (A'2, R1-2, R2-2, R3-1, R4-2, G5),
(A'2, R1-2, R2-2, R3-2, R4-1, G1), (A'2, R1-2, R2-2, R3-2, R4-1, G2),
(A'2, R1-2, R2-2, R3-2, R4-1, G3), (A'2, R1-2, R2-2, R3-2, R4-1, G4),
(A'2, R1-2, R2-2, R3-2, R4-1, G5), (A'2, R1-2, R2-2, R3-2, R4-2, G1),
(A'2, R1-2, R2-2, R3-2, R4-2, G2), (A'2, R1-2, R2-2, R3-2, R4-2, G3),
(A'2, R1-2, R2-2, R3-2, R4-2, G4), (A'2, R1-2, R2-2, R3-2, R4-2, G5),
(A'2, R1-2, R2-2, R3-3, R4-1, G1), (A'2, R1-2, R2-2, R3-3, R4-1, G2),
(A'2, R1-2, R2-2, R3-3, R4-1, G3), (A'2, R1-2, R2-2, R3-3, R4-1, G4),
(A'2, R1-2, R2-2, R3-3, R4-1, G5), (A'2, R1-2, R2-2, R3-3, R4-2, G1),
(A'2, R1-2, R2-2, R3-3, R4-2, G2), (A'2, R1-2, R2-2, R3-3, R4-2, G3),
(A'2, R1-2, R2-2, R3-3, R4-2, G4), (A'2, R1-2, R2-2, R3-3, R4-2, G5),
(A'3, R1-1, R2-1, R3-1, R4-1, G1), (A'3, R1-1, R2-1, R3-1, R4-1, G2),
(A'3, R1-1, R2-1, R3-1, R4-1, G3), (A'3, R1-1, R2-1, R3-1, R4-1, G4),
(A'3, R1-1, R2-1, R3-1, R4-1, G5), (A'3, R1-1, R2-1, R3-1, R4-2, G1),
(A'3, R1-1, R2-1, R3-1, R4-2, G2), (A'3, R1-1, R2-1, R3-1, R4-2, G3),
(A'3, R1-1, R2-1, R3-1, R4-2, G4), (A'3, R1-1, R2-1, R3-1, R4-2, G5),
(A'3, R1-1, R2-1, R3-2, R4-1, G1), (A'3, R1-1, R2-1, R3-2, R4-1, G2),
(A'3, R1-1, R2-1, R3-2, R4-1, G3), (A'3, R1-1, R2-1, R3-2, R4-1, G4),
(A'3, R1-1, R2-1, R3-2, R4-1, G5), (A'3, R1-1, R2-1, R3-2, R4-2, G1),
(A'3, R1-1, R2-1, R3-2, R4-2, G2), (A'3, R1-1, R2-1, R3-2, R4-2, G3),
(A'3, R1-1, R2-1, R3-2, R4-2, G4), (A'3, R1-1, R2-1, R3-2, R4-2, G5),
(A'3, R1-1, R2-1, R3-3, R4-1, G1), (A'3, R1-1, R2-1, R3-3, R4-1, G2),
(A'3, R1-1, R2-1, R3-3, R4-1, G3), (A'3, R1-1, R2-1, R3-3, R4-1, G4),
(A'3, R1-1, R2-1, R3-3, R4-1, G5), (A'3, R1-1, R2-1, R3-3, R4-2, G1),
(A'3, R1-1, R2-1, R3-3, R4-2, G2), (A'3, R1-1, R2-1, R3-3, R4-2, G3),
(A'3, R1-1, R2-1, R3-3, R4-2, G4), (A'3, R1-1, R2-1, R3-3, R4-2, G5),
(A'3, R1-1, R2-2, R3-1, R4-1, G1), (A'3, R1-1, R2-2, R3-1, R4-1, G2), (A'3, R1-1, R2-2, R3-1, R4-1, G3), (A'3, R1-1, R2-2, R3-1, R4-1, G4),
(A'3, R1-1, R2-2, R3-1, R4-1, G5), (A'3, R1-1, R2-2, R3-1, R4-2, G1),
(A'3, R1-1, R2-2, R3-1, R4-2, G2), (A'3, R1-1, R2-2, R3-1, R4-2, G3),
(A'3, R1-1, R2-2, R3-1, R4-2, G4), (A'3, R1-1, R2-2, R3-1, R4-2, G5),
(A'3, R1-1, R2-2, R3-2, R4-1, G1), (A'3, R1-1, R2-2, R3-2, R4-1, G2),
(A'3, R1-1, R2-2, R3-2, R4-1, G3), (A'3, R1-1, R2-2, R3-2, R4-1, G4),
(A'3, R1-1, R2-2, R3-2, R4-1, G5), (A'3, R1-1, R2-2, R3-2, R4-2, G1),
(A'3, R1-1, R2-2, R3-2, R4-2, G2), (A'3, R1-1, R2-2, R3-2, R4-2, G3),
(A'3, R1-1, R2-2, R3-2, R4-2, G4), (A'3, R1-1, R2-2, R3-2, R4-2, G5),
(A'3, R1-1, R2-2, R3-3, R4-1, G1), (A'3, R1-1, R2-2, R3-3, R4-1, G2),
(A'3, R1-1, R2-2, R3-3, R4-1, G3), (A'3, R1-1, R2-2, R3-3, R4-1, G4),
(A'3, R1-1, R2-2, R3-3, R4-1, G5), (A'3, R1-1, R2-2, R3-3, R4-2, G1),
(A'3, R1-1, R2-2, R3-3, R4-2, G2), (A'3, R1-1, R2-2, R3-3, R4-2, G3),
(A'3, R1-1, R2-2, R3-3, R4-2, G4), (A'3, R1-1, R2-2, R3-3, R4-2, G5),
(A'3, R1-2, R2-1, R3-1, R4-1, G1), (A'3, R1-2, R2-1, R3-1, R4-1, G2),
(A'3, R1-2, R2-1, R3-1, R4-1, G3), (A'3, R1-2, R2-1, R3-1, R4-1, G4),
(A'3, R1-2, R2-1, R3-1, R4-1, G5), (A'3, R1-2, R2-1, R3-1, R4-2, G1),
(A'3, R1-2, R2-1, R3-1, R4-2, G2), (A'3, R1-2, R2-1, R3-1, R4-2, G3),
(A'3, R1-2, R2-1, R3-1, R4-2, G4), (A'3, R1-2, R2-1, R3-1, R4-2, G5),
(A'3, R1-2, R2-1, R3-2, R4-1, G1), (A'3, R1-2, R2-1, R3-2, R4-1, G2),
(A'3, R1-2, R2-1, R3-2, R4-1, G3), (A'3, R1-2, R2-1, R3-2, R4-1, G4),
(A'3, R1-2, R2-1, R3-2, R4-1, G5), (A'3, R1-2, R2-1, R3-2, R4-2, G1),
(A'3, R1-2, R2-1, R3-2, R4-2, G2), (A'3, R1-2, R2-1, R3-2, R4-2, G3),
(A'3, R1-2, R2-1, R3-2, R4-2, G4), (A'3, R1-2, R2-1, R3-2, R4-2, G5),
(A'3, R1-2, R2-1, R3-3, R4-1, G1), (A'3, R1-2, R2-1, R3-3, R4-1, G2),
(A'3, R1-2, R2-1, R3-3, R4-1, G3), (A'3, R1-2, R2-1, R3-3, R4-1, G4),
(A'3, R1-2, R2-1, R3-3, R4-1, G5), (A'3, R1-2, R2-1, R3-3, R4-2, G1),
(A'3, R1-2, R2-1, R3-3, R4-2, G2), (A'3, R1-2, R2-1, R3-3, R4-2, G3),
(A'3, R1-2, R2-1, R3-3, R4-2, G4), (A'3, R1-2, R2-1, R3-3, R4-2, G5),
(A'3, R1-2, R2-2, R3-1, R4-1, G1), (A'3, R1-2, R2-2, R3-1, R4-1, G2),
(A'3, R1-2, R2-2, R3-1, R4-1, G3), (A'3, R1-2, R2-2, R3-1, R4-1, G4),
(A'3, R1-2, R2-2, R3-1, R4-1, G5), (A'3, R1-2, R2-2, R3-1, R4-2, G1),
(A'3, R1-2, R2-2, R3-1, R4-2, G2), (A'3, R1-2, R2-2, R3-1, R4-2, G3),
(A'3, R1-2, R2-2, R3-1, R4-2, G4), (A'3, R1-2, R2-2, R3-1, R4-2, G5),
(A'3, R1-2, R2-2, R3-2, R4-1, G1), (A'3, R1-2, R2-2, R3-2, R4-1, G2),
(A'3, R1-2, R2-2, R3-2, R4-1, G3), (A'3, R1-2, R2-2, R3-2, R4-1, G4),
(A'3, R1-2, R2-2, R3-2, R4-1, G5), (A'3, R1-2, R2-2, R3-2, R4-2, G1),
(A'3, R1-2, R2-2, R3-2, R4-2, G2), (A'3, R1-2, R2-2, R3-2, R4-2, G3),
(A'3, R1-2, R2-2, R3-2, R4-2, G4), (A'3, R1-2, R2-2, R3-2, R4-2, G5),
(A'3, R1-2, R2-2, R3-3, R4-1, G1), (A'3, R1-2, R2-2, R3-3, R4-1, G2),
(A'3, R1-2, R2-2, R3-3, R4-1, G3), (A'3, R1-2, R2-2, R3-3, R4-1, G4),
(A'3, R1-2, R2-2, R3-3, R4-1, G5), (A'3, R1-2, R2-2, R3-3, R4-2, G1),
(A'3, R1-2, R2-2, R3-3, R4-2, G2), (A'3, R1-2, R2-2, R3-3, R4-2, G3),
(A'3, R1-2, R2-2, R3-3, R4-2, G4), (A'3, R1-2, R2-2, R3-3, R4-2, G5),
(A'4, R1-1, R2-1, R3-1, R4-1, G1), (A'4, R1-1, R2-1, R3-1, R4-1, G2),
(A'4, R1-1, R2-1, R3-1, R4-1, G3), (A'4, R1-1, R2-1, R3-1, R4-1, G4),
(A'4, R1-1, R2-1, R3-1, R4-1, G5), (A'4, R1-1, R2-1, R3-1, R4-2, G1),
(A'4, R1-1, R2-1, R3-1, R4-2, G2), (A'4, R1-1, R2-1, R3-1, R4-2, G3),
(A'4, R1-1, R2-1, R3-1, R4-2, G4), (A'4, R1-1, R2-1, R3-1, R4-2, G5),
(A'4, R1-1, R2-1, R3-2, R4-1, G1), (A'4, R1-1, R2-1, R3-2, R4-1, G2),
(A'4, R1-1, R2-1, R3-2, R4-1, G3), (A'4, R1-1, R2-1, R3-2, R4-1, G4),
(A'4, R1-1, R2-1, R3-2, R4-1, G5), (A'4, R1-1, R2-1, R3-2, R4-2, G1),
(A'4, R1-1, R2-1, R3-2, R4-2, G2), (A'4, R1-1, R2-1, R3-2, R4-2, G3),
(A'4, R1-1, R2-1, R3-2, R4-2, G4), (A'4, R1-1, R2-1, R3-2, R4-2, G5),
(A'4, R1-1, R2-1, R3-3, R4-1, G1), (A'4, R1-1, R2-1, R3-3, R4-1, G2),
(A'4, R1-1, R2-1, R3-3, R4-1, G3), (A'4, R1-1, R2-1, R3-3, R4-1, G4),
(A'4, R1-1, R2-1, R3-3, R4-1, G5), (A'4, R1-1, R2-1, R3-3, R4-2, G1),
(A'4, R1-1, R2-1, R3-3, R4-2, G2), (A'4, R1-1, R2-1, R3-3, R4-2, G3),
(A'4, R1-1, R2-1, R3-3, R4-2, G4), (A'4, R1-1, R2-1, R3-3, R4-2, G5),
(A'4, R1-1, R2-2, R3-1, R4-1, G1), (A'4, R1-1, R2-2, R3-1, R4-1, G2),
(A'4, R1-1, R2-2, R3-1, R4-1, G3), (A'4, R1-1, R2-2, R3-1, R4-1, G4),
(A'4, R1-1, R2-2, R3-1, R4-1, G5), (A'4, R1-1, R2-2, R3-1, R4-2, G1),
(A'4, R1-1, R2-2, R3-1, R4-2, G2), (A'4, R1-1, R2-2, R3-1, R4-2, G3),
(A'4, R1-1, R2-2, R3-1, R4-2, G4), (A'4, R1-1, R2-2, R3-1, R4-2, G5),
(A'4, R1-1, R2-2, R3-2, R4-1, G1), (A'4, R1-1, R2-2, R3-2, R4-1, G2),
(A'4, R1-1, R2-2, R3-2, R4-1, G3), (A'4, R1-1, R2-2, R3-2, R4-1, G4), (A'4, R1-1, R2-2, R3-2, R4-1, G5), (A'4, R1-1, R2-2, R3-2, R4-2, G0,
(A'4, R1-1, R2-2, R3-2, R4-2, G2), (A'4, R1-1, R2-2, R3-2, R4-2, G3),
(A'4, R1-1, R2-2, R3-2, R4-2, G4), (A'4, R1-1, R2-2, R3-2, R4-2, G5),
(A'4, R1-1, R2-2, R3-3, R4-1, G1), (A'4, R1-1, R2-2, R3-3, R4-1, G2),
(A'4, R1-1, R2-2, R3-3, R4-1, G3), (A'4, R1-1, R2-2, R3-3, R4-1, G4),
(A'4, R1-1, R2-2, R3-3, R4-1, G5), (A'4, R1-1, R2-2, R3-3, R4-2, G1),
(A'4, R1-1, R2-2, R3-3, R4-2, G2), (A'4, R1-1, R2-2, R3-3, R4-2, G3),
(A'4, R1-1, R2-2, R3-3, R4-2, G4), (A'4, R1-1, R2-2, R3-3, R4-2, G5),
(A'4, R1-2, R2-1, R3-1, R4-1, G1), (A'4, R1-2, R2-1, R3-1, R4-1, G2),
(A'4, R1-2, R2-1, R3-1, R4-1, G3), (A'4, R1-2, R2-1, R3-1, R4-1, G4),
(A'4, R1-2, R2-1, R3-1, R4-1, G5), (A'4, R1-2, R2-1, R3-1, R4-2, G1),
(A'4, R1-2, R2-1, R3-1, R4-2, G2), (A'4, R1-2, R2-1, R3-1, R4-2, G3),
(A'4, R1-2, R2-1, R3-1, R4-2, G4), (A'4, R1-2, R2-1, R3-1, R4-2, G5),
(A'4, R1-2, R2-1, R3-2, R4-1, G1), (A'4, R1-2, R2-1, R3-2, R4-1, G2),
(A'4, R1-2, R2-1, R3-2, R4-1, G3), (A'4, R1-2, R2-1, R3-2, R4-1, G4),
(A'4, R1-2, R2-1, R3-2, R4-1, G5), (A'4, R1-2, R2-1, R3-2, R4-2, G0,
(A'4, R1-2, R2-1, R3-2, R4-2, G2), (A'4, R1-2, R2-1, R3-2, R4-2, G3),
(A'4, R1-2, R2-1, R3-2, R4-2, G4), (A'4, R1-2, R2-1, R3-2, R4-2, G5),
(A'4, R1-2, R2-1, R3-3, R4-1, G1), (A'4, R1-2, R2-1, R3-3, R4-1, G2),
(A'4, R1-2, R2-1, R3-3, R4-1, G3), (A'4, R1-2, R2-1, R3-3, R4-1, G4),
(A'4, R1-2, R2-1, R3-3, R4-1, G5), (A'4, R1-2, R2-1, R3-3, R4-2, G1),
(A'4, R1-2, R2-1, R3-3, R4-2, G2), (A'4, R1-2, R2-1, R3-3, R4-2, G3),
(A'4, R1-2, R2-1, R3-3, R4-2, G4), (A'4, R1-2, R2-1, R3-3, R4-2, G5),
(A'4, R1-2, R2-2, R3-1, R4-1, G1), (A'4, R1-2, R2-2, R3-1, R4-1, G2),
(A'4, R1-2, R2-2, R3-1, R4-1, G3), (A'4, R1-2, R2-2, R3-1, R4-1, G4),
(A'4, R1-2, R2-2, R3-1, R4-1, G5), (A'4, R1-2, R2-2, R3-1, R4-2, G1),
(A'4, R1-2, R2-2, R3-1, R4-2, G2), (A'4, R1-2, R2-2, R3-1, R4-2, G3),
(A'4, R1-2, R2-2, R3-1, R4-2, G4), (A'4, R1-2, R2-2, R3-1, R4-2, G5),
(A'4, R1-2, R2-2, R3-2, R4-1, G1), (A'4, R1-2, R2-2, R3-2, R4-1, G2),
(A'4, R1-2, R2-2, R3-2, R4-1, G3), (A'4, R1-2, R2-2, R3-2, R4-1, G4),
(A'4, R1-2, R2-2, R3-2, R4-1, G5), (A'4, R1-2, R2-2, R3-2, R4-2, G1),
(A'4, R1-2, R2-2, R3-2, R4-2, G2), (A'4, R1-2, R2-2, R3-2, R4-2, G3),
(A'4, R1-2, R2-2, R3-2, R4-2, G4), (A'4, R1-2, R2-2, R3-2, R4-2, G5),
(A'4, R1-2, R2-2, R3-3, R4-1, G1), (A'4, R1-2, R2-2, R3-3, R4-1, G2),
(A'4, R1-2, R2-2, R3-3, R4-1, G3), (A'4, R1-2, R2-2, R3-3, R4-1, G4),
(A'4, R1-2, R2-2, R3-3, R4-1, G5), (A'4, R1-2, R2-2, R3-3, R4-2, G1),
(A'4, R1-2, R2-2, R3-3, R4-2, G2), (A'4, R1-2, R2-2, R3-3, R4-2, G3),
(A'4, R1-2, R2-2, R3-3, R4-2, G4), (A'4, R1-2, R2-2, R3-3, R4-2, G5).

The present compounds are useful in disease induced by the generation, secretion or deposition of amyloid β protein, and are effective in treatment and/or prevention, and symptom improvement of such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, amyloid angiopathy and so on.

Since the present compound has high inhibitory activity on β secretase, and/or has high selectivity on other enzymes, it can be a medicament with reduced side effect. Further, since the compound has high effect of reducing amyloid β production in a cell system, particularly, has high effect of reducing amyloid β production in brain, it can be an excellent medicament. In addition, by converting the compound into an optically active body having suitable stereochemistry, the compound can be a medicament having a wider safety margin on the side effect. In addition, the present compound also has advantages that metabolism stability is high, solubility is high, oral absorbability is high, good bioavailability is exhibited, clearance is good, brain transference is high, a half life is high, non-protein binding rate is high, hERG channel inhibition is low, CYP inhibition is low, and/or an Ames test is negative.

The present compounds can be administered in combination with other pharmaceutical agents such as other therapeutic drugs for Alzheimer's disease, e.g., acetylcholinesterase inhibitors and the like. The present compounds can be treated with concomitantly with the anti-dementia agents such as Donepezil Hydrochloride, Tacrine, Galantamine, Rivastigmine, Zanapezil, Memantine, and Vinpocetine.

When the present compound is administered to a human, it can be administered orally as powders, granules, tablets, capsules, pills, solutions, or the like, or parenterally as injectables, suppositories, transdermal absorbable agents, absorbable agents, or the like. In addition, the present compound can be formulated into pharmaceutical preparations by adding pharmaceutical additives such as excipients, binders, wetting agents, disintegrating agents, lubricants and the like, which are suitable for formulations and an effective amount of the present compound.

A dose is different depending on state of disease, an administration route, and an age and a weight of a patient, and is usually 0.1 μg to 1 g/day, preferably 0.01 to 200 mg/day when orally administered to an adult, and is usually 0.1 μg to 10 g/day, preferably 0.1 to 2 g/day when parenterally administered.

EXAMPLES

Following examples and test examples illustrate the present invention in more detail, but the present invention is not limited by these examples.

In example, the meaning of each abbreviation is following.
Me methyl
Et ethyl
iPr or Pri isopropyl
Ph phenyl
Bn benzyl
Bz benzoyl
Boc t-butoxycarbonyl
Fmoc 9-fluorenylmethyloxycarbonyl
Trt trityl
TFA trifluoroacetyl
DMAC dimethylacetamide
THF tetrahydrofuran
DMSO dimethyl sulfoxide
DMT-MM 4-(4,6-dimethoxy-1,3,5-triazine-2-yl)-4-methyl-morpholinium chloride
DMF N,N-dimethylformamide
mCPBA metachloroperbenzoic acid
Secondary generation Grubbs' catalyst benzylidene[1,3-bis(2,4,6-trimethylphenyl)-2-imidazolidi-nylidene]dichloro(tricyclohexylphosphine)ruthenium LCMS data of the present compound were measured under any of the following conditions (Methods A and B), and a retention time and [M+H]$^+$ are shown.

(Method A)
Column: Waters XBridge C18 5 μm
Size: 4.6×50 mm
Flow rate: 3 mL/min
Column oven: 50° C.
UV detection wavelength: PDA (254 mm)
Linear gradient of 10% to 100% solvent (0.1% formic acid-containing acetonitrile solution) for 3 minutes was performed, and 100% solvent (0.1% formic acid-containing acetonitrile solution) was maintained for 0.5 minutes.

(Method B)
Column: Shimadzu Shim pack XR-ODS 50L×3.0
Size: 50×3.0 mm
Flow rate: 1.6 mL/min
Column oven: 50° C.
UV detection wavelength: PDA (254 mm)
Linear gradient of 10% to 100% solvent (0.1% formic acid-containing acetonitrile solution) for 3 minutes was performed, and 100% solvent (0.1% formic acid-containing acetonitrile solution) was maintained for 0.5 minute.

Reference Example 1

Synthesis of Intermediate Compound (21)

[Chemical formula 27]

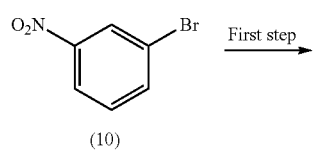

(10)

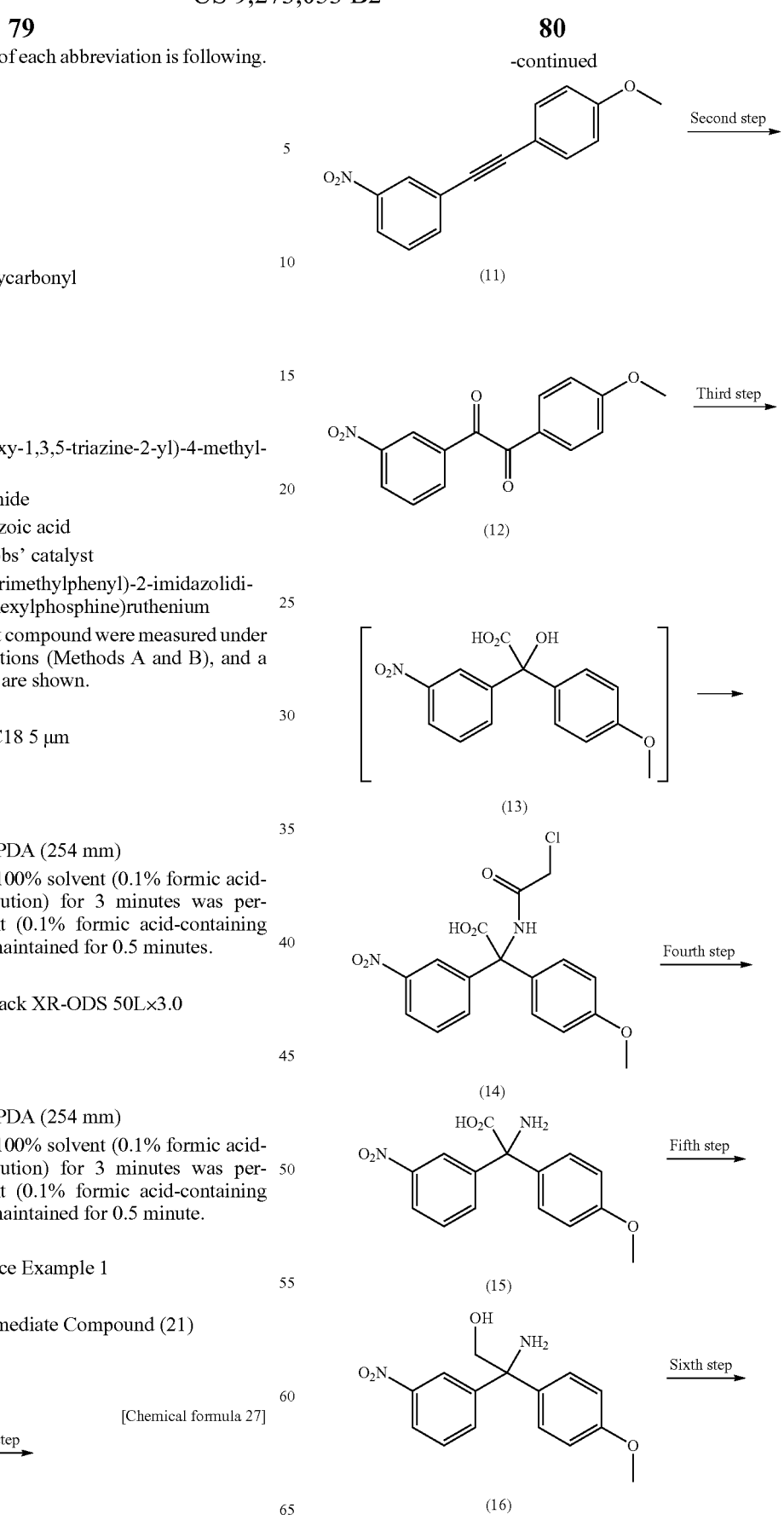

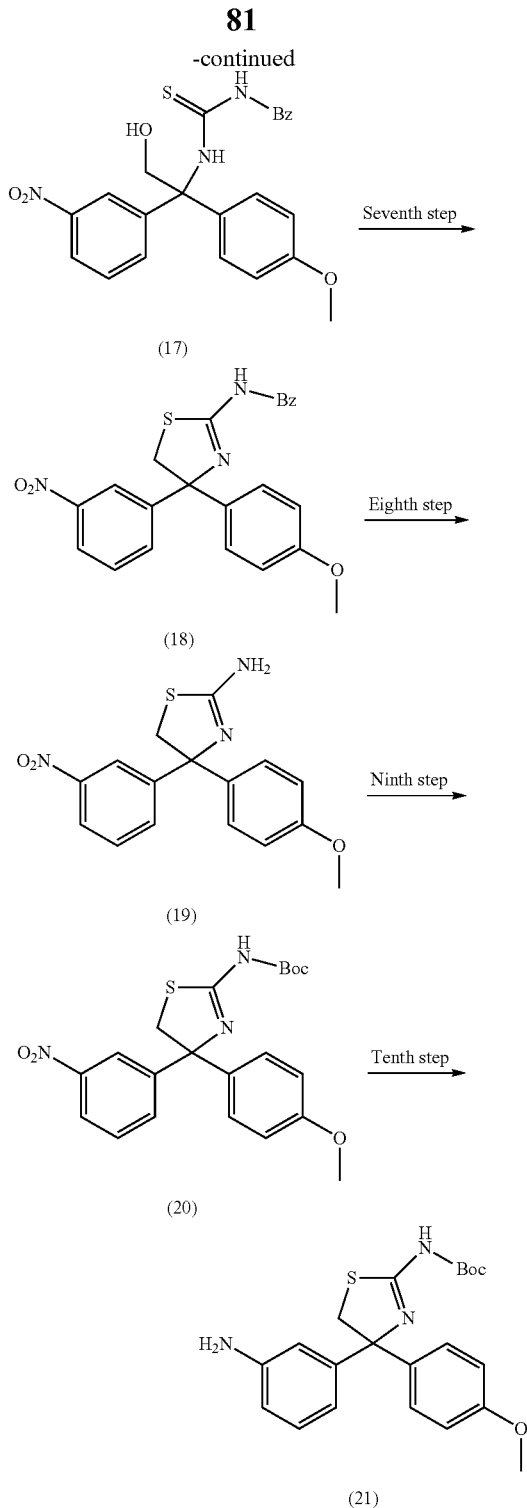

First Step

The compound (10) (7.17 g) was dissolved in tetrahydrofuran (70.0 ml), 1-ethynyl-4-methoxybenzene (5.63 g), tetrakistriphenylphosphine palladium (4.10 g), copper iodide (338 mg), and diisopropylamine (70.0 ml) were added, and the mixture was stirred at reflux for 30 minutes. The solvent was evaporated under reduced pressure, dichloromethane was added, and insolubles were removed. The residue was purified by column chromatography, dichloromethane and n-hexane were added, and the precipitated solid was collected by filtration to afford the compound (11) (8.99 g).

$^1$H-NMR (DMSO-d$_6$) δ: 3.81 (3H, s), 7.02 (2H, d, J=8.6 Hz), 7.57 (2H, d, J=8.6 Hz), 7.71 (1H, t, J=8.0 Hz), 7.96 (1H, d, J=7.6 Hz), 8.22 (1H, d, J=8.1 Hz), 8.30 (1H, s).

Second Step

The compound (11) (1.00 g) was dissolved in dimethyl sulfoxide (10.0 ml), iodine (501 mg) was added, and the mixture was heated to 165° C. and stirred for 2 hours. The reaction solvent was extracted with ethyl acetate, and the organic layer was washed with a sodium thiosulfate aqueous solution and distilled water. The organic layer was dried over anhydrous magnesium sulfate and the solvent was evaporated under reduced pressure. To the residue were added dichloromethane and diisopropyl ether, and the precipitated solid was collected by filtration to afford the compound (12) (532 mg).

$^1$H-NMR (DMSO-d$_6$) δ 3.89 (3H, s), 7.16 (2H, d, J=8.6 Hz), 7.91 (1H, t, J=8.0 Hz), 7.98 (2H, d, J=8.8 Hz), 8.33 (1H, d, J=7.3 Hz), 8.58-8.61 (2H, m).

Third Step

The compound (12) (2.00 g) was dissolved in ethanol (10.0 ml), potassium hydroxide (7.87 g) and distilled water (10.0 ml) were added, and the mixture was stirred at reflux for 3 hours. The reaction solution was extracted with distilled water and a potassium hydroxide aqueous solution, and the aqueous layer was washed with chloroform. The aqueous layer was neutralized with hydrochloric acid, and was extracted into the organic layer with a mixture of chloroform and methanol. The organic layer was dried over anhydrous sodium sulfate and under reduced pressure to afford the compound (13) (2.02 g). To the resulting compound (13) (2.02 g) were added 2-chloroacetonitrile (10.1 ml), acetic acid (12.8 ml), and concentrated sulfuric acid (12.8 ml), and the mixture was stirred at room temperature for 2 hours. The reaction solution was poured into ice-water, and the precipitated solid was collected by filtration to afford the compound (14) (2.34 g).

$^1$H-NMR (DMSO-d$_6$) δ: 3.74 (30H, s), 4.26 (2H, dd, J=20.5, 13.1 Hz), 6.94 (2H, d, J=8.8 Hz), 7.21 (2H, d, J=8.8 Hz), 7.62 (1H, t, J=8.0 Hz), 7.77 (1H, d, J=7.3 Hz), 8.14 (1H, d, J=7.6 Hz), 8.25 (1H, s), 9.22 (1H, s).

Fourth Step

To the compound (14) (2.34 g) were added thiourea (564 mg), ethanol (12.0 ml), and acetic acid (2.40 ml), and the mixture was heated at 80° C. and stirred overnight. The solvent was evaporated under reduced pressure, distilled water was added to the residue, and the precipitated solid was collected by filtration to afford the compound (15) (4.76 g).

$^1$H-NMR (DMSO-d$_6$) δ: 3.75 (3H, s), 3.89 (2H, s), 6.89 (2H, d, J=8.8 Hz), 7.22 (2H, br s), 7.30 (2H, d, J=8.8 Hz), 7.58 (1H, t, J=8.0 Hz), 7.81 (1H, d, J=8.3 Hz), 8.11 (1H, d, J=8.1 Hz), 8.34 (1H, s).

Fifth Step

The compound (15) (455 mg) was dissolved in tetrahydrofuran (5.00 ml), and a 0.99 mol/L borane/tetrahydrofuran complex (10.0 ml) was added. After stirred at 0° C. for 1 hour, the mixture was stirred at room temperature for additional 3 hours. To the reaction solution was added 2 mol/L hydrochloric acid (6.8 ml), the solvent was concentrated, and the insolubles were removed by filtration. The resulting filtrate was extracted with distilled water, and washed with dichloromethane. The resulting aqueous layer was neutralized with hydrochloric acid, extracted with a mixture of dichloromethane and methanol, and the solvent was evaporated under reduced pressure to afford the compound (16) (300 mg).

¹H-NMR (DMSO-d₆) δ: 3.71 (3H, s), 3.83 (1H, d, J=9.9 Hz), 4.04 (1H, d, J=6.6 Hz), 5.10 (1H, s), 5.75 (2H, s), 6.84 (2H, d, J=8.6 Hz), 7.33 (2H, d, J=8.6 Hz), 7.55 (1H, t, J=8.0 Hz), 7.83 (1H, d, J=8.1 Hz), 8.04 (1H, d, J=7.1 Hz), 8.34 (1H, s).

Sixth Step

The compound (16) (300 mg) was dissolved in acetone (3.00 ml), benzoyl isothiocyanate (187 mg) was added, and the mixture was stirred at room temperature for 1 hour. The solvent was evaporated under reduced pressure, and the residue was purified by chromatography to afford the compound (17) (470 mg).

¹H-NMR (DMSO-d₆) δ: 3.76 (3H, s), 4.54 (2H, s), 5.42 (1H, s), 6.94 (2H, d, J=8.8 Hz), 7.34 (2H, d, J=8.8 Hz), 7.53 (2H, t, J=7.8 Hz), 7.64 (2H, dd, J=13.6, 7.6 Hz), 7.86 (1H, d, J=8.6 Hz), 7.98 (2H, d, J=7.3 Hz), 8.13 (1H, d, J=8.1 Hz), 8.22 (1H, s), 8.31 (2H, s), 11.20 (1H, s), 12.15 (1H, s).

Seventh Step

The compound (17) (31.2 mg) was dissolved in dichloromethane (1.00 ml), 1-chloro-2-trimethylpropenylamine (0.0183 ml) was added, and the mixture was stirred at room temperature for 2 hours. The reaction solution was extracted with dichloromethane, the organic layer was washed with distilled water, and the solvent was evaporated under reduced pressure to afford the compound (18) (15.6 mg).

¹H-NMR (DMSO-d₆) δ: 3.74 (3H, s), 3.97 (2H, dd, J=20.2, 11.6 Hz), 6.94 (2H, d, J=8.3 Hz), 7.43 (2H, d, J=8.6 Hz), 7.49 (2H, t, J=7.5 Hz), 7.59 (1H, t, J=7.1 Hz), 7.68 (1H, t, J=8.0 Hz), 7.94 (1H, d, J=7.3 Hz), 8.08 (2H, d, J=7.3 Hz), 8.15 (1H, d, J=8.6 Hz), 8.36 (1H, s).

Eighth Step

The compound (18) (320 mg) was dissolved in methanol (3.00 ml), hydrazine monohydrate (0.107 ml) was added, and the mixture was stirred at 40° C. for 3 hours and stirred at room temperature for additional 14 hours. The solvent was evaporated under reduced pressure, and the residue was purified by column chromatography to afford the compound (19) (128 mg).

¹H-NMR (DMSO-d₆) δ: 3.71 (3H, s), 3.93 (2H, s), 6.78 (2H, s), 6.85 (2H, d, J=8.8 Hz), 7.40 (2H, d, J=8.8 Hz), 7.58 (1H, t, J=8.2 Hz), 7.89 (1H, d, J=7.6 Hz), 8.04 (1H, d, J=8.8 Hz), 8.32 (1H, s).

Ninth Step

The compound (19) (120 mg) was dissolved in dichloromethane (1.20 ml), di-t-butyl dicarbonate (564 mg) was added, and the mixture was stirred at room temperature for 6 hours. The solvent was evaporated under reduced pressure, and the residue was purified by column chromatography to afford the compound (20) (105 mg).

¹H-NMR (DMSO-d₆) δ: 1.41 (9H, s), 3.72 (3H, s), 3.90 (2H, dd, J=22.7, 12.6 Hz), 6.89 (2H, d, J=7.8 Hz), 7.37 (2H, d, J=8.8 Hz), 7.64 (1H, s), 7.88 (1H, d, J=6.6 Hz), 8.10 (1H, s), 8.30 (1H, d, J=9.1 Hz).

Tenth Step

The compound (20) (106 mg) was dissolved in methanol, 10% palladium carbon (52.5 mg) was added, and the mixture was stirred for 5 hours under the hydrogen atmosphere. The insolubles were removed by filtration with Celite, and the solvent was evaporated under reduced pressure to afford the compound (21) (98.7 mg).

¹H-NMR (DMSO-d₆) δ: 1.40 (9H, s), 3.70-3.73 (4H, m), 3.84 (1H, d, J=11.4 Hz), 6.85-6.89 (3H, m), 6.96-6.99 (2H, m), 7.20 (1H, t, J=7.2 Hz), 7.33 (2H, d, J=8.8 Hz).

Reference Example 2

Synthesis of Intermediate Compound (31)

[Chemical formula 28]

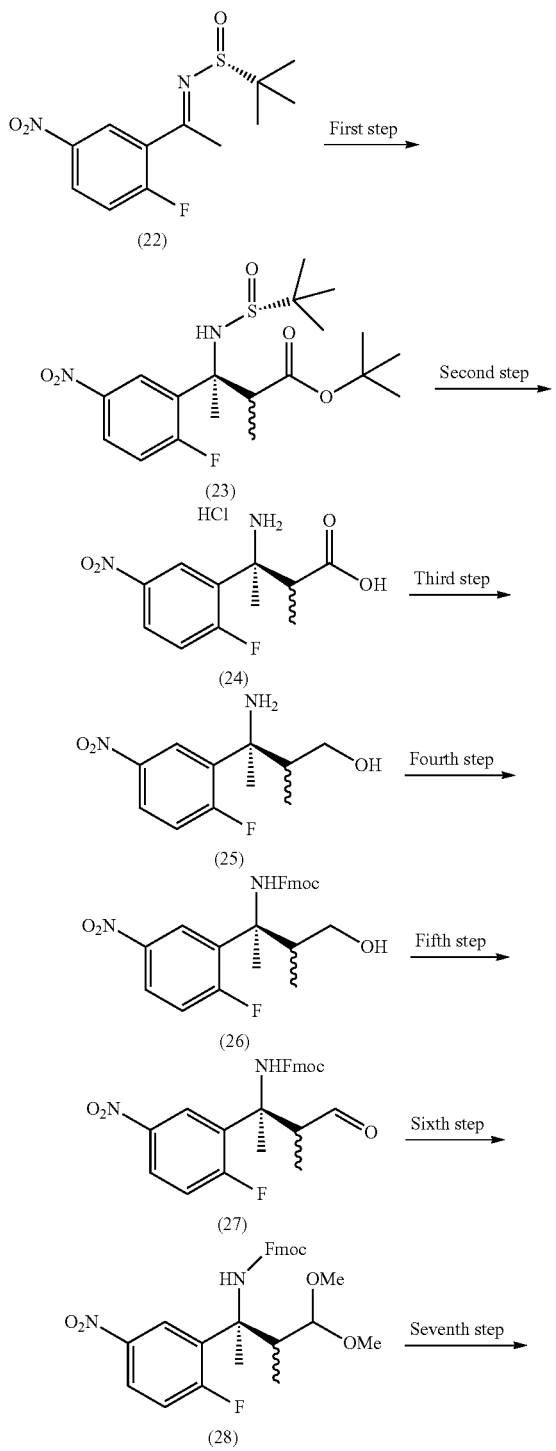

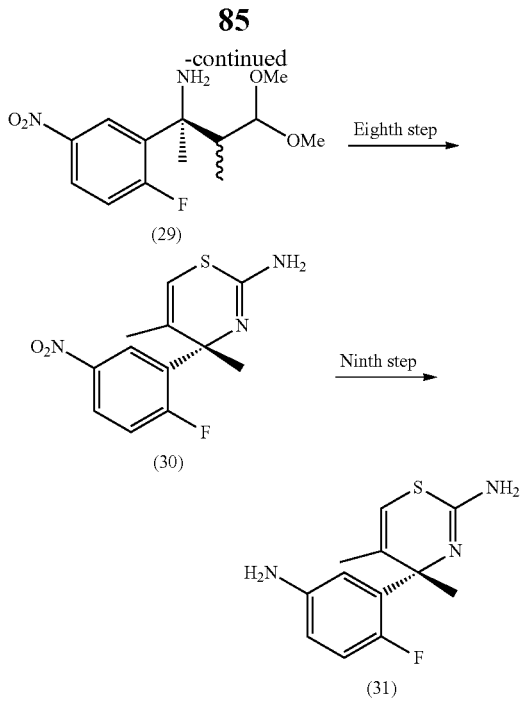

First Step

To a stirred solution of 2.0 mol/L lithium diisopropylamide in normal heptane/ethylbenzene/tetrahydrofuran (16.2 ml) at −78° C. was added dropwise over 10 minutes a solution of t-butyl propionate (4.73 ml) in tetrahydrofuran (10 ml). After stirred at −78° C. for 1 hour and 20 minutes, a solution of chlorotitanium triisopropoxide (12.0 g) in tetrahydrofuran (20 ml) was added dropwise over 40 minutes. After stirred at −78° C. for 1 hour, a solution of a compound (22) (3.00 g) in tetrahydrofuran (10 ml) was added dropwise over 30 minutes. After stirred at −78° C. for 1 hour, the mixture was added to a saturated ammonium chloride aqueous solution in portions in an ice bath, and the resulting insolubles were separated by filtration. The insolubles were washed with ethyl acetate, and the organic layer was dried over anhydrous magnesium sulfate. The solvent was evaporated under reduced pressure to afford the compound (23) (5.00 g) as a crude product.

Second Step

To the compound (23) (5.00 g) obtained in the first step were added a 4 mol/L hydrochloric acid/dioxane solution (39 ml) and methanol (1.2 ml), and the mixture was stirred at room temperature overnight. Diethyl ether (60 ml) was added, and the precipitate was collected by filtration to afford the compound (24) (2.37 g) as a crude product.

Third Step

The compound (24) (2.37 g) obtained in the second step was suspended in tetrahydrofuran (8 ml), and a 1 mol/L borane/tetrahydrofuran solution (24 ml) was added at 0° C. After stirred at room temperature for 3.5 hours, the mixture was poured into ice water, and a 1 mol/L sodium hydroxide aqueous solution was added to make alkaline. The mixture was extracted with ethyl acetate, and the organic layer was dried over anhydrous magnesium sulfate. The solvent was evaporated under reduced pressure to afford the compound (25) (1.67 g) as a crude product.

Fourth Step

To a solution of the compound (25) (1.67 g) obtained in the third step in tetrahydrofuran (16 ml) were added water (8 ml), sodium hydrogen carbonate (1.74 g) and N-(fluorenyl-methoxycarbonyloxy)succinic acid imide (1.74 g), the mixture was stirred at room temperature for 2 hours and 20 minutes, followed by extraction with ethyl acetate. The organic layer was dried over anhydrous magnesium sulfate, and the solvent was evaporated under reduced pressure to afford the compound (26) (3.72 g) as a crude product.

Fifth Step

To a solution of the compound (26) (3.72 g) obtained in the fourth step in dimethyl sulfoxide (15 ml) was added 2-iodoxybenzoic acid (1.93 g), and the mixture was stirred at room temperature for 2 hours and 30 minutes. Water and ethyl acetate were added, the resulting insolubles were removed by filtration, the organic layer was dried over anhydrous magnesium sulfate, and the solvent was evaporated under reduced pressure to afford the compound (27) (3.77 g) as a crude product.

Sixth Step

To a solution of the compound (27) (3.77 g) obtained in the fifth step in methanol (60 ml) were added methyl orthoformate (38 μl) and p-toluene sulfonic acid monohydrate (66 mg), and the mixture was stirred and heated at reflux for 30 minutes. The solvent was evaporated under reduced pressure, and the residue was diluted with ethyl acetate. The mixture was washed with a saturated sodium hydrogen carbonate aqueous solution, and the organic layer was dried over anhydrous magnesium sulfate. The solvent was evaporated under reduced pressure to afford the compound (28) (3.55 g) as a crude product.

Seventh Step

To a solution of the compound (28) (3.55 g) obtained in the sixth step in dimethylformamide (14 ml) was added piperidine (1 ml), and the mixture was stirred at room temperature for 30 minutes. Water was added, the mixture was extracted with ethyl acetate, and the organic layer was dried over anhydrous magnesium sulfate. The solvent was evaporated under reduced pressure, and the residue was subjected to column chromatography to afford the diastereomer mixture (29) (985 mg) at about 2:3 calculated from a proton ratio of $^1$H-NMR. $^1$H-NMR (diastereomer mixture, CDCl$_3$) δ 0.80 (d, J=7.2 Hz), 1.06 (d, J=7.2 Hz), 1.48 (d, J=1.4 Hz), 1.62 (d, J=1.7 Hz), 2.40-2.60 (m), 3.17 (s), 3.21 (s), 3.36 (s), 3.41 (s), 3.72 (d, J=2.6 Hz), 4.34 (d, J=3.8 Hz), 7.11-7.20 (m), 8.10-8.19 (m), 8.59 (dd, J=6.9, 3.0 Hz), 8.71 (dd, J=6.9, 2.9 Hz).

Eighth Step

To a solution of the compound (29) (985 mg) in acetone (5 ml) was added benzoyl isothiocyanate (497 μl) at 0° C., the mixture was stirred at 0° C. for 20 minutes, and the solvent was evaporated under reduced pressure. To the residue was added concentrated sulfuric acid (6 ml), the mixture was stirred at 50° C. overnight, an ice was added, and the mixture was made alkaline with a 28% ammonia aqueous solution while stirred under ice-cooling. The mixture was extracted with ethyl acetate, washed with water, and the organic layer was dried over anhydrous magnesium sulfate. The solvent was evaporated under reduced pressure to afford the compound (30) (968 mg).

$^1$H-NMR (CDCl$_3$) δ: 1.77 (3H, d, J=1.1 Hz), 1.82 (1H, d, J=1.4 Hz), 6.07 (1H, d, J=1.4 Hz), 7.15 (1H, dd, J=10.3, 8.9 Hz), 8.16 (1H, ddd, J=8.9, 4.0, 2.9 Hz), 8.30 (1H, dd, J=6.9, 2.9 Hz).

Ninth Step

To a solution of the compound (30) (968 mg) in acetic acid (8 ml) and water (1 ml) was added iron (769 mg), and the mixture was stirred at 60° C. The mixture was made alkaline with 28% aqueous ammonia, the resulting insolubles were removed by filtration, the filtrate was extracted with ethyl acetate, and dried over anhydrous magnesium sulfate. The solvent was evaporated under reduced pressure to afford the compound (31) (968 mg).

$^1$H-NMR (CDCl$_3$) δ: 1.66 (3H, s), 1.78 (3H, d, J=1.3 Hz), 3.51 (2H, br), 5.94 (1H, d, J=4.7, 1.5 Hz), 6.51 (1H, ddd, J=8.5, 3.8, 2.8 Hz), 6.66 (1H, dd, J=6.6, 2.8 Hz), 6.79 (1H, dd, J=11.4, 8.5 Hz).

Reference Example 3

Synthesis of Intermediate Compound (39)

[Chemical formula 29]

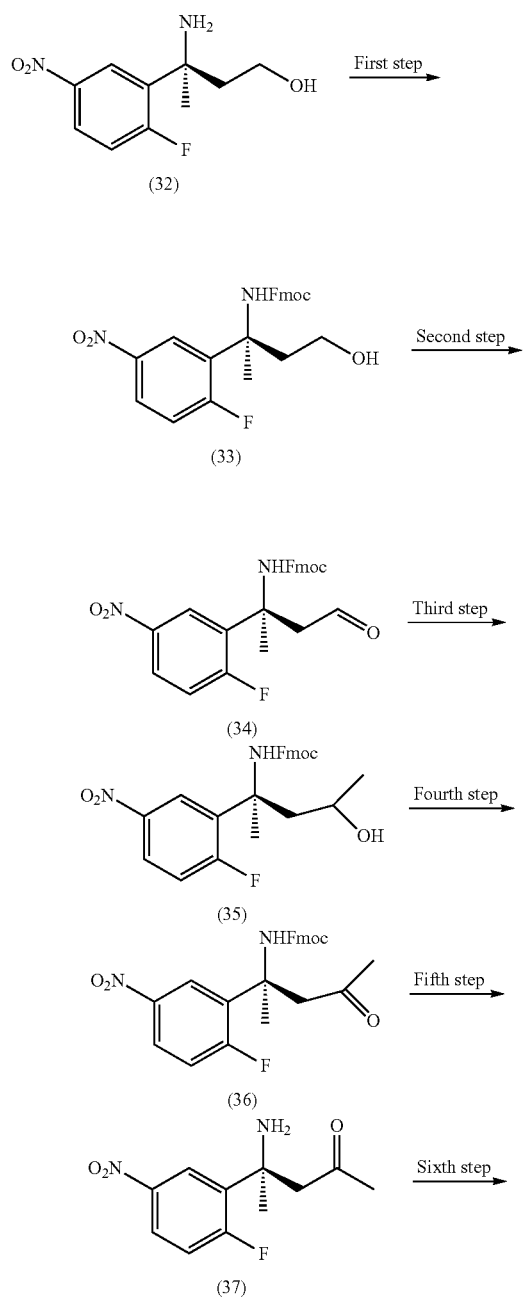

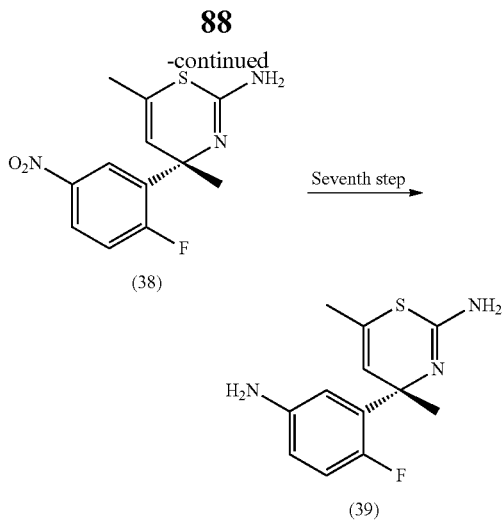

First Step

To a solution of a compound (32) (5.14 g) in tetrahydrofuran (50 ml) were added water (40 ml), sodium hydrogen carbonate (7.57 g) and N-(fluorenylmethoxycarbonyloxy) succinic acid imide (8.36 g), the mixture was stirred at room temperature for 2.5 hours, and extracted with ethyl acetate. The organic layer was dried over anhydrous magnesium sulfate, and the solvent was evaporated under reduced pressure to afford the compound (33) (11.0 g) as a crude product.

Second Step

To a solution of the compound (33) (11.0 g) obtained in first step in dimethyl sulfoxide (40 ml) was added 2-iodoxybenzoic acid (6.94 g), and the mixture was stirred at room temperature for 2 hours. Water and ethyl acetate were added, and the resulting insolubles were removed by filtration. The organic layer was washed with water, dried over anhydrous magnesium sulfate, and the solvent was evaporated under reduced pressure. The residue was subjected to column chromatography to afford the compound (34) (6.06 g).

MS (M+1) 449.00

Third Step

To diethyl ether (60 ml) was added titanium tetrachloride (3.1 ml) at −78° C., and to the resulting yellow suspension was added dropwise a solution of 3 mol/L methyl magnesium bromide in diethyl ether (9.5 ml). After the mixture was raised to −40° C., a solution of the compound (34) (3.18 g) in diethyl ether (15 ml) was added dropwise over 30 minutes. After stirred for 2.5 hours, an ice was added, and the mixture was warmed to room temperature. The mixture was extracted with ethyl acetate, and the organic layer was dried over anhydrous magnesium sulfate. The solvent was evaporated under reduced pressure to afford the compound (35) (3.4 g) as a crude product.

Fourth Step

To a solution of the compound (35) (3.4 g) obtained in third step in dimethyl sulfoxide (16 ml) was added 2-iodoxybenzoic acid (1.98 g), and the mixture was stirred at room temperature for 2 days. Water and ethyl acetate were added, and the resulting insolubles were removed by filtration. The organic layer was washed with water, dried over anhydrous magnesium sulfate, and the solvent was evaporated under reduced pressure. The residue was subjected to column chromatography to afford the compound (36) (2.34 g).

MS (M+1) 463.16

Fifth Step

To a solution of the compound (36) (2.34 g) in dimethylformamide (10 ml) was added piperidine (600 μl), and the mixture was stirred at room temperature for 20 minutes.

Water was added, and the mixture was extracted with ethyl acetate. The organic layer was dried over anhydrous magnesium sulfate, the solvent was evaporated under reduced pressure. The residue was subjected to column chromatography to afford the compound (37) (928 mg).

$^1$H-NMR (CDCl$_3$) δ: 1.51 (3H, s), 2.08 (3H, s), 2.93 (1H, d, J=18 Hz), 3.44 (1H, d, J=18 Hz), 7.13 (1H, dd, J=11.0, 8.9 Hz), 8.13 (1H, ddd, J=8.9, 4.0, 2.9 Hz), 8.59 (1H, dd, J=7.2, 2.9 Hz).

Sixth Step

To a solution of the compound (37) (928 mg) in acetone (4 ml) was added benzoyl isothiocyanate (497 µl) at 0° C., the mixture was stirred for 20 minutes, and the solvent was evaporated under reduced pressure. To the residue was added concentrated sulfuric acid (6 ml), and the mixture was stirred at room temperature for 3 hours. An ice was added, and the mixture was made alkaline with a 28% ammonia aqueous solution while stirred under ice-cooling. The mixture was extracted with ethyl acetate, the organic layer was washed with water, and dried over anhydrous magnesium sulfate. The solvent was evaporated under reduced pressure, the resulting residue was dissolved in ethanol (6 ml), and hydrazine monohydrate (290 mg) was added. After stirred at 50° C. for 2 hours, water was added, the mixture was extracted with ethyl acetate, and the organic layer was dried over anhydrous magnesium sulfate. The solvent was evaporated under reduced pressure, and the residue was subjected to column chromatography to afford the compound (38) (523 mg).

$^1$H-NMR (CDCl$_3$) δ: 1.68 (3H, d, J=1.2 Hz), 1.99 (3H, d, J=1.5 Hz), 4.63 (2H, br), 5.93 (2H, dd, J=4.7, 1.5 Hz), 7.15 (1H, dd, J=10.3, 8.9 Hz), 8.11 (1H, ddd, J=8.9, 4.1, 2.9 Hz), 8.38 (1H, dd, J=6.7, 2.9 Hz).

Seventh Step

To a solution of the compound (38) (523 mg) in acetic acid (5 ml) and water (0.5 ml) was added iron (415 mg), the mixture was stirred at 50° C. for 2 hours. The mixture was made alkaline with 28% aqueous ammonia, the resulting insolubles were removed by filtration, and the filtrate was extracted with ethyl acetate. After the organic layer was dried over anhydrous magnesium sulfate, the solvent was evaporated under reduced pressure to afford the compound (39) (407 mg).

$^1$H-NMR (CDCl$_3$) δ: 1.66 (3H, d, J=1.1 Hz), 1.96 (3H, d, J=1.5 Hz), 3.51 (2H, br), 5.95 (2H, dd, J=4.7, 1.5 Hz), 6.48 (1H, ddd, J=8.5, 3.6, 2.9 Hz), 6.73 (1H, dd, J=6.7, 2.9 Hz), 6.81 (1H, dd, J=11.4, 8.5 Hz).

Reference Example 4

Synthesis of Intermediate Compound (53)

[Chemical formula 30]

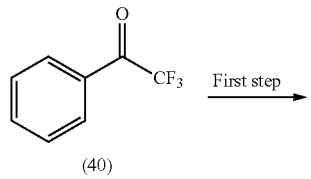

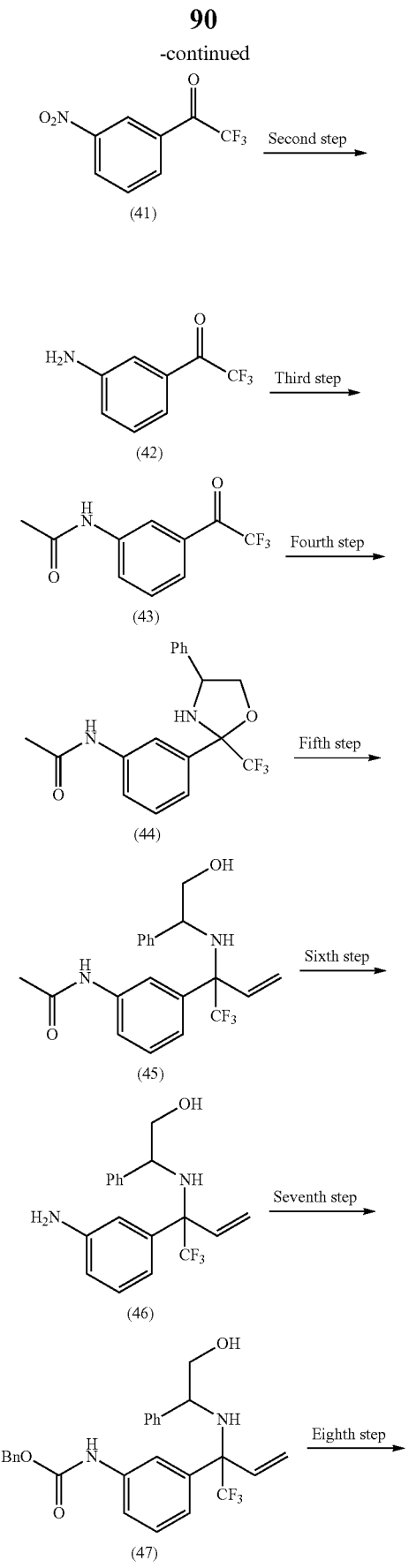

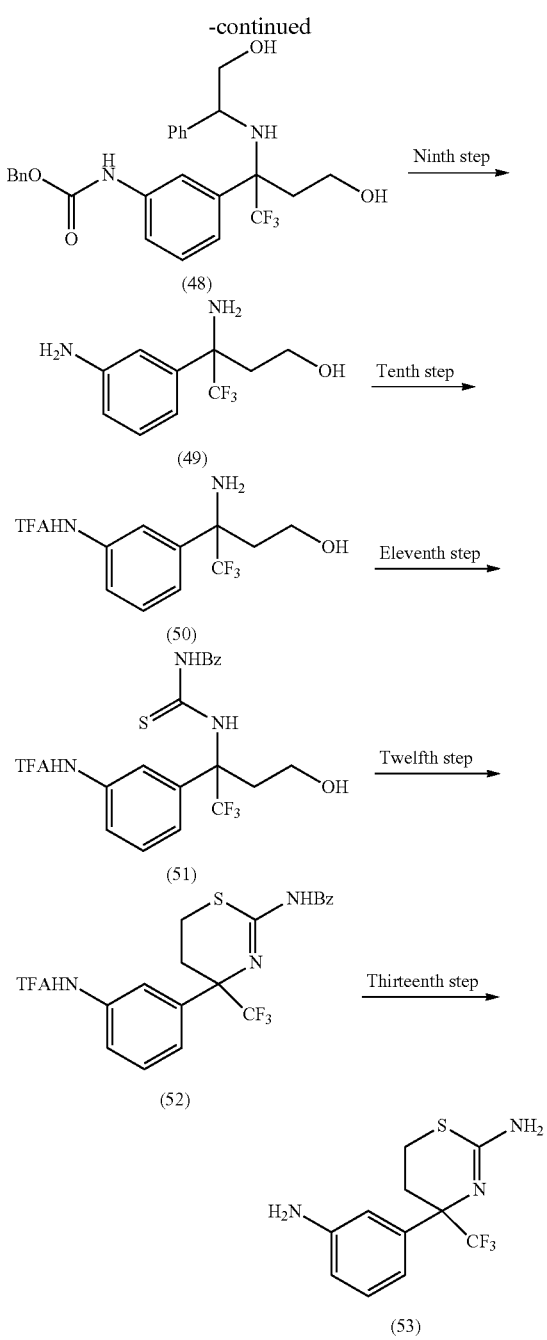

First Step

To cooled concentrated sulfuric acid (61 ml) in an ice bath was added dropwise nitric acid (20 ml) to prepare a reagent. At −38° C., to the compound (40) (50 g) was added dropwise concentrated sulfuric acid (137 ml), followed by dissolution. To this solution was added dropwise the previously prepared reagent at −25° C. over 1 hour. Thereupon, an internal temperature was maintained from −15° C. to −20° C. After stirred for 1 hour, the reaction solution was added to ice water, vigorously stirred for 40 minutes under ice-cooling, and the mixture was extracted with diethyl ether. The organic layer was washed with water, dried over anhydrous sodium sulfate, and the solvent was evaporated under reduced pressure. The residue was purified by silica gel column chromatography to afford the compound (41) (72.3 g).

$^1$H-NMR (mixture with hydrate body, CDCl$_3$) δ: 8.81 (1H, s), 8.51 (1H, d, J=8.1 Hz), 8.44 (1.5H, s), 8.33 (1H, d, J=7.6 Hz), 8.20 (1.5H, d, J=6.8 Hz), 7.93 (1.5H, d, J=7.8 Hz), 7.77 (1H, t, J=8.1 Hz), 7.56 (1.5H, t, J=16.8 Hz).

Second Step

The compound (41) (10 g) was dissolved in methanol (200 ml), iron (15 g) was added, and concentrated hydrochloric acid (23 ml) was added dropwise under ice-cooling. After stirred for 5 hours, the resulting insolubles were removed by filtration through Celite, and to the resulting filtrate was added a 4 mol/L sodium hydroxide aqueous solution (69 ml) under ice-cooling. After the mixture was filtered through Celite, the filtrate was extracted with ethyl acetate. The organic layer was washed with an aqueous sodium chloride solution, dried over anhydrous sodium sulfate, and the solvent was evaporated under reduced pressure. The residue was purified by silica gel column chromatography to afford the compound (42) (8.63 g).

$^1$H-NMR (CDCl$_3$) δ: 7.43 (1H, d, J=7.6 Hz), 7.32-7.28 (2H, m), 6.99 (1H, d, J=8.1 Hz), 3.93 (2H, br s).

Third Step

The compound (42) (37.2 g) was dissolved in ethyl acetate (200 ml), acetic anhydride (19.5 ml) was added, the mixture was stirred at room temperature for 2 hours, and the solvent was evaporated under reduced pressure. To the residue was added isopropyl ether, the resulting solid was collected by filtration, and washed with isopropyl ether to afford the compound (43) (15.8 g). In addition, to the resulting filtrate were added water and ethyl acetate, and the mixture was extracted with ethyl acetate. The organic layer was washed with an aqueous sodium chloride solution, dried over anhydrous sodium sulfate, and the solvent was evaporated under reduced pressure. The residue was purified by silica gel column chromatography to afford the compound (43) (10.5 g).

$^1$H-NMR (mixture with hydrate compound, DMSO-d$_6$) δ: 10.33 (1H, s), 10.01 (0.7H, s), 8.41 (1H, s), 7.97 (1H, d, J=7.8 Hz), 7.78 (0.7H, s), 7.73-7.70 (1.7H, m), 7.59 (1H, t, J=8.0 Hz), 7.52 (1.4H, s), 7.32-7.27 (1.4H, m), 2.08 (3H, s), 2.04 (2.1H, s).

Fourth Step

The compound (43) (2.0 g) was dissolved in toluene (100 ml), 2-amino-2-phenylethanol (1.2 g) and pyridinium para-toluenesulfonate (0.22 g) were added, and the mixture was heated at 130° C. in the vessel equipped with a Dean-Stark apparatus to dehydrate. The mixture was stirred at the same temperature for 10 hours, cooled to room temperature, an aqueous sodium hydrate carbonate solution was added, and the mixture was extracted with ethyl acetate. The organic layer was washed with an aqueous sodium chloride solution, dried over anhydrous sodium sulfate, and the solvent was evaporated under reduced pressure. The residue was purified by amino silica gel column chromatography to afford the compound (44) (1.8 g).

$^1$H-NMR (DMSO-d$_6$) δ: 10.07 (1H, s), 7.84 (1H, s), 7.73 (1H, d, J=8.3 Hz), 7.38-7.27 (7H, m), 4.68-4.61 (1H, m), 4.52 (1H, t, J=7.1 Hz), 4.08 (1H, d, J=8.8 Hz), 3.59 (1H, t, J=8.3 Hz), 2.04 (3H, s).

Fifth Step

To tetravinyltin (10 ml) was added dropwise butyllithium (42.2 ml: 2.6 mol/L) under nitrogen stream, pentane was added to the resulting white solid, the supernatant was decanted off, and dissolved in THF (25 ml). On the other hand, the compound (44) (3.2 g) was dissolved in THF (32 ml), and the previously prepared vinyllithium solution (22.1 ml) was added dropwise at −78° C. After stirred for 1.5 hours, the mixture was added to the ice-cooled saturated ammonium chloride aqueous solution, and extracted with ethyl acetate.

The organic layer was washed with an aqueous sodium chloride solution, dried over anhydrous sodium sulfate, and the solvent was evaporated under reduced pressure. The residue was purified by amino silica gel column chromatography to afford the compound (45) (1.7 g).

$^1$H-NMR (CDCl$_3$) δ: 7.88 (1H, s), 7.80 (1H, s), 7.39-7.37 (1H, m), 7.24-7.19 (7H, m), 5.74 (1H, dd, J=17.7, 11.1 Hz), 5.23 (2H, dd, J=17.7, 11.1 Hz), 3.97-3.95 (1H, m), 3.68-3.66 (1H, m), 3.47-3.45 (1H, m), 3.25-3.23 (1H, m), 2.86-2.84 (1H, m), 2.10 (3H, s).

Sixth Step

The compound (45) (1.1 g) was dissolved in ethanol (11 ml), hydrochloric acid (5.5 ml: 6 mol/L) was added, the mixture was stirred at 90° C. for 5 hours, and sodium hydroxide (8.7 ml: 4 mol/L) was added. The mixture was extracted with ethyl acetate, the organic layer was washed with an aqueous sodium chloride solution, dried over anhydrous sodium sulfate, and the solvent was evaporated under reduced pressure. The residue was purified by silica gel column chromatography to afford the crude product (46) (728 mg).

Seventh Step

The compound (46) (728 mg) was dissolved in dichloromethane (7 ml), and diisopropylethylamine (0.42 ml) and benzyl chloroformate (0.308 ml) were added under ice-cooling under a nitrogen stream. After stirred for 1 hour, a saturated ammonium chloride aqueous solution was added under ice-cooling, and the mixture was extracted with ethyl acetate. The organic layer was washed with an aqueous saturated sodium chloride solution, dried over anhydrous sodium sulfate, and the solvent was evaporated under reduced pressure. The residue was purified by silica gel column chromatography to afford the compound (47) (839 mg).

$^1$H-NMR (DMSO-d$_6$) δ: 9.79 (1H, s), 7.79 (1H, s), 7.48-7.14 (13H, m), 5.80 (1H, dd, J=18.1, 11.2 Hz), 5.42-5.38 (2H, dd, J=18.1, 11.2 Hz), 5.15 (2H, s), 5.08 (1H, s), 3.89-3.87 (1H, m), 3.35-3.25 (2H, m), 3.03-3.00 (1H, m).

Eighth Step

The compound (47) (4.8 g) was dissolved in THF (48 ml), a borane/dimethyl sulfide complex (15.3 ml: 2 mol/L) was added under ice-cooling under a nitrogen stream, and the mixture was stirred at the same temperature for 30 minutes. The mixture was warmed to room temperature, and stirred for 30 minutes. Further, the mixture was warmed to 40° C., stirred for 2.5 hours, and ice-cooled. After water (4.8 ml) was added to the reaction solution, a sodium hydroxide aqueous solution (25.5 ml: 4 mol/L) and aqueous hydrogen peroxide (10.4 ml: 30%) were added. After stirred at room temperature overnight, the mixture was extracted with ethyl acetate. The organic layer was washed with an aqueous sodium chloride solution, dried over anhydrous sodium sulfate, and the solvent was evaporated under reduced pressure. The residue was purified by silica gel column chromatography to afford the compound (48) (1.7 g).

$^1$H-NMR (DMSO-d$_6$) δ: 9.77 (1H, s), 7.81 (1H, s), 7.49-7.12 (13H, m), 5.16 (2H, s), 4.98-4.96 (1H, m), 4.52-4.49 (1H, m), 3.86-3.84 (1H, m), 3.37-3.18 (4H, m), 2.90-2.87 (1H, m), 2.28-2.25 (1H, m), 2.12-2.10 (1H, m).

Ninth Step

The compound (48) (50 mg) was dissolved in methanol (0.5 ml), 20% Pd(OH)$_2$ (28 mg: 50% wet) was added, and the mixture was stirred for 8 hours under a hydrogen stream. The solvent of the filtrate obtained by Celite filtration was evaporated to afford the crude product (49) (33 mg).

Tenth Step

The compound (49) (24 mg) was dissolved in THF (0.5 ml), trifluoroacetic anhydride (0.029 ml) was added under ice-cooling, the mixture was stirred at room temperature for 5.5 hours, and an aqueous sodium hydrogen carbonate solution was added. Further, the mixture was extracted with ethyl acetate, the organic layer was washed with an aqueous sodium chloride solution, dried over anhydrous sodium sulfate, and the solvent was evaporated under reduced pressure. The residue was purified by silica gel column chromatography to afford the compound (50) (12 mg).

$^1$H-NMR (CDCl$_3$) δ: 8.53 (1H, s), 7.76 (1H, s), 7.68 (1H, d, J=8.1 Hz), 7.45 (1H, t, J=8.0 Hz), 7.40 (1H, d, J=7.8 Hz), 3.61-3.58 (1H, m), 3.46-3.39 (1H, m), 2.22 (2H, t, J=5.2 Hz).

Eleventh Step

The compound (50) (68 mg) was dissolved in acetone (1 ml), and benzoyl isothiocyanate (0.043 ml) was added under ice-cooling. After stirred for 15 minutes, the mixture was warmed to room temperature, stirred for 2.5 hours and further stirred at 40° C. for 4 hours. The solvent was evaporated under reduced pressure, and the residue was purified by silica gel column chromatography to afford the compound (51) (80 mg).

$^1$H-NMR (DMSO-d$_6$) δ: 12.40 (1H, s), 11.69 (1H, s), 11.30 (1H, s), 8.03-8.01 (2H, m), 7.84-7.81 (2H, m), 7.68-7.66 (1H, m), 7.56-7.54 (2H, m), 7.45-7.43 (1H, m), 7.34-7.33 (1H, m), 4.81-4.79 (1H, m), 3.73-3.62 (2H, m), 3.48-3.45 (1H, m), 2.67-2.65 (1H, m).

Twelfth Step

The compound (51) (80 mg) was dissolved in dichloromethane (2 ml), and 1-chloro-2-trimethylpropenylamine (0.043 ml) was added under a nitrogen stream. After the mixture was stirred at room temperature for 1 hour, an aqueous sodium hydrogen carbonate solution was added, and the mixture was extracted with ethyl acetate. The organic layer was washed with water and an aqueous sodium chloride solution, dried over anhydrous sodium sulfate, and the solvent was evaporated under reduced pressure. The residue was purified by silica gel thin layer chromatography to afford the compound (52) (58 mg). $^1$H-NMR (DMSO-d$_6$) δ: 11.42 (1H, s), 11.23 (1H, s), 8.01 (2H, d, J=6.6 Hz), 7.84-7.81 (2H, m), 7.70-7.46 (5H, m), 3.10-2.99 (1H, m), 2.92-2.82 (1H, m), 2.65-2.59 (1H, m), 2.12-2.05 (1H, m).

Thirteenth Step

The compound (52) (57 mg) was dissolved in ethanol (1 ml), and a 2 mol/L sodium hydroxide aqueous solution (0.6 ml) was added. After warmed and stirred at 70° C. for 7.5 hours, the mixture was cooled to room temperature, and extracted with ethyl acetate. The solvent was evaporated under reduced pressure to afford the compound (53) (7.7 mg).

$^1$H-NMR (DMSO-d$_6$) δ: 7.01 (1H, t, J=7.8 Hz), 6.67 (1H, s), 6.59 (1H, d, J=7.6 Hz), 6.51 (1H, d, J=7.8 Hz), 6.29 (2H, s), 5.07 (2H, s), 2.90 (1H, d, J=10.6 Hz), 2.59-2.49 (2H, m), 1.74 (1H, t, J=13.4 Hz).

Reference Example 5

Synthesis of Intermediate Compound (58)

[Chemical formula 31]

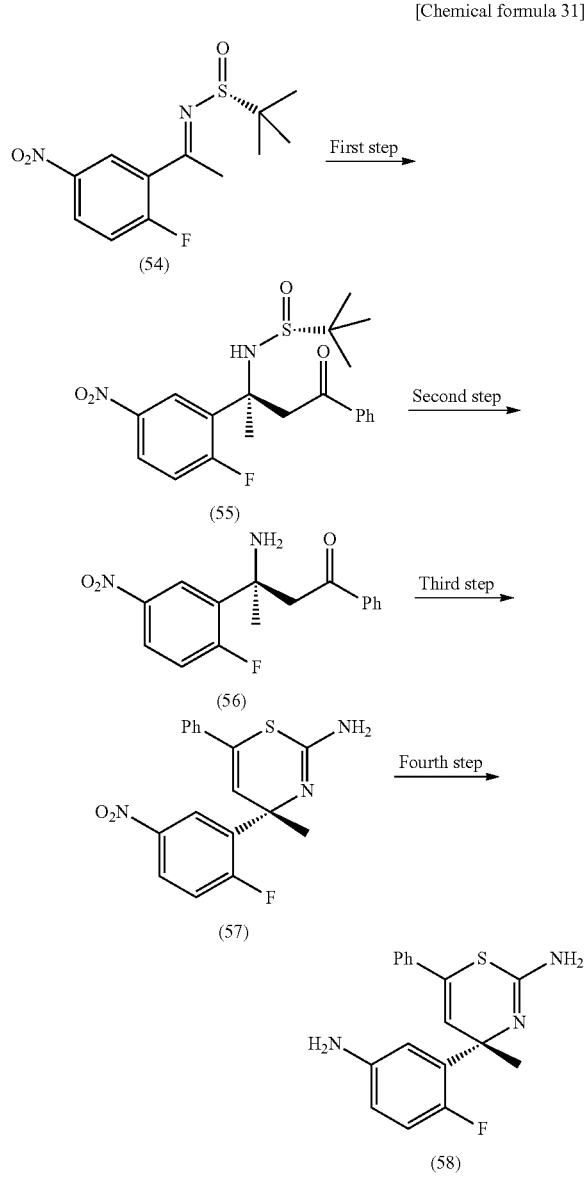

First Step

To a solution of 0.5 mol/L potassium hexamethyldisilazide in toluene (7.3 ml) was added tetrahydrofuran (30 ml), and acetophenone (407 μl) was slowly added dropwise while stirring at −78° C. After stirred at −78° C. for 1 hour, a solution of the compound (54) (500 mg) in tetrahydrofuran (3 ml) was added dropwise. After the mixture was stirred at −78° C. for 1 hour, a saturated ammonium chloride aqueous solution was added, and the mixture was warmed to room temperature. The mixture was extracted with ethyl acetate, and the organic layer was dried over anhydrous magnesium sulfate. The solvent was evaporated under reduced pressure, and the residue was purified by column chromatography to afford the compound (55) (380 mg) as the diastereomer mixture.

Second Step

To the mixture of the compound (55) (380 mg) obtained in first step were added a 4 mol/L hydrochloric acid/dioxane solution (1.8 ml) and methanol (45 μl), and the mixture was stirred at room temperature for 1.5 hours. Diethyl ether and water were added, the aqueous layer was made alkaline with 28% aqueous ammonia, and the mixture was extracted with ethyl acetate. The organic layer was dried over anhydrous magnesium sulfate, and the solvent was evaporated under reduced pressure to afford the compound (56) (181 mg).

$^1$H-NMR (CDCl$_3$) δ: 1.62 (3H, s, J=1.7 Hz), 3.43 (1H, d, J=18.8 Hz), 4.02 (1H, d, J=18.8 Hz), 7.08 (1H, dd, J=11.1, 9.0 Hz), 7.41-7.59 (3H, m), 7.85-7.90 (2H, m), 8.11 (1H, ddd, J=9.0, 4.0, 2.8 Hz), 8.69 (1H, dd, J=7.2, 2.8 Hz).

Third Step

To a solution of the compound (56) (181 mg) in acetone (1.5 ml) was added benzoyl isothiocyanate (81 μl) at 0° C., the mixture was stirred at 0° C. for 30 minutes, and the solvent was evaporated under reduced pressure. To the residue was added concentrated sulfuric acid (1.1 ml), the mixture was stirred at room temperature overnight, water (500 μl) was added, and the mixture was stirred at 50° C. for 6 hours. The mixture was made alkaline with a 28% ammonia aqueous solution while stirring under ice-cooling. The mixture was extracted with ethyl acetate, the organic layer was washed with water, and dried over anhydrous magnesium sulfate. The solvent was evaporated under reduced pressure, and the residue was purified by column chromatography to afford the compound (57) (112 mg).

$^1$H-NMR (CDCl$_3$) δ: 1.81 (3H, d, J=0.9 Hz), 4.80 (2H, s), 6.46 (1H, d, J=5.5 Hz), 7.17 (1H, dd, J=10.5, 8.9 Hz), 7.34-7.49 (5H, m), 8.13 (1H, ddd, J=8.9, 4.0, 3.0 Hz), 8.45 (1H, dd, J=6.8, 3.0 Hz).

Fourth Step

To a solution of the compound (57) (112 mg) in acetic acid (1 ml) and water (0.1 ml) was added iron (91 mg), and the mixture was stirred at 50° C. for 2.5 hours. The resulting insolubles were removed by filtration, the filtrate was made alkaline with 28% aqueous ammonia, extracted with ethyl acetate, and the organic layer was dried over anhydrous magnesium sulfate. The solvent was evaporated under reduced pressure to afford the compound (58) (98.7 mg) as a crude product.

Reference Example 6

Synthesis of Intermediate Compound (63)

[Chemical formula 32]

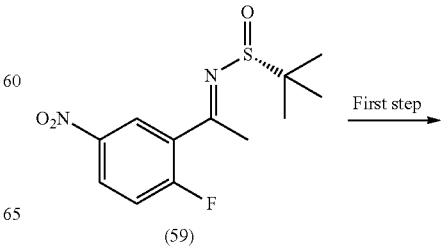

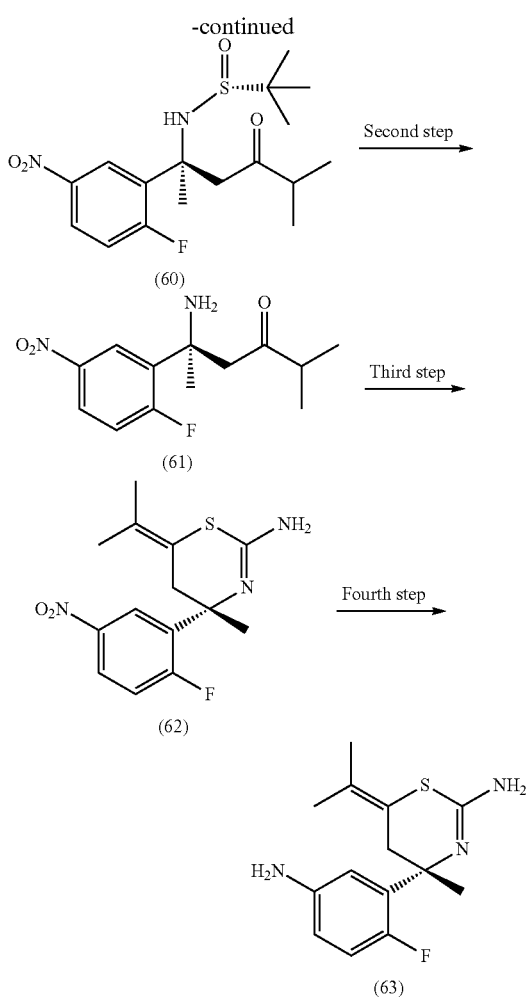

acetate. The organic layer was dried over anhydrous magnesium sulfate, and the solvent was evaporated under reduced pressure to afford the compound (61) (209 mg).

Third Step

To a solution of the compound (61) (209 mg) in acetone (1 ml) was added benzoyl isothiocyanate (105 μl) at 0° C., the mixture was stirred at 0° C. for 30 minutes, and the solvent was evaporated under reduced pressure. To the residue was added concentrated sulfuric acid (1.6 ml), the mixture was stirred at room temperature overnight, and the mixture was made alkaline with a 28% ammonia aqueous solution while stirring under ice-cooling. The mixture was extracted with ethyl acetate, the organic layer was washed with water, and dried over anhydrous magnesium sulfate. The solvent was evaporated under reduced pressure, and the residue was purified by column chromatography to afford the compound (62) (96 mg).

$^1$H-NMR (CDCl$_3$) δ: 1.57 (3H, s), 1.68 (3H, s), 1.77 (3H, s), 2.70 (1H, d, J=14.2 Hz), 2.87 (1H, d, J=14.2 Hz), 4.80 (2H, s), 6.46 (1H, d, J=5.5 Hz), 7.14 (1H, dd, J=11.0, 8.9 Hz), 8.12 (1H, ddd, J=8.9, 4.0, 3.0 Hz), 8.44 (1H, dd, J=6.9, 3.0 Hz).

Fourth Step

To a solution of the compound (62) (96 mg) in acetic acid (1 ml) and water (0.1 ml) was added iron (87 mg), and the mixture was stirred at 50° C. for 2 hours. The mixture was made alkaline with 28% aqueous ammonia, the resulting insolubles was removed by filtration. The filtrate was extracted with ethyl acetate, and dried over anhydrous magnesium sulfate. The solvent was evaporated under reduced pressure to afford the compound (63) (78.3 mg) as a crude product.

Reference Example 7

Synthesis of Intermediate Compound (70)

First Step

To a solution of 0.5 mol/L potassium hexamethyldisilazide in toluene (8 ml) was added diethyl ether (30 ml), and 3-methyl-2-butanone (376 μl) was slowly added dropwise while stirring at −78° C. After stirred at −78° C. for 1 hour, a solution of the compound (59) (500 mg) in diethyl ether (8 ml) was added dropwise. After stirred at −78° C. for 1.5 hours, a saturated ammonium chloride aqueous solution was added, and the mixture was warmed to room temperature. The mixture was extracted with ethyl acetate, and the organic layer was dried over anhydrous magnesium sulfate. The solvent was evaporated under reduced pressure, and the residue was purified by column chromatography to afford the compound (60) (307 mg).

$^1$H-NMR (CDCl$_3$) δ: 1.02 (3H, d, J=6.9 Hz), 1.06 (3H, d, J=6.9 Hz), 1.34 (9H, s), 1.77 (3H, s), 2.55 (1H, septet, J=6.9 Hz), 3.41 (1H, d, J=18.8 Hz), 3.72 (1H, d, J=18.8 Hz), 5.46 (1H, s), 7.12 (1H, dd, J=11.3, 8.9 Hz), 8.13 (1H, ddd, J=8.9, 4.0, 2.8 Hz), 8.56 (1H, dd, J=6.9, 2.8 Hz).

Second Step

To the compound (60) (307 mg) obtained in the first step were added a 4 mol/L hydrochloric acid/dioxane solution (1.65 ml) and methanol (40 μl), and the mixture was stirred at room temperature for 1 hour. Diethyl ether and water were added, the aqueous layer was made alkaline with 28% aqueous ammonia, and the mixture was extracted with ethyl

[Chemical formula 33]

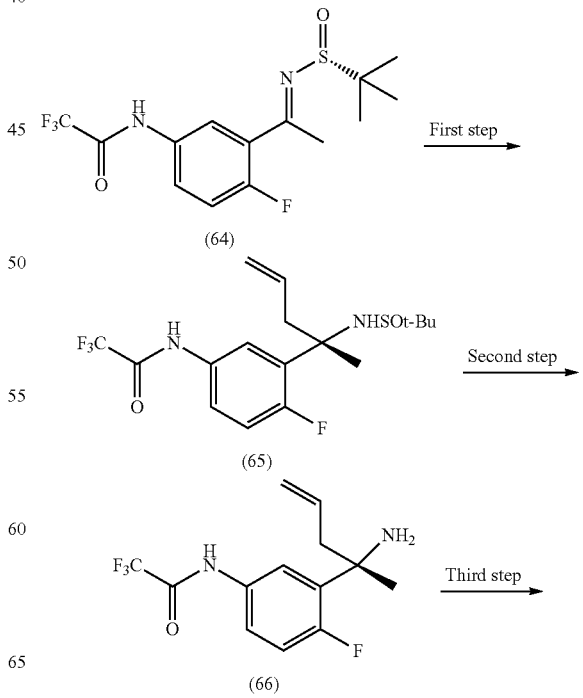

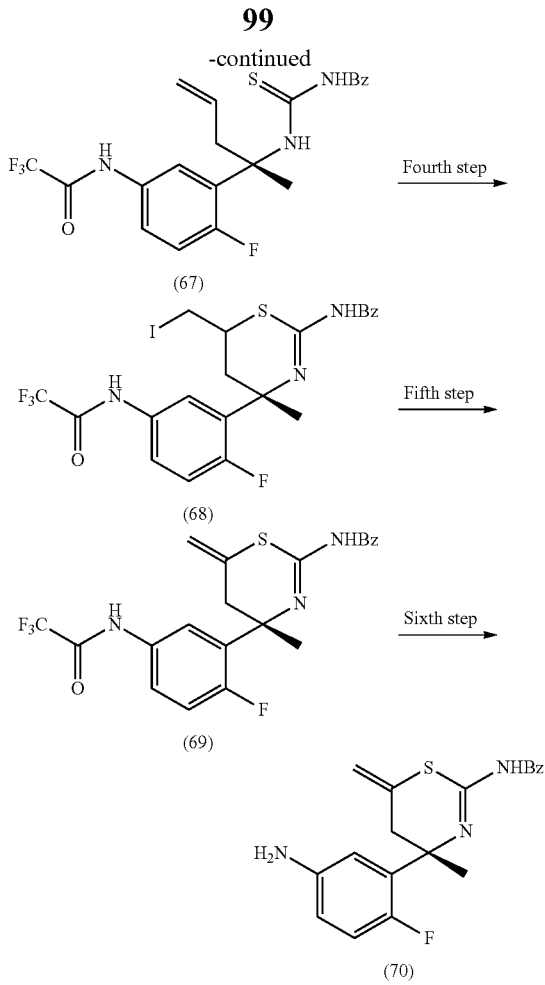

First Step

The compound (64) (12 g) was dissolved in tetrahydrofuran (240 ml), and a 1 mol/L allylmagnesium bromide/ether solution was added dropwise at −78° C. over 1 hour under stirring. After further stirred at −78° C. for 1 hour, the mixture was transferred to a saturated ammonium chloride aqueous solution, extracted with ethyl acetate, and the organic layer was dried over anhydrous sodium sulfate. The inorganic substance was removed by filtration, the solvent was evaporated under reduced pressure, and the residue was subjected to column chromatography to afford the compound (65) (9.7 g).

$^1$H-NMR (CDCl$_3$) δ: 1.21 (9H, s), 1.68 (3H, s), 2.79 (1H, dd, J=13.4, 7.3 Hz), 2.92 (1H, dd, J=13.4, 6.8 Hz), 4.16 (1H, s), 5.10 (1H, d, J=9.6 Hz), 5.13 (1H, d, J=17.2 Hz), 5.52-5.66 (1H, m), 6.95 (1H, dd, J=10.6, 10.1 Hz), 7.55-7.62 (1H, m), 7.67-7.72 (1H, m), 9.96 (1H, s).

Second Step

The compound (65) (3.99 g) was dissolved in ethanol (20 ml), a 1 mol/L hydrochloric acid-ethanol solution was added at room temperature under stirring, and the mixture was stirred at room temperature for 1 hour. The solvent was evaporated under reduced pressure, the residue was diluted with ethyl acetate, and the mixture was extracted with 2 mol/L hydrochloric acid. The resulting aqueous layer was made basic with potassium carbonate (pH=8 to 9), the mixture was extracted with ethyl acetate, and the organic layer was dried over anhydrous sodium sulfate. The inorganic substance was removed by filtration, and the solvent was evaporated under reduced pressure to afford the compound (66). A total amount of this was used in the next reaction without a purification.

$^1$H-NMR (CDCl$_3$) δ: 1.51 (3H, s), 1.75-1.89 (2H, br), 2.47 (1H, dd, J=13.1, 8.1 Hz), 2.76 (1H, dd, J=13.1, 7.1 Hz), 5.03-5.11 (2H, m), 5.46-5.58 (1H, m), 7.01-7.08 (1H, m), 7.52-7.60 (2H, m), 8.25-8.36 (1H, br).

Third Step

The resulting compound (66) was dissolved in methylene chloride (20 ml), and benzoyl isothiocyanate (1.43 ml) was added dropwise while stirring under ice-cooling. The mixture was stirred for 5 minutes under ice-cooling, and stirred at room temperature for 45 minutes. The solvent was evaporated under reduced pressure, and the residue was subjected to column chromatography to afford the compound (67) (4.34 g).

$^1$H-NMR (CDCl$_3$) δ: 2.00 (3H, s), 2.73 (1H, dd, J=13.1, 6.6 Hz), 3.18 (1H, dd, J=13.1, 7.6 Hz), 5.24 (1H, d, J=10.6 Hz), 5.29 (1H, J=17.2 Hz), 5.67-5.79 (1H, m), 6.99-7.07 (1H, dd, J=10.4, 10.4 Hz), 7.45-7.53 (3H, m), 7.57-7.65 (2H, m), 7.83 (2H, d J=7.07 Hz), 8.39 (1H, s), 8.86 (1H, s), 11.36 (1H, s).

Fourth Step

The compound (67) (4.34 g) was dissolved in methylene chloride (220 ml), iodine (3.64 g) was added at once while stirring under ice-cooling, and the mixture was further stirred for 30 minutes under ice-cooling. After diluted with water, remaining iodine was reduced with sodium hyposulfite, the aqueous layer was neutralized (pH=8) with sodium hydrogen carbonate. The mixture was extracted with ethyl acetate, and the organic layer was dried over sodium sulfate. The inorganic substance was removed by filtration, and the solvent was evaporated under reduced pressure to afford the compound (68). A total amount of this was used in the next reaction without a purification.

Fifth Step

The compound (68) was dissolved in tetrahydrofuran (130 ml), pyrrolidine (4 ml) was added, the mixture was heated at reflux for 2 hours. Water was added, the mixture was extracted with ethyl acetate, and the organic layer was dried over sodium sulfate. The inorganic substance was removed by filtration, and the solvent was evaporated under reduced pressure. The residue was subjected to column chromatography to afford the compound (69) (3.44 g).

$^1$H-NMR (CDCl$_3$) δ: 1.71 (3H, s), 2.71 (1H, d, J=14.1 Hz), 3.39 (1H, d, J=14.1 Hz), 5.01 (1H, s), 5.09 (1H, s), 7.10 (1H, dd, J=10.6, 10.1 Hz), 7.31-7.40 (4H, m), 7.47 (1H, t, J=7.0 Hz), 8.05 (2H, d, J=7.6 Hz), 8.08-8.13 (1H, m).

Sixth Step

The compound (69) (459 mg) was dissolved in ethanol (9.2 ml), hydrazine monohydrate (0.986 ml) was added, and the mixture was stirred at 50° C. for 4.5 hours. Water was added, the mixture was extracted with chloroform, and the organic layer was dried over sodium sulfate. The inorganic substance was removed by filtration, and the solvent was evaporated under reduced pressure. The residue was subjected to column chromatography to afford the compound (70) (158 mg).

$^1$H-NMR (CDCl$_3$) δ: 1.54 (3H, s), 2.53 (1H, d, J=13.6 Hz), 2.89 (1H, d, J=13.6 Hz), 4.97 (1H, s), 5.09 (1H, s), 6.45-6.51 (1H, m), 6.73-6.84 (2H, m).

Reference Example 8

Synthesis of Intermediate Compound (76)

[Chemical formula 34]

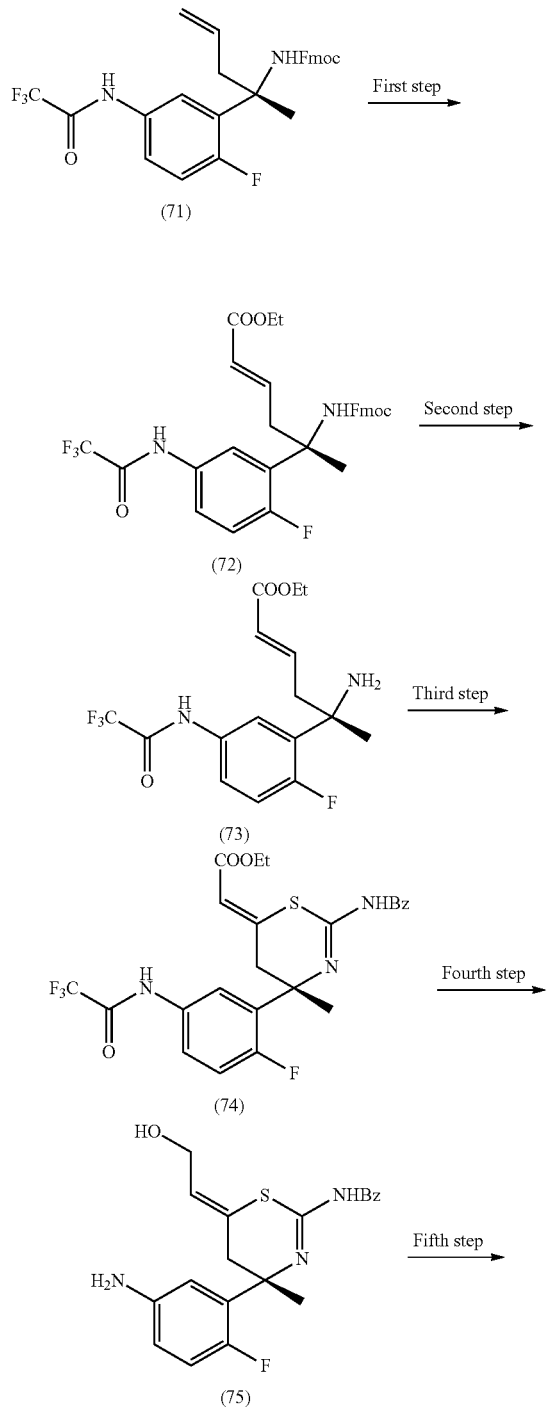

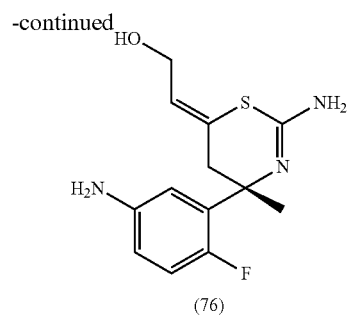

First Step

The compound (71) (8.00 g) was dissolved in methylene chloride (20 ml), ethyl acrylate (40 ml) and a second generation Grubbs' catalyst (0.412 g) were added, and the mixture was stirred at room temperature for 2 hours under the nitrogen atmosphere. The solvent was evaporated under reduced pressure, and the residue was subjected to column chromatography to afford the compound (72) (8.34 g).

$^1$H-NMR (CDCl$_3$) δ: 1.26 (3H, t, J=6.6 Hz), 1.53-1.78 (3H, br), 2.72-2.92 (1H, br), 3.14-3.38 (1H, br), 4.23 (2H, q, J=6.6 Hz), 4.25-4.50 (2H, br), 5.44-5.67 (1H, br), 5.82-5.98 (1H, br), 6.73-6.93 (1H, br), 6.97 (1H, dd, J=9.6, 9.6 Hz), 7.19-7.85 (11H, m), 8.67-8.82 (1H, br).

Second Step

The compound (72) (8.32 g) was dissolved in N,N-dimethylformamide, piperidine (0.125 ml) was added, and the mixture was stirred at room temperature for 15 hours. Water was added to the reaction solution, the mixture was extracted with ethyl acetate, and the organic layer was dried over anhydrous sodium sulfate. After filtration, the solvent was evaporated under reduced pressure, and the residue was subjected to column chromatography to afford the compound (73) (4.81 g).

$^1$H-NMR (CDCl$_3$) δ: 1.26 (3H, t, J=7.1 Hz), 1.55 (3H, s), 1.65-1.88 (2H, br), 2.66 (1H, dd, J=14.1, 8.1 Hz), 2.89 (1H, dd, J=14.1, 8.1 Hz), 4.15 (2H, q, J=7.1 Hz), 5.86 (1H, d, J=15.2 Hz), 6.69 (1H, ddd, J=15.2, 8.1, 8.1 Hz), 7.07 (1H, dd, J=10.1, 8.1 Hz), 7.56-7.64 (2H, m), 8.14-8.26 (1H, br).

Third Step

The compound (73) (0.950 g) was dissolved in methylene chloride (14 ml), benzoyl isothiocyanate (0.370 ml) was added dropwise over 10 minutes under ice-cooling, and the mixture was stirred for 30 minutes under ice-cooling. Thereafter, iodine (0.732 g) was added at once under ice-cooling, and the mixture was stirred at room temperature for 45 minutes. The mixture was ice-cooled again, and a solution of 1,8-bicyclo[5.4.0]undec-7-ene (1.581 ml) dissolved in methylene chloride (10 ml) was added dropwise over 5 minutes. The mixture was warmed to room temperature, and the mixture was stirred for 4 hours. The reaction solution was diluted with ethyl acetate and water, sodium sulfite was added, the mixture was neutralized with sodium hydrogen carbonate, and extracted with ethyl acetate. The organic layer was dried over anhydrous sodium sulfate, filtered, and the solvent was evaporated under reduced pressure. The residue was subjected to column chromatography to afford the compound (74) (0.939 g).

$^1$H-NMR (CDCl$_3$) δ: 1.22 (3H, t, J=7.1 Hz), 1.73 (3H, s), 2.93 (1H, d, J=14.7 Hz), 3.58 (1H, d, J=14.7 Hz), 4.09 (2H, q, J=7.1 Hz), 5.83 (1H, s), 7.14 (1H, dd, J=11.1, 9.1 Hz), 7.31-7.45 (3H, m), 7.58 (1H, t, J=7.1 Hz), 8.00 (2H, d, J=7.1 Hz), 8.10-8.16 (1H, m), 9.62-9.76 (1H, br).

Fourth Step

The compound (74) (0.700 mg) was dissolved in toluene, and the internal temperature was maintained under −50° C. A 1 mol/L solution of diisobutyl aluminum hydride in toluene was added dropwise over 5 minutes, the mixture was cooled in an acetone-dry ice bath, and further stirred for 30 minutes. After quenched with methanol, the mixture was warmed to room temperature, filtered, and the solvent was evaporated under reduced pressure. The residue was subjected to column chromatography to afford the compound (75) (0.183 g).

$^1$H-NMR (CDCl$_3$) δ: 1.52-1.98 (1H, br), 1.78 (3H, s), 2.75 (1H, d, J=13.9 Hz), 3.40 (1H, d, J=13.9 Hz), 3.44-3.87 (2H, br), 4.07 (1H, dd, J=13.1, 5.1 Hz), 4.14 (1H, dd, J=13.1, 3.5 Hz), 5.63 (1H, dd, J=5.1, 3.5 Hz), 6.46-6.59 (2H, m), 6.87 (1H, dd, J=11.1, 9.1 Hz), 7.46 (2H, dd, J=7.1, 7.1 Hz), 7.53 (1H, t, J=7.1 Hz), 8.25 (2H, d, J=7.1 Hz).

Fifth Step

The compound (75) (60.4 mg) was dissolved in ethanol (600 hydrazine monohydrate (38 μl) was added, and the mixture was stirred at room temperature overnight. The reaction solution was diluted with a saturated sodium chloride aqueous solution, extracted with chloroform, and the organic layer was dried over anhydrous sodium sulfate. After filtration, the solvent was evaporated under reduced pressure to afford the compound (76) as a mixture with benzoylhydrazine. The compound (76) was used in the next reaction without a purification.

$^1$H-NMR (CDCl$_3$) δ: 1.45 (3H, s), 2.41 (1H, d, J=14.2 Hz), 2.82 (1H, d, J=14.2 Hz), 3.29-3.80 (4H, br), 3.98 (2H, d, J=6.6 Hz), 5.49 (1H, m), 6.36-6.41 (1H, m), 6.60-6.65 (1H, m), 6.70 (1H, dd, J=12.1, 9.1 Hz).

Reference Example 9

Synthesis of Intermediate Compound (79)

First Step

A compound (77) (500 mg) was dissolved in dimethylacetamide (7.5 ml), potassium carbonate (440 mg) and 1H-1,2,4-triazole (200 mg) were added, and the mixture was stirred at 130° C. for 10 minutes under microwave irradiation. Water was added, the mixture was extracted with ethyl acetate, the organic layer was washed with water and a saturated sodium chloride aqueous solution. The organic layer was dried over anhydrous magnesium sulfate, and the solvent was evaporated under reduced pressure. The residue was washed with diisopropyl alcohol to afford the compound (78) (451 mg).

$^1$H-NMR (DMSO-d$_6$) δ: 3.96 (3H, s), 8.48 (1H, s), 9.16 (1H, d, J=1.5 Hz), 9.29 (1H, d, J=1.5 Hz), 9.56 (1H, s).

Second Step

The compound (78) (50 mg) was dissolved in tetrahydrofuran (1 ml) and methanol (1 ml), a 2 mol/L sodium hydroxide aqueous solution (0.12 ml) was added, and the mixture was stirred at room temperature for 2 hours. 2 mol/L hydrochloric acid (0.12 ml) was added, the solvent was evaporated under reduced pressure, and chloroform was added to the residue, to afford the compound (79) (27 mg) (containing sodium chloride) by filtration.

$^1$H-NMR (DMSO-d$_6$) δ: 8.48 (1H, s), 9.13 (1H, s), 9.27 (1H, s), 9.55 (1H, s), 14.18 (1H, s).

Reference Example 10

Synthesis of Intermediate Compound (84)

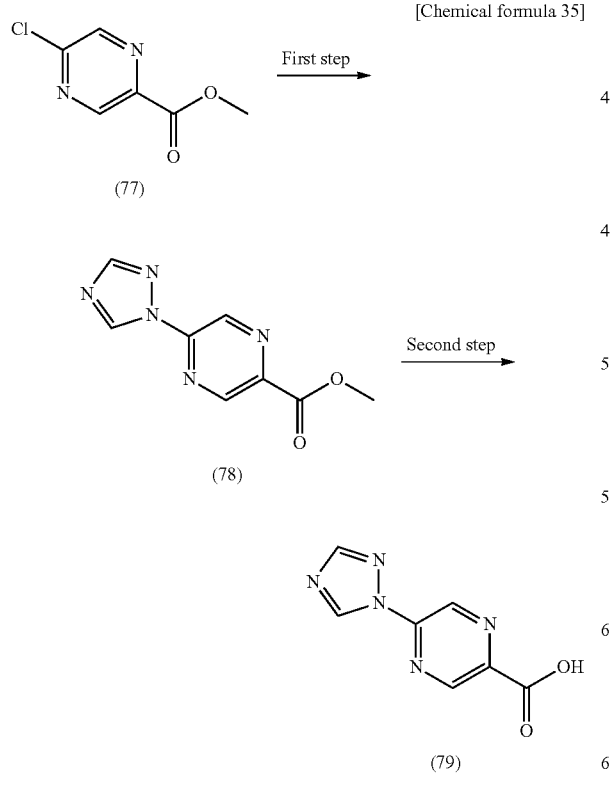

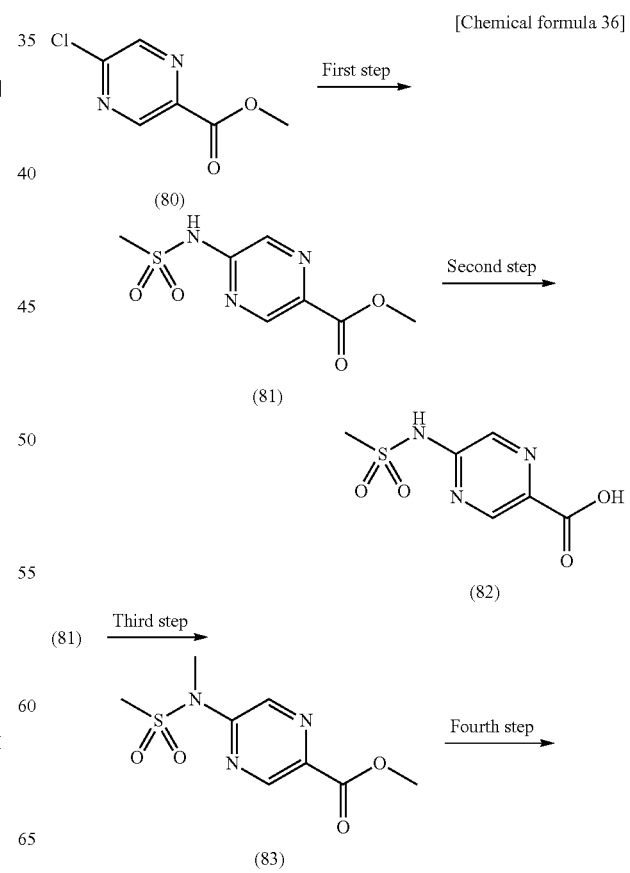

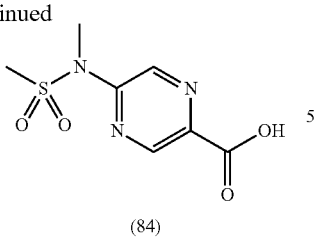

(84)

First Step

The compound (80) (1.0 g) was dissolved in dimethyl sulfoxide (10 ml), methanesulfoneamide (0.66 g) and potassium carbonate (1.6 g) were added, and the mixture was stirred at 120° C. for 1 hour. 0.2 mol/L hydrochloric acid was added to adjust pH to 4, and the mixture was extracted with ethyl acetate. The organic layer was washed with water and a saturated sodium chloride aqueous solution in order, the organic layer was dried over anhydrous magnesium sulfate, and the solvent was evaporated under reduced pressure. The residue was washed with diethyl ether to afford the compound (81) (1.1 g).

$^1$H-NMR (DMSO-$d_6$) δ: 3.40 (3H, s), 3.88 (3H, s), 8.35 (1H, d, J=1.0 Hz), 8.90 (1H, d, J=1.0 Hz), 11.68 (1H, s).

Second Step

The compound (81) (200 mg) was dissolved in tetrahydrofuran (4 ml) and methanol (4 ml), a 2 mol/L sodium hydroxide aqueous solution (1.3 ml) was added, and the mixture was stirred at room temperature for 3 hours. 2 mol/L hydrochloric acid (1.3 ml) was added, and the organic solvent was evaporated under reduced pressure. Water was added, and the residue was collected by filtration, and washed with tetrahydrofuran to afford the compound (82) (161 mg).

$^1$H-NMR (DMSO-$d_6$) δ: 3.39 (3H, s), 8.34 (1H, d, J=1.5 Hz), 8.87 (1H, d, J=1.0 Hz), 11.62 (1H, s), 13.35 (1H, s).

Third Step

The compound (81) (300 mg) and potassium carbonate (197 mg) were dissolved in dimethylformamide (3 ml), methyl iodide (203 mg) was added, and the mixture was stirred at 60° C. for 2 hours. Water was added, the mixture was extracted with ethyl acetate, the organic layer was washed with water and a saturated sodium chloride aqueous solution. The organic layer was dried over anhydrous sodium sulfate, and the solvent was evaporated under reduced pressure. The residue was subjected to silica gel chromatography to afford the compound (83) (162 mg).

$^1$H-NMR (DMSO-$d_6$) δ: 3.39 (3H, s), 3.42 (3H, s), 3.91 (3H, s), 8.87 (1H, d, J=1.5 Hz), 8.99 (1H, d, J=1.5 Hz).

Fourth Step

The compound (83) (153 mg) was dissolved in tetrahydrofuran (3 ml) and methanol (3 ml), a 2 mol/L sodium hydroxide aqueous solution (0.31 ml) was added, and the mixture was stirred at room temperature for 1 hour. 2 mol/L hydrochloric acid (0.31 ml) was added, the organic solvent was evaporated under reduced pressure, and water was added. The residue was collected by filtration, and washed with water to afford the compound (84) (121 mg).

$^1$H-NMR (DMSO-$d_6$) δ: 3.37 (3H, s), 3.41 (3H, s), 8.85 (1H, d, J=1.0 Hz), 8.97 (1H, d, J=1.5 Hz), 13.53 (1H, s).

Reference Example 11

Synthesis of Intermediate Compound (88)

[Chemical formula 37]

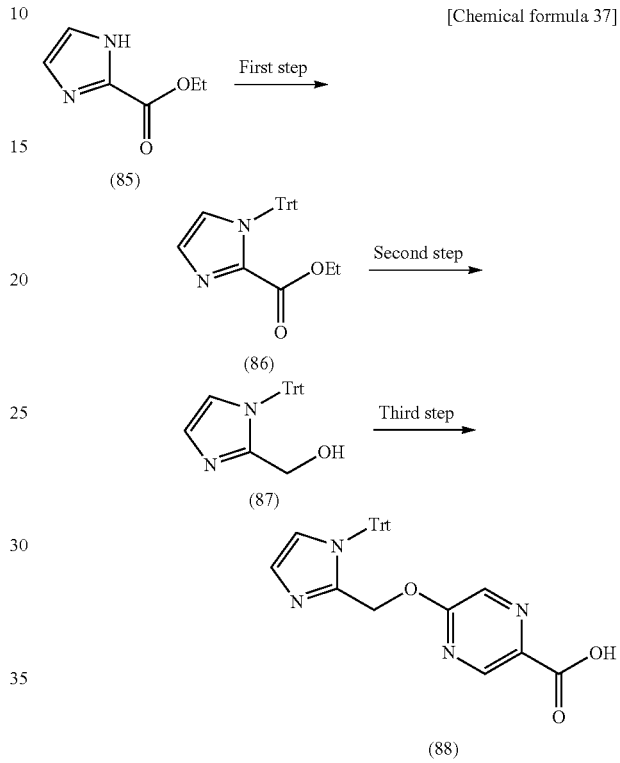

First Step

The compound (85) (2.50 g) was dissolved in pyridine (25 ml), trityl chloride (5.47 g) and dimethylaminopyridine (2.40 g) were added, the mixture was stirred at 100° C. for 22 hours. Water was added, the mixture was extracted with ethyl acetate, the organic layer was dried over anhydrous sodium sulfate, and the solvent was evaporated under reduced pressure. The residue was subjected to silica gel column chromatography to afford the compound (86) (2.81 g).

$^1$H-NMR (CDCl$_3$) δ: 0.94 (3H, t, J=7.1 Hz), 3.82 (2H, q, J=7.1 Hz), 6.97 (1H, d, J=1.0 Hz), 7.12 (7H, m), 7.28-7.30 (9H, m).

Second Step

To ice-cooled and stirred tetrahydrofuran (25 mL), aluminum lithium hydride (333 mg) was added, and a solution of the compound (86) (2.80 g) in tetrahydrofuran (40 mL) was added dropwise. After reacted at room temperature for 1 hour, water (0.35 mL), a 2 mol/L sodium hydroxide aqueous solution (0.35 mL), and water (1.05 mL) were added while stirring under ice-cooling, and the mixture was stirred at room temperature for 1 hour. The resulting insolubles were removed through Celite, and the insolubles on the Celite were washed with hot chloroform and methanol. These washing solutions were evaporated under reduced pressure to afford the compound (87) (960 mg).

$^1$H-NMR (CDCl$_3$) δ: 3.09 (1H, s), 3.65 (2H, d, J=3.5 Hz), 6.80 (1H, s), 7.00 (1H, s), 7.11 (6H, m), 7.34 (9H, m).

Third Step

The compound (87) (681 mg), and 5-chloropyrazine-2-carboxylic acid (317 mg) were dissolved in DMF (20 ml), sodium hydride (240 mg) was added while stirring under ice-cooling, and the mixture was stirred at 75° C. for 3 hours. After reacted, a saturated ammonium chloride aqueous solution (50 mL) was added, and the reaction solution was concentrated under reduced pressure. To the residue was added hot ethanol, the mixture was extracted, and the solvent was evaporated under reduced pressure. The residue was subjected to silica gel column chromatography to afford the compound (88) (497 mg, containing impurities).

$^1$H-NMR (CDCl$_3$) δ: 4.85 (2H, s), 6.88 (1H, s), 7.00-7.42 (16H, m), 7.84 (1H, s), 8.59 (1H, s).

Reference Example 12

Synthesis of Intermediate Compound (95)

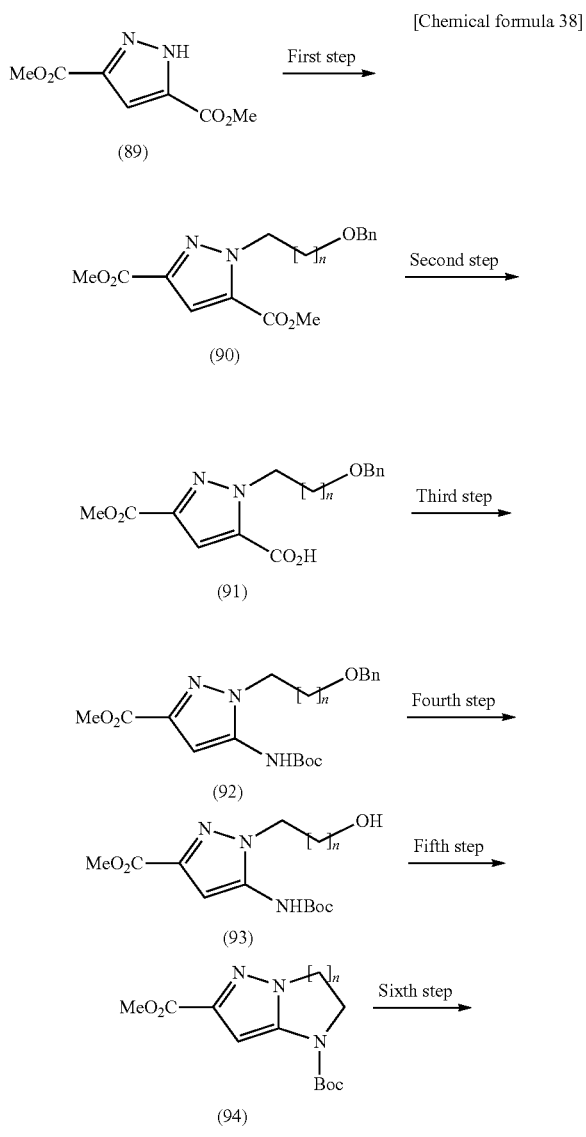

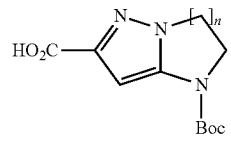

wherein, n represents 1 or 2.

First Step

When n is 1,

The compound (89) (10.0 g) was dissolved in acetonitrile (200 ml), benzyl 2-bromoethyl ether (9.5 ml) and potassium carbonate (11.3 g) were added, and the mixture was stirred at 85° C. for 1.5 hours. After allowed to cool to room temperature, the solvent was evaporated under reduced pressure, and water was added. The mixture was extracted with ethyl acetate, the organic layer was dried over anhydrous sodium sulfate, and the solvent was evaporated under reduced pressure to afford the compound (90) (17.0 g). $^1$H-NMR (CDCl$_3$) δ: 3.84 (3H, d, J=2.5 Hz), 3.86 (2H, t, J=5.8 Hz), 3.94 (3H, s), 4.47 (2H, s), 4.90 (2H, t, J=5.8 Hz), 7.19-7.36 (6H, m).

When n is 2

The compound (89) (10.0 g) was dissolved in acetonitrile (100 ml), benzyl 3-bromopropyl ether (11.2 ml) and potassium carbonate (11.3 g) were added, and the mixture was stirred at 85° C. for 1.5 hours. After allowed to cool to room temperature, the solvent was evaporated under reduced pressure, and water was added. The mixture was extracted with ethyl acetate, the organic layer was dried over anhydrous sodium sulfate, and the solvent was evaporated under reduced pressure to afford the compound (90) (18.0 g).

$^1$H-NMR (CDCl$_3$) δ: 2.16-2.23 (2H, m), 3.50 (2H, t, J=6.1 Hz), 3.87 (3H, s), 3.93 (3H, s), 4.48 (2H, s), 4.77 (2H, t, J=7.4 Hz), 7.26-7.35 (6H, m).

Second Step

When n is 1

The compound (90) (17.0 g) was dissolved in MeOH, and a 0.7 mol/L sodium hydroxide aqueous solution (32 ml) was added while stirring under ice-cooling. After stirred at room temperature for 18 hours, the reaction solution was concentrated under reduced pressure. 0.2 mol/L hydrochloric acid was added, The mixture was extracted with ethyl acetate, and the organic layer was dried over anhydrous sodium sulfate. The solvent was evaporated under reduced pressure to afford the compound (91) (16.0 g) as a crude product.

When n is 2, the compound was similarly synthesized.

A spectrum of the crude product was not measured.

Third Step

When n=1

The compound (91) (16.0 g) was dissolved in t-butyl alcohol, diphenylphosphoryl azide (14 ml) and triethylamine (10 ml) were added, and the mixture was stirred and heated at reflux for 4 hours. The reaction solution was concentrated under reduced pressure. Water was added, the mixture was extracted with ethyl acetate, the organic layer was dried over anhydrous sodium sulfate, and the solvent was evaporated under reduced pressure. The residue was subjected to silica gel column chromatography to afford the compound (92) (15.0 g).

$^1$H-NMR (CDCl$_3$) δ: 1.44 (9H, s), 3.85 (2H, t, J=4.3 Hz), 3.92 (3H, s), 4.37 (2H, t, J=4.3 Hz), 4.52 (2H, s), 6.82 (1H, s), 7.28 (5H, m), 7.90 (1H, s).

When n is 2, the compound was similarly synthesized.

¹H-NMR (CDCl₃) δ: 1.48 (9H, s), 2.08-2.14 (2H, m), 3.35 (2H, t, J=5.6 Hz), 3.90 (3H, s), 4.23 (2H, t, J=6.1 Hz), 4.57 (2H, s), 6.80 (1H, s), 7.35 (5H, m, Hz), 7.75 (1H, s).

Fourth Step

When n=1

The compound (92) (15.0 g) was dissolved in methanol (150 ml), palladium hydroxide (1.40 g) was added, and the mixture was vigorously stirred at room temperature under a hydrogen stream. After five hours, the insolubles were removed by filtration with Celite, and the filtrate was concentrated under reduced pressure to afford the compound (93) (11.4 g) as a crude product.

¹H-NMR (CDCl₃) δ: 1.51 (9H, s), 3.89 (3H, s), 4.03-4.05 (2H, m), 4.28-4.31 (2H, m), 6.77 (1H, s), 7.75 (1H, s).

When n is 2, the compound was similarly synthesized.

¹H-NMR (CDCl₃) δ: 1.48 (9H, d, J=19.8 Hz), 2.07-2.12 (2H, m), 3.56 (2H, t, J=5.3 Hz), 3.90 (3H, s), 4.26 (2H, t, J=6.1 Hz), 6.76 (1H, s), 7.76 (1H, s).

Fifth Step

When n=1

The compound (93) (11.4 g) was dissolved in THF (400 ml), 1,1'-(azodicarbonyl)dipiperazine (12.1 g) and tributylphosphine (13 ml) were added, and the mixture was stirred at 75° C. for 15 minutes. After reacted, the mixture was allowed to cool to room temperature. The precipitated insolubles were removed by filtration, and the filtrate was concentrated under reduced pressure. To the residue was added water, the mixture was extracted with ethyl acetate, the organic layer was dried over anhydrous sodium sulfate, and the solvent was evaporated under reduced pressure. The residue was subjected to silica gel column chromatography to afford the compound (94) (7.60 g).

¹H-NMR (CDCl₃) δ: 1.57 (9H, s), 3.91 (3H, s), 4.39 (4H, s), 6.17 (1H, s).

When n is 2, the compound was similarly synthesized.

¹H-NMR (CDCl₃) δ: 1.58 (9H, s), 2.20 (2H, m), 3.84 (2H, t, J=5.6 Hz), 3.91 (3H, s), 4.24 (2H, t, J=6.1 Hz), 6.80 (1H, s).

Sixth Step

When n=1

The compound (94) (1.01 g) was dissolved in THF (10 ml) and MeOH (10 ml), a 4 mol/L lithium hydroxide aqueous solution (1.9 ml) was added, and the mixture was stirred at room temperature for 4.5 hours. To the reaction solution was added a 0.1 mol/L hydrochloric acid, the mixture was extracted with chloroform, and the organic layer was dried over anhydrous sodium sulfate. The solvent was evaporated under reduced pressure to afford the compound (95) (844 mg) as a crude product.

1H-NMR (CDCl₃) δ: 1.59 (9H, s), 4.41 (4H, s), 6.21 (1H, s).

When n is 2, the compound was similarly synthesized.

1H-NMR (CDCl₃) δ: 1.56 (9H, s), 2.18-2.24 (2H, m), 3.85 (2H, t, J=5.8 Hz), 4.25 (2H, t, J=6.1 Hz), 6.82 (1H, s).

Reference Example 13

Synthesis of Intermediate Compound (101)

[Chemical formula 39]

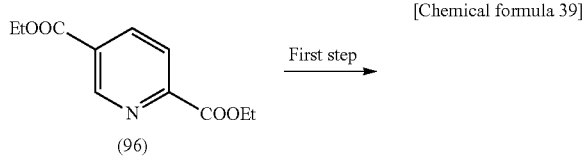

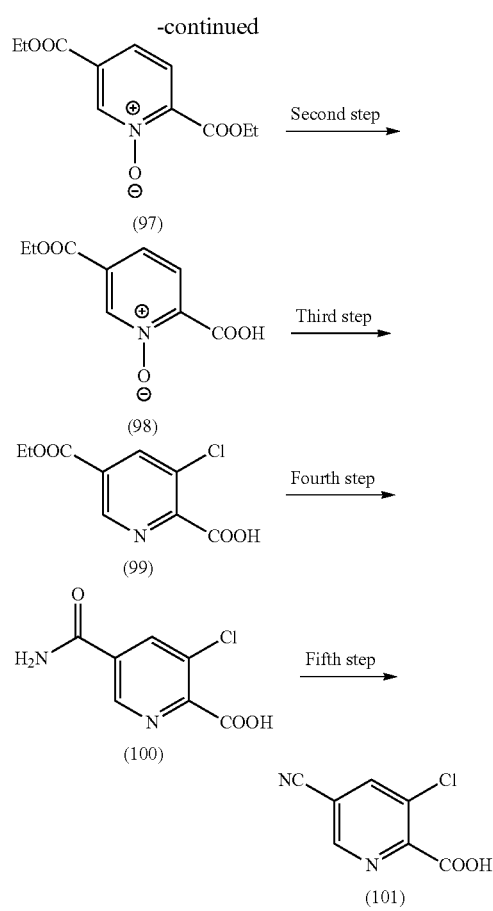

First Step

A compound (96) (15 g) was dissolved in dichloromethane (150 ml), mCPBA (21.4 g) was added, and the mixture was stirred at room temperature for 24 hours. A saturated sodium, hydrogen carbonate aqueous solution was added, the mixture was extracted with dichloromethane. The organic layer was washed with a saturated sodium hydrogen carbonate aqueous solution, dried over sodium sulfate, and the solvent was evaporated under reduced pressure. The residue was subjected to silica gel column chromatography to afford the compound (97) (14.3 g).

¹H-NMR (DMSO-d₆) δ: 8.60-8.58 (1.0H, m), 7.85-7.83 (2.0H, m), 4.40-4.32 (4.0H, m), 1.33-1.31 (6.0H, m).

Second Step

The compound (97) (14.3 g) was dissolved in ethanol (72 ml) and water (72 ml), concentrated hydrochloric acid (14.3 ml) was added, and the mixture was stirred at 60° C. for 14.5 hours. After ice-cooled, the resulting solid was collected by filtration, and washed with water to afford the compound (98) (9.8 g).

¹H-NMR (DMSO-d₆) δ: 9.00-8.97 (1.0H, m), 8.41-8.39 (1.0H, m), 8.28-8.26 (1.0H, m), 4.40 (2.0H, q, J=6.91 Hz), 1.36 (3.0H, t, J=6.95 Hz).

Third Step

Thionyl chloride (13.5 ml) was dissolved in dichloromethane (200 ml), DMF (4.7 ml) was added under ice-cooling, the compound (98) (9.7 g) was added, at the same temperature, and the mixture was stirred at 65° C. for 2.5 hours. After allowed to cool to room temperature, and water (31 ml) was added under ice-cooling. Dichloromethane was evaporated under reduced pressure, the precipitated solid was collected by filtration, and washed with water to afford the compound (99) (9.3 g).

$^1$H-NMR (DMSO-$d_6$) δ: 8.99 (1.0H, d, J=1.68 Hz), 8.42 (1.0H, d, J=1.68 Hz), 4.36 (2.0H, q, J=7.07 Hz), 1.34 (3.0H, t, J=7.09 Hz).

Fourth Step

To the compound (99) (6 g) was added 28% aqueous ammonia (40.2 ml), the mixture was stirred at room temperature for 2 hours, and concentrated hydrochloric acid (44.1 ml) was added dropwise under ice-cooling. The precipitated solid was collected by filtration, and washed with water to afford the compound (100) (4.6 g).

$^1$H-NMR (DMSO-$d_6$) δ: 8.97-8.95 (1.0H, m), 8.43-8.40 (1.0H, m), 8.33 (1.0H, br s), 7.84 (1.0H, br s).

Fifth Step

The compound (100) (1.5 g) was dissolved in DMF (15 ml), oxalyl chloride (1.9 ml) was added under ice-cooling, the mixture was stirred at the same temperature for 1.5 hours, and 4 mol/L sodium hydroxide (9.4 ml) was added. The precipitated solid was collected by filtration, and washed with water to afford the compound (6) (706 mg). In addition, the filtrate was extracted with ethyl acetate ester, the organic layer was dried over anhydrous sodium sulfate, and the solvent was evaporated under reduced pressure. The residue was washed with water, and collected by filtration to afford the compound (101) (305 mg).

$^1$H-NMR (DMSO-$d_6$) δ: 9.03-9.00 (1.0H, m), 8.75-8.72 (1.0H, m).

Reference Example 14

Synthesis of Intermediate Compound (105)

[Chemical formula 40]

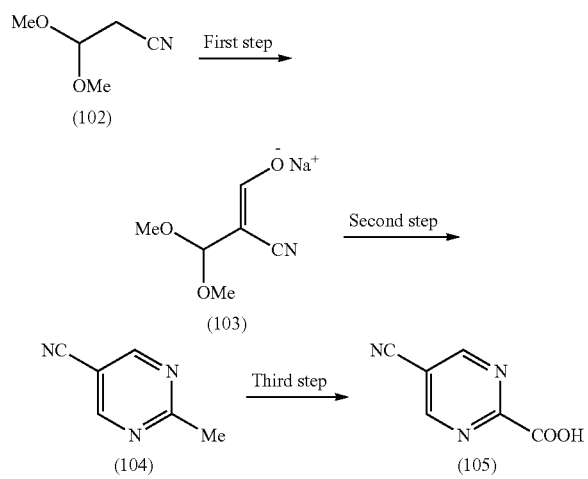

First Step

To a suspension of sodium hydride (3.90 g) in tetrahydrofuran (30 ml) were added a compound (102) (9.8 ml) and ethyl formate (10.8 ml) at 15° C., and the mixture was stirred at room temperature for 5 days. The resulting solid was collected by filtration, washed with ether, and naturally dried to afford the compound (103) (11.7 g).

Second Step

The compound (103) (1.05 g) was dissolved in ethanol (3 ml), and acetamidine hydrochloride (500 mg) was added, the mixture was heated at reflux for 7 hours. After the solvent was evaporated under reduced pressure, water was added, and the mixture was extracted with ethyl acetate. After the solvent was evaporated under reduced pressure, the residue was subjected to silica gel column chromatography to afford the compound (104) (294 mg).

$^1$H-NMR (CDCl$_3$) δ: 2.84 (3H, s), 8.90 (2H, s).

Third Step

To a solution of the compound (104) (2.15 g) in pyridine (20 ml) was added selenium dioxide (4.01 g), and the mixture was stirred at 80° C. for 4 hours. The mixture was allowed to stand at room temperature overnight, the resulting insolubles were removed by filtration, and the solvent was evaporated under reduced pressure. The residue was dissolved in water, the mixture was passed through HP-20SS column chromatography, and the solvent was evaporated under reduced pressure. The residue was washed with acetone to afford the compound (105) (491 mg).

$^1$H-NMR (DMSO-$d_6$) δ: 9.44 (2H, s).

Reference Example 15

Synthesis of Intermediate Compound (107)

[Chemical formula 41]

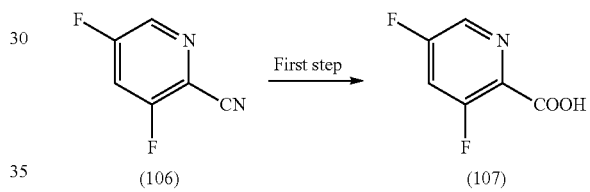

First Step

A solution of a compound (106) (1.0 g) in concentrated sulfuric acid (5.4 ml) and water (600 was stirred at 110° C. for 22 hours, the mixture was poured into ice water, and the precipitated solid was collected by filtration. The solid was washed with water, and naturally dried to afford the compound (107) (1.02 g).

$^1$H-NMR (DMSO-$d_6$) δ: 8.08 (1H, m), 8.60 (1H, m).

Example 1

Synthesis of Compound 2

[Chemical formula 42]

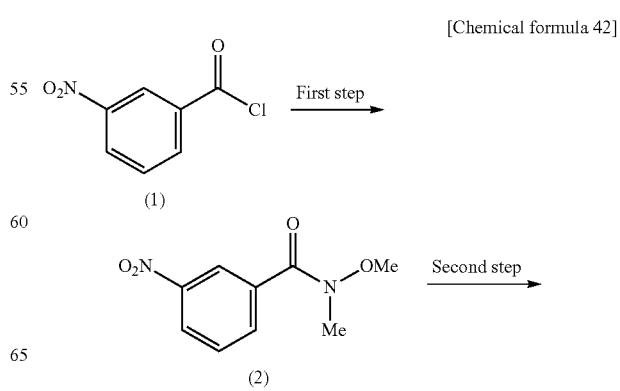

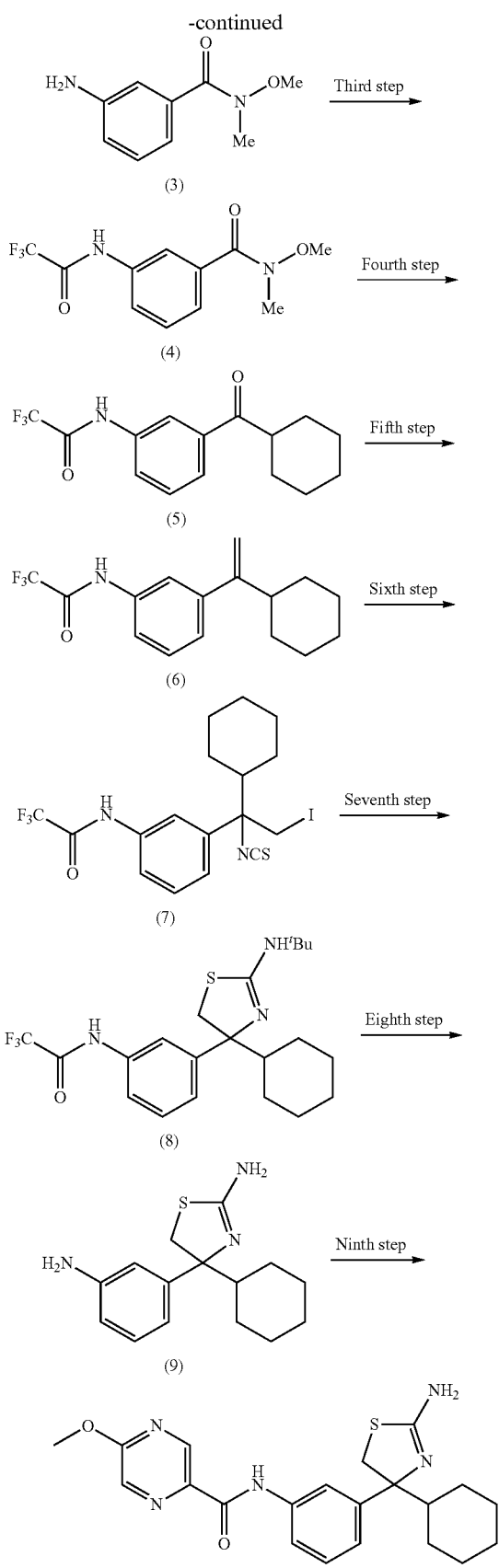

First Step

The compound (1) (21.25 g) was dissolved in dichloromethane (106 ml), N,O-dimethylhydroxylamine hydrochloride (12.29 g) and pyridine (23.2 ml) were added under ice-cooling, and the mixture was stirred for 20 minutes. Dilute hydrochloric acid was added, the mixture was extracted with dichloromethane. The organic layer was washed with dilute hydrochloric acid, a saturated sodium hydrogen carbonate aqueous solution, and a saturated sodium chloride aqueous solution in order, dried over anhydrous sodium sulfate, and the solvent was evaporated under reduced pressure. To the residue was added hexane, and the precipitated solid was collected by filtration to afford the compound (2) (22.47 g).

$^1$H-NMR (CDCl$_3$) δ: 3.41 (3H, s), 3.57 (3H, s), 7.62 (1H, t, J=8.1 Hz), 8.05 (1H, dt, J=8.1, 1.2 Hz), 8.33 (1H, ddd, J=8.1, 2.1, 1.2 Hz), 8.59 (1H, t, J=2.1 Hz).

Second Step

The compound (2) (22.26 g) was dissolved in methanol (111 ml), 5% palladium carbon (6.68 g) was added, and the mixture was stirred for 7 hours under the hydrogen atmosphere. Further, 5% palladium carbon (4.45 g) was added, the mixture was stirred for 1.5 hours under the hydrogen atmosphere, the reaction solution was filtered, and the mother liquor wad concentrated under reduced pressure to afford the residue (15.86 g) of the compound (3).

$^1$H-NMR (CDCl$_3$) δ: 3.33 (3H, s), 3.58 (3H, s), 3.74 (2H, brs), 6.76 (1H, ddd, J=7.8, 2.4, 1.2 Hz), 6.95 (1H, t, J=2.4 Hz), 7.02 (1H, dt, J=7.8, 1.2 Hz), 7.17 (1H, t, J=7.8 Hz).

Third Step

The compound (3) (15.81 g) was dissolved in dichloromethane (79 ml), trifluoroacetic anhydride (13.6 ml) and pyridine (7.8 ml) were added under ice-cooling, and the mixture was stirred for 30 minutes, Dilute hydrochloric was added, the mixture was extracted with dichloromethane. The organic layer was washed with dilute hydrochloric acid, a saturated sodium hydrogen carbonate aqueous solution, and a saturated sodium chloride aqueous solution, and dried over anhydrous sodium sulfate, and the solvent was evaporated under reduced pressure. To the residue was added hexane, and the precipitated solid was collected by filtration to afford the compound (4) (14.92 g).

$^1$H-NMR (CDCl$_3$) δ: 3.37 (3H, s), 3.58 (3H, s), 7.42 (1H, t, J=7.8 Hz), 7.52 (1H, dt, J=7.8, 1.2 Hz), 7.80-7.88 (2H, m), 8.78 (1H, brs).

Fourth Step

The compound (4) (4.00 g) was dissolved in tetrahydrofuran (32 ml), a 1 mol/L cyclohexylmagnesium bromide-tetrahydrofuran solution (43.5 ml) was added under ice-cooling, and the mixture was stirred at room temperature for 16.5 hours. An ammonium chloride aqueous solution was added under ice-cooling, the mixture was extracted with ethyl acetate, and the insolubles were removed by filtration. The organic layer was washed with water, and a saturated sodium chloride aqueous solution in order, dried over anhydrous sodium sulfate, and the solvent was evaporated under reduced pressure. The residue was purified by chromatography to afford the compound (5) (833 mg).

$^1$H-NMR (CDCl$_3$) δ 1.20-1.96 (10H, m), 3.20-3.28 (1H, m), 7.52 (1H, t, J=8.1 Hz), 7.76 (1H, dt, J=8.1, 1.2 Hz), 7.92 (1H, ddd, J=8.1, 1.7, 1.2 Hz), 8.03 (1H, t, J=1.7 Hz), 8.07 (1H, brs).

Fifth Step

Methyltriphenylphosphonium iodide (5.73 g) was suspended in tetrahydrofuran (21 ml), and a 1.57 mol/L n-butyllithium-hexane solution (9.0 ml) was added dropwise under ice-cooling. After stirred at room temperature for 50 minutes, a solution of the compound (5) (1.42 g) in tetrahydrofuran (8 ml) was added under ice-cooling, and the mixture was stirred at room temperature for 45 minutes. Ethyl acetate and water were added, the mixture was extracted with ethyl acetate. The organic layer was washed with water, and a saturated sodium chloride aqueous solution in order, dried over anhydrous sodium sulfate, and the solvent was evaporated under reduced pressure. The residue was purified by chromatography to afford the compound (6) (1.47 g).

$^1$H-NMR (CDCl$_3$) δ: 1.10-1.88 (10H, m), 2.34-2.43 (1H, m), 5.05 (1H, t, J=1.2 Hz), 5.14 (1H, s), 7.21 (1H, dt, J=7.8, 1.2 Hz), 7.34 (1H, t, J=7.8 Hz), 7.47 (1H, t, J=2.1 Hz), 7.52 (1H, ddd, J=7.8, 2.1, 1.2 Hz), 7.85 (1H, brs).

Sixth Step

The compound (6) (1.20 g) was dissolved in chloroform (60 ml), iodine (2.46 g), potassium thiocyanate (1.96 g), tetra n-butylammonium chloride (50 mg) and water (3 ml) were added, and the mixture was stirred at 60° C. for 45.5 hours. A sodium thiosulfate aqueous solution was added under ice-cooling, and the mixture was extracted with chloroform. The organic layer was washed with water and a saturated sodium chloride aqueous solution in order, dried over anhydrous sodium sulfate, and the solvent was evaporated under reduced pressure. The residue was purified by chromatography to afford the compound (7) (619 mg).

$^1$H-NMR (CDCl$_3$) δ: 1.10-2.10 (11H, m), 3.67, 4.00 (2H, ABq, J=10.7 Hz), 7.15 (111, d, J=8.3 Hz), 7.41-7.48 (2H, m), 7.65 (1H, d, J=8.3 Hz), 8.03 (1H, brs).

Seventh Step

The compound (7) (70 mg) was dissolved in tetrahydrofuran (0.7 ml), t-butylamine (0.046 ml) was added, and the mixture was stirred at 60° C. for 26 hours. Ethyl acetate and water were added, the mixture was extracted. The organic layer was washed with water, and a saturated sodium chloride aqueous solution in order, dried over anhydrous sodium sulfate, and the solvent was evaporated under reduced pressure. Similarly, using the compound (7) (578 mg), tetrahydrofuran (5.8 ml), and t-butylamine (0.378 ml), a reaction was performed. Both reaction residues were combined, and purified by chromatography to afford the compound (8) (511 mg).

$^1$H-NMR (CDCl$_3$) δ: 0.90-2.00 (11H, m), 1.47 (9H, s), 3.35, 3.63 (2H, ABq, J=10.4 Hz), 7.26-7.37 (2H, m), 7.47-7.60 (2H, m).

Eighth Step

The compound (8) (464 mg) was suspended in concentrated hydrochloric acid (4.6 ml), and the mixture was stirred at 100° C. for 2.5 hours. A 5 mol/L sodium hydroxide aqueous solution was added, the mixture was extracted with ethyl acetate. The organic layer was washed with water, and a saturated sodium chloride aqueous solution in order, dried over anhydrous sodium sulfate, and the solvent was evaporated under reduced pressure. The residue was purified by chromatography to afford the compound (9) (280 mg).

$^1$H-NMR (CDCl$_3$) δ: 0.94-1.95 (11H, m), 3.52, 3.71 (2H, ABq, J=10.7 Hz), 3.63 (1H, brs), 4.63 (1H, brs), 6.55 (1H, ddd, J=7.8, 2.0, 1.2 Hz), 6.73 (1H, dt, J=7.8, 1.2 Hz), 6.76 (1H, t, J=2.0 Hz), 7.09 (1H, t, J=7.8 Hz).

Ninth Step

5-Methoxypyrazine-2-carboxylic acid (47 mg) was suspended in methanol (1.4 ml), DMT-MM (88 mg) and methanol (0.7 ml) were added, followed by the compound (9) (70 mg), and the mixture was stirred at room temperature for 1 hour. Ethyl acetate and a 5% potassium carbonate aqueous solution were added, the mixture was extracted with ethyl acetate. The organic layer was washed with water, and a saturated sodium chloride aqueous solution in order, dried over anhydrous sodium sulfate, and the solvent was evaporated under reduced pressure. The residue was purified by chromatography to afford the compound (2) (63 mg).

$^1$H-NMR (CDCl$_3$) δ: 0.80-2.10 (11H, m), 3.59, 3.79 (2H, ABq, J=11.1 Hz), 4.07 (3H, s), 4.67 (1H, brs), 7.15 (1H, dt, J=8.1, 1.2 Hz), 7.33 (1H, t, J=8.1 Hz), 7.68 (1H, t, J=1.8 Hz), 7.74 (1H, ddd, J=8.1, 1.8, 1.2 Hz), 8.15 (1H, d, J=1.2 Hz), 9.03 (1H, d, J=1.2 Hz), 9.53 (1H, s).

Example 2

Synthesis of Compound 56

[Chemical formula 43]

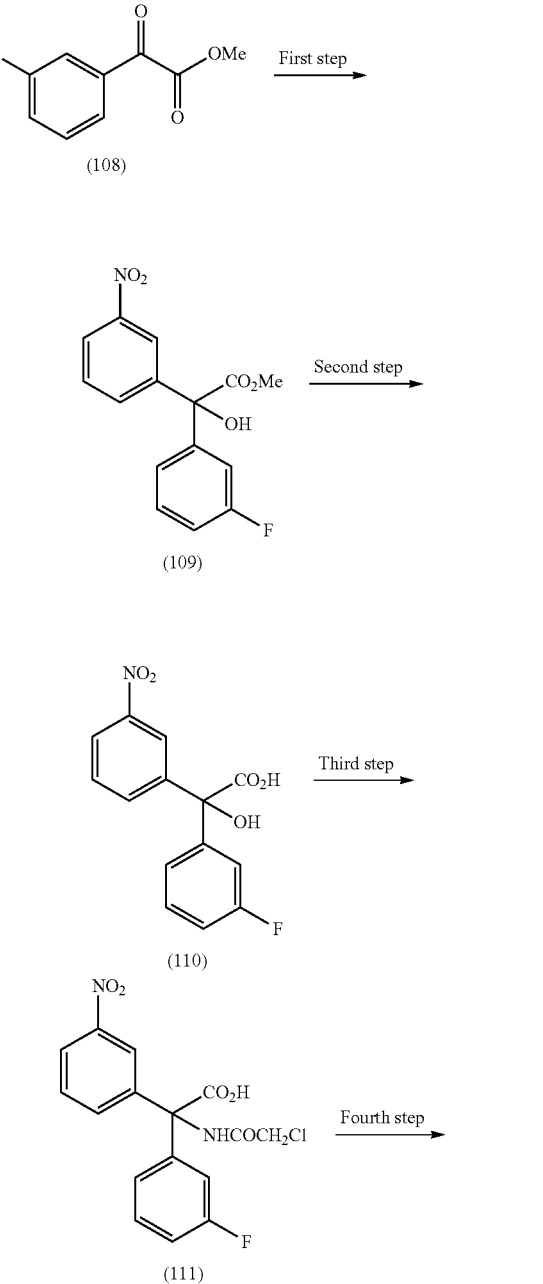

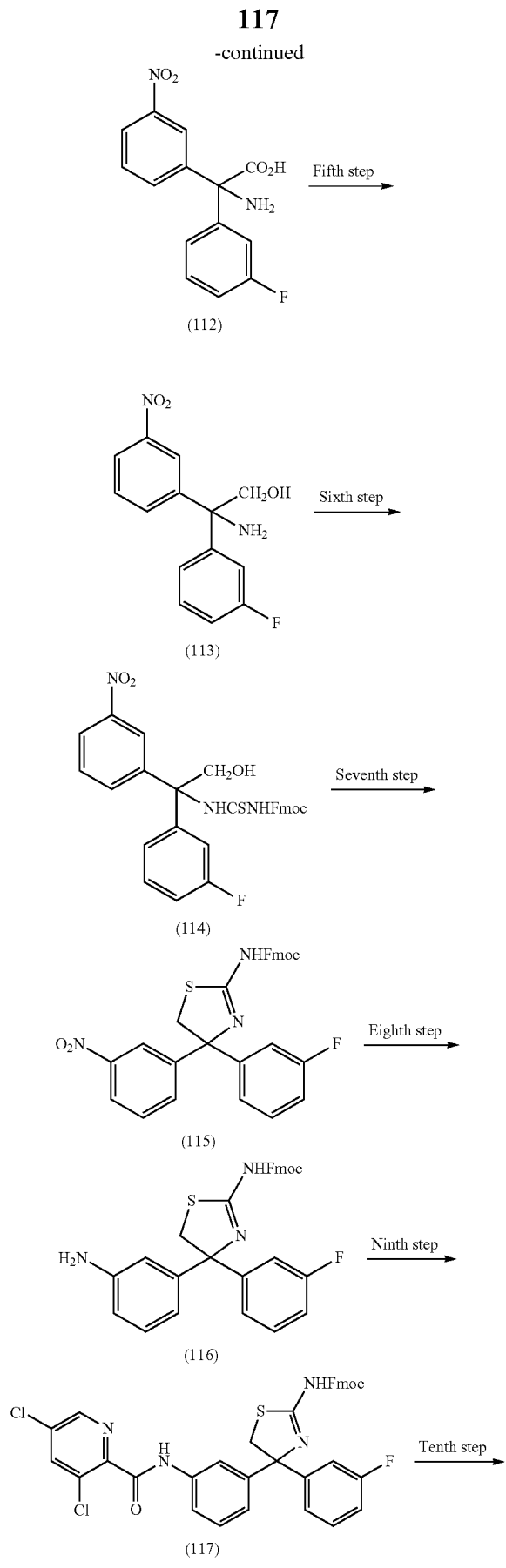

First Step

To a stirred under ice-cooling solution of a compound (108) (4.00 g) in tetrahydrofuran (40 ml) was added dropwise a 1 mol/L 3-bromophenylmagnesium bromide/tetrahydrofuran solution (24.9 ml). After reacted for 1 hour, a saturated ammonium chloride aqueous solution was added. The mixture was extracted with ethyl acetate, the organic layer was dried over anhydrous sodium sulfate, and the solvent was evaporated under reduced pressure. The residue was subjected to silica gel column chromatography to afford the compound (109) (3.24 g).

$^1$H-NMR (CDCl$_3$) δ: 3.92 (3H, s), 4.37 (1H, s), 7.02-7.19 (3H, m), 7.31-7.38 (1H, m), 7.52 (1H, t, J=8.2 Hz), 7.78 (1H, dq, J=8.2, 1.0 Hz), 8.19 (1H, dq, J=8.2, 1.0 Hz), 8.35 (1H, t, J=2.1 Hz).

Second Step

To a stirred under ice-cooling solution of the compound (109) (3.24 g) in methanol (32 ml) was added dropwise a 2 mol/L sodium hydroxide aqueous solution (15.9 ml), and the mixture was stirred for 30 minutes. To the reaction solution was added 2 mol/L hydrochloric acid to make the solution acidic, and the mixture was extracted with chloroform. The organic layer was dried over anhydrous sodium sulfate, the solvent was evaporated under reduced pressure, and the residue was subjected to silica gel column chromatography to afford the compound (110) (2.77 g).

$^1$H-NMR (CDCl$_3$) δ: 7.04-7.40 (4H, m), 7.54 (1H, t, J=8.2 Hz), 7.84 (1H, dq, J=8.2, 1.1 Hz), 8.21 (1H, dq, J=8.2, 1.1 Hz), 8.43 (1H, t, J=1.9 Hz).

Third Step

To a stirred under ice-cooling solution of the compound (110) (0.96 g) in 2-chloroacetonitrile (4.98 g) was added concentrated sulfuric acid (3.23 g), and the mixture was stirred for 4 hours. To the reaction solution was added water, the mixture was extracted with chloroform. The organic layer was dried over anhydrous sodium sulfate, and the solvent was evaporated under reduced pressure to afford the compound (111) as a crude product.

Fourth Step

To a stirred under ice-cooling solution of the compound (111) obtained in the third step in dichloromethane (24 ml), N,N-dimethylformamide (0.024 g) and oxalyl chloride (1.16 ml) were added, and the mixture was stirred at room temperature for 3 hours. The reaction solution was poured into methanol (20 ml), and the solvent was evaporated under reduced pressure to afford the compound (112) as a crude product.

Fifth Step

To a stirred under ice-cooling solution of the compound (112) obtained in the fourth step in tetrahydrofuran (10 ml) was added dropwise a 1 mol/L borane/tetrahydrofuran solution (66.0 ml), and the mixture was stirred at room temperature for 3 hours. The reaction solution was poured into ice, concentrated hydrochloric acid was added to make the solution acidic, and the mixture was stirred at room temperature for 15 minutes. A 4 mol/L sodium hydroxide aqueous solution was added to make the solution basic, the mixture was extracted with chloroform. The organic layer was dried over anhydrous sodium sulfate, and the solvent was evaporated under reduced pressure to afford the compound (113) as a crude product.

Sixth Step

To a stirred under ice-cooling solution of the compound (113) obtained in the fifth step in acetone (3.6 ml) was added Fmoc-isothiocyanate (0.40 g), and the mixture was stirred for 1.5 hours. The reaction solution was evaporated under reduced pressure, and the residue was subjected to silica gel column chromatography to afford the compound (114) (0.57 g).

Seventh step

The compound (114) (0.57 g) was dissolved in dichloromethane (31 ml), and 1-chloro-N,N-2-trimethyl-1-propenylamine (0.27 g) was added while stirring under ice-cooling. After stirred at room temperature for 2 hours, water was added, the mixture was extracted with dichloromethane. The organic layer was dried over anhydrous magnesium sulfate, the solvent was evaporated under reduced pressure, and the residue was subjected to silica gel column chromatography to afford the compound (115) (0.24 g).

$^1$H-NMR (CDCl$_3$) δ: 3.90 (1H, d, J=11.9 Hz), 3.95 (1H, d, J=11.9 Hz), 4.25 (1H, t, J=6.5 Hz), 4.52 (2H, d, J=6.5 Hz), 6.96-6.99 (1H, m), 7.08-7.13 (2H, m), 7.29-7.34 (3H, m), 7.40-7.42 (2H, m), 7.49 (1H, t, J=8.0 Hz), 7.57 (2H, d, J=7.5 Hz), 7.69 (1H, dt, J=8.0, 2.0 Hz), 7.76 (2H, d, J=7.5 Hz), 8.12 (1H, d, J=8.0 Hz), 8.29 (1H, t, J=2.0 Hz).

Eighth Step

To a solution of the compound (115) (0.22 g) in ethyl acetate (2.2 ml) and methanol (2.2 ml) was added 10% palladium carbon powder (0.07 g), and the mixture was stirred at room temperature for 7 hours. The insolubles were removed by filtration, the filtrate was evaporated under reduced pressure, and the residue was subjected to silica gel column chromatography to afford the compound (116) (0.18 g).

$^1$H-NMR (CDCl$_3$) δ: 3.73 (2H, br s), 3.82 (1H, d, J=11.8 Hz), 3.91 (1H, d, J=11.8 Hz), 4.27 (1H, t, J=7.1 Hz), 4.46 (2H, d, J=7.1 Hz), 6.59-6.71 (2H, m), 6.94-7.18 (4H, m), 7.29-7.32 (4H, m), 7.40 (2H, t, J=7.7 Hz), 7.62 (2H, d, J=7.7 Hz), 7.76 (2H, d, J=7.7 Hz).

Ninth Step

To a stirred under ice-cooling solution of 3,5-dichloropyridine-2-carboxylic acid in N,N-dimethylformamide (0.5 ml), 2-(1H-7-azabenzotriazol-1-yl)-1,1,3,3-tetramethyluronium hexafluorophosphate (0.05 mg) and triethylamine (0.01 mg) were added. After stirred for 10 minutes, a solution of the compound (116) (0.05 g) in N,N-dimethylformamide (2 ml) was added, and the mixture was stirred at room temperature for 2.5 hours. Water was added, the mixture was extracted with ethyl acetate, and the organic layer was dried over anhydrous sodium sulfate. The solvent was evaporated under reduced pressure, and the residue was subjected to silica gel column chromatography to afford the compound (117) (0.05 g).

$^1$H-NMR (CDCl$_3$) δ: 3.89 (1H, d, J=11.7 Hz), 3.99 (1H, d, J=11.7 Hz), 4.26 (1H, t, J=6.8 Hz), 4.47 (3H, d, J=6.8 Hz), 6.96 (1H, dd, J=8.9, 7.2 Hz), 7.10-7.14 (2H, m), 7.28-7.42 (9H, m), 7.60 (2H, d, J=7.3 Hz), 7.74-7.76 (2H, m), 7.90 (1H, d, J=2.0 Hz), 8.46 (1H, d, J=2.0 Hz), 9.77 (1H, s).

Tenth Step

To a stirred under ice-cooling solution of the compound (117) (0.05 g) in dichloromethane (0.5 ml) was added piperidine (0.03 mg), and the mixture was stirred for 1 hour. Water was added, the mixture was extracted with dichloromethane, and the organic layer was dried over anhydrous sodium sulfate. The solvent was evaporated under reduced pressure, and the residue was subjected to silica gel column chromatography to afford the compound (56) (0.02 g).

$^1$H-NMR (CDCl$_3$) δ: 3.97 (1H, d, J=11.2 Hz), 4.06 (1H, d, J=11.2 Hz), 4.78 (2H, br s), 6.88-6.94 (1H, m), 7.17-7.21 (4H, m), 7.33 (1H, t, J=7.9 Hz), 7.69 (1H, t, J=1.9 Hz), 7.78-7.81 (1H, m), 7.89 (1H, d, J=2.2 Hz), 8.46 (1H, d, J=2.2 Hz), 9.73 (1H, s).

Reference Example 16

Synthesis of Compound 203

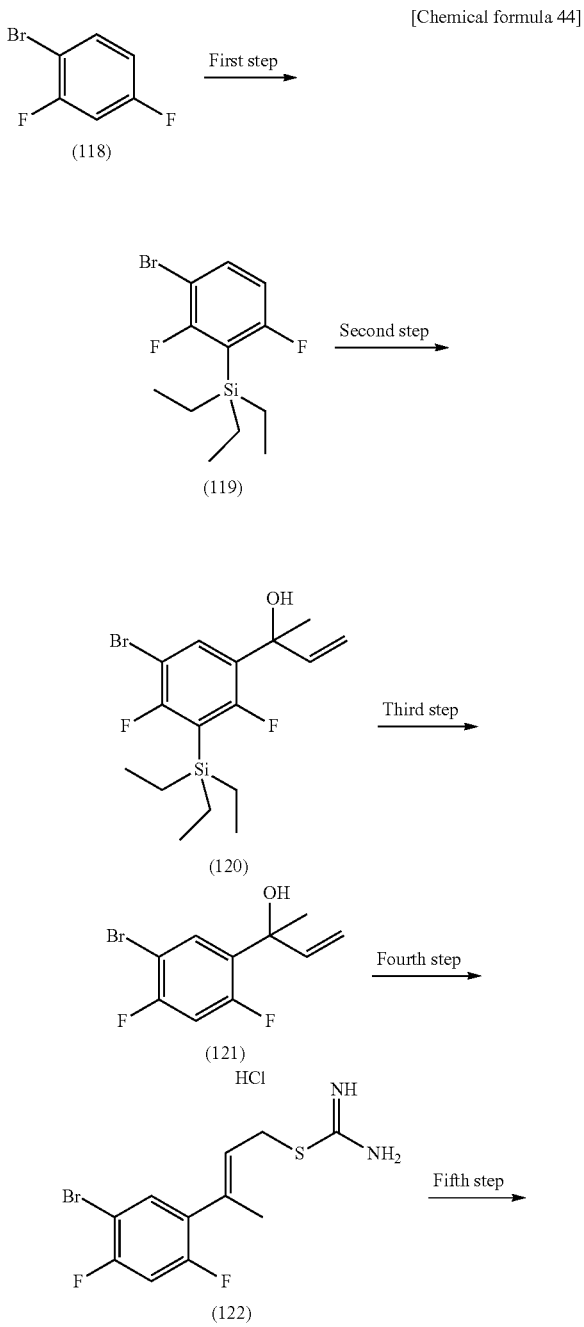

[Chemical formula 44]

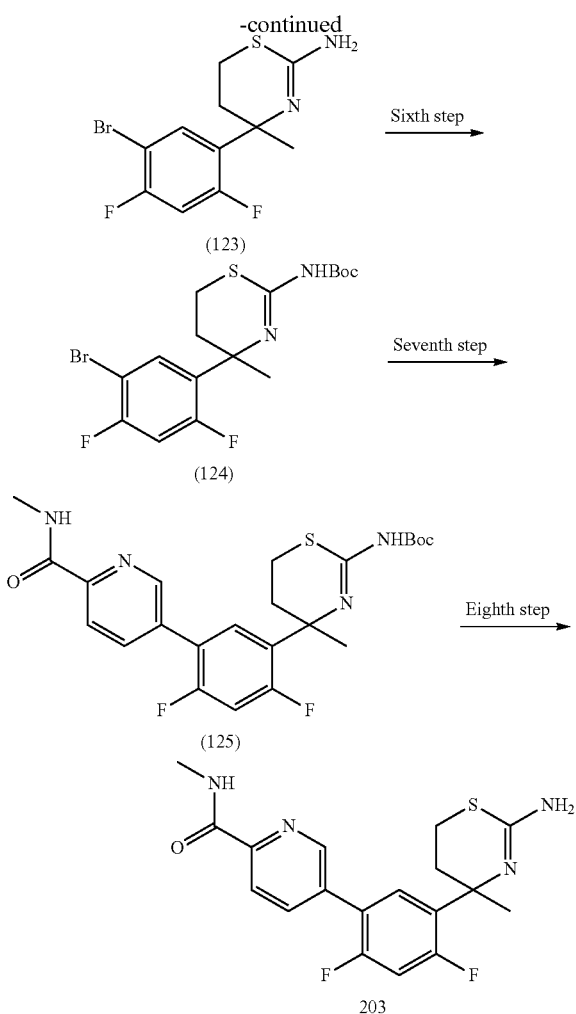

After cooled to room temperature, the mixture was concentrated, water, ethyl acetate and ether were added, and the mixture was extracted with ether. After washed with a sodium chloride aqueous solution, the organic layer was dried over sodium sulfate, and the resulting residue was subjected to chromatography to afford the crude product (121) (200 mg).

Fourth Step

To the crude product (121) (200 mg) were added a hydrochloric acid acetic acid solution (1 mol/L: 1.901 mL) and thiourea (63.7 mg), the mixture was stirred at 40° C. for 4.5 hours, and warmed to 50° C. After stirred overnight, the reaction solution was concentrated to afford the crude product (122) (272 mg).

Fifth Step

To the crude product (122) (272 mg) were added trifluoroacetic acid (3 mL) and concentrated sulfuric acid (0.162 mL), and the mixture was stirred at 60° C. for about 7 hours. After cooled to room temperature, the reaction solution was concentrated, neutralized with a potassium carbonate aqueous solution, and the mixture was extracted with ethyl acetate. The organic layer was washed with an aqueous sodium chloride solution, and dried over sodium sulfate. The resulting residue was purified by chromatography to afford the compound (123) (146 mg).

$^1$H-NMR (CDCl$_3$) δ: 7.62 (1.0H, t, J=8.24 Hz), 6.86 (1.0H, dd, J=11.44, 8.08 Hz), 4.40 (2.0H, br s), 3.00 (1.0H, ddd, J=12.35, 7.32, 3.66 Hz), 2.71 (1.0H, ddd, J=12.35, 9.76, 3.66 Hz), 2.26 (1.0H, ddd, J=14.03, 7.32, 3.66 Hz), 1.95 (1.0H, ddd, J=14.03, 9.76, 3.66 Hz), 1.56 (3.0H, d, J=1.53 Hz).

Sixth Step

The compound (123) (146 mg) was dissolved in tetrahydrofuran (1.5 mL), Boc$_2$O (298 mg) was added, and the mixture was stirred at room temperature for about 1 hour. Water was added, the mixture was extracted with ethyl acetate, the organic layer was washed with a sodium chloride aqueous solution, and dried over sodium sulfate. The resulting residue was purified by chromatography to afford the compound (124) (174 mg).

$^1$H-NMR (CDCl$_3$) δ 7.50 (1.0H, t, J=8.08 Hz), 6.94-6.89 (1.0H, m), 2.89-2.85 (1.0H, m), 2.66-2.59 (2.0H, m), 2.12-2.05 (1.0H, m), 1.68 (3.0H, s), 1.52 (9.0H, s).

Seventh Step

To the compound (124) (47 mg), N-methyl-5-(4,4,5,5-tetramethyl-1,3,2-dioxaborolan-2-yl)picolinamide (38 mg) and PdCl$_2$ (dppf) (9.11 mg) was added DME (1 mL), a sodium carbonate aqueous solution (1 mol/L: 0.335 mL) was added, microwave was irradiated at 70° C., and the mixture was stirred for 30 minutes. The resulting reaction solution was subjected to chromatography to afford the crude product (125) (24 mg).

Eighth Step

The crude product (125) (24 mg) was dissolved in chloroform (0.5 mL), trifluoroacetic acid (0.5 mL) was added, and the mixture was stirred at room temperature for 3 hours. The reaction solution was concentrated, neutralized with a sodium carbonate aqueous solution, and extracted with ethyl acetate. The organic layer was washed with an sodium chloride aqueous solution, and dried over sodium sulfate. The resulting residue was purified by chromatography, and washed with isopropyl ether to afford the compound (203) (3.5 mg).

$^1$H-NMR (DMSO-d$_6$) δ: 8.85 (1.0H, s), 8.71 (1.0H, s), 8.15-8.08 (2.0H, m), 7.64 (1.0H, t, J=9.09 Hz), 7.45-7.39 (1.0H, m), 6.00 (2.0H, br s), 3.09-2.99 (1.0H, m), 2.85 (3.0H,

First Step

A starting material (118) (500 mg) was dissolved in tetrahydrofuran (10 mL), LDA (2 mol/L: 2.59 mL) was added dropwise at −78° C., and the mixture was stirred for about 1 hour. Thereafter, chlorotriethylsilane (0.527 mL) was added dropwise, the mixture was stirred for about 5 hours, warmed to 0° C., and a saturated ammonium chloride aqueous solution was added. After extracted with ether, the organic layer was washed with a sodium chloride aqueous solution, and dried over sodium sulfate. The resulting residue was subjected to chromatography to afford the crude product (119) (932 mg).

Second Step

Diisopropylamine (0.554 mL) was dissolved in tetrahydrofuran (8 mL), butyllithium (1.66 mol/L: 1.873 mL) was added dropwise at −78° C., and the mixture was stirred for 10 minutes. Then, a solution of the crude product (119) (796 mg) in tetrahydrofuran (4 mL) was added dropwise, the mixture was stirred for 10 minutes, methyl vinyl ketone (0.315 mL) was added dropwise, and the mixture was stirred for about 3 hours. The mixture was warmed to 0° C., a saturated ammonium chloride aqueous solution was added, and the mixture was extracted with ethyl acetate. The organic layer was washed with a sodium chloride aqueous solution, and dried over sodium sulfate to afford the crude product (120) (1.26 g).

Third Step

The crude product (120) (978 mg) was dissolved in ethanol (8 mL) and water (2 mL), potassium hydroxide (291 mg) was added, and the mixture was heated at reflux for about 4 hours.

d, J=3.54 Hz), 2.71-2.59 (1.0H, m), 2.15-2.02 (1.0H, m), 1.96-1.85 (1.0H, m), 1.49 (3.0H, s).

Reference Example 17

Synthesis of Compound 205

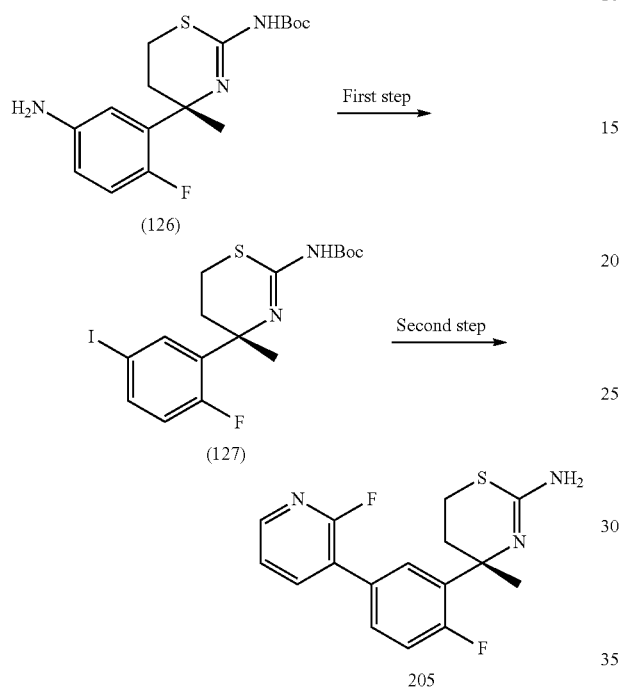

First Step

The compound (126) (200 mg) was dissolved in acetonitrile (4 mL), and a tetrafluoroboric acid aqueous solution (0.096 mL) was added. Thereafter, isopentyl nitrite (0.098 mL) was added at 0° C., the mixture was stirred for 30 minutes, a potassium iodide (293 mg) aqueous solution was added, and the mixture was stirred at room temperature for about 3.5 hours. Sodium hydrogen carbonate was added, and the mixture was extracted with ethyl acetate. The organic layer was washed with water and a sodium chloride aqueous solution, dried over sodium sulfate, and purified by chromatography to afford the compound (127) (87 mg).

$^1$H-NMR (DMSO-$d_6$) δ: 9.75 (1.0H, s), 7.76-7.61 (2.0H, m), 7.07-6.98 (1.0H, m), 3.03-2.93 (1.0H, m), 2.63-2.54 (1.0H, m), 2.25-2.03 (2.0H, m), 1.50 (3.0H, s), 1.42 (9.0H, s).

Second Step

To the compound (127) (100 mg), 2-fluoropyridine-3-boronic acid (40.7 mg), Pd(PPh$_3$)$_4$ (25.7 mg) and sodium carbonate (47.1 mg) were added DME (2 mL) and water (0.5 mL), the mixture was stirred at 50° C. overnight, warmed to 70° C., and stirred for about 7.5 hours. After cooled to room temperature, 2 mol/L hydrochloric acid was added, the mixture was stirred overnight, trifluoroacetic acid was added, and stirred for 9 hours. A saturated sodium carbonate aqueous solution was added, and the mixture was extracted with ethyl acetate. The organic layer was washed with a sodium chloride aqueous solution, and dried over sodium sulfate. This was purified by chromatography, washed with isopropyl ether, and purified by MS triggering to afford the compound (205) (9.3 mg).

$^1$H-NMR (DMSO-$d_6$) δ: 8.31-8.23 (2.0H, m), 8.10-8.03 (1.0H, m), 7.53-7.45 (2.0H, m), 7.42-7.34 (1.0H, m), 3.16-3.09 (1.0H, m), 2.66-2.57 (2.0H, m), 2.08-1.98 (1.0H, m), 1.65 (3.0H, s).

Reference Example 18

Synthesis of Intermediate Compound (135)

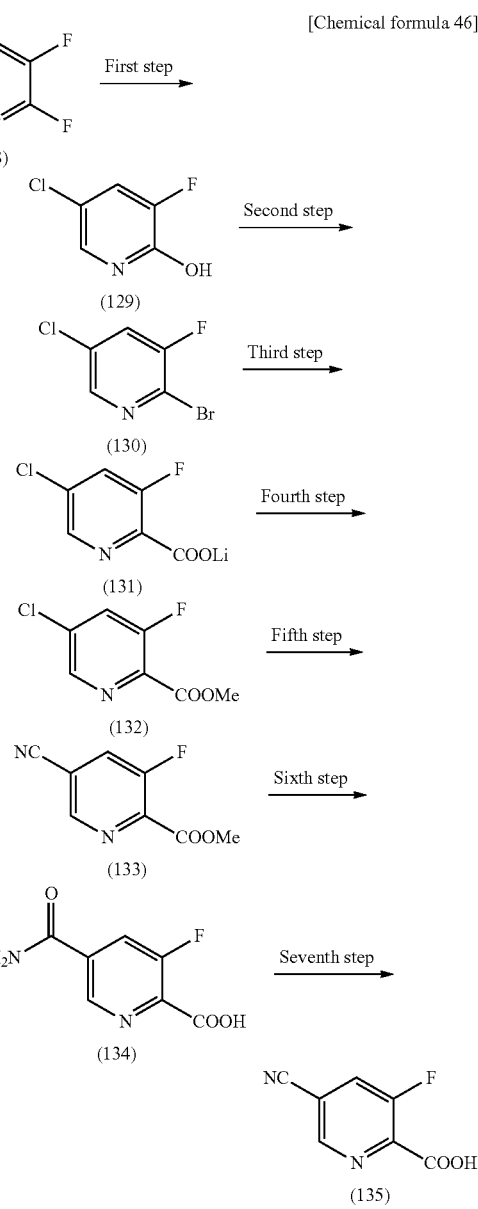

First step

A starting material (128) (35 g) and sodium hydroxide (20.6 g) were dissolved in water (300 mL), and the mixture was heated at reflux for 2.5 hours. After cooled to 0° C., concentrated hydrochloric acid (44.7 mL) was added, water (120 mL) was added, and the precipitated solid was collected by filtration to afford the crude product (129) (25.9 g). To the filtrate was added a 4 mol/L sodium hydroxide aqueous solution to make the solution neutral, and the mixture was extracted with ethyl acetate. The organic layer was dried over sodium sulfate to afford the crude product (2) (5.29 g).

Second Step

Phosphorus oxybromide (100 g) was dissolved in toluene (100 mL), and the mixture was heated and dissolved at 60° C. The crude product (129) (25.7 g) was slowly added at the same temperature, and the mixture was stirred at the 110° C. for 4 hours. After cooled to room temperature, ice water was added at 0° C., 10 mol/L sodium hydroxide (174 mL) was added at the same temperature, and the mixture was extracted with ethyl acetate. The organic layer was washed with sodium hydrogen carbonate and a sodium chloride aqueous solution, and dried over sodium sulfate to afford the crude product (130) (40.3 g).

Third Step

Butyllithium (2.73 mol/L: 0.914 mL) was dissolved in toluene (5 mL) and hexane (3 mL), and a solution of the crude product (130) (500 mg) in toluene (1 mL) was added dropwise at −78° C. After stirred for 45 minutes, dry ice was slowly added, the mixture was stirred for 40 minutes, and warmed to room temperature. After ether was added, the precipitated solid was collected by filtration to afford the crude product (131) (461 mg).

Fourth Step

The crude product (131) (361 mg) was dissolved in methanol (8 mL), thionyl chloride (0.218 mL) was added, and the mixture was heated at reflux for about 2 hours. After cooled to room temperature, the solution was concentrated, and sodium hydrogen carbonate was added, the mixture was extracted with ethyl acetate. The organic layer was washed with a sodium chloride aqueous solution, and dried over sodium sulfate to afford the crude product (132) (243.6 mg).

Fifth Step

The crude product (132) (100 mg), Pd(OCOCF$_3$)$_2$ (17.54 mg), zinc powder (6.55 mg), 1,1'-binaphthyl-2-yldi-tert-butylphosphine (18.5 mg) and zinc cyanide (57.8 mg) were dissolved in DMAC (3 mL) under a nitrogen stream, and the mixture was stirred at 80° C. for about 3 hours. After cooled to room temperature, ethyl acetate was added, the resulting solid was filtered, water was added to the filtrate, the mixture was extracted with ethyl acetate. The organic layer was washed with a sodium chloride aqueous solution, and dried over sodium sulfate. This was purified by chromatography to afford the compound (133) (54.3 mg).

$^1$H-NMR (DMSO-d$_6$) δ: 8.97 (1.0H, S), 8.62 (1.0H, d, J=9.35 Hz), 3.93 (3.0H, s).

Sixth Step

The compound (133) (64 mg) was dissolved in tetrahydrofuran (1 mL), a 1 mol/L sodium hydroxide aqueous solution (0.391 mL) was added at 0° C., and the mixture was stirred at room temperature for 2.5 hours. The solution was concentrated, 2 mol/L hydrochloric acid (0.195 mL) was added at 0° C., and the resulting solid was collected by filtration to afford the crude product (134) (47 mg).

Seventh Step

The crude product (134) (47 mg) was dissolved in DMF (1 mL), oxalyl chloride (0.066 mL) was added at 0° C., and the mixture was stirred for 2 hours. A 2 mol/L sodium hydroxide aqueous solution (0.638 mL) was added at the same temperature, and the mixture was extracted with ethyl acetate ester. The organic layer was washed with water and a sodium chloride aqueous solution, and dried over sodium sulfate to afford the crude product (135) (8 mg). On the other hand, the aqueous layer at extraction was concentrated, tetrahydrofuran was added to the resulting residue, and the mixture was filtered. The filtrate was concentrated to afford the crude product (135) (28 mg).

Reference Example 19

Synthesis of Intermediate Compound 145

[Chemical formula 47]

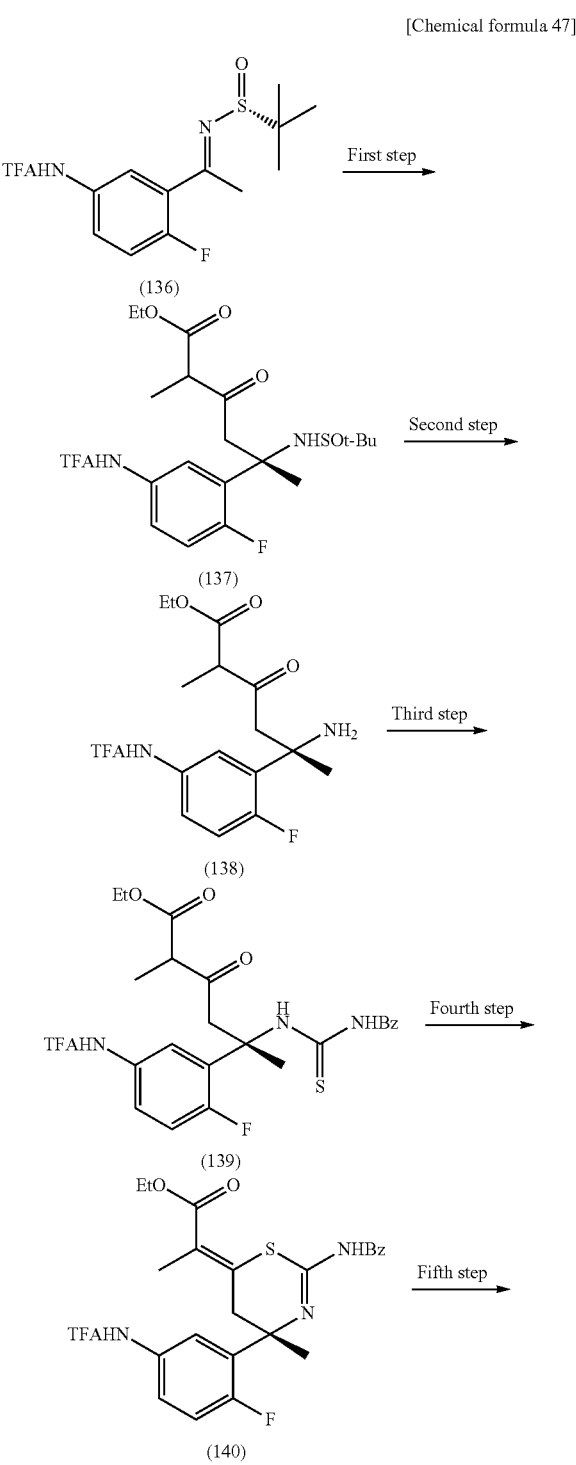

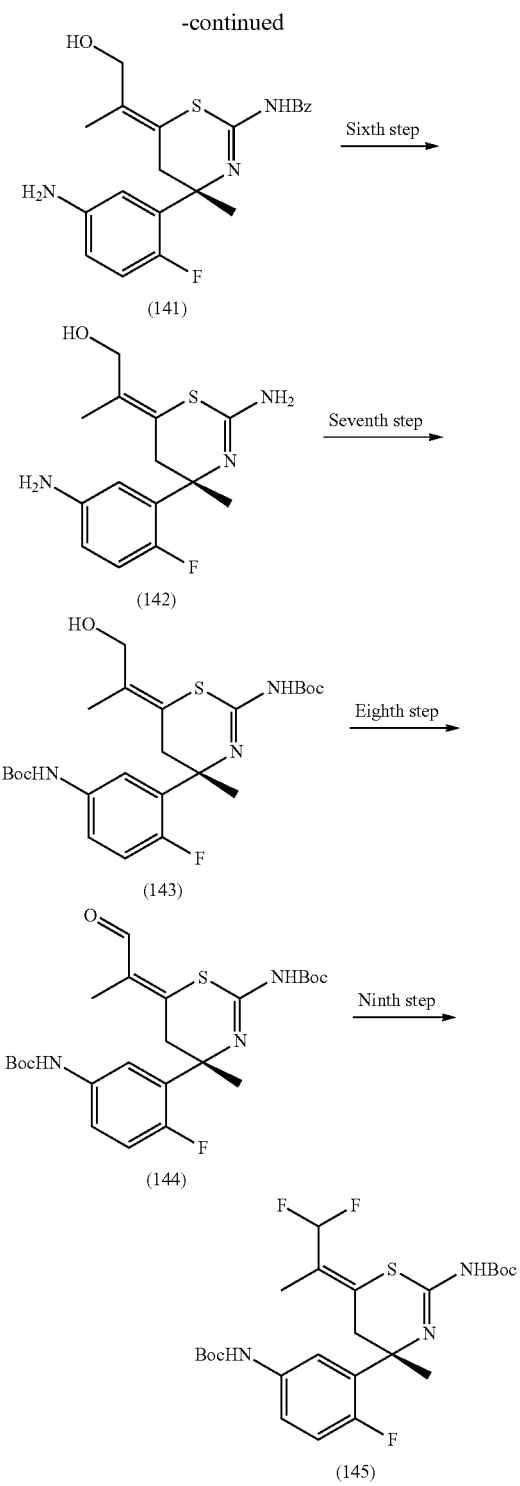

(141)
(142)
(143)
(144)
(145)

First Step

To a solution of diisopropylamine (13.1 g) diluted with tetrahydrofuran (75 ml) was added dropwise a 2.67 mol/L n-butyllithium/hexane solution (48.6 ml) at −25 to −40° C. over 5 minutes while stirring. Further, the mixture was stirred at the same temperature for 20 minutes, and a solution of ethyl 2-methyl-3-oxobutanoate (9.36 g) diluted with tetrahydrofuran (75 ml) was added over 10 minutes. The mixture was stirred for 50 minutes, and a solution of the compound (136) (7.63 g) dissolved in tetrahydrofuran (150 ml) was added dropwise over 10 minutes. The mixture was stirred at the same temperature for 75 minutes, transferred to a saturated ammonium chloride aqueous solution, and extracted with ethyl acetate. The organic layer was dried over anhydrous sodium sulfate. After filtration, the filtrate was evaporated under the reduced pressure, and the residue was subjected to column chromatography to afford the compound (137) (6.57 g).

$^1$H-NMR (d6-DNSO) δ: 1.03-1.21 (15H, m), 1.69-1.77 (3H, m), 3.41-3.70 (3H, m), 4.01-4.12 (2H, m), 5.23-5.33 (1H, m), 7.11-7.23 (1H, m), 7.62-7.69 (1H, m), 7.87-7.96 (1H, m), 11.28-11.37 (1H, m).

Second Step

The compound (137) (7.57 g) was dissolved in 22 ml of ethanol, a 2 mol/L hydrochloric acid/ethanol solution (22 ml) was added, and the mixture was stirred at room temperature for 30 minutes. The mixture was diluted with water, washed with hexane-diethyl ether (1:1), the aqueous layer was made basic with potassium carbonate, and extracted with chloroform. The organic layer was dried over anhydrous sodium sulfate. After filtration, the filtrate was evaporated under reduced pressure to afford the compound (138). A total amount was used in the next reaction without a purification.

Third Step

The compound (138) was dissolved in methylene chloride (30 ml), benzoyl isothiocyanate (2.05 ml) was added under ice-cooling, and the mixture was stirred at the same temperature for 30 minutes. The solvent was evaporated under reduced pressure to afford the compound (139). A total amount was used in the next reaction without a purification.

Fourth Step

To the compound (139) was added pre-ice-cooled concentrated sulfuric acid (30 ml) to dissolve gradually it, and the solution was stirred at 15° C. for 40 minutes. Further, pre-ice-cooled concentrated sulfuric acid (10 ml) was added, and the mixture was stirred at 20° C. for 20 minutes. The reaction solution was transferred to ice water, neutralized with potassium carbonate, and extracted with ethyl acetate. The organic layer was dried over anhydrous sodium sulfate. After filtration, the filtrate was evaporated under reduced pressure, and the residue was subjected to column chromatography to afford the compound (140) (2.86 g).

$^1$H-NMR (CDCl$_3$) δ: 1.25 (3H, t, J=7.0 Hz), 1.74 (3H, s), 1.93 (3H, s), 2.71 (1H, d, J=14.9 Hz), 3.97 (1H, d, J=14.9 Hz), 4.09 (2H, q, J=7.0 Hz), 7.13 (1H, dd, J=11.6, 9.1 Hz), 7.29-7.38 (3H, m), 7.48 (1H, t, J=7.1 Hz), 8.00 (2H, d, J=7.1 Hz), 8.10-8.16 (1H, m), 9.55-9.68 (1H, br), 12.06-12.36 (1H, br).

Fifth Step

The compound (140) (296.6 g) was dissolved in toluene (3 ml), a 1 mol/L diisobutylaluminum hydride/toluene solution (3.31 ml) was added dropwise at −78° C. over 5 minutes. The mixture was stirred at the same temperature for additional 1 hour, and stirred for 1 hour under ice-cooling. 10 ml of a 20 w/w % potassium sodium tartarate aqueous solution-10 ml of ethyl acetate was added, the mixture was stirred at room temperature for 30 minutes, and extracted with ethyl acetate. The organic layer was dried over anhydrous sodium sulfate. After filtration, the filtrate was evaporated under reduced pressure to afford the compound (141). A total amount was used in the next reaction without a purification.

Sixth Step

The compound (141) was dissolved in ethanol (3.0 ml), hydrazine monohydrate (0.268 ml) was added, and the mixture was stirred at room temperature overnight. After diluted with a saturated sodium chloride aqueous solution, the mixture was extracted with chloroform. The organic layer was dried over anhydrous sodium sulfate, filtered, and the filtrate was evaporated under reduced pressure. The residue was subjected to column chromatography to afford the compound (142) (94.4 mg).

$^1$H-NMR (CDCl$_3$) δ: 1.60 (3H, s), 1.77 (3H, s), 2.46 (1H, d, J=13.9 Hz), 3.20 (1H, d, J=13.9 Hz), 2.79-3.69 (5H, br), 4.00 (1H, d, J=12.1 Hz), 4.08 (1H, d, J=12.1 Hz), 6.42-6.50 (1H, m), 6.63-6.69 (1H, m), 6.79 (1H, dd, J=11.1, 8.6 Hz).

Seventh Step

The compound (142) (94 mg) was dissolved in tetrahydrofuran (2 ml), t-butyl dicarbonate (209 mg) was added, and the mixture was stirred at 60° C. for 2 hours. The solvent was evaporated under reduced pressure, and the residue was subjected to column chromatography to afford the compound (143) (111 mg).

$^1$H-NMR (CDCl$_3$) δ: 1.44 (3H, s), 1.46-1.50 (21H, m), 1.69-1.75 (1H, br), 2.55 (1H, d, J=14.2 Hz), 3.51 (1H, d, J=14.2 Hz), 4.00 (1H, d, J=12.6 Hz), 4.08 (1H, d, J=12.6 Hz), 6.94 (1H, dd, J=10.6, 9.6 Hz), 6.98-7.06 (1H, m), 7.34-7.41 (1H, m), 7.41-7.52 (1H, m), 7.77-7.85 (1H, m).

Eighth Step

The compound (143) (110 mg) was dissolved in methylene chloride (2 ml), manganese dioxide (510 mg) was added, and the mixture was stirred at room temperature for 2 hours. The reaction solution was filtered through Celite, and the filtrate was evaporated under reduced pressure to afford the compound (144). A total amount was used in the next reaction without a purification.

Ninth Step

The compound (144) was dissolved in methylene chloride (2 ml), N,N-diethylaminosulfur trifluoride (88 ul) was added under ice cooling, and the mixture was stirred at the same temperature for 1 hour, at 50° C. for 3 hours, and at 65° C. for 3 hours. To the reaction solution was added a saturated sodium bicarbonate aqueous solution, and the mixture was extracted with ethyl acetate. The organic layer was dried over anhydrous sodium sulfate, filtered, and the filtrate was evaporated under reduced pressure. The residue was subjected to column chromatography to afford the compound (145) (30.2 mg).

$^1$H-NMR (CDCl$_3$) δ: 1.51 (9H, s), 1.52 (3H, s), 1.53 (9H, s), 1.74 (3H, s), 2.73 (1H, d, J=11.6 Hz), 3.00 (1H, d, J=11.6 Hz), 6.49 (1H, t, J=53.8 Hz), 6.50-6.54 (1H, m), 6.91-7.07 (3H, m), 7.47-7.62 (1H, m).

Reference Example 20

Synthesis of Intermediate Compound (147)

[Chemical formula 48]

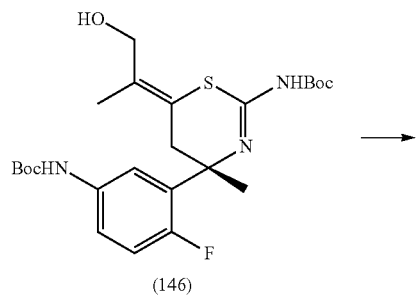

(146)

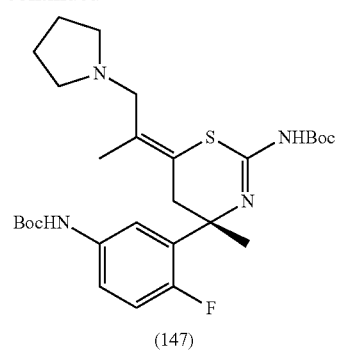

(147)

The compound (146) (126 mg) was dissolved in methylene chloride (1.3 ml), manganese dioxide (600 mg) was added, and the mixture was stirred at room temperature over night. The mixture was filtered through Celite, and the solvent of the filtrate was evaporated under reduced pressure. The resulting residue was dissolved in methylene chloride-acetic acid (9:1) (1.3 ml), pyrrolidine (210 μl) and sodium triacetylborohydride (109 mg) were added, and the mixture was stirred at room temperature for 2 hours. The mixture was diluted with a saturated sodium hydrogen carbonate aqueous solution, and extracted with ethyl acetate. The organic layer was dried over anhydrous sodium sulfate, filtrated, and the filtrate was evaporated under reduced pressure. The residue was subjected to column chromatography to afford the compound (147) (65.4 mg).

$^1$H-NMR (CDCl$_3$) δ: 1.51 (9H, s), 1.52 (1H, s), 1.53 (9H, s), 1.67-1.73 (2H, m), 1.77 (3H, s), 1.94-2.03 (2H, m), 2.12-2.23 (2H, m), 2.42-2.56 (3H, m), 2.91 (1H, d, J=13.1 Hz), 3.00 (1H, d, J=13.1 Hz), 3.70 (1H, d, J=15.2 Hz), 6.47-6.63 (1H, m), 6.69-6.77 (1H, m), 6.92-7.08 (3H, m), 7.57-7.68 (1H, m).

Reference Example 21

Synthesis of Compound 200

[Chemical formula 49]

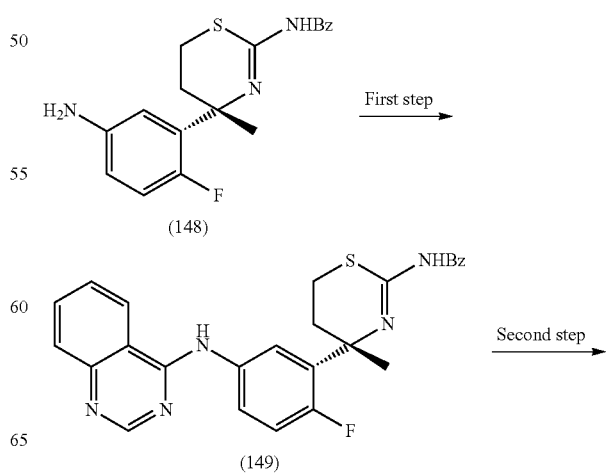

(148)

(149)

-continued

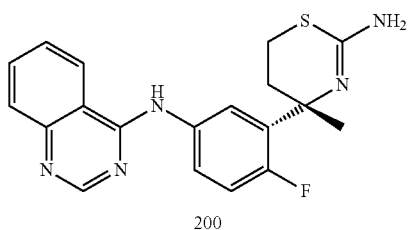

200

First Step

The compound (148) (100 mg) was dissolved in 2-propanol (2 ml), 4-chloroquinazoline (52.7 mg) was added, and the mixture was stirred and heated at reflux. After 6 hours, 4-chloroquinazoline (24.0 mg) was added, and the mixture was stirred and heated at reflux for 2 hours. After cooled to room temperature, water was added, and the mixture was extracted with ethyl acetate. The organic layer was dried over anhydrous sodium sulfate, and the solvent was evaporated under reduced pressure. The residue was subjected to silica gel column chromatography to afford the compound (149) (126 mg).

$^1$H-NMR (CDCl$_3$) δ: 1.83 (3H, s), 2.11-2.18 (1H, m), 2.75-2.82 (1H, m), 2.90-2.92 (1H, m), 2.98-3.02 (1H, m), 7.19 (1H, dd, J=11.4, 8.9 Hz), 7.40-7.51 (6H, m), 7.60 (1H, s), 7.77 (1H, t, J=7.9 Hz), 7.88-7.90 (2H, m), 8.11-8.14 (1H, m), 8.24 (2H, d, J=8.1 Hz), 8.71 (1H, s).

Second Step

The compound (149) (131 mg) was dissolved in ethanol (1 ml), hydrazine hydrate (0.067 ml) was added, and the mixture was stirred at room temperature for 3 days. The reaction solution was concentrated under reduced pressure, and the residue was subjected to silica gel column chromatography to afford the compound 200 (57 mg).

$^1$H-NMR (DMSO-d$_6$) δ: 1.50 (3H, s), 1.81-1.87 (1H, m), 2.18-2.20 (1H, m), 2.60-2.66 (1H, m), 2.98-3.02 (1H, m), 5.84 (2H, s), 7.16 (1H, dd, J=11.9, 8.9 Hz), 7.62 (1H, t, J=7.6 Hz), 7.69-7.73 (1H, m), 7.76-7.80 (2H, m), 7.85 (1H, t, J=7.6 Hz), 8.54 (2H, t, J=4.1 Hz), 9.89 (1H, s).

Similarly, the following compounds were synthesized. If necessary, a condensing reaction was performed with a precursor in which an amino group of a thiazole ring part was protected, for example, as the compound (21) described in Reference Example 1, and finally, the protecting group was removed to obtain an objective substance.

TABLE 1

| Compound No. | Structure | MS [M + 1] | NMR (solvent, δ) | uv |
|---|---|---|---|---|
| 1 | 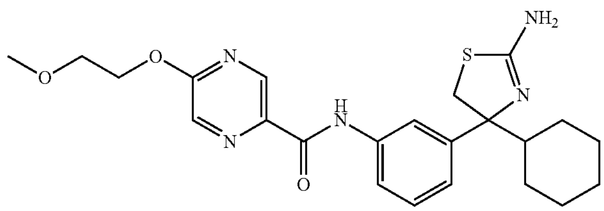 [SMILES: COCCOc1cnc(C(=O)Nc2cccc(C3(C4CCCCC4)CSC(N)=N3)c2)cn1] | 456 | | |
| 2 | 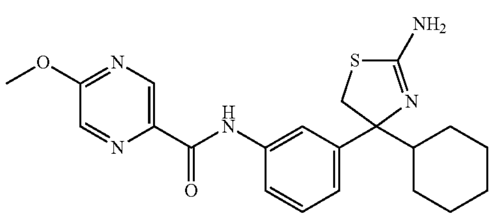 [SMILES: COc1cnc(C(=O)Nc2cccc(C3(C4CCCCC4)CSC(N)=N3)c2)cn1] | 412 | $^1$H-NMR (CDCl$_3$) d: 0.82-2.10 (11H, m), 3.59, 3.79 (2H, ABq, J = 11.1 Hz), 4.07 (3H, s), 4.67 (1H, brs), 7.15 (1H, dt, J = 8.1, 1.2 Hz), 7.33 (1H, t, J = 8.1 Hz), 7.68 (1H, t, J = 1.8 Hz), 7.74 (1H, ddd, J = 8.1, 1.8, 1.2 Hz), 8.15 (1H, d, J = 1.2 Hz), 9.03 (1H, d, J = 1.2 Hz), 9.53 (1H, s). | |
| 3 | 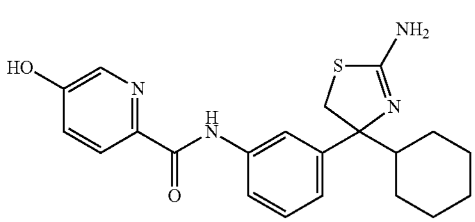 [SMILES: NC1=NC(c2cccc(NC(=O)c3ccc(O)cn3)c2)(C2CCCCC2)CS1] | 397 | | |

TABLE 1-continued
| Compound No. | Structure | MS [M + 1] | NMR (solvent, δ) | uv |
|---|---|---|---|---|
| 4 | 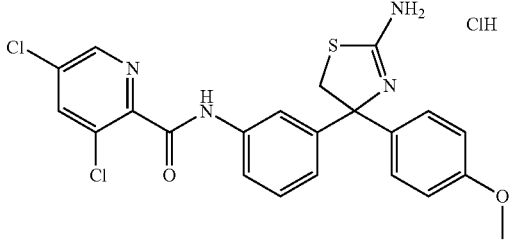 [SMILES: COc1ccc(C2(c3cccc(NC(=O)c4ncc(Cl)cc4Cl)c3)CSC(N)=N2)cc1 ; Cl] | 473 | | |
| 5 | 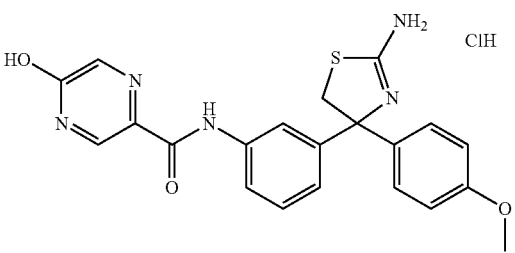 [SMILES: COc1ccc(C2(c3cccc(NC(=O)c4cnc(O)cn4)c3)CSC(N)=N2)cc1 ; Cl] | 422 | | |
| 6 | 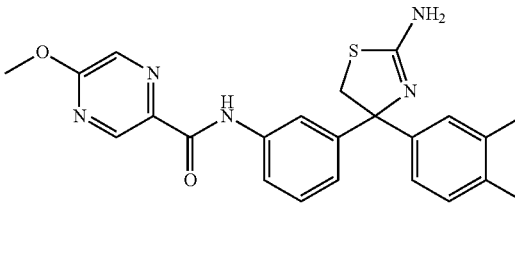 | | | |
| 7 | 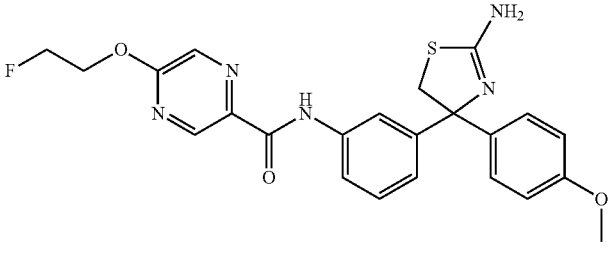 [SMILES: COc1ccc(C2(c3cccc(NC(=O)c4cnc(OCCF)cn4)c3)CSC(N)=N2)cc1] | | | |
TABLE 2
| Compound No. | Structure | MS [M + 1] | NMR (solvent, δ) | uv |
|---|---|---|---|---|
| 8 | 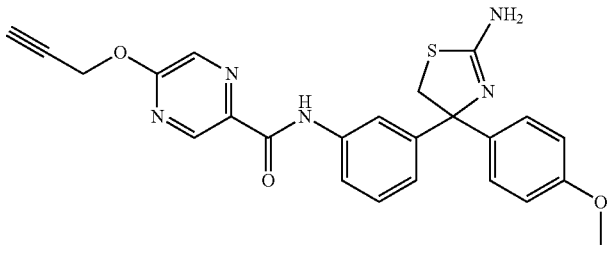 [SMILES: C#CCOc1cnc(C(=O)Nc2cccc(C3(c4ccc(OC)cc4)CSC(N)=N3)c2)cn1] | | | |

TABLE 2-continued

| Compound No. | Structure | MS [M + 1] | NMR (solvent, δ) | uv |
|---|---|---|---|---|
| 9 | 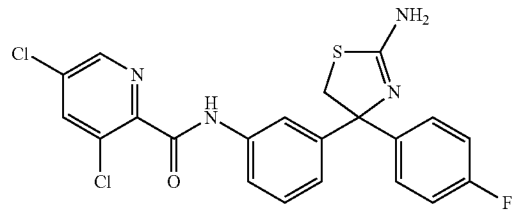 [SMILES: NC1=NC(c2ccc(F)cc2)(c2cccc(NC(=O)c3ncc(Cl)cc3Cl)c2)CS1] | 461 | | |
| 10 | 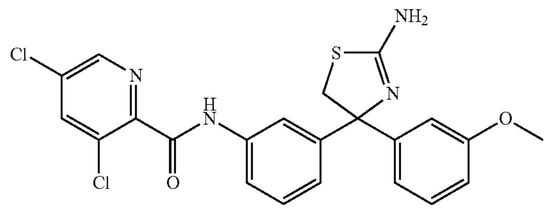 [SMILES: COc1cccc(C2(c3cccc(NC(=O)c4ncc(Cl)cc4Cl)c3)CSC(N)=N2)c1] | 473 | | |
| 11 | 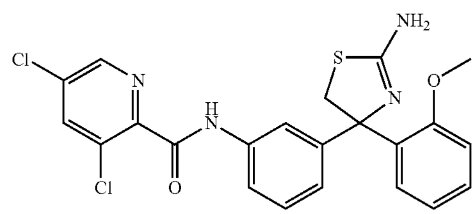 [SMILES: COc1ccccc1C1(c2cccc(NC(=O)c3ncc(Cl)cc3Cl)c2)CSC(N)=N1] | 473 | | |
| 12 | 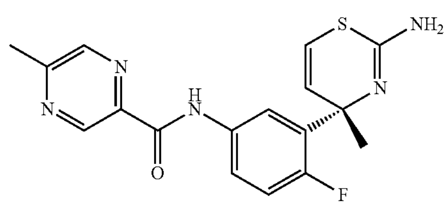 [SMILES: Cc1cnc(C(=O)Nc2ccc(F)c([C@]3(C)C=CSC(N)=N3)c2)cn1] | 358 | | |
| 13 | 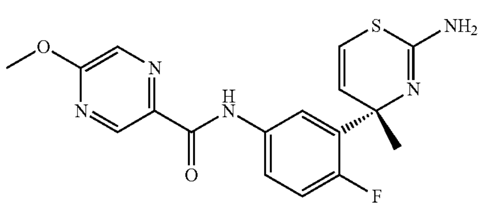 [SMILES: COc1cnc(C(=O)Nc2ccc(F)c([C@]3(C)C=CSC(N)=N3)c2)cn1] | | 1H-NMR (CDCl3) d: 1.71 (3H, s), 4.06 (3H, s), 6.28 (2H, d, J = 2.1 Hz), 7.04 (1H, dd, J = 11.2, 8.8 Hz), 7.60 (2H, dd, J = 6.8, 2.8 Hz), 7.83 (1H, ddd, J = 8.8, 4.1, 2.8 Hz), 8.14 (1H, d, J = 1.2 Hz), 9.00 (1H, d, J = 1.2 Hz), 9.45 (1H, s). | |
| 14 | 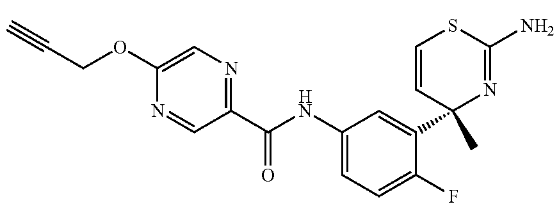 [SMILES: C#CCOc1cnc(C(=O)Nc2ccc(F)c([C@]3(C)C=CSC(N)=N3)c2)cn1] | 398 | | 231, 259 |

TABLE 3

| Compound No. | Structure | MS [M + 1] | NMR (solvent, δ) | uv |
|---|---|---|---|---|
| 15 | 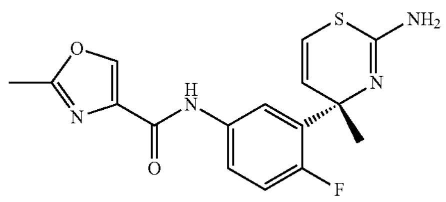 [SMILES: Cc1nc(C(=O)Nc2ccc(F)c([C@]3(C)C=CSC(N)=N3)c2)co1] | | 1H-NMR (CDCl3) d: 1.70 (3H, s), 2.52 (3H, s), 6.27 (2H, d, J = 2.0 Hz), 7.02 (1H, dd, J = 11.3, 8.8 Hz), 7.56 (2H, dd, J = 6.9, 2.8 Hz), 7.74 (1H, ddd, J = 8.8, 4.0, 2.8 Hz), 8.15 (1H, s), 8.61 (1H, s). | |
| 16 | 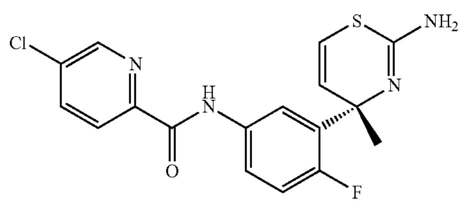 [SMILES: C[C@@]1(c2cc(NC(=O)c3ccc(Cl)cn3)ccc2F)C=CSC(N)=N1] | 377 | | |
| 17 | 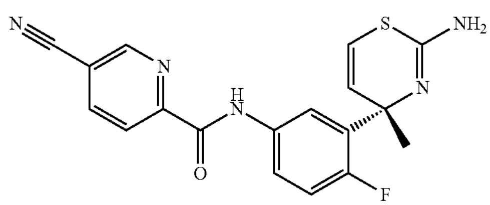 [SMILES: C[C@@]1(c2cc(NC(=O)c3ccc(C#N)cn3)ccc2F)C=CSC(N)=N1] | | 1H-NMR (CDCl3) d: 1.71 (3H, s), 4.06 (3H, s), 6.29 (2H, d, J = 2.4 Hz), 7.07 (1H, dd, J = 11.3, 8.8 Hz), 7.65 (2H, dd, J = 6.8, 2.8 Hz), 7.86 (1H, ddd, J = 8.8, 4.1, 2.8 Hz), 8.19 (1H, dd, J = 8.1, 2.0 Hz), 8.43 (1H, d, J = 8.1 Hz), 8.89 (1H, d, J = 2.0 Hz), 9.81 (1H, s). | |
| 18 | 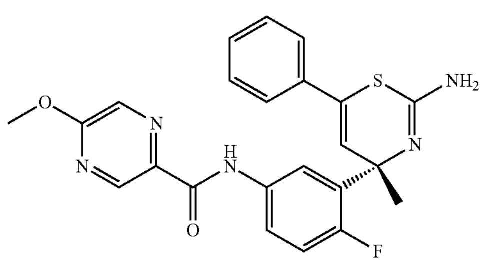 [SMILES: COc1cnc(C(=O)Nc2ccc(F)c([C@]3(C)C=C(c4ccccc4)SC(N)=N3)c2)cn1] | | 1H-NMR (CDCl3) d: 1.81 (3H, s), 4.06 (3H, s), 6.52 (1H, d, J = 5.5 Hz), 7.06 (1H, dd, J = 11.2, 8.8 Hz), 7.30-7.39 (3H, m), 7.48 (2H, dd, J = 6.9, 2.8 Hz), 7.62 (2H, dd, J = 6.8, 2.8 Hz), 7.83 (1H, ddd, J = 8.8, 4.2, 2.8 Hz), 8.14 (1H, d, J = 1.4 Hz), 9.01 (1H, d, J = 1.4 Hz), 9.45 (1H, s). | |
| 19 | 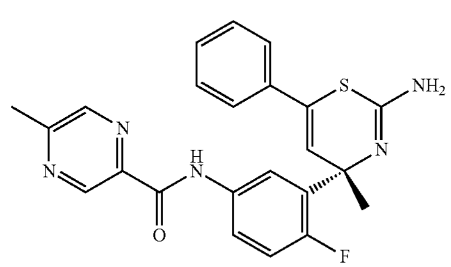 [SMILES: Cc1cnc(C(=O)Nc2ccc(F)c([C@]3(C)C=C(c4ccccc4)SC(N)=N3)c2)cn1] | | | 201, 203 |
| 20 | 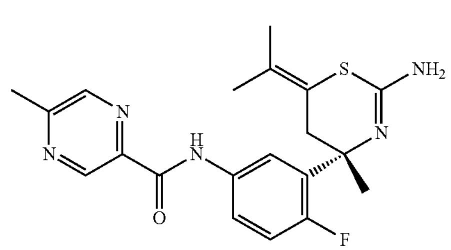 [SMILES: CC(C)=C1C[C@@](C)(c2cc(NC(=O)c3cnc(C)cn3)ccc2F)N=C(N)S1] | | 1H-NMR (CDCl3) d: 1.56 (3H, s), 1.67 (3H, s), 1.76 (3H, s), 2.65 (1H, d, J = 14.2 Hz), 2.69 (3H, s), 2.96 (1H, d, J = 14.2 Hz), 7.04 (1H, dd, J = 11.8, 8.8 Hz), 7.45 (1H, dd, J = 7.0, 2.9 Hz), 7.98 (1H, ddd, J = 8.8, 3.9, 2.9 Hz), 8.43 (1H, d, J = 1.2 Hz), 9.35 (1H, d, J = 1.2 Hz), 9.59 (1H, s). | |

TABLE 3-continued

| Compound No. | Structure | MS [M + 1] | NMR (solvent, δ) | uv |
|---|---|---|---|---|
| 21 | 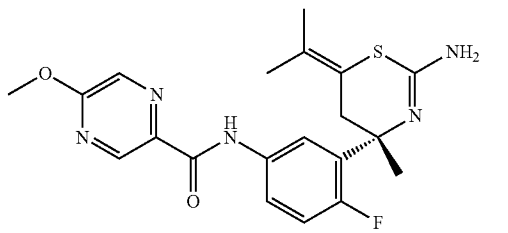 [SMILES: COc1cnc(C(=O)Nc2ccc(F)c([C@]3(C)CC(=C(C)C)SC(N)=N3)c2)cn1] | | 1H-NMR (CDCl3) d: 1.58 (3H, s), 1.68 (3H, s), 1.76 (3H, s), 2.65 (1H, d, J = 14.2 Hz), 2.99 (1H, d, J = 14.2 Hz), 4.07 (3H, s), 7.04 (1H, dd, J = 11.8, 8.6 Hz), 7.42 (1H, dd, J = 6.9, 2.8 Hz), 7.98 (1H, ddd, J = 8.6, 3.9, 2.8 Hz), 8.15 (1H, d, J = 1.2 Hz), 9.01 (1H, d, J = 1.2 Hz), 9.47 (1H, s). | |

TABLE 4

| Compound No. | Structure | MS [M + 1] | NMR (solvent, δ) | uv |
|---|---|---|---|---|
| 22 | 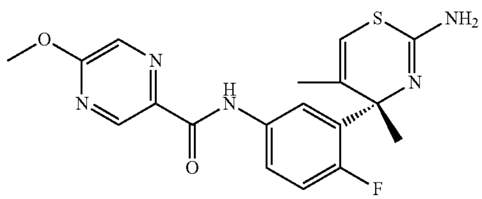 [SMILES: COc1cnc(C(=O)Nc2ccc(F)c([C@@]3(C)N=C(N)SC=C3C)c2)cn1] | | | 193 |
| 23 | 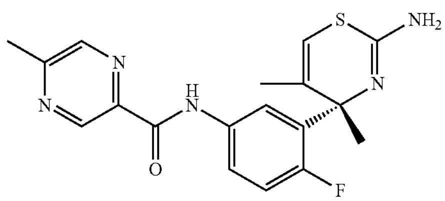 [SMILES: CC1=CSC(N)=N[C@]1(C)c1cc(NC(=O)c2cnc(C)cn2)ccc1F] | | | 201, 212 |
| 24 | 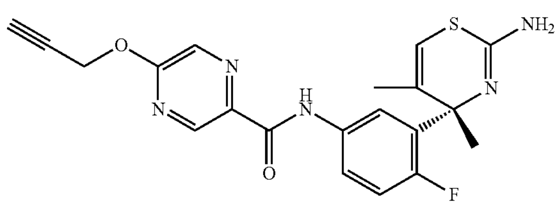 [SMILES: C#CCOc1cnc(C(=O)Nc2ccc(F)c([C@@]3(C)N=C(N)SC=C3C)c2)cn1] | | 1H-NMR (CDCl3) d: 1.74 (3H, s), 1.80 (3H, s), 2.56 (1H, t, J = 2.4 Hz), 5.09 (2H, d, J = 2.4 Hz), 6.01 (1H, s), 7.04 (1H, dd, J = 11.2, 8.8 Hz), 7.65-7.74 (2H, m), 8.23 (1H, d, J = 1.3 Hz), 9.04 (1H, d, J = 1.3 Hz), 9.46 (1H, s). | |
| 25 | 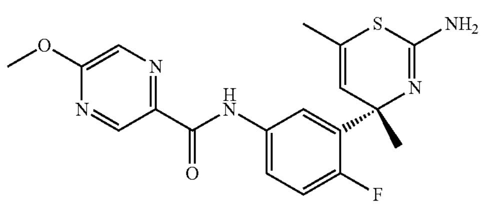 [SMILES: COc1cnc(C(=O)Nc2ccc(F)c([C@]3(C)C=C(C)SC(N)=N3)c2)cn1] | | | 222 |
| 26 | 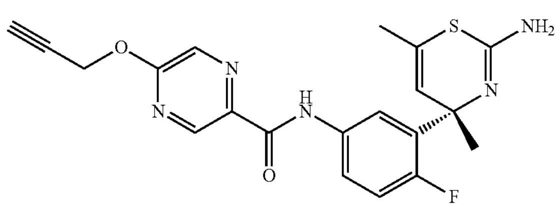 [SMILES: C#CCOc1cnc(C(=O)Nc2ccc(F)c([C@]3(C)C=C(C)SC(N)=N3)c2)cn1] | | | 196, 207 |

TABLE 4-continued

| Compound No. | Structure | MS [M + 1] | NMR (solvent, δ) | uv |
|---|---|---|---|---|
| 27 | 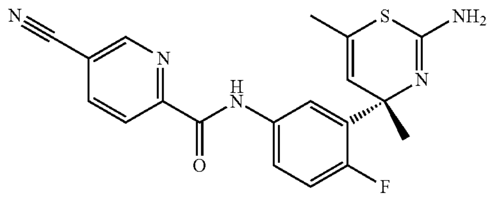 [SMILES: CC1=C[C@@](C)(c2cc(NC(=O)c3ccc(C#N)cn3)ccc2F)N=C(N)S1] | | 1H-NMR (CDCl3) d: 1.69 (3H, s), 1.98 (3H, d, J = 1.5 Hz), 5.98 (2H, dd, J = 4.6, 1.5 Hz), 7.06 (1H, dd, J = 11.2, 8.8 Hz), 7.58 (1H, dd, J = 7.0, 2.8 Hz), 7.86 (1H, ddd, J = 8.8, 4.1, 2.8 Hz), 8.19 (1H, dd, J = 8.1, 2.0 Hz), 8.42 (1H, d, J = 8.1, 0.9 Hz), 8.88 (1H, dd, J = 2.0, 0.9 Hz), 9.80 (1H, s). | |
| 28 | 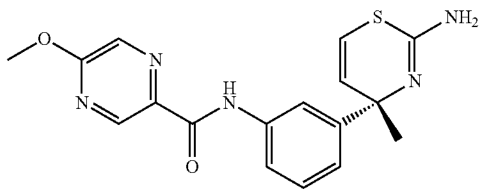 [SMILES: COc1cnc(C(=O)Nc2cccc([C@]3(C)C=CSC(N)=N3)c2)cn1] | | | 201, 211 |

TABLE 5

| Compound No. | Structure | MS [M + 1] | NMR (solvent, δ) | uv |
|---|---|---|---|---|
| 29 | 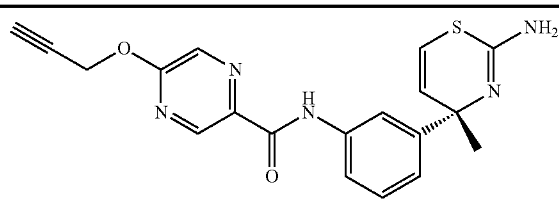 | | | 193 |
| 30 | 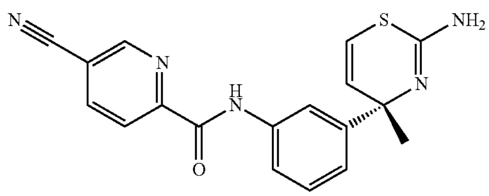 [SMILES: C[C@@]1(c2cccc(NC(=O)c3ccc(C#N)cn3)c2)C=CSC(N)=N1] | | | 199 |
| 31 | 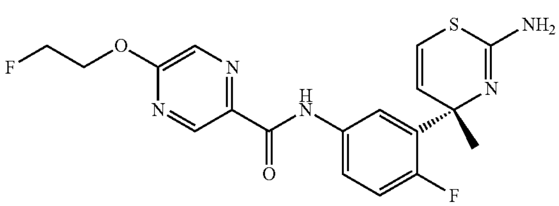 [SMILES: C[C@@]1(c2cc(NC(=O)c3cnc(OCCF)cn3)ccc2F)C=CSC(N)=N1] | | 1H-NMR (DMSO-d6) d: 155 (3H, s), 4.63 (1H, t, J = 3.8 Hz), 4.71 (1H, t, J = 3.8 Hz), 4.76 (1H, t, J = 3.8 Hz), 4.88 (1H, t, J = 3.8 Hz), 6.15 (1H, dd, J = 9.4, 4.3 Hz), 6.29 (2H, s), 6.47 (1H, d, J = 9.6 Hz), 7.12 (1H, dd, J = 11.7, 9.1 Hz), 7.72 (1H, dt, J = 8.3, 3.6 Hz), 7.91 (1H, dd, J = 7.1, 2.5 Hz), 8.47 (1H, d, J = 1.5 Hz), 8.87 (1H, d, J = 1.0 Hz), 10.45 (1H, s). | |
| 32 | 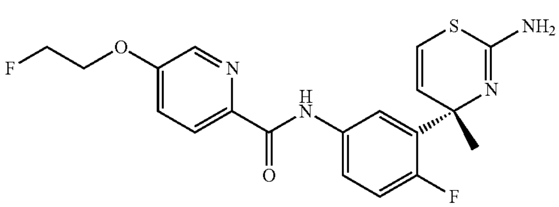 [SMILES: C[C@@]1(c2cc(NC(=O)c3ccc(OCCF)cn3)ccc2F)C=CSC(N)=N1] | | 1H-NMR (DMSO-d6) d: 1.55 (3H, s), 4.41 (1H, t, J = 3.8 Hz), 4.49 (1H, t, J = 3.8 Hz), 4.75 (1H, t, J = 3.8 Hz), 4.87 (1H, t, J = 3.8 Hz), 6.15 (1H, dd, J = 9.6, 4.6 Hz), 6.30 (2H, s), 6.47 (1H, d, J = 9.6 Hz), 7.11 (1H, dd, J = 11.4, 8.9 Hz), 7.65 (1H, dd, J = 8.6, 2.5 Hz), 7.75 (1H, dt, J = 8.3, 3.6 Hz), 7.88 (1H, dd, J = 7.6, 2.5 Hz), 8.12 (1H, d, J = 8.6 Hz), 8.43 (1H, d, J = 2.5 Hz), 10.39 (1H, s). | |
| 33 | 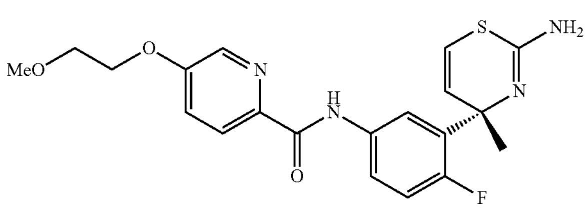 [SMILES: COCCOc1ccc(C(=O)Nc2ccc(F)c([C@]3(C)C=CSC(N)=N3)c2)nc1] | | 1H-NMR (DMSO-d6) d: 1.55 (3H, s), 3.71 (2H, t, J = 4.3 Hz), 4.29 (2H, dd, J = 5.3, 3.3 Hz), 6.15 (1H, dd, J = 9.6, 4.6 Hz), 6.30 (2H, s), 6.46 (1H, d, J = 9.6 Hz), 7.11 (1H, dd, J = 11.7, 9.1 Hz), 7.62 (1H, dd, J = 8.6, 3.0 Hz), 7.75 (1H, dt, J = 8.3, 3.6 Hz), 7.88 (1H, dd, J = 7.4, 2.8 Hz), 8.10 (1H, d, J = 8.6 Hz), 8.40 (1H, d, J = 3.0 Hz), 10.37 (1H, s). | |

TABLE 5-continued

| Compound No. | Structure | MS [M + 1] | NMR (solvent, δ) | uv |
|---|---|---|---|---|
| 34 | 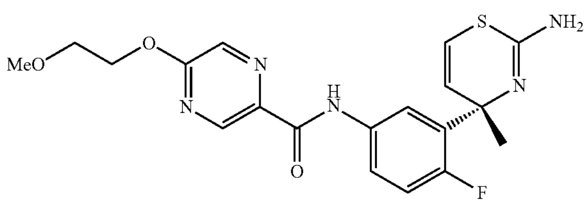 [SMILES: COCCOc1cnc(C(=O)Nc2ccc(F)c([C@]3(C)C=CSC(N)=N3)c2)cn1] | | 1H-NMR (DMSO-d6) d: 1.55 (3H, s), 3.72 (2H, t, J = 4.6 Hz), 4.53 (2H, t, J = 4.6 Hz), 6.15 (1H, dd, J = 9.6, 4.1 Hz), 6.29 (2H, s), 6.46 (1H, d, J = 9.1 Hz), 7.12 (1H, dd, J = 11.4, 8.9 Hz), 7.72 (1H, t, J = 3.8 Hz), 7.9 (1H, dd, J = 7.4, 2.8 Hz), 8.43 (1H, d, J = 1.0 Hz), 8.86 (1H, s), 10.43 (1H, s). | |
| 35 | 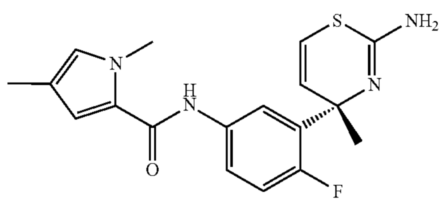 [SMILES: Cc1cc(C(=O)Nc2ccc(F)c([C@]3(C)C=CSC(N)=N3)c2)n(C)c1] | | 1H-NMR (DMSO-d6) d: 1.54 (3H, s), 2.19 (3H, s), 3.99 (3H, s), 6.15 (1H, dd, J = 9.6, 4.6 Hz), 6.29 (2H, s), 6.47 (1H, d, J = 9.6 Hz), 6.80 (1H, s), 7.11 (1H, dd, J = 11.7, 9.1 Hz), 7.57-7.61 (1H, m), 7.71 (1H, dd, J = 7.4, 2.8 Hz), 10.16 (1H, s). | |

TABLE 6

| Compound No. | Structure | MS [M + 1] | NMR (solvent, δ) | uv |
|---|---|---|---|---|
| 36 | 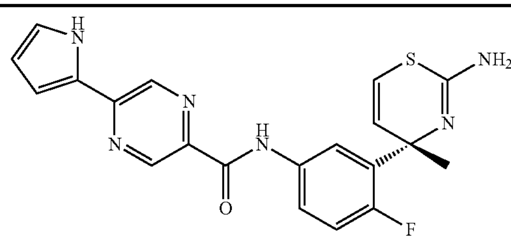 | | 1H-NMR (DMSO-d6) d: 1.56 (3H, s), 6.16 (1H, dd, J = 9.6, 4.6 Hz), 6.30 (3H, s), 6.47 (1H, d, J = 9.1 Hz), 7.10-7.17 (3H, m), 7.74 (1H, dt, J = 8.8, 3.6 Hz), 7.93 (1H, dd, J = 7.1, 2.5 Hz), 9.08 (2H, d, J = 13.2 Hz), 10.50 (1H, s), 11.97 (1H, s). | |
| 37 | 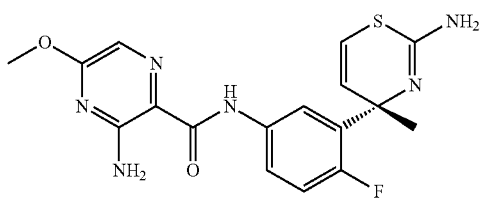 [SMILES: COc1cnc(C(=O)Nc2ccc(F)c([C@]3(C)C=CSC(N)=N3)c2)c(N)n1] | | 1H-NMR (DMSO-d6) d: 1.54 (3H, s), 3.90 (3H, s), 6.15 (1H, dd, J = 9.4, 4.3 Hz), 6.31 (2H, s), 6.46 (1H, d, J = 9.6 Hz), 7.09 (1H, dd, J = 11.7, 9.1 Hz), 7.52 (1H, s), 7.63-7.67 (1H, m), 7.80 (1H, dd, J = 7.6, 2.5 Hz), 10.08 (1H, s). | |
| 38 | 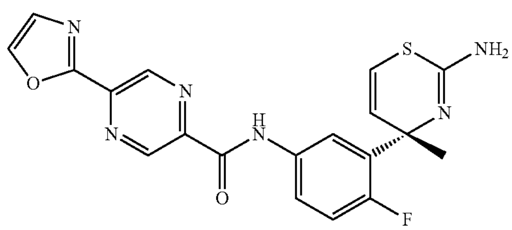 [SMILES: C[C@@]1(c2cc(NC(=O)c3cnc(-c4ncco4)cn3)ccc2F)C=CSC(N)=N1] | | 1H-NMR (DMSO-d6) d: 1.57 (3H, s), 6.16 (1H, dd, J = 9.6, 4.6 Hz), 6.31 (2H, s), 6.48 (1H, d, J = 9.6 Hz), 7.15 (1H, dd, J = 11.4, 8.9 Hz), 7.64 (1H, s), 7.74-7.76 (1H, m), 7.97 (1H, dd, J = 7.6, 2.5 Hz), 8.49 (1H, s), 9.37 (2H, dd, J = 3.5, 1.5 Hz), 10.84 (1H, s). | |
| 39 | 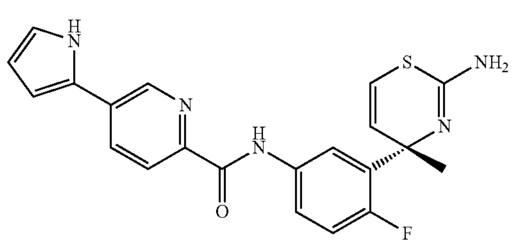 [SMILES: C[C@@]1(c2cc(NC(=O)c3ccc(-c4ccc[nH]4)cn3)ccc2F)C=CSC(N)=N1] | | 1H-NMR (DMSO-d6) d: 1.56 (3H, s), 6.16 (1H, dd, J = 9.6, 4.6 Hz), 6.23 (1H, dd, J = 5.6, 2.5 Hz), 6.32 (2H, s), 6.47 (1H, d, J = 9.6 Hz), 6.85 (1H, s), 7.05 (1H, dd, J = 4.1, 2.5 Hz), 7.13 (1H, dd, J = 11.4, 8.9 Hz), 7.76-7.79 (1H, m), 7.90 (1H, dd, J = 7.4, 2.8 Hz), 8.09 (1H, d, J = 8.1 Hz), 8.21 (1H, dd, J = 8.4, 2.3 Hz), 8.99 (1H, d, J = 2.0 Hz), 10.45 (1H, s), 11.70 (1H, s). | |

TABLE 6-continued

| Compound No. | Structure | MS [M + 1] | NMR (solvent, δ) | uv |
|---|---|---|---|---|
| 40 | 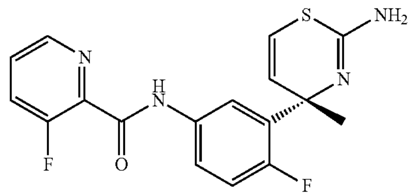 [SMILES: C[C@@]1(c2cc(NC(=O)c3ncccc3F)ccc2F)C=CSC(N)=N1] | | | |
| 41 | 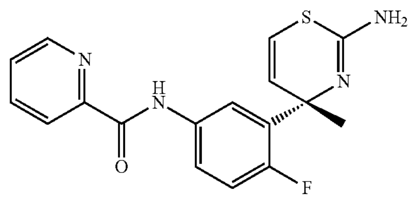 [SMILES: C[C@@]1(c2cc(NC(=O)c3ccccn3)ccc2F)C=CSC(N)=N1] | | | |
| 42 | 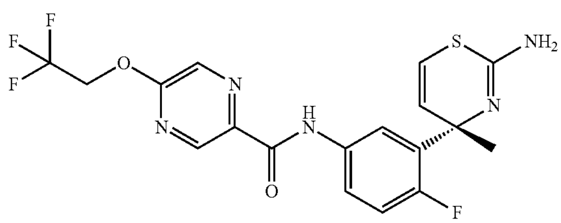 [SMILES: C[C@@]1(c2cc(NC(=O)c3cnc(OCC(F)(F)F)cn3)ccc2F)C=CSC(N)=N1] | | | |

TABLE 7

| Compound No. | Structure | MS [M + 1] | LC/MS retention time (measurement condition) or NMR (solvent, shift value: ascending order) |
|---|---|---|---|
| 43 | 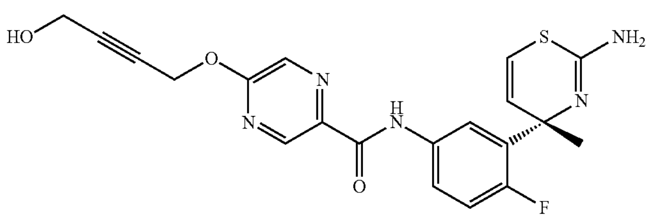 [SMILES: C[C@@]1(c2cc(NC(=O)c3cnc(OCC#CCO)cn3)ccc2F)C=CSC(N)=N1] | | |
| 44 | 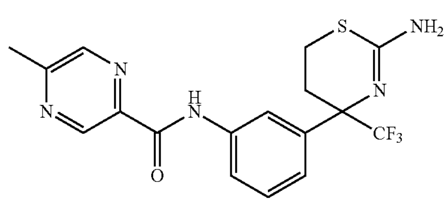 [SMILES: Cc1cnc(C(=O)Nc2cccc(C3(C(F)(F)F)CCSC(N)=N3)c2)cn1] | 396 | 0.98 (Method A) |
| 45 | 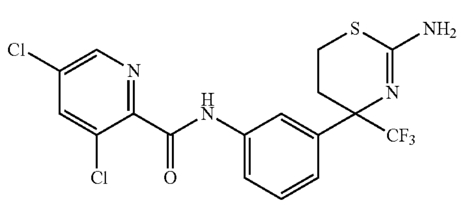 [SMILES: NC1=NC(c2cccc(NC(=O)c3ncc(Cl)cc3Cl)c2)(C(F)(F)F)CCS1] | 449 | 1.29 (Method A) |

TABLE 7-continued

| Compound No. | Structure | MS [M + 1] | LC/MS retention time (measurement condition) or NMR (solvent, shift value: ascending order) |
|---|---|---|---|
| 46 | 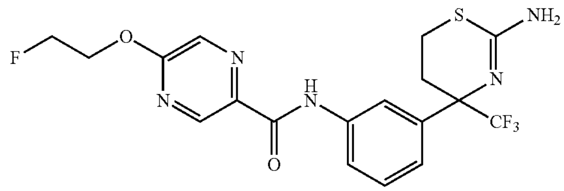 [SMILES: NC1=NC(c2cccc(NC(=O)c3cnc(OCCF)cn3)c2)(C(F)(F)F)CCS1] | 444 | 1.2 (Method A) |
| 47 | 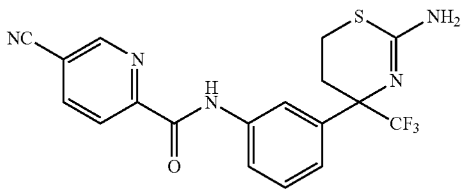 [SMILES: N#Cc1ccc(C(=O)Nc2cccc(C3(C(F)(F)F)CCSC(N)=N3)c2)nc1] | 406 | 1.17 (Method B) |
| 48 | 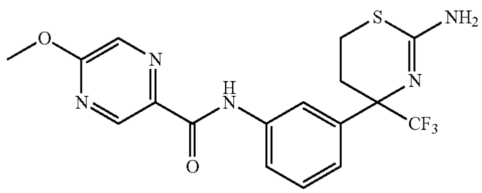 [SMILES: COc1cnc(C(=O)Nc2cccc(C3(C(F)(F)F)CCSC(N)=N3)c2)cn1] | 412 | 1.12 (Method A) |
| 49 | 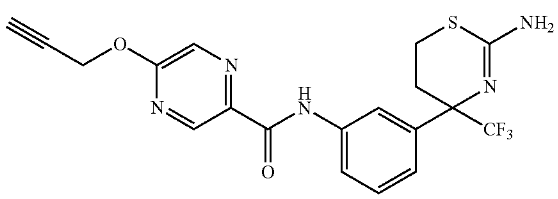 [SMILES: C#CCOc1cnc(C(=O)Nc2cccc(C3(C(F)(F)F)CCSC(N)=N3)c2)cn1] | 436 | 1.32 (Method B) |

TABLE 8

| Compound No. | Structure | MS [M + 1] | LC/MS retention time (measurement condition) or NMR (solvent, shift value: ascending order) |
|---|---|---|---|
| 50 | 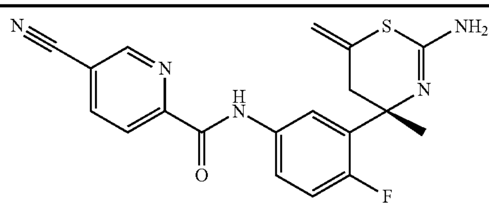 | 382 | 1.22 (Method B) |
| 51 | 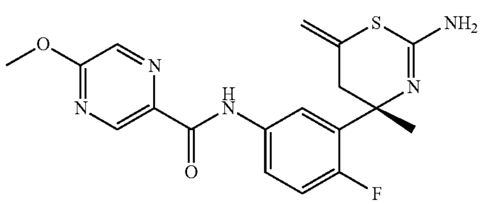 [SMILES: C=C1C[C@@](C)(c2cc(NC(=O)c3cnc(OC)cn3)ccc2F)N=C(N)S1] | 388 | 1.25 (Method B) |
| 52 | 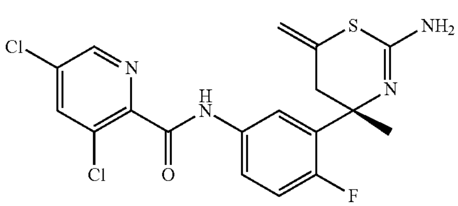 [SMILES: C=C1C[C@@](C)(c2cc(NC(=O)c3ncc(Cl)cc3Cl)ccc2F)N=C(N)S1] | 425 | 1.35 (Method B) |

TABLE 8-continued
| Compound No. | Structure | MS [M + 1] | LC/MS retention time (measurement condition) or NMR (solvent, shift value: ascending order) |
|---|---|---|---|
| 53 | 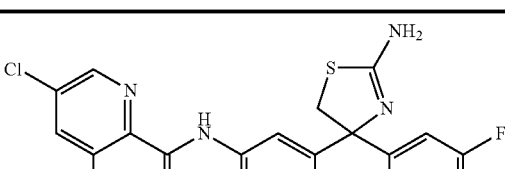 | 372 | 1.37 (Method B) |
| 54 | 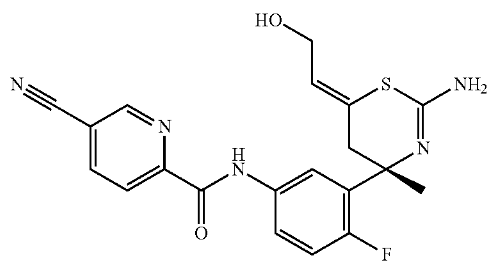 [SMILES: C[C@@]1(c2cc(NC(=O)c3ccc(C#N)cn3)ccc2F)C/C(=C/CO)SC(N)=N1] | 412 | 1.19 (Method B) |
| 55 | 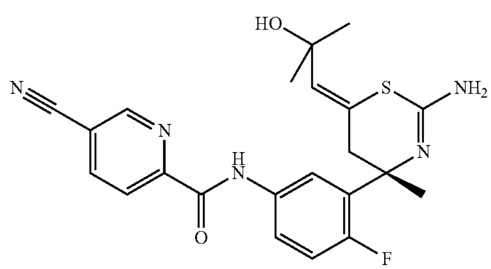 [SMILES: CC(C)(O)/C=C1/C[C@@](C)(c2cc(NC(=O)c3ccc(C#N)cn3)ccc2F)N=C(N)S1] | 440 | 1.24 (Method B) |
TABLE 9
| Compound No. | Structure | MS [M + 1] | LC/MS retention time (measurement condition) or NMR (solvent, shift value: ascending order) |
|---|---|---|---|
| 56 | 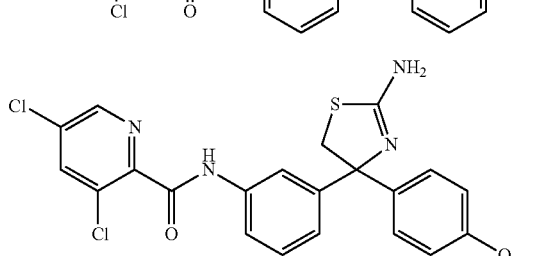 | 461 | |
| 57 | 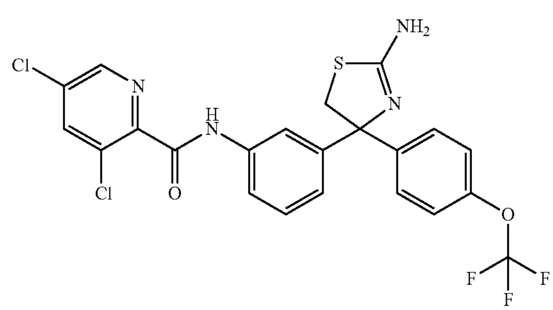 [SMILES: NC1=NC(c2ccc(OC(F)(F)F)cc2)(c2cccc(NC(=O)c3ncc(Cl)cc3Cl)c2)CS1] | 527 | |

TABLE 9-continued

| Compound No. | Structure | MS [M + 1] | LC/MS retention time (measurement condition) or NMR (solvent, shift value: ascending order) |
|---|---|---|---|
| 58 | 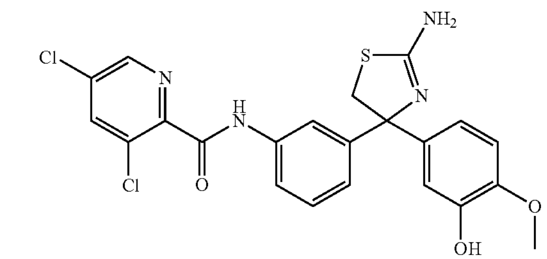 [SMILES: COc1ccc(C2(c3cccc(NC(=O)c4ncc(Cl)cc4Cl)c3)CSC(N)=N2)cc1O] | 489 | |
| 59 | 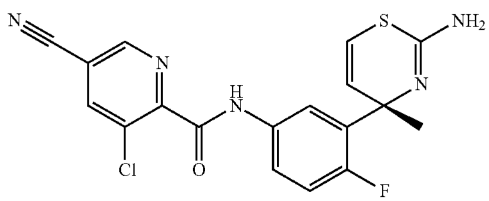 [SMILES: C[C@@]1(c2cc(NC(=O)c3ncc(C#N)cc3Cl)ccc2F)C=CSC(N)=N1] | 402 | 1.05 (Method A) |
| 60 | 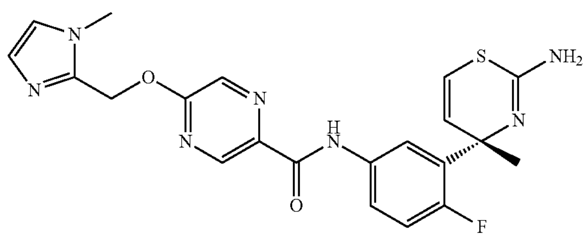 [SMILES: Cn1ccnc1COc1cnc(C(=O)Nc2ccc(F)c([C@]3(C)C=CSC(N)=N3)c2)cn1] | | 1H-NMR (DMSO-d6) d: 1.55 (3H, s), 3.73 (3H, s), 5.50 (2H, s), 6.15 (1H, dd, J = 9.6, 4.6 Hz), 6.29 (2H, s), 6.47 (1H, d, J = 9.6 Hz), 6.91 (1H, d, J = 1.0 Hz), 7.12 (1H, dd, J = 11.4, 8.9 Hz), 7.23 (1H, d, J = 1.0 Hz), 7.71-7.73 (1H, m), 7.91 (1H, dd, J = 7.4, 2.8 Hz), 8.46 (1H, d, J = 1.0 Hz), 8.91 (1H, d, J = 1.0 Hz), 10.45 (1H, s). |
| 61 | 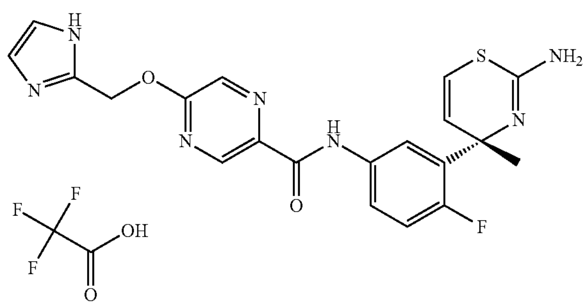 [SMILES: C[C@@]1(c2cc(NC(=O)c3cnc(OCc4ncc[nH]4)cn3)ccc2F)C=CSC(N)=N1 ; O=C(O)C(F)(F)F] | | 1H-NMR (DMSO-d6) d: 1.83 (3H, s), 5.68 (2H, s), 6.38 (1H, dd, J = 9.6, 2.5 Hz), 6.64 (1H, d, J = 9.6 Hz), 7.29 (1H, dd, J = 11.4, 8.9 Hz), 7.55 (2H, s), 7.92-7.96 (1H, m), 8.01 (1H, dd, J = 7.1, 2.5 Hz), 8.53 (1H, d, J = 1.0 Hz), 8.91 (1H, d, J = 1.0 Hz), 10.78 (1H, s). |

TABLE 10

| Compound No. | Structure | MS [M + 1] | LC/MS retention time (measurement condition) or NMR (solvent, shift value: ascending order) |
|---|---|---|---|
| 62 | 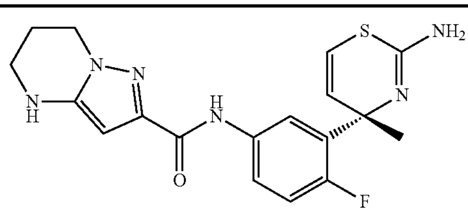 | | 1H-NMR (DMSO-d6) d: 1.53 (3H, s), 2.00-2.06 (2H, m), 3.18-3.19 (2H, m), 4.08 (2H, t, J = 6.1 Hz), 5.65 (1H, s), 6.13 (1H, dd, J = 9.6, 4.1 Hz), 6.26 (3H, s), 6.45 (1H, d, J = 9.6 Hz), 7.04 (1H, dd, J = 11.4, 8.9 Hz), 7.62-7.64 (1H, m), 7.81 (1H, dd, J = 7.4, 2.8 Hz), 9.67 (1H, s). |

TABLE 10-continued

| Compound No. | Structure | MS [M + 1] | LC/MS retention time (measurement condition) or NMR (solvent, shift value: ascending order) |
|---|---|---|---|
| 63 | 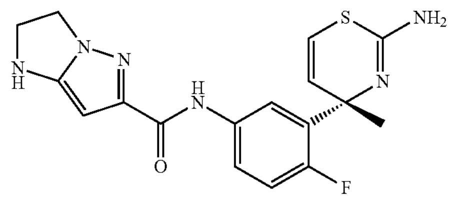 [SMILES: C[C@@]1(c2cc(NC(=O)c3cc4n(n3)CCN4)ccc2F)C=CSC(N)=N1] | | 1H-NMR (DMSO-d6) d: 1.53 (3H, s), 3.88-3.90 (2H, m), 4.16-4.19 (2H, m), 5.71 (1H, s), 5.91 (1H, t, J = 2.5 Hz), 6.13 (1H, dd, J = 9.4, 4.3 Hz), 6.25 (2H, s), 6.45 (1H, d, J = 9.6 Hz), 7.05 (1H, dd, J = 11.7, 9.1 Hz), 7.60-7.64 (1H, m), 7.84 (1H, dd, J = 7.6, 2.5 Hz), 9.76 (1H, s). |
| 64 | 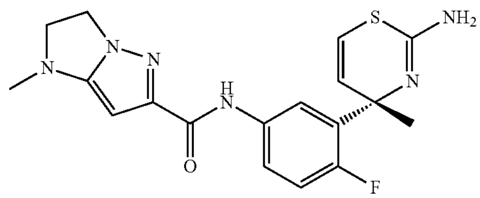 [SMILES: CN1CCn2nc(C(=O)Nc3ccc(F)c([C@]4(C)C=CSC(N)=N4)c3)cc21] | | 1H-NMR (DMSO-d6) d: 1.54 (3H, s), 2.77 (3H, s), 3.73 (2H, t, J = 7.6 Hz), 4.20 (2H, t, J = 7.9 Hz), 5.85 (1H, s), 6.13 (1H, dd, J = 9.6, 4.1 Hz), 6.24 (2H, s), 6.45 (1H, d, J = 9.1 Hz), 7.05 (1H, dd, J = 11.7, 9.1 Hz), 7.62-7.64 (1H, m), 7.82 (1H, dd, J = 7.4, 2.8 Hz), 9.78 (1H, s). |
| 65 | 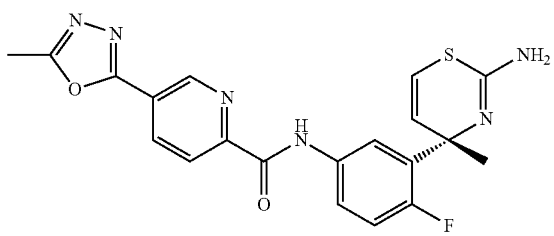 [SMILES: Cc1nnc(-c2ccc(C(=O)Nc3ccc(F)c([C@]4(C)C=CSC(N)=N4)c3)nc2)o1] | | 1H-NMR (DMSO-d6) d: 1.56 (3H, s), 2.65 (3H, s), 6.11-6.20 (1H, m), 6.31 (2H, s), 6.42-6.51 (1H, m), 7.08-7.20 (1H, m), 7.72-7.82 (1H, m), 7.95 (1H, dd, J = 6.8, 2.8 Hz), 8.33 (1H, d, J = 8.1 Hz), 8.54-8.62 (1H, m), 9.26 (1H, d, J = 1.5 Hz), 10.76 (1H, s). |
| 66 | 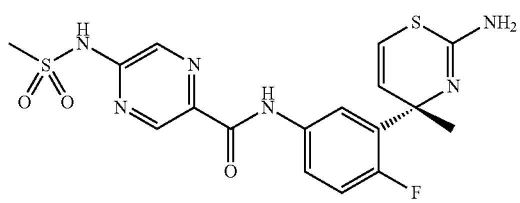 [SMILES: C[C@@]1(c2cc(NC(=O)c3cnc(NS(C)(=O)=O)cn3)ccc2F)C=CSC(N)=N1] | | 1H-NMR (DMSO-d6) d: 1.80 (3H, s), 3.39 (3H, s), 6.36 (1H, dd, J = 9.6, 3.0 Hz), 6.62 (1H, d, J = 9.6 Hz), 7.27 (1H, dd, J = 11.7, 9.1 Hz), 7.86-7.92 (1H, m), 8.03 (1H, dd, J = 7.6, 2.5 Hz), 8.34 (1H, d, J = 1.0 Hz), 8.94 (1H, d, J = 1.0 Hz), 10.69 (1H, s), 11.26 (1H, s). |
| 67 | 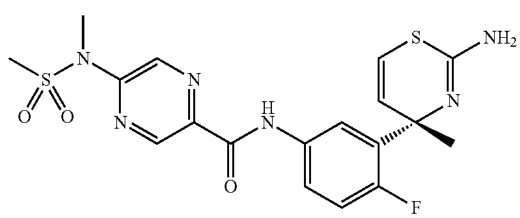 [SMILES: CN(c1cnc(C(=O)Nc2ccc(F)c([C@]3(C)C=CSC(N)=N3)c2)cn1)S(C)(=O)=O] | | 1H-NMR (DMSO-d6) d: 1.56 (3H, s), 3.36 (3H, s), 3.43 (3H, s), 6.15 (1H, dd, J = 9.6, 4.6 Hz), 6.29 (2H, s), 6.47 (1H, d, J = 9.6 Hz), 7.13 (1H, dd, J = 11.7, 8.6 Hz), 7.69-7.75 (1H, m), 7.93 (1H, dd, J = 7.4, 2.8 Hz), 8.84 (1H, d, J = 1.5 Hz), 9.06 (1H, d, J = 1.5 Hz), 10.59 (1H, s). |

TABLE 11

| Compound No. | Structure | MS [M + 1] | NMR (solvent, δ) |
|---|---|---|---|
| 68 | 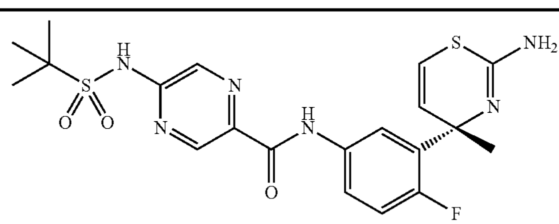 | | 1H-NMR (DMSO-d6) d: 1.37 (9H, s), 1.74 (3H, s), 6.31 (1H, dd, J = 9.6. 3.0 Hz), 6.58 (1H, d, J = 9.6 Hz), 7.24 (1H, dd, J = 11.4, 8.9 Hz), 7.82-7.88 (1H, m), 7.98 (1H, dd, J = 7.4, 2.3 Hz), 8.64 (1H, s), 8.91 (1H, s), 10.66 (1H, s), 11.14 (1H, s). |

TABLE 11-continued

| Compound No. | Structure | MS [M + 1] | NMR (solvent, δ) |
|---|---|---|---|
| 69 | 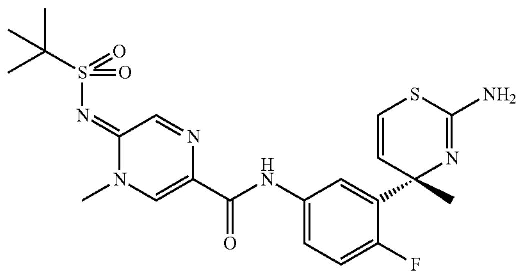 [SMILES: Cn1cc(C(=O)Nc2ccc(F)c([C@]3(C)C=CSC(N)=N3)c2)nc/c1=N\S(=O)(=O)C(C)(C)C] | | 1H-NMR (DMSO-d6) d: 1.40 (9H, s), 1.55 (3H, s), 3.68 (3H, s), 6.14 (1H, dd, J = 9.6, 4.1 Hz), 6.27 (2H, s), 6.46 (1H, d, J = 9.6 Hz), 7.11 (1H, dd, J = 11.4, 8.9 Hz), 7.65-7.71 (1H, m), 7.88 (1H, dd, J = 7.4, 2.8 Hz), 8.76 (1H, s), 6.90 (1H, s), 10.37 (1H, s). |
| 70 | 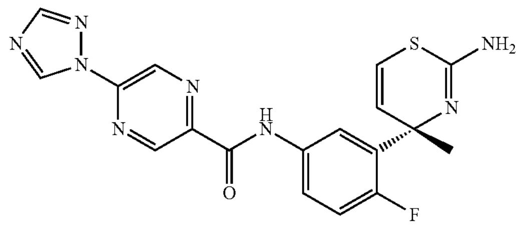 [SMILES: C[C@@]1(c2cc(NC(=O)c3cnc(-n4cncn4)cn3)ccc2F)C=CSC(N)=N1] | | 1H-NMR (DMSO-d6) d: 1.56 (3H, s), 6.16 (1H, dd, J = 9.6, 4.6 Hz), 6.30 (2H, s), 6.48 (1H, d, J = 9.6 Hz), 7.15 (1H, dd, J = 11.7, 8.6 Hz), 7.71-7.78 (1H, m), 7.96 (1H, dd, J = 7.4, 2.8 Hz), 8.49 (1H, s), 9.22 (2H, dd, J = 10.9, 1.3 Hz), 9.58 (1H, s), 10.79 (1H, s). |
| 71 | 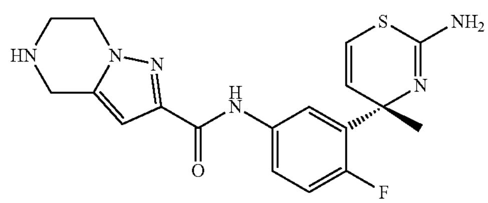 [SMILES: C[C@@]1(c2cc(NC(=O)c3cc4n(n3)CCNC4)ccc2F)C=CSC(N)=N1] | | 1H-NMR (DMSO-d6) d: 1.54 (3H, s), 1.99 (1H, s), 3.15 (2H, t, J = 5.6 Hz), 3.92 (2H, s), 4.08 (2H, t, J = 5.3 Hz), 6.13 (1H, dd, J = 9.6, 4.1 Hz), 6.26 (2H, s), 6.45 (1H, d, J = 9.6 Hz), 6.48 (1H, s), 7.06 (1H, dd, J = 11.7, 9.1 Hz), 7.61-7.68 (1H, m), 7.85 (1H, dd, J = 7.4, 2.8 Hz), 9.93 (1H, s). |
| 72 | 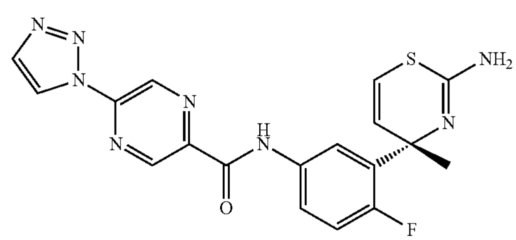 [SMILES: C[C@@]1(c2cc(NC(=O)c3cnc(-n4ccnn4)cn3)ccc2F)C=CSC(N)=N1] | | 1H-NMR (DMSO-d6) d: 1.57 (3H, s), 6.16 (1H, dd, J = 9.6, 4.1 Hz), 6.29 (2H, s), 6.48 (1H, d, J = 9.6 Hz), 7.15 (1H, dd, J = 11.4, 8.9 Hz), 7.72-7.79 (1H, m), 7.97 (1H, dd, J = 7.4, 2.8 Hz), 8.13 (1H, s), 9.04 (1H, s), 9.27 (1H, s), 9.50 (1H, s), 10.83 (1H, s). |
| 73 | 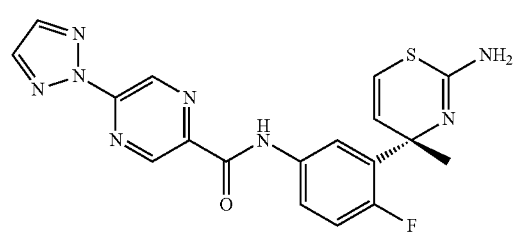 [SMILES: C[C@@]1(c2cc(NC(=O)c3cnc(-n4nccn4)cn3)ccc2F)C=CSC(N)=N1] | | 1H-NMR (DMSO-d6) d: 1.57 (3H, s), 6.16 (1H, dd, J = 9.6, 4.1 Hz), 6.29 (2H, s), 6.48 (1H, d, J = 9.6 Hz), 7.15 (1H, dd, J = 11.4, 8.9 Hz), 7.72-7.78 (1H, m), 7.96 (1H, dd, J = 7.4, 2.8 Hz), 8.38 (2H, s), 9.25 (1H, d, J = 1.0 Hz), 9.39 (1H, d, J = 1.5 Hz), 10.78 (1H, s). |

TABLE 12

| Compound No. | Structure | MS [M + 1] | NMR (solvent, δ) |
|---|---|---|---|
| 74 | 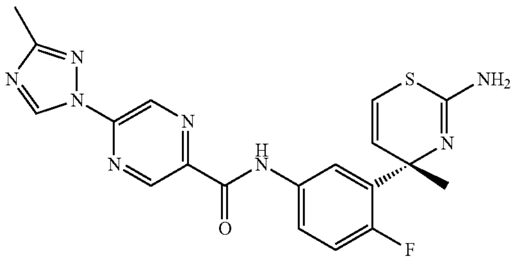 [SMILES: Cc1ncn(-c2cnc(C(=O)Nc3ccc(F)c([C@]4(C)C=CSC(N)=N4)c3)cn2)n1] | | 1H-NMR (DMSO-d6) d: 1.56 (3H, s), 2.46 (3H, s), 6.16 (1H, dd, J = 9.4, 4.3 Hz), 6.30 (2H, s), 6.48 (1H, d, J = 9.6 Hz), 7.14 (1H, dd, J = 11.4, 8.9 Hz), 7.71-7.77 (1H, m), 7.96 (1H, dd, J = 7.4, 2.8 Hz), 9.16 (2H, dd, J = 9.4, 1.3 Hz), 9.42 (1H, s), 10.78 (1H, s). |
| 75 | 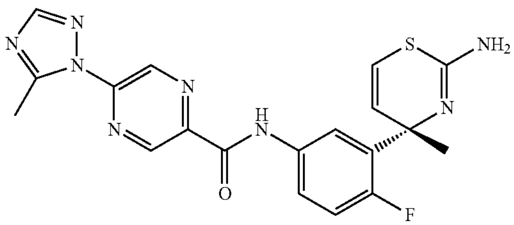 [SMILES: Cc1ncnn1-c1cnc(C(=O)Nc2ccc(F)c([C@]3(C)C=CSC(N)=N3)c2)cn1] | | 1H-NMR (DMSO-d6) d: 1.57 (3H, s), 2.83 (3H, s), 6.16 (1H, dd, J = 9.1, 3.5 Hz), 6.32 (2H, s), 6.48 (1H, d, J = 9.6 Hz), 7.14 (1H, t, J = 9.9 Hz), 7.70-7.79 (1H, m), 7.96 (1H, d, J = 5.6 Hz), 8.25 (1H, s), 9.21 (2H, d, J = 6.6 Hz), 10.78 (1H, s). |
| 76 | 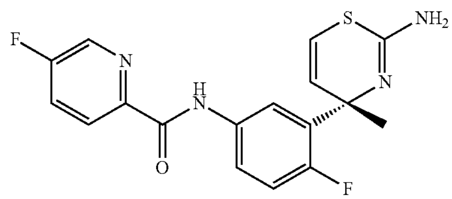 [SMILES: C[C@@]1(c2cc(NC(=O)c3ccc(F)cn3)ccc2F)C=CSC(N)=N1] | | 1H-NMR (DMSO-d6) d: 1.56 (3H, s), 6.16 (1H, dd, J = 9.6, 4.2 Hz), 6.30 (2H, s), 6.47 (1H, d, J = 9.6 Hz) 1, 7.13 (1H, dd, J = 11.2, 9.2 Hz), 7.74 (1H, m), 7.90 (1H, m), 7.98 (1H, m), 8.22 (1H, m), 8.65 (1H, s), 10.54 (1H, s) |
| 77 | 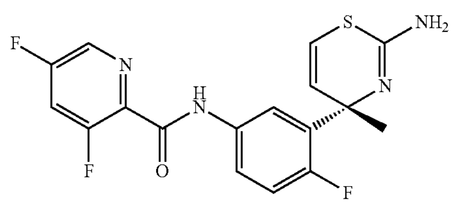 [SMILES: C[C@@]1(c2cc(NC(=O)c3ncc(F)cc3F)ccc2F)C=CSC(N)=N1] | | 1H-NMR (DMSO-d6) d: 1.55 (3H, s), 6.16 (1H, dd, J = 9.6, 4.2 Hz), 6.31 (2H, s), 6.47 (1H, d, J = 9.6 Hz), 7.13 (1H, dd, J = 11.4, 8.8 Hz), 7.69 (1H, m), 7.79 (1H, m), 8.15 (1H, t, J = 9.2 Hz), 8.65 (1H, s), 10.57 (1H, s) |
| 78 | 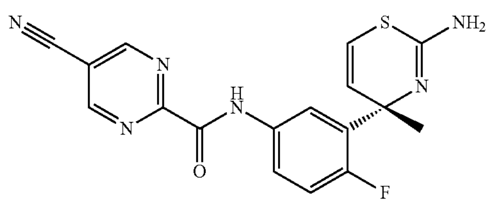 [SMILES: C[C@@]1(c2cc(NC(=O)c3ncc(C#N)cn3)ccc2F)C=CSC(N)=N1] | | 1H-NMR (DMSO-d6) d: 1.56 (3H. s), 6.16 (1H, dd, J = 9.6, 4.2 Hz), 6.31 (2H, s). 6.48 (1H, d, J = 9.6 Hz), 7.15 (1H, dd, J = 11.4, 8.8 Hz), 7.75 (1H, m), 7.86 (1H, m), 9.52 (2H, s), 10.90 (1H, s) |
| 79 | 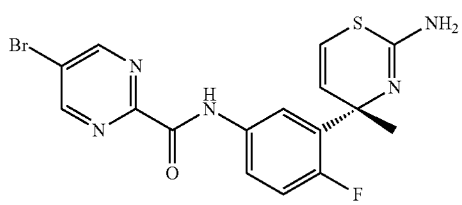 | | 1H-NMR (DMSO-d6) d: 1.56 (3H, s), 6.16 (1H, dd, J = 9.6, 3.6 Hz), 6.32 (2H, s), 6.47 (1H, d, J = 9.6 Hz), 7.14 (1H, dd, J = 11.4, 8.8 Hz), 7.75 (1H, m), 7.84 (1H, m), 9.21 (2H, s), 10.74 (1H, s) |
| 80 | 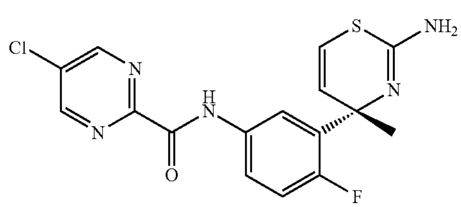 [SMILES: C[C@@]1(c2cc(NC(=O)c3ncc(Cl)cn3)ccc2F)C=CSC(N)=N1] | | 1H-NMR (DMSO-d6) d: 1.56 (3H, s), 6.17 (1H, dd, J = 9.6, 4.0 Hz), 6.33 (2H, s), 6.47 (1H, d, J = 9.6 Hz), 7.14 (1H, dd, J = 11.4, 8.8 Hz), 7.75 (1H, m), 7.85 (1H, m), 9.14 (2H, s), 10.74 (1H, s) |

TABLE 13

| Compound No. | Structure | MS [M + 1] | LC/MS retention time (measurement condition) or NMR (solvent, shift value: ascending order) |
|---|---|---|---|
| 81 | 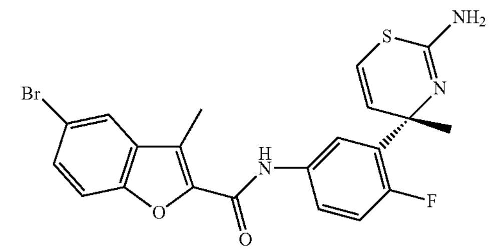 [SMILES: Cc1c(C(=O)Nc2ccc(F)c([C@]3(C)C=CSC(N)=N3)c2)oc2ccc(Br)cc12] | | 1H-NMR (CDCl3) d: 1.72 (3H, s), 2.51 (3H, s), 4.77 (2H, brs), 6.28 (2H, m), 6.98 (1H, m), 7.25 (1H, m), 7.49 (1H, m), 7.61 (1H, m), 7.73 (2H, m), 8.28 (1H, brs) |
| 82 | 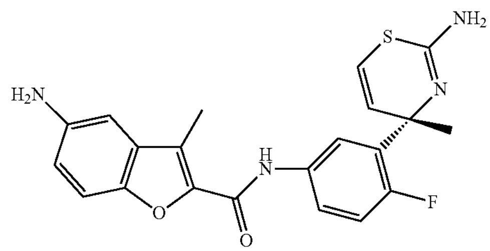 [SMILES: Cc1c(C(=O)Nc2ccc(F)c([C@]3(C)C=CSC(N)=N3)c2)oc2ccc(N)cc12] | | |
| 83 | 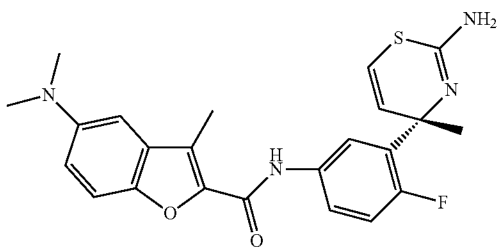 [SMILES: Cc1c(C(=O)Nc2ccc(F)c([C@]3(C)C=CSC(N)=N3)c2)oc2ccc(N(C)C)cc12] | | |
| 84 | 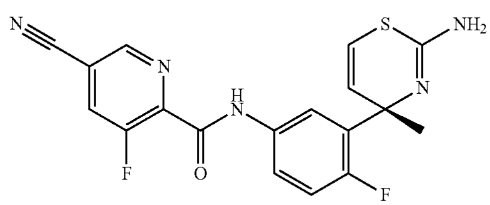 [SMILES: C[C@@]1(c2cc(NC(=O)c3ncc(C#N)cc3F)ccc2F)C=CSC(N)=N1] | 386 | 1.04 (Method B) |
| 85 | 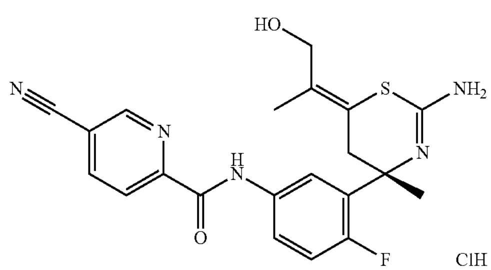 [SMILES: C/C(CO)=C1\C[C@@](C)(c2cc(NC(=O)c3ccc(C#N)cn3)ccc2F)N=C(N)S1 ; Cl] | 426 | 1.21 (Method B) |
| 86 | 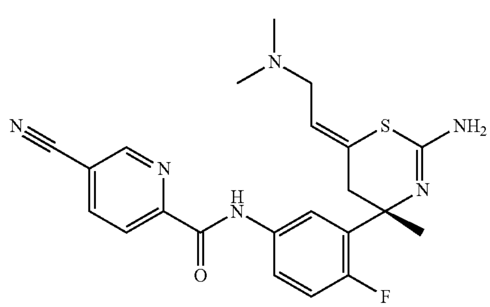 [SMILES: CN(C)C/C=C1/C[C@@](C)(c2cc(NC(=O)c3ccc(C#N)cn3)ccc2F)N=C(N)S1] | | |

TABLE 14

| Compound No. No. | Structure | MS [M + 1] | LC/MS retention time (measurement condition) or NMR (solvent, shift value: ascending order) |
|---|---|---|---|
| 87 | 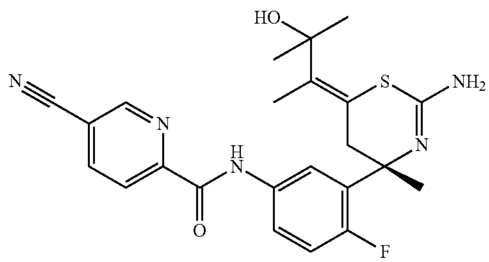 [SMILES: C/C(=C1\C[C@@](C)(c2cc(NC(=O)c3ccc(C#N)cn3)ccc2F)N=C(N)S1)C(C)(C)O] | 454 | 1.36 (Method B) |
| 88 | 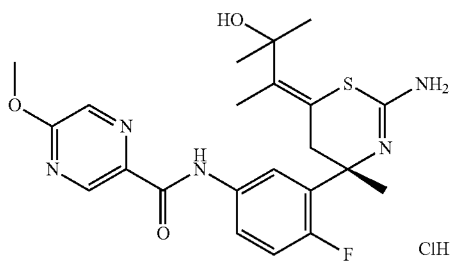 [SMILES: COc1cnc(C(=O)Nc2ccc(F)c([C@]3(C)C/C(=C(\C)C(C)(C)O)SC(N)=N3)c2)cn1 ; Cl] | 460 | 1.38 (Method B) |
| 89 | 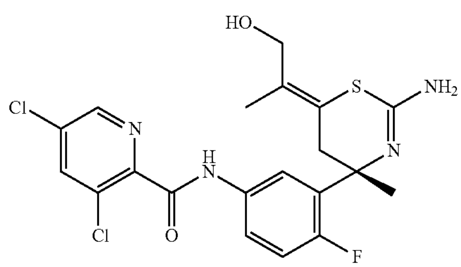 [SMILES: C/C(CO)=C1\C[C@@](C)(c2cc(NC(=O)c3ncc(Cl)cc3Cl)ccc2F)N=C(N)S1] | 469 | 1.3 (Method B) |
| 90 | 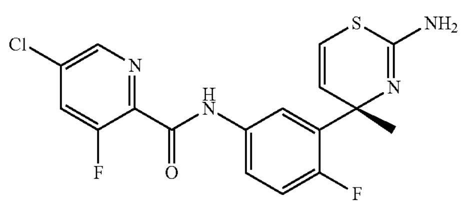 [SMILES: C[C@@]1(c2cc(NC(=O)c3ncc(Cl)cc3F)ccc2F)C=CSC(N)=N1] | 395 | 1.14 (Method A) |
| 91 | 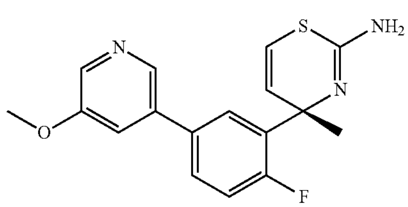 | 330 | 0.8 (Method A) |
| 92 | 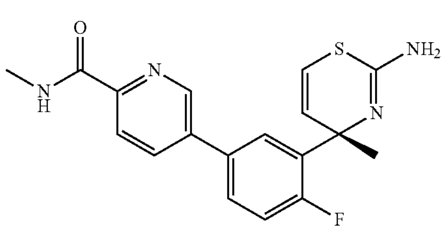 [SMILES: CNC(=O)c1ccc(-c2ccc(F)c([C@]3(C)C=CSC(N)=N3)c2)cn1] | 357 | 0.92 (Method A) |

TABLE 14-continued

| Compound No. No. | Structure | MS [M + 1] | LC/MS retention time (measurement condition) or NMR (solvent, shift value: ascending order) |
|---|---|---|---|
| 93 | 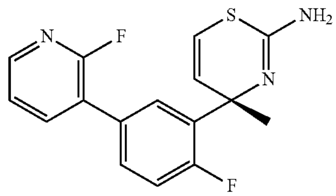 [SMILES: C[C@@]1(c2cc(-c3cccnc3F)ccc2F)C=CSC(N)=N1] | 318 | 0.99 (Method A) |

TABLE 15

| Compound No. | Structure | MS [M + 1] | LC/MS retention time (measurement condition) or NMR (solvent, shift value: ascending order) |
|---|---|---|---|
| 94 | 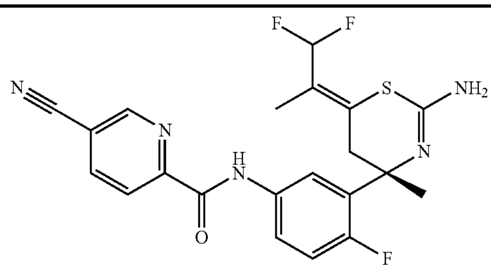 | 446 | 1.38 (Method B) |
| 95 | 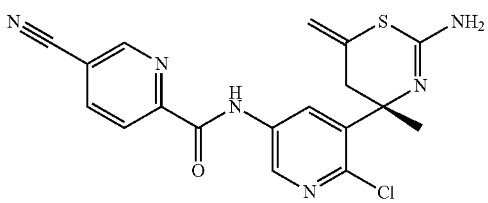 [SMILES: C=C1C[C@@](C)(c2cc(NC(=O)c3ccc(C#N)cn3)cnc2Cl)N=C(N)S1] | 399 | 1.08 (Method B) |
| 96 | 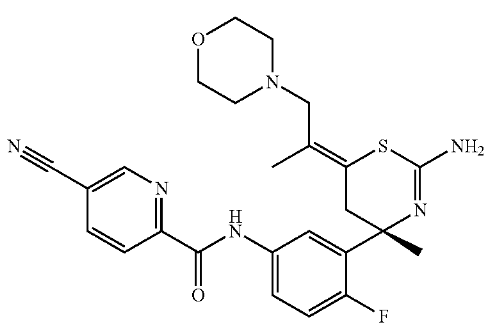 [SMILES: C/C(CN1CCOCC1)=C1\C[C@@](C)(c2cc(NC(=O)c3ccc(C#N)cn3)ccc2F)N=C(N)S1] | 495 | 0.89 (Method B) |
| 97 | ClH ClH | 512 | 1.43 (Method B) |

TABLE 15-continued

| Compound No. | Structure | MS [M + 1] | LC/MS retention time (measurement condition) or NMR (solvent, shift value: ascending order) |
|---|---|---|---|
| 98 | 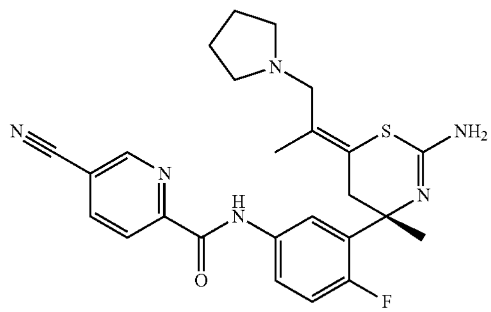 [SMILES: C/C(CN1CCCC1)=C1\C[C@@](C)(c2cc(NC(=O)c3ccc(C#N)cn3)ccc2F)N=C(N)S1] | 479 | 0.81 (Method B) |
| 99 | 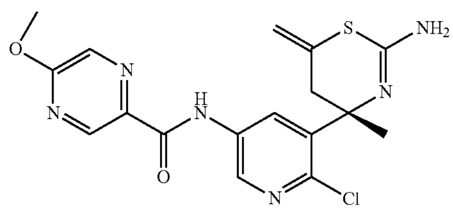 | 405 | 1.18 (Method B) |
| 100 | 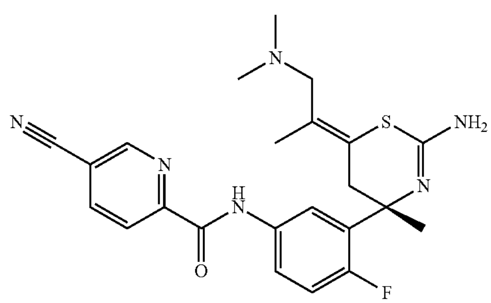 [SMILES: C/C(CN(C)C)=C1\C[C@@](C)(c2cc(NC(=O)c3ccc(C#N)cn3)ccc2F)N=C(N)S1] | 453 | 0.88 (Method B) |
| 101 | 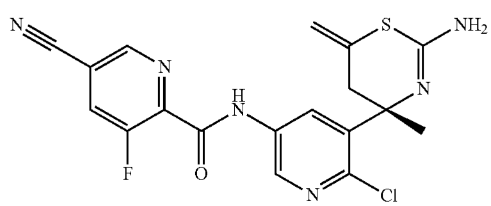 [SMILES: C=C1C[C@@](C)(c2cc(NC(=O)c3ncc(C#N)cc3F)cnc2Cl)N=C(N)S1] | 417 | 1.02 (Method B) |

TABLE 16

| Compound No. | Structure | MS [M + 1] | LC/MS retention time (measurement condition) or NMR (solvent, shift value: ascending order) |
|---|---|---|---|
| 102 | 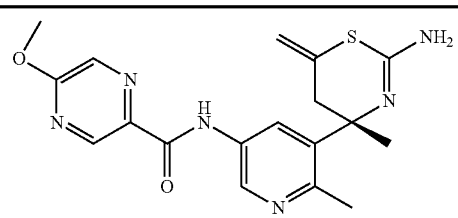 | 385 | 0.88 (Method B) |

TABLE 16-continued

| Compound No. | Structure | MS [M + 1] | LC/MS retention time (measurement condition) or NMR (solvent, shift value: ascending order) |
|---|---|---|---|
| 103 | 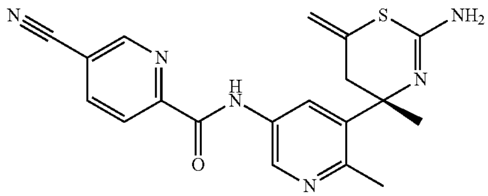 [SMILES: C=C1C[C@@](C)(c2cc(NC(=O)c3ccc(C#N)cn3)cnc2C)N=C(N)S1] | 379 | 0.85 (Method B) |
| 104 | 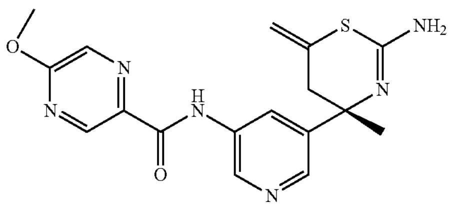 [SMILES: C=C1C[C@@](C)(c2cncc(NC(=O)c3cnc(OC)cn3)c2)N=C(N)S1] | 371 | 0.98 (Method B) |
| 105 | 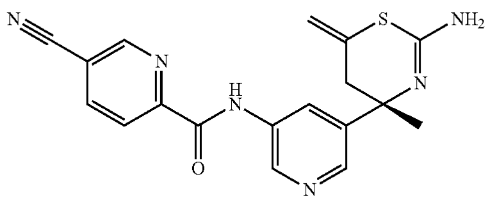 [SMILES: C=C1C[C@@](C)(c2cncc(NC(=O)c3ccc(C#N)cn3)c2)N=C(N)S1] | 365 | 0.92 (Method B) |
| 106 | 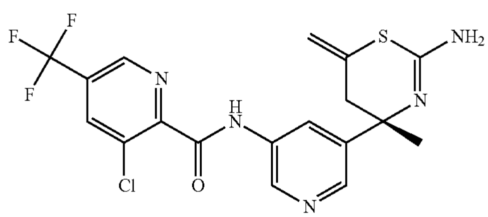 | 442 | 1.26 (Method B) |
| 107 | 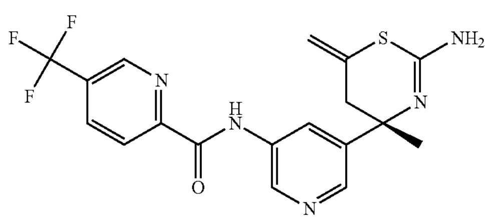 [SMILES: C=C1C[C@@](C)(c2cncc(NC(=O)c3ccc(C(F)(F)F)cn3)c2)N=C(N)S1] | 408 | 1.23 (Method B) |
| 108 | 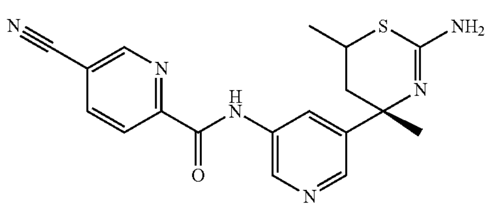 [SMILES: CC1C[C@@](C)(c2cncc(NC(=O)c3ccc(C#N)cn3)c2)N=C(N)S1] | 365 | 0.96 (Method B) |
| 109 | 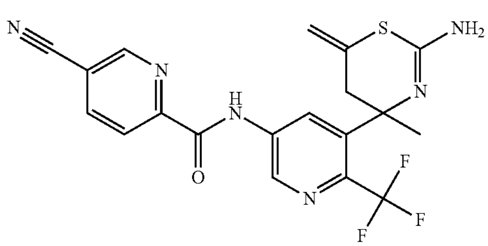 [SMILES: C=C1CC(C)(c2cc(NC(=O)c3ccc(C#N)cn3)cnc2C(F)(F)F)N=C(N)S1] | 433 | 1.34 (Method B) |

TABLE 17

| Compound No. | Structure | MS [M + 1] | LC/MS retention time (measurement condition) or NMR (solvent, shift value: ascending order) |
|---|---|---|---|
| 200 | 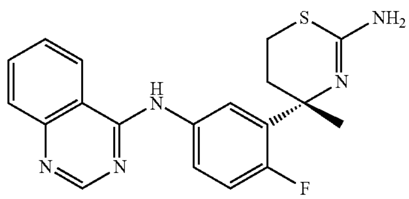 [SMILES: C[C@@]1(c2cc(Nc3ncnc4ccccc34)ccc2F)CCSC(N)=N1] | | 1H-NMR (DMSO-d6) d: 1.50 (3H, s), 1.81-1.87 (1H, m), 2.18-2.20 (1H, m), 2.60-2.66 (1H, m), 2.98-3.02 (1H, m), 5.84 (2H, s), 7.16 (1H, dd, J = 11.9, 8.9 Hz), 7.62 (1H, t, J = 7.6 Hz), 7.69-7.73 (1H, m), 7.76-7.80 (2H, m), 7.85 (1H, t, J = 7.6 Hz), 8.54 (2H, t, J = 4.1 Hz), 9.89 (1H, s). |
| 201 | 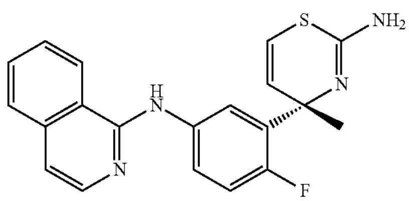 [SMILES: C[C@@]1(c2cc(Nc3nccc4ccccc34)ccc2F)C=CSC(N)=N1] | | 1H-NMR (DMSO-d6) d: 1.51 (3H, s), 1.79-1.81 (1H, m), 2.22-2.22 (1H, m), 2.60-2.66 (1H, m), 2.96-3.00 (1H, m), 5.87 (2H, br s), 7.08 (1H, dd, J = 12.2, 8.6 Hz), 7.13 (1H, d, J = 6.1 Hz), 7.59 (1H, t, J = 7.6 Hz), 7.69-7.73 (2H, m), 7.79-7.81 (2H, m), 7.94 (1H, d, J = 5.6 Hz), 8.53 (1H, d, J = 8.6 Hz), 9.19 (1H, s). |
| 202 | 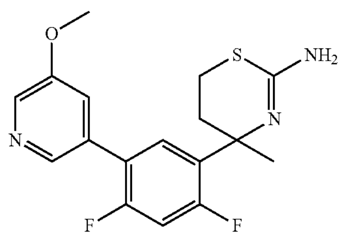 [SMILES: COc1cncc(-c2cc(C3(C)CCSC(N)=N3)c(F)cc2F)c1] | 350 | 0.91 (Method A) |
| 203 | 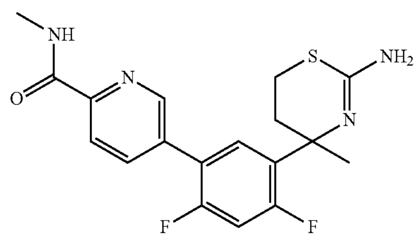 [SMILES: CNC(=O)c1ccc(-c2cc(C3(C)CCSC(N)=N3)c(F)cc2F)cn1] | 377 | 0.97 (Method A) |
| 204 | 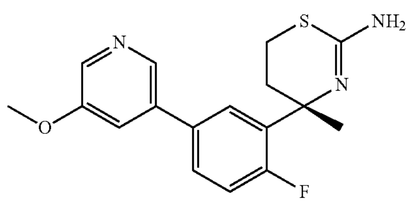 [SMILES: COc1cncc(-c2ccc(F)c([C@]3(C)CCSC(N)=N3)c2)c1] | 332 | 0.82 (Method A) |
| 205 | 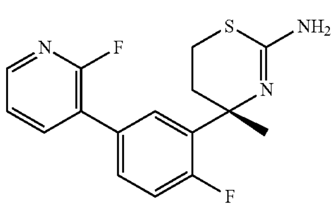 [SMILES: C[C@@]1(c2cc(-c3cccnc3F)ccc2F)CCSC(N)=N1] | 320 | 1.03 (Method A) |
| 206 | 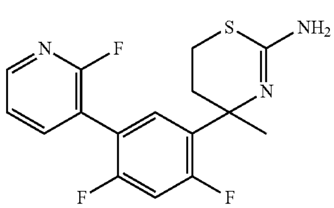 [SMILES: CC1(c2cc(-c3cccnc3F)c(F)cc2F)CCSC(N)=N1] | 338 | 0.16 (Method A) |

TABLE 17-continued
| Compound No. | Structure | MS [M + 1] | LC/MS retention time (measurement condition) or NMR (solvent, shift value: ascending order) |
|---|---|---|---|
| 207 | 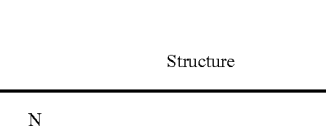 | 347 | 1.27 (Method A) |
TABLE 18
| Compound No. | Structure | MS [M + 1] | LC/MS retention time (measurement condition) or NMR (solvent, shift value: ascending order) |
|---|---|---|---|
| 208 | 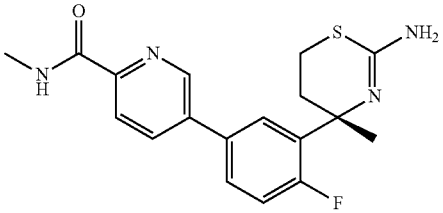 [SMILES: CNC(=O)c1ccc(-c2ccc(F)c([C@]3(C)CCSC(N)=N3)c2)cn1] | 359 | 0.93 (Method A) |
| 209 | 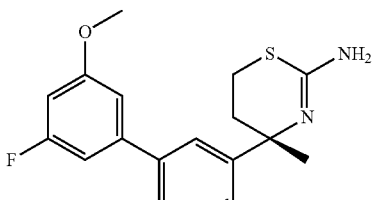 | 331 | 1.33 (Method A) |
| 210 | 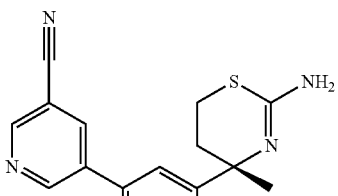 | 327 | 0.96 (Method A) |
| 211 | 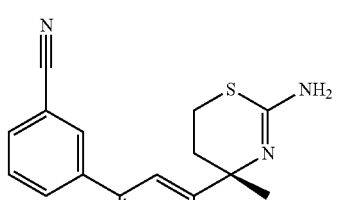 | 308 | 1.13 (Method A) |

TABLE 18-continued

| Compound No. | Structure | MS [M + 1] | LC/MS retention time (measurement condition) or NMR (solvent, shift value: ascending order) |
|---|---|---|---|
| 212 | 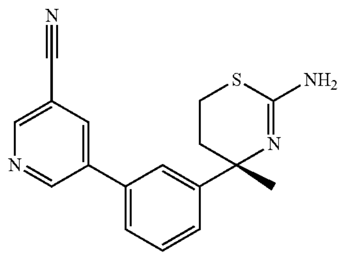 [SMILES: C[C@@]1(c2cccc(-c3cncc(C#N)c3)c2)CCSC(N)=N1] | 309.0 | 0.88 (Method A) |
| 213 | 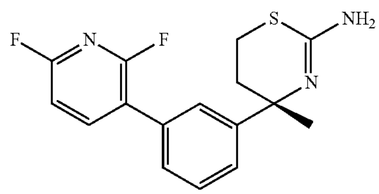 [SMILES: C[C@@]1(c2cccc(-c3ccc(F)nc3F)c2)CCSC(N)=N1] | 320 | 1.11 (Method A) |
| 214 | 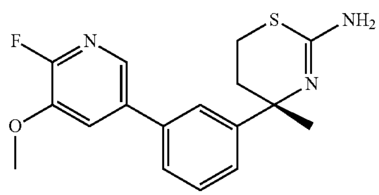 [SMILES: COc1cc(-c2cccc([C@]3(C)CCSC(N)=N3)c2)cnc1F] | 332 | 1.06 (Method A) |
| 215 | 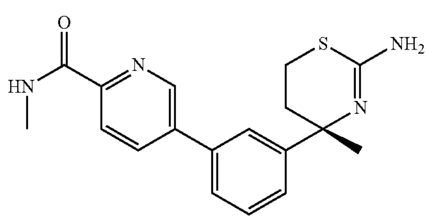 [SMILES: CNC(=O)c1ccc(-c2cccc([C@]3(C)CCSC(N)=N3)c2)cn1] | 341 | 0.96 (Method B) |

TABLE 19

| Compound No. | Structure | MS [M + 1] | LC/MS retention time (measurement condition) or NMR (solvent, shift value: ascending order) |
|---|---|---|---|
| 216 | 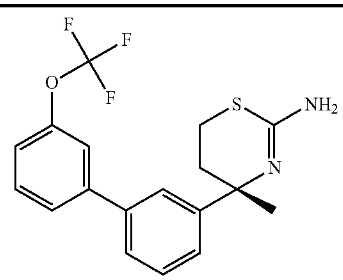 | 367 | 1.4 (Method A) |
| 217 | 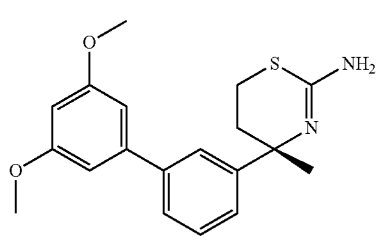 [SMILES: COc1cc(OC)cc(-c2cccc([C@]3(C)CCSC(N)=N3)c2)c1] | 343 | 1.37 (Method A) |

TABLE 19-continued

| Compound No. | Structure | MS [M + 1] | LC/MS retention time (measurement condition) or NMR (solvent, shift value: ascending order) |
|---|---|---|---|
| 218 | 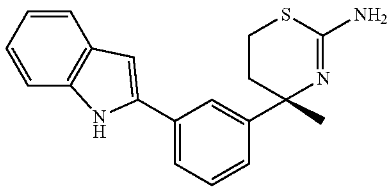 [SMILES: C[C@@]1(c2cccc(-c3cc4ccccc4[nH]3)c2)CCSC(N)=N1] | 322 | 1.34 (Method A) |
| 219 | 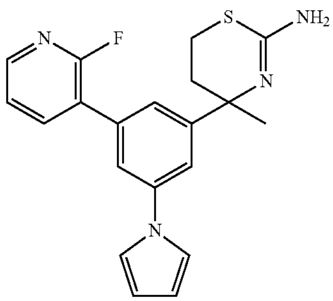 [SMILES: CC1(c2cc(-c3cccnc3F)cc(-n3cccc3)c2)CCSC(N)=N1] | 367 | 1.43 (Method A) |
| 220 | 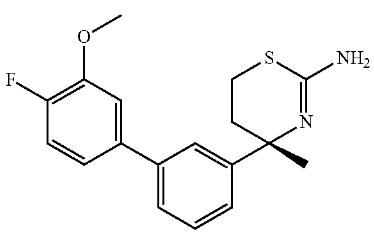 [SMILES: COc1cc(-c2cccc([C@]3(C)CCSC(N)=N3)c2)ccc1F] | 331 | 1.32 (Method A) |
| 221 | 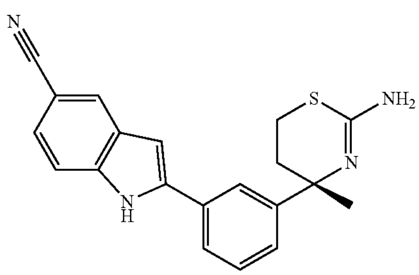 [SMILES: C[C@@]1(c2cccc(-c3cc4cc(C#N)ccc4[nH]3)c2)CCSC(N)=N1] | 347 | 1.25 (Method A) |
| 222 | 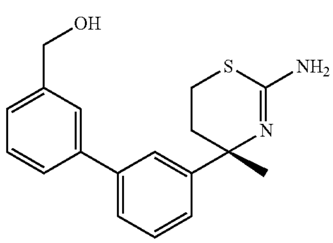 [SMILES: C[C@@]1(c2cccc(-c3cccc(CO)c3)c2)CCSC(N)=N1] | 313 | 1.02 (Method A) |
| 223 | 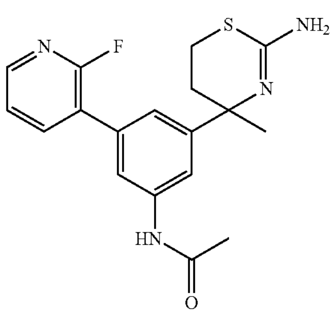 [SMILES: CC(=O)Nc1cc(-c2cccnc2F)cc(C2(C)CCSC(N)=N2)c1] | 359 | 0.87 (Method B) |

TABLE 20

| Compound No. | Structure | MS [M + 1] | LC/MS retention time (measurement condition) or NMR (solvent, shift value: ascending order) |
|---|---|---|---|
| 224 | 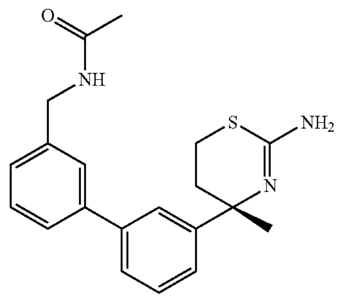 [SMILES: CC(=O)NCc1cccc(-c2cccc([C@]3(C)CCSC(N)=N3)c2)c1] | 354 | 0.94 (Method A) |
| 225 | 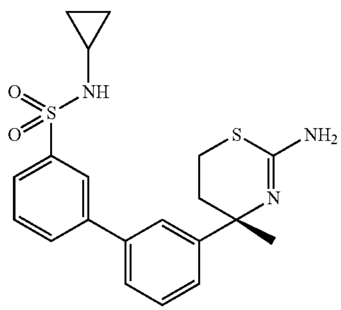 [SMILES: C[C@@]1(c2cccc(-c3cccc(S(=O)(=O)NC4CC4)c3)c2)CCSC(N)=N1] | 402 | 1.11 (Method A) |
| 226 | 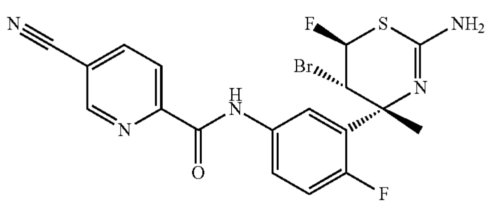 [SMILES: C[C@]1(c2cc(NC(=O)c3ccc(C#N)cn3)ccc2F)N=C(N)S[C@H](F)[C@H]1Br] | 466 | 1.51 (Method B) |

The effect of the present compound was confirmed by the following test Examples.

Test Example 1

Assay of δ-Secretase-Inhibiting Activity 48.5 μL of substrate peptide solution (Biotin-XSEVNLDAEFRHDSGC-Eu: X=ε-amino-n-capronic acid, Eu=Europium cryptate) was added to each well of 96-hole half-area plate (a black plate: Corning Incorporated), and after addition of 0.5 μl of the test sample (dissolved in N,N'-dimethylformaldehyde) and 1 μl of Recombinant human BACE-1 (R&D Systems), the reaction mixture was incubated at 30° C. for 3 hours. The substrate peptide was synthesized by reacting Cryptate TBPCOOH mono SMP (CIS bio international) with Biotin-XSEVNLDAEFRHDSGC (Peptide Institute, Inc.). The final concentrations of the substrate peptide and Recombinant human BACE-1 were adjusted to 18 nM and 7.4 nM respectively, and the reaction was performed in sodium acetate buffer (50 mM sodium acetate, pH 5.0, 0.008% Triton X-10).

After the incubation for reaction, 50 μl of 8.0 μg/ml Streptavidin-XL665 (CIS bio international) dissolved in phosphate buffer (150 mM $K_2HPO_4$—$KH_2PO_4$, pH 7.0, 0.008% Triton X-100, 0.8 M KF) was added to each well and left stand at 30° C. for an hour. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000×Count 665/Count 620) and 50% inhibitory concentration against the enzymatic activity was calculated. $IC_{50}$ values of the test compounds are indicated in Table 21.

TABLE 21

| Compound No. | $IC_{50}$ (μM) |
|---|---|
| 2 | 0.514 |
| 3 | 0.966 |
| 16 | 0.010 |
| 20 | 0.095 |
| 21 | 0.019 |
| 22 | 0.572 |
| 23 | 5.280 |
| 24 | 0.054 |
| 33 | 0.073 |
| 35 | 0.096 |
| 38 | 0.304 |
| 39 | 0.097 |
| 44 | 2.130 |
| 46 | 0.611 |
| 47 | 0.091 |
| 48 | 0.273 |
| 51 | 0.016 |
| 53 | 0.076 |
| 56 | 0.352 |

TABLE 21-continued

| Compound No. | IC$_{50}$ (µM) |
|---|---|
| 58 | 0.186 |
| 59 | 0.019 |
| 60 | 0.243 |
| 61 | 0.169 |
| 63 | 0.435 |
| 66 | 0.296 |
| 70 | 0.036 |
| 72 | 0.250 |
| 73 | 0.234 |
| 75 | 0.697 |
| 76 | 0.062 |
| 79 | 0.024 |
| 81 | 0.007 |
| 99 | 0.014 |
| 101 | 0.022 |
| 102 | 0.036 |
| 104 | 0.063 |
| 106 | 0.102 |

The following compounds showed the IC$_{50}$ value of 1 µM or less by the similar test.
Compounds 1, 4, 5, 12, 13, 14, 15, 17, 18, 19, 25, 26, 27, 28, 29, 30, 31, 32, 34, 36, 37, 45, 49, 50, 52, 54, 55, 57, 74, 77, 78, 80, 84, 85, 94, 95, 96, 97, 98, 100, 103, 105, 107 and 108.

Test Example 2

Lowering Effect on Brain β Amyloid in Rats

A test compound was suspended in 0.5% methylcellulose, the final concentration was adjusted to 2 mg/mL, and this was orally administered to male Crg:SD rat (7 to 9 week old) at 10 mg/kg. In a vehicle control group, only 0.5% methylcellulose was administered, and an administration test was performed at 3 to 8 animals per group. A brain was isolated 3 hours after administration, a cerebral hemisphere was isolated, a weight thereof was measured, the hemisphere was rapidly frozen in liquid nitrogen, and stored at −80° C. until extraction date. The frozen cerebral hemisphere was transferred to a homogenizer manufactured by Teflon (registered trade mark) under ice cooling, a 5-fold volume of a weight of an extraction buffer (containing 1% CHAPS ({3-[(3-chloroamidopropyl) dimethylammonio]-1-propanesulfonate}), 20 mM Tris-HCl (pH 8.0), 150 mM NaCl, Complete (Roche) protease inhibitor) was added, up and down movement was repeated, and this was homogenized to solubilize for 2 minutes. The suspension was transferred to a centrifugation tube, allowed to stand on an ice for 3 hours or more and, thereafter centrifuged at 100,000×g and 4° C. for 20 minutes. After centrifugation, the supernatant was transferred to an ELISA plate (product No. 27730, Immuno-Biological Laboratories Co., Ltd.) for measuring β amyloid 1-40. ELISA measurement was performed according to the attached instruction. The lowering effect was calculated as a ratio compared to the brain β amyloid 1-40 level of vehicle control group of each test.

The present compound exhibited the extremely excellent effect in the test, and it was shown that the compound had high intrabrain β amyloid inhibitory activity.

Test Example 3

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was ¹/₁₀ diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was ¹/₁₀ diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm). Addition of only DMSO which is a solvent dissolving a drug to a reaction system was adopted as a control (100%), remaining activity (%) was calculated at each concentration of a test drug added as the solution, and IC$_{50}$ was calculated by reverse-presumption by a logistic model using a concentration and an inhibition rate. When a difference between IC$_{50}$ values is 5 µM or more, this was defined as (+) and, when the difference is 3 µM or less, this was defined as (−).
(Result)
Compound 99: (−)
Compound 108 (−)

Test Example 4

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and 1050 was calculated by reverse presumption by a logistic model using a concentration and an inhibition rate.

(Result)
Compound No. 35: five kinds>20 µM
Compound No. 63: five kinds>20 µM
Compound No. 68: five kinds>20 µM
Compound No. 104: five kinds>20
Compound No. 106: five kinds>20 µM Test Example 5

Solubility Test

A 2-fold dilution series (12 points) of a 10 mM solution of a test compound in DMSO was added to a medium (JP-I, JP-II) (2%), and solubility was assessed by 3 stages (High; >40 µM, Medium; 3-40 µM, Low; <3 µM) from a turbidity after 4 hours (crystallization information).
(Result)
Compound No. 2: High (JP-I)
Compound No. 9: High (JP-I)
Compound No. 23: High (JP-I)
Compound No. 32: High (JP-I)
Compound No. 60: High (JP-I)
Compound No. 70: High (JP-I)

Test Example 6

Metabolism Stability Test

Using a commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v) mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%.
(Result)
Compound No. 38: 95%
Compound No. 70: 94%
Compound No. 212: 95%
Compound No. 213: 98%

Test Example 7 hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +50 mV for 2 seconds and, further, repolarization pulse stimulation at −50 mV for 2 seconds was recorded. After the generated current was stabilized, extracellular solution (NaCl: 137 mmol/L, KCl: 4 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.
(Result)
Compound 92: 7.9%
Compound 102: 2.3%

Test Example 8

FAT Test

Each 20 µL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate 0.25 g/L, $MgSO_4.7H_2O$: 0.1 g/L), and the suspension is added to 110 mL of Exposure medium (Micro F buffer containing Biotin: 8 µg/mL, histidine: 0.2 µg/mL, glucose: 8 mg/mL). 3.16 mL of TA100 culture is added to 120 mL of Exposure medium to prepare the test bacterial solution. 588 µL of the test bacterial solution (or mixed solution of 498 µl of the test bacterial solution and 90 µL of the S9 mix in the case with metabolic activation system) are mixed with each 12 µL of the following solution: DMSO solution of the test substance (eight dose levels from maximum dose 50 mg/mL at 2-fold ratio); DMSO as negative control; 50 µg/mL of 4-nitroquinoline-1-oxide DMSO solution as positive control for TA98 without metabolic activation system; 0.25 µg/mL of 2-(furyl)-3-(5-nitro-2-furyl)acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. 12 μL of the solution and 588 μL of the test bacterial solution (a mixed solution of 498 μl of the test bacterial solution and 90 μL of S9 mix with metabolic activation condition) were mixed and incubated at 37° C. under shaking for 90 minutes. 460 μL of the bacterial solution exposed to the test substance is mixed with 2300 μL of Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into 48 wells per dose in the microwell plates, and was subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose is counted, and evaluate the mutagenicity by comparing with the negative control group. (−) means that mutagenicity is negative and (+) means positive.

Preparation Example 1

A granule containing the following ingredients is produced.

| Ingredient | |
| --- | --- |
| Compound represented by the formula (I) | 10 mg |
| Lactose | 700 mg |
| Corn starch | 274 mg |
| HPC-L | 16 mg |
| | 1000 mg |

The compound represented by the formulae (I), and lactose are passed through a 60 mesh sieve. Corn starch is passed through a 120 mesh sieve. These are mixed with a V-type mixer. To the mixed powder is added a HPC-L (low viscosity hydroxypropylcellulose) aqueous solution, this is kneaded, granulated (extrusion granulation, pore diameter 0.5 to 1 mm), and dried. The resulting dry granule is passed through a vibration sieve (12/60 mesh) to obtain a granule.

Preparation Example 2

A granule for filling a capsule containing the following ingredients is produced.

| Ingredient | |
| --- | --- |
| Compound represented by the formula (I) | 15 mg |
| Lactose | 90 mg |
| Corn starch | 42 mg |
| HPC-L | 3 mg |
| | 150 mg |

The compound represented by the formula (I), and lactose are passed through a 60 mesh sieve. Corn starch is passed through a 120 mesh sieve. These are mixed, a HPC-L solution is added to the mixed powder, this is kneaded, granulated, and dried. The resulting dry granule is adjusted in a size, and 150 mg of it is filled into a No. 4 hard gelatin capsule.

Preparation Example 3

A tablet containing the following ingredients is produced.

| Ingredient | |
| --- | --- |
| Compound represented by the formula (I) | 10 mg |
| Lactose | 90 mg |
| Microcrystalline cellulose | 30 mg |
| CMC-Na | 15 mg |
| Magnesium stearate | 5 mg |
| | 150 mg |

The compound represented by the formula (I), lactose, microcrystalline cellulose, and CMC-Na (carboxymethylcellulose sodium salt) are passed through a 60 mesh sieve, and mixed. Magnesium stearate is mixed into the mixed powder to obtain a mixed powder for tabletting. The present mixed powder is directly compressed to obtain a 150 mg of a tablet.

Preparation Example 4

The following ingredients are warmed, mixed, and sterilized to obtain an injectable.

| Ingredient | |
| --- | --- |
| Compound represented by the formula (I) | 3 mg |
| Nonionic surfactant | 15 mg |
| Purified water for injection | 1 ml |

INDUSTRIAL APPLICABILITY

The present compound can be a medicament useful as an agent for treating a disease induced by production, secretion and/or deposition of amyloid β protein.

The invention claimed is:
1. A compound represented by the following formula (III):

[Chemical formula 3]

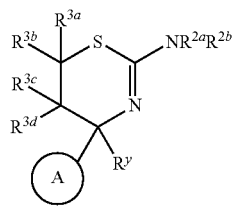

(III)

wherein $R^y$ is halogeno lower alkyl;
$R^{3a}$, $R^{3b}$, $R^{3c}$ and $R^{3d}$ are each independently hydrogen, halogen, hydroxy, optionally substituted lower alkyl, optionally substituted lower alkenyl, optionally substituted lower alkynyl, optionally substituted acyl, optionally substituted lower alkoxy, optionally substituted aryl lower alkyl, optionally substituted heteroaryl lower alkyl, optionally substituted aryl lower alkoxy, optionally substituted heteroaryl lower alkoxy, optionally substituted lower alkylthio, carboxy, cyano, optionally substituted lower alkoxycarbonyl, optionally substituted amino, optionally substituted carbamoyl, an optionally substituted carbocyclic group or an optionally substituted heterocyclic group; and
ring A is

[Chemical formula 5]

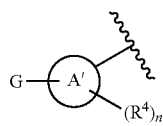

wherein ring A' is a carbocyclic group or a heterocyclic group,
G is (ii')

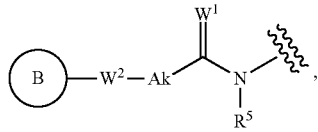

(ii'')

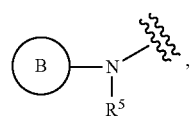

(iv')

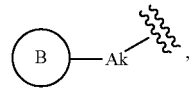

(v')

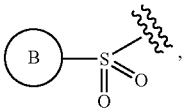

(x')

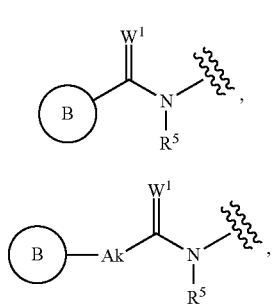

(xiii')

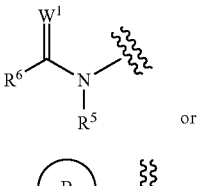

(xiv')

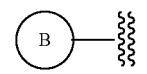
or (xixi')

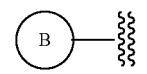

wherein $R^5$ is hydrogen, lower alkyl or acyl;
$R^6$ is optionally substituted lower alkyl, optionally substituted lower alkenyl, or optionally substituted lower alkynyl;
$W^1$ is O;
$W^2$ is O, S or $NR^5$;
Ak is optionally substituted lower alkylene, optionally substituted lower alkenylene, or optionally substituted lower alkynylene;
ring B is an optionally substituted carbocyclic group or an optionally substituted heterocyclic group;
$R^4$ is each independently halogen, hydroxy, mercapto, halogeno lower alkyl, lower alkyl, lower alkoxy, optionally substituted amino, or lower alkylthio, and n is an integer of 0 to 2;
$R^{2a}$ and $R^{2b}$ are each independently hydrogen, optionally substituted lower alkyl or optionally substituted acyl,
the substituents of "optionally substituted lower alkyl", "optionally substituted lower alkenyl", "optionally substituted lower alkynyl", "optionally substituted lower alkoxy", "optionally substituted lower alkylthio", "optionally substituted lower alkoxycarbonyl", "optionally substituted lower alkylene", "optionally substituted lower alkenylene" and "optionally substituted lower alkynylene" are one or more selected from a substituent group α, the substituent group α is a group consisting of halogen, hydroxy, lower alkoxy, halogeno lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfinyl, lower alkylsulfonylamino, lower alkylsulfonyl lower alkylamino, lower alkylsulfonylimino, lower alkylsulfonylamino, lower alkylsulfinyl lower alkylamino, lower alkylsulfinylimino, cyano, nitro, a carbocyclic group and a heterocyclic group wherein the carbocycle and the heterocycle may be each substituted with halogen and/or hydroxy, the "acyl" includes aliphatic acyl of a carbon number of 1 to 10, carbocyclylcarbonyl and heterocyclylcarbonyl, the substituent of "optionally substituted acyl" is one or more substituents selected from the substituent group α and a ring part of the carbocyclylcarbonyl and the heterocyclylcarbonyl may be substituted with one or more substituents selected from lower alkyl, a substituent group α, and lower alkyl substituted with one or more groups selected from the substituent group α, the substituent of "optionally substituted amino" and "optionally substituted carbamoyl" is 1 to 2 substituents selected from lower alkyl, acyl, hydroxy, lower alkoxy, lower alkoxycarbonyl, a carbocyclic group and a heterocyclic group, the substituents of "optionally substituted aryl lower alkyl", "optionally substituted heteroaryl lower alkyl", "optionally substituted aryl lower alkoxy", "optionally substituted heteroaryl lower alkoxy", "optionally substituted carbocyclic group" and "optionally substituted heterocyclic group" is one or more selected from lower alkyl optionally substituted with one or more groups selected from the substituent group α and the substituent group α, each of "carbocyclic group" and "carbocyclyl" is C3-C10 cycloalkyl, C3-C10 cycloalkenyl, aryl, or non-aromatic fused carbocyclic group, aryl is phenyl, naphthyl, anthryl or phenanthryl, the non-aromatic fused carbocyclic group is a non-aromatic group in which two or more cyclic groups selected from "C3-C10 cycloalkyl", "C3-C10 cycloalkenyl" and "aryl" are fused, each of the "heterocyclic group" and "heterocyclyl" is a heterocyclic group having one or more hetero atoms optionally selected from O, S and N in a ring, the "heteroaryl" is an aromatic cyclic group among the "heterocyclic group", or its pharmaceutically acceptable salt or a solvate thereof.

2. The compound according to claim 1, wherein $R^{3a}$, $R^{3b}$, $R^{3c}$ and $R^{3d}$ are all hydrogen, or its pharmaceutically acceptable salt, or a solvate thereof.

3. The compound according to claim 1, wherein $R^{2a}$ and $R^{2b}$ are both hydrogen, or its pharmaceutically acceptable salt, or a solvate thereof.

4. The compound according to claim 1, wherein ring A' is phenyl or a nitrogen-containing aromatic heterocyclic group, or its pharmaceutically acceptable salt, or a solvate thereof.

5. The compound according to claim 1, wherein ring A' is a nitrogen-containing aromatic heteromonocyclic group, or its pharmaceutically acceptable salt, or a solvate thereof.

6. The compound according to claim 1, wherein ring B is a nitrogen-containing aromatic heteromonocyclic group, or its pharmaceutically acceptable salt, or a solvate thereof.

7. A pharmaceutical composition comprising, as an active ingredient, the compound according to claim 3, or its pharmaceutically acceptable salt, or a solvate thereof.

8. A pharmaceutical composition having β secretase inhibitory activity, comprising, as an active ingredient, the compound according to claim 1, or its pharmaceutically acceptable salt, or a solvate thereof.

9. A method for inhibiting β secretase activity, comprising administering the compound according to claim 1, or its pharmaceutically acceptable salt, or a solvate thereof.

10. The compound according to claim 2, wherein $R^{2a}$ and $R^{2b}$ are both hydrogen, or its pharmaceutically acceptable salt, or a solvate thereof.

11. A method for treating dementia of the Alzheimer's type, Alzheimer's disease, senile dementia of Alzheimer type, Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, or amyloid angiopathy, comprising administering the compound according to claim 1, or a pharmaceutically acceptable salt thereof.

12. The compound according to claim 1, wherein ring A is

[Chemical formula 7]

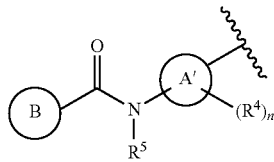

wherein ring A' is a carbocyclic group or a heterocyclic group;

$R^5$ is hydrogen, lower alkyl or acyl;

ring B is an optionally substituted carbocyclic group or an optionally substituted heterocyclic group;

$R^4$ is each independently halogen, hydroxy, mercapto, halogeno lower alkyl, lower alkyl, lower alkoxy, optionally substituted amino, or lower alkylthio, and n is an integer of 0 to 2;

or its pharmaceutically acceptable salt, or a solvate thereof.

13. A method for treating dementia of the Alzheimer's type, Alzheimer's disease, senile dementia of Alzheimer type, Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, or amyloid angiopathy, comprising administering the compound according to claim 12, or a pharmaceutically acceptable salt thereof.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:

```
<223> OTHER INFORMATION: Peptide sequence in a biotinylated peptide

<400> SEQUENCE: 1

Ser Glu Val Asn Leu Asp Ala Glu Phe Arg His Asp Ser Gly Cys
1               5                   10                  15
```